United States Patent
Klempner et al.

(10) Patent No.: US 11,732,032 B2
(45) Date of Patent: Aug. 22, 2023

(54) ANTI-ETEC ADHESIN PROTEIN ANTIBODIES AND METHODS OF USE

(71) Applicant: University of Massachusetts, Boston, MA (US)

(72) Inventors: Mark S. Klempner, Boston, MA (US); Yang Wang, Wellesley, MA (US); Lisa Cavacini, Natick, MA (US); Alla Amcheslavsky, Harvard, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 17/358,669

(22) Filed: Jun. 25, 2021

(65) Prior Publication Data

US 2022/0025022 A1 Jan. 27, 2022

Related U.S. Application Data

(60) Provisional application No. 63/044,691, filed on Jun. 26, 2020.

(51) Int. Cl.

| | |
|---|---|
| *C07K 16/12* | (2006.01) |
| *G01N 33/569* | (2006.01) |
| *A61P 31/04* | (2006.01) |
| *A61K 39/00* | (2006.01) |

(52) U.S. Cl.
CPC .......... *C07K 16/1232* (2013.01); *A61P 31/04* (2018.01); *G01N 33/56916* (2013.01); *A61K 2039/505* (2013.01); *A61K 2039/54* (2013.01); *A61K 2039/545* (2013.01); *C07K 2317/14* (2013.01); *C07K 2317/24* (2013.01); *C07K 2317/522* (2013.01); *C07K 2317/53* (2013.01); *C07K 2317/565* (2013.01); *C07K 2317/567* (2013.01); *C07K 2317/569* (2013.01); *C07K 2317/76* (2013.01); *C07K 2317/92* (2013.01); *G01N 2333/245* (2013.01); *G01N 2469/10* (2013.01)

(58) Field of Classification Search
None
See application file for complete search history.

(56) References Cited

U.S. PATENT DOCUMENTS

| | | |
|---|---|---|
| 8,481,043 B2 | 7/2013 | Bergenhem et al. |
| 2005/0250196 A1 | 11/2005 | Paton et al. |

FOREIGN PATENT DOCUMENTS

| | | |
|---|---|---|
| WO | WO-2004/074491 A2 | 9/2004 |
| WO | WO-2017/219004 A2 | 12/2017 |
| WO | WO-2020/097627 A1 | 5/2020 |

OTHER PUBLICATIONS

International Search Report and Written Opinion for International Application No. PCT/US2021/039091, dated Oct. 28, 2021 (22 pages).
International Preliminary Report on Patentability for International Patent Application No. PCT/US2021/039091, dated Dec. 13, 2022 (11 pages).

*Primary Examiner* — Oluwatosin A Ogunbiyi
(74) *Attorney, Agent, or Firm* — Clark & Elbing LLP

(57) ABSTRACT

The invention provides anti-ETEC adhesin protein antibodies and methods of using the same.

26 Claims, 27 Drawing Sheets
(13 of 27 Drawing Sheet(s) Filed in Color)
Specification includes a Sequence Listing.

Fig. 1A

Llama immunization with 8 CFAs

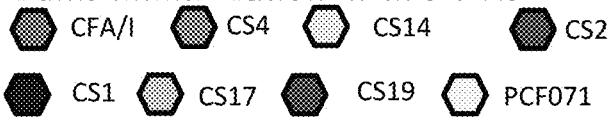

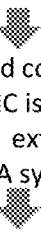

- Blood collection
- PBMC isolation
- RNA extraction
- cDNA synthesis

- Cloning into pUR8100 phagemid vector
- Generation of two phage libraries(~ 5x10e8 each)

- Panning and selection (3 rounds- CS1, CS2, CfaE)
- Sequencing of 2 masterplates
- Selection of clones for further characterization

Fig. 1B

Naïve yeast surface display library

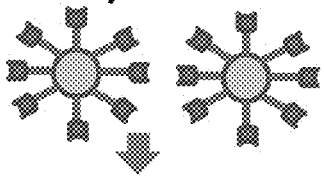

- Induce nanobody expression
- Bind to antigen (CFA/I)
- Select binders by MACS
- Amplify binding clones and repeat selection

- FACS to select for high affinity binders to CfaE

- Panning against CS1 and CS2
- Sequencing of binding clones
- Selection of clones for further characterization

FIG. 10

|       | D40 | Y58 | H62 | L64 | Y65 | D66 | R67 | T91 | Y156 | R181 | R182 | Y183 |
|-------|-----|-----|-----|-----|-----|-----|-----|-----|------|------|------|------|
| 2R215 |     | ++  |     | ++  | +   |     | ++  | ++  | ++   | ++   | ++   | ++   |
| 1D7   | ++  | -   | ++  | -   | +++ | ++  | ++  |     | ++   | +    | ++   | ++   |
| 2R23  | -   | +   | +   | +   | +   |     | -   | +   | +    | -    | +    | +    |
| 1H4   |     | -   |     | -   | +   |     | +   |     | -    | +    | +    | -    |

SEQUENCE LISTING

```
<160> NUMBER OF SEQ ID NOS: 266

<210> SEQ ID NO 1
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1

Asn Ile Phe Gln Asp Ala Glu
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic Construct

<400> SEQUENCE: 2

Phe Val Ala Thr Ile Ala Tyr Gly Gly Asn Thr Asn
1               5                   10

<210> SEQ ID NO 3
<211> LENGTH: 18
<212> TYPE: PRT
<213> ORGANISM: Artificial Sequence
```

```
<220> FEATURE:
<223> OTHER INFORMATION: Synthetic Construct

<400> SEQUENCE: 3

Val Tyr Thr Gly Val Tyr Tyr Asp Arg Thr Thr Gly Gly Tyr Val Ala
1               5                   10                  15

Phe Glu

<210> SEQ ID NO 4
<211> LENGTH: 126
<212> TYPE: PRT
<213> ORGANISM: Artificial Sequence
<220> FEATURE:
<223> OTHER INFORMATION: Synthetic Construct

<400> SEQUENCE: 4

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Phe Gln Asp Ala
            20                  25                  30

Glu Met Gly Trp Tyr Arg Gln Ala Pro Gly Lys Glu Arg Glu Phe Val
        35                  40                  45

Ala Thr Ile Ala Tyr Gly Gly Asn Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Tyr Thr Gly Val Tyr Tyr Asp Arg Thr Thr Gly Gly Tyr Val Ala
            100                 105                 110

Phe Glu Tyr Trp Gly Gln Gly Thr Gln Val Thr Val Ser Ser
        115                 120                 125

<210> SEQ ID NO 5
<211> LENGTH: 26
<212> TYPE: PRT
<213> ORGANISM: Artificial Sequence
<220> FEATURE:
<223> OTHER INFORMATION: Synthetic Construct

<400> SEQUENCE: 5

Gln Val Gln Leu Gln Glu Ser Gly Gly Gly Leu Val Gln Ala Gly Gly
1               5                   10                  15

Ser Leu Arg Leu Ser Cys Ala Ala Ser Gly
            20                  25

<210> SEQ ID NO 6
<211> LENGTH: 13
<212> TYPE: PRT
<213> ORGANISM: Artificial Sequence
<220> FEATURE:
<223> OTHER INFORMATION: Synthetic Construct

<400> SEQUENCE: 6

Met Gly Trp Tyr Arg Gln Ala Pro Gly Lys Glu Arg Glu
1               5                   10

<210> SEQ ID NO 7
<211> LENGTH: 38
<212> TYPE: PRT
<213> ORGANISM: Artificial Sequence
<220> FEATURE:
```

<223> OTHER INFORMATION: Synthetic Construct

<400> SEQUENCE: 7

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala
        35

<210> SEQ ID NO 8
<211> LENGTH: 12
<212> TYPE: PRT
<213> ORGANISM: Artificial Sequence
<220> FEATURE:
<223> OTHER INFORMATION: Synthetic Construct

<400> SEQUENCE: 8

Tyr Trp Gly Gln Gly Thr Gln Val Thr Val Ser Ser
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Synthetic Construct

<400> SEQUENCE: 9

Glu Arg Thr Phe Ser Tyr Tyr Val
1               5

<210> SEQ ID NO 10
<211> LENGTH: 13
<212> TYPE: PRT
<213> ORGANISM: Artificial Sequence
<220> FEATURE:
<223> OTHER INFORMATION: Synthetic Construct

<400> SEQUENCE: 10

Phe Val Ala Gly Ile Ser Met Ser Gly Asp Ser Thr Lys
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic Construct

<400> SEQUENCE: 11

Ala Asp Arg Asp Ile Arg Gly Asn Phe Arg Ser
1               5                   10

<210> SEQ ID NO 12
<211> LENGTH: 121
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Val Glu Ser Gly Gly Gly Leu Val Gln Ala Gly Gly
1               5                   10                  15

Ser Leu Thr Leu Ser Cys Ala Ala Ser Glu Arg Thr Phe Ser Tyr Tyr

```
                    20                  25                  30
Val Met Ala Trp Phe Arg Gln Ala Pro Gly Lys Glu Arg Glu Phe Val
                35                  40                  45

Ala Gly Ile Ser Met Ser Gly Asp Ser Thr Lys Tyr Ala Asp Ser Val
         50                  55                  60

Lys Gly Arg Phe Thr Ile Ser Arg Asp Asn Ala Glu Asn Thr Gly Tyr
 65                  70                  75                  80

Leu Gln Met Asn Gly Leu Lys Pro Glu Asp Thr Ala Val Tyr Tyr Cys
                 85                  90                  95

Ala Ala Asp Arg Asp Ile Arg Gly Asn Phe Arg Ser Trp Gly Arg Gly
            100                 105                 110

Thr Gln Val Thr Val Ser Ser Ala Ala
        115                 120

<210> SEQ ID NO 13
<211> LENGTH: 25
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Val Glu Ser Gly Gly Gly Leu Val Gln Ala Gly Gly
 1               5                  10                  15

Ser Leu Thr Leu Ser Cys Ala Ala Ser
            20                  25

<210> SEQ ID NO 14
<211> LENGTH: 13
<212> TYPE: PRT
<213> ORGANISM: Artificial Sequence
<220> FEATURE:
<223> OTHER INFORMATION: Synthetic Construct

<400> SEQUENCE: 14

Met Ala Trp Phe Arg Gln Ala Pro Gly Lys Glu Arg Glu
 1               5                  10

<210> SEQ ID NO 15
<211> LENGTH: 38
<212> TYPE: PRT
<213> ORGANISM: Artificial Sequence
<220> FEATURE:
<223> OTHER INFORMATION: Synthetic Construct

<400> SEQUENCE: 15

Tyr Ala Asp Ser Val Lys Gly Arg Phe Thr Ile Ser Arg Asp Asn Ala
 1               5                  10                  15

Glu Asn Thr Gly Tyr Leu Gln Met Asn Gly Leu Lys Pro Glu Asp Thr
             20                  25                  30

Ala Val Tyr Tyr Cys Ala
         35

<210> SEQ ID NO 16
<211> LENGTH: 13
<212> TYPE: PRT
<213> ORGANISM: Artificial Sequence
<220> FEATURE:
<223> OTHER INFORMATION: Synthetic Construct

<400> SEQUENCE: 16

Trp Gly Arg Gly Thr Gln Val Thr Val Ser Ser Ala Ala
```

-continued

```
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Synthetic Construct

<400> SEQUENCE: 17

Tyr Ile Phe Trp Ser Tyr Gly Tyr
1               5

<210> SEQ ID NO 18
<211> LENGTH: 12
<212> TYPE: PRT
<213> ORGANISM: Artificial Sequence
<220> FEATURE:
<223> OTHER INFORMATION: Synthetic Construct

<400> SEQUENCE: 18

Leu Val Ala Thr Ile Ser Arg Gly Gly Thr Thr Asn
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic Construct

<400> SEQUENCE: 19

Ala Gly Arg Tyr Ala Phe Gly Tyr Phe Lys
1               5                   10

<210> SEQ ID NO 20
<211> LENGTH: 119
<212> TYPE: PRT
<213> ORGANISM: Artificial Sequence
<220> FEATURE:
<223> OTHER INFORMATION: Synthetic Construct

<400> SEQUENCE: 20

Gln Val Gln Leu Gln Glu Ser Gly Gly Gly Leu Val Gln Ala Gly Gly
1               5                   10                  15

Ser Leu Arg Leu Ser Cys Ala Ala Ser Gly Tyr Ile Phe Trp Ser Tyr
            20                  25                  30

Gly Tyr Met Gly Trp Tyr Arg Gln Ala Pro Gly Lys Glu Arg Glu Leu
        35                  40                  45

Val Ala Thr Ile Ser Arg Gly Gly Thr Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Arg Tyr Ala Phe Gly Tyr Phe Lys Tyr Trp Gly Gln Gly
            100                 105                 110

Thr Gln Val Thr Val Ser Ser
        115

<210> SEQ ID NO 21
<211> LENGTH: 26
<212> TYPE: PRT
```

```
<213> ORGANISM: Artificial Sequence
<220> FEATURE:
<223> OTHER INFORMATION: Synthetic Construct

<400> SEQUENCE: 21

Gln Val Gln Leu Gln Glu Ser Gly Gly Gly Leu Val Gln Ala Gly Gly
1               5                   10                  15

Ser Leu Arg Leu Ser Cys Ala Ala Ser Gly
            20                  25

<210> SEQ ID NO 22
<211> LENGTH: 13
<212> TYPE: PRT
<213> ORGANISM: Artificial Sequence
<220> FEATURE:
<223> OTHER INFORMATION: Synthetic Construct

<400> SEQUENCE: 22

Met Gly Trp Tyr Arg Gln Ala Pro Gly Lys Glu Arg Glu
1               5                   10

<210> SEQ ID NO 23
<211> LENGTH: 38
<212> TYPE: PRT
<213> ORGANISM: Artificial Sequence
<220> FEATURE:
<223> OTHER INFORMATION: Synthetic Construct

<400> SEQUENCE: 23

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala
        35

<210> SEQ ID NO 24
<211> LENGTH: 12
<212> TYPE: PRT
<213> ORGANISM: Artificial Sequence
<220> FEATURE:
<223> OTHER INFORMATION: Synthetic Construct

<400> SEQUENCE: 24

Tyr Trp Gly Gln Gly Thr Gln Val Thr Val Ser Ser
1               5                   10

<210> SEQ ID NO 25
<211> LENGTH: 8
<212> TYPE: PRT
<213> ORGANISM: Artificial Sequence
<220> FEATURE:
<223> OTHER INFORMATION: Synthetic Construct

<400> SEQUENCE: 25

Ser Arg Thr Phe Asn His Tyr Asn
1               5

<210> SEQ ID NO 26
<211> LENGTH: 13
<212> TYPE: PRT
<213> ORGANISM: Artificial Sequence
<220> FEATURE:
<223> OTHER INFORMATION: Synthetic Construct

<400> SEQUENCE: 26
```

Phe Ala Ala Ala Ile Thr Trp Asn Gly Arg Ser Thr Leu
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthetic Construct

<400> SEQUENCE: 27

Thr Leu Thr Thr Trp Glu His Lys Trp Glu Tyr Asn Ser
1               5                   10

<210> SEQ ID NO 28
<211> LENGTH: 123
<212> TYPE: PRT
<213> ORGANISM: Artificial Sequence
<220> FEATURE:
<223> OTHER INFORMATION: Synthetic Construct

<400> SEQUENCE: 28

Glu Val Gln Leu Val Glu Ser Gly Gly Gly Leu Val Gln Ala Gly Gly
1               5                   10                  15

Ser Leu Arg Leu Ser Cys Ala Ala Ser Ser Arg Thr Phe Asn His Tyr
            20                  25                  30

Asn Ile Gly Trp Phe Arg Gln Ala Pro Gly Lys Glu Arg Glu Phe Ala
        35                  40                  45

Ala Ala Ile Thr Trp Asn Gly Arg Ser Thr Leu Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Thr Leu Thr Thr Trp Glu His Lys Trp Glu Tyr Asn Ser Gln Gly
            100                 105                 110

Gln Gly Thr Gln Val Thr Val Ser Ser Ala Ala
        115                 120

<210> SEQ ID NO 29
<211> LENGTH: 25
<212> TYPE: PRT
<213> ORGANISM: Artificial Sequence
<220> FEATURE:
<223> OTHER INFORMATION: Synthetic Construct

<400> SEQUENCE: 29

Glu Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 30
<211> LENGTH: 13
<212> TYPE: PRT
<213> ORGANISM: Artificial Sequence
<220> FEATURE:
<223> OTHER INFORMATION: Synthetic Construct

<400> SEQUENCE: 30

Ile Gly Trp Phe Arg Gln Ala Pro Gly Lys Glu Arg Glu
1               5                   10

<210> SEQ ID NO 31
<211> LENGTH: 38
<212> TYPE: PRT
<213> ORGANISM: Artificial Sequence
<220> FEATURE:
<223> OTHER INFORMATION: Synthetic Construct

<400> SEQUENCE: 31

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala
        35

<210> SEQ ID NO 32
<211> LENGTH: 13
<212> TYPE: PRT
<213> ORGANISM: Artificial Sequence
<220> FEATURE:
<223> OTHER INFORMATION: Synthetic Construct

<400> SEQUENCE: 32

Gln Gly Gln Gly Thr Gln Val Thr Val Ser Ser Ala Ala
1               5                   10

<210> SEQ ID NO 33
<211> LENGTH: 6
<212> TYPE: PRT
<213> ORGANISM: Artificial Sequence
<220> FEATURE:
<223> OTHER INFORMATION: Synthetic Construct

<400> SEQUENCE: 33

Ser Ile Phe Cys Arg Ser
1               5

<210> SEQ ID NO 34
<211> LENGTH: 12
<212> TYPE: PRT
<213> ORGANISM: Artificial Sequence
<220> FEATURE:
<223> OTHER INFORMATION: Synthetic Construct

<400> SEQUENCE: 34

Phe Val Ala Gly Ile Gly Leu Gly Ala Asn Thr Tyr
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic Construct

<400> SEQUENCE: 35

Ala Arg Ser Phe Ser Val Leu Gly His Tyr
1               5                   10

<210> SEQ ID NO 36
<211> LENGTH: 116
<212> TYPE: PRT
<213> ORGANISM: Artificial Sequence
<220> FEATURE:
<223> OTHER INFORMATION: Synthetic Construct

<400> SEQUENCE: 36

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Cys Arg Ser
            20                  25                  30

Met Gly Trp Tyr Arg Gln Ala Pro Gly Lys Glu Arg Glu Phe Val Ala
        35                  40                  45

Gly Ile Gly Leu Gly Ala Asn Thr Tyr Tyr Ala Asp Ser Val Lys Gly
    50                  55                  60

Arg Phe Thr Ile Ser Arg Asp Asn Ala Lys Asn Thr Val Tyr Leu Gln
65                  70                  75                  80

Met Asn Ser Leu Lys Pro Glu Asp Thr Ala Val Tyr Tyr Cys Ala Ala
                85                  90                  95

Arg Ser Phe Ser Val Leu Gly His Tyr Tyr Trp Gly Gln Gly Thr Gln
            100                 105                 110

Val Thr Ser Ser
        115

<210> SEQ ID NO 37
<211> LENGTH: 26
<212> TYPE: PRT
<213> ORGANISM: Artificial Sequence
<220> FEATURE:
<223> OTHER INFORMATION: Synthetic Construct

<400> SEQUENCE: 37

Gln Val Gln Leu Gln Glu Ser Gly Gly Gly Leu Val Gln Ala Gly Gly
1               5                   10                  15

Ser Leu Arg Leu Ser Cys Ala Ala Ser Gly
            20                  25

<210> SEQ ID NO 38
<211> LENGTH: 13
<212> TYPE: PRT
<213> ORGANISM: Artificial Sequence
<220> FEATURE:
<223> OTHER INFORMATION: Synthetic Construct

<400> SEQUENCE: 38

Met Gly Trp Tyr Arg Gln Ala Pro Gly Lys Glu Arg Glu
1               5                   10

<210> SEQ ID NO 39
<211> LENGTH: 38
<212> TYPE: PRT
<213> ORGANISM: Artificial Sequence
<220> FEATURE:
<223> OTHER INFORMATION: Synthetic Construct

<400> SEQUENCE: 39

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala
        35

<210> SEQ ID NO 40
<211> LENGTH: 11
<212> TYPE: PRT

```
<213> ORGANISM: Artificial Sequence
<220> FEATURE:
<223> OTHER INFORMATION: Synthetic Construct

<400> SEQUENCE: 40

Tyr Trp Gly Gln Gly Thr Gln Val Thr Ser Ser
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Synthetic Construct

<400> SEQUENCE: 41

Thr Ile Phe Tyr Gly Ala Tyr
1               5

<210> SEQ ID NO 42
<211> LENGTH: 12
<212> TYPE: PRT
<213> ORGANISM: Artificial Sequence
<220> FEATURE:
<223> OTHER INFORMATION: Synthetic Construct

<400> SEQUENCE: 42

Leu Val Ala Gly Ile Thr Ile Gly Ala Asn Thr Asn
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic Construct

<400> SEQUENCE: 43

Val Gln Tyr Trp Arg Lys Arg Leu His Gln
1               5                   10

<210> SEQ ID NO 44
<211> LENGTH: 118
<212> TYPE: PRT
<213> ORGANISM: Artificial Sequence
<220> FEATURE:
<223> OTHER INFORMATION: Synthetic Construct

<400> SEQUENCE: 44

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Tyr Gly Ala
            20                  25                  30

Tyr Met Gly Trp Tyr Arg Gln Ala Pro Gly Lys Glu Arg Glu Leu Val
        35                  40                  45

Ala Gly Ile Thr Ile Gly Ala Asn Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Gln Tyr Trp Arg Lys Arg Leu His Gln Tyr Trp Gly Gln Gly Thr
            100                 105                 110
```

Gln Val Thr Val Ser Ser
        115

<210> SEQ ID NO 45
<211> LENGTH: 26
<212> TYPE: PRT
<213> ORGANISM: Artificial Sequence
<220> FEATURE:
<223> OTHER INFORMATION: Synthetic Construct

<400> SEQUENCE: 45

Gln Val Gln Leu Gln Glu Ser Gly Gly Gly Leu Val Gln Ala Gly Gly
1               5                   10                  15

Ser Leu Arg Leu Ser Cys Ala Ala Ser Gly
            20                  25

<210> SEQ ID NO 46
<211> LENGTH: 13
<212> TYPE: PRT
<213> ORGANISM: Artificial Sequence
<220> FEATURE:
<223> OTHER INFORMATION: Synthetic Construct

<400> SEQUENCE: 46

Met Gly Trp Tyr Arg Gln Ala Pro Gly Lys Glu Arg Glu
1               5                   10

<210> SEQ ID NO 47
<211> LENGTH: 38
<212> TYPE: PRT
<213> ORGANISM: Artificial Sequence
<220> FEATURE:
<223> OTHER INFORMATION: Synthetic Construct

<400> SEQUENCE: 47

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala
        35

<210> SEQ ID NO 48
<211> LENGTH: 12
<212> TYPE: PRT
<213> ORGANISM: Artificial Sequence
<220> FEATURE:
<223> OTHER INFORMATION: Synthetic Construct

<400> SEQUENCE: 48

Tyr Trp Gly Gln Gly Thr Gln Val Thr Val Ser Ser
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Synthetic Construct

<400> SEQUENCE: 49

Thr Ile Phe Gln Asp Ala Tyr
1               5

<210> SEQ ID NO 50

-continued

```
<211> LENGTH: 12
<212> TYPE: PRT
<213> ORGANISM: Artificial Sequence
<220> FEATURE:
<223> OTHER INFORMATION: Synthetic Construct

<400> SEQUENCE: 50

Phe Val Ala Thr Ile Ala Tyr Gly Gly Asn Thr Asn
1               5                   10

<210> SEQ ID NO 51
<211> LENGTH: 18
<212> TYPE: PRT
<213> ORGANISM: Artificial Sequence
<220> FEATURE:
<223> OTHER INFORMATION: Synthetic Construct

<400> SEQUENCE: 51

Val Tyr Thr Gly Val Tyr Tyr Asp Arg Thr Thr Gly Gly Tyr Val Ala
1               5                   10                  15

Phe Glu

<210> SEQ ID NO 52
<211> LENGTH: 126
<212> TYPE: PRT
<213> ORGANISM: Artificial Sequence
<220> FEATURE:
<223> OTHER INFORMATION: Synthetic Construct

<400> SEQUENCE: 52

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Gln Asp Ala
                20                  25                  30

Tyr Met Gly Trp Tyr Arg Gln Ala Pro Gly Lys Glu Arg Glu Phe Val
            35                  40                  45

Ala Thr Ile Ala Tyr Gly Gly Asn Thr Asn Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Tyr Thr Gly Val Tyr Tyr Asp Arg Thr Thr Gly Gly Tyr Val Ala
            100                 105                 110

Phe Glu Tyr Trp Gly Gln Gly Thr Gln Val Thr Val Ser Ser
        115                 120                 125

<210> SEQ ID NO 53
<211> LENGTH: 26
<212> TYPE: PRT
<213> ORGANISM: Artificial Sequence
<220> FEATURE:
<223> OTHER INFORMATION: Synthetic Construct

<400> SEQUENCE: 53

Gln Val Gln Leu Gln Glu Ser Gly Gly Gly Leu Val Gln Ala Gly Gly
1               5                   10                  15

Ser Leu Arg Leu Ser Cys Ala Ala Ser Gly
                20                  25

<210> SEQ ID NO 54
<211> LENGTH: 13
```

```
<212> TYPE: PRT
<213> ORGANISM: Artificial Sequence
<220> FEATURE:
<223> OTHER INFORMATION: Synthetic Construct

<400> SEQUENCE: 54

Met Gly Trp Tyr Arg Gln Ala Pro Gly Lys Glu Arg Glu
1               5                   10

<210> SEQ ID NO 55
<211> LENGTH: 38
<212> TYPE: PRT
<213> ORGANISM: Artificial Sequence
<220> FEATURE:
<223> OTHER INFORMATION: Synthetic Construct

<400> SEQUENCE: 55

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala
        35

<210> SEQ ID NO 56
<211> LENGTH: 12
<212> TYPE: PRT
<213> ORGANISM: Artificial Sequence
<220> FEATURE:
<223> OTHER INFORMATION: Synthetic Construct

<400> SEQUENCE: 56

Tyr Trp Gly Gln Gly Thr Gln Val Thr Val Ser Ser
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Synthetic Construct

<400> SEQUENCE: 57

Tyr Ile Phe Gly His Ser Lys
1               5

<210> SEQ ID NO 58
<211> LENGTH: 12
<212> TYPE: PRT
<213> ORGANISM: Artificial Sequence
<220> FEATURE:
<223> OTHER INFORMATION: Synthetic Construct

<400> SEQUENCE: 58

Phe Val Ala Gly Ile Ser Leu Gly Ala Asn Thr Tyr
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic Construct

<400> SEQUENCE: 59

Ala Arg Phe Phe Ser Val Leu Gly His Tyr
```

<210> SEQ ID NO 60
<211> LENGTH: 118
<212> TYPE: PRT
<213> ORGANISM: Artificial Sequence
<220> FEATURE:
<223> OTHER INFORMATION: Synthetic Construct

<400> SEQUENCE: 60

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Tyr Ile Phe Gly His Ser
            20                  25                  30

Lys Met Gly Trp Tyr Arg Gln Ala Pro Gly Lys Glu Arg Glu Phe Val
        35                  40                  45

Ala Gly Ile Ser Leu Gly Ala Asn Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Arg Phe Phe Ser Val Leu Gly His Tyr Tyr Trp Gly Gln Gly Thr
            100                 105                 110

Gln Val Thr Val Ser Ser
        115
```

<210> SEQ ID NO 61
<211> LENGTH: 26
<212> TYPE: PRT
<213> ORGANISM: Artificial Sequence
<220> FEATURE:
<223> OTHER INFORMATION: Synthetic Construct

<400> SEQUENCE: 61

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly
            20                  25
```

<210> SEQ ID NO 62
<211> LENGTH: 13
<212> TYPE: PRT
<213> ORGANISM: Artificial Sequence
<220> FEATURE:
<223> OTHER INFORMATION: Synthetic Construct

<400> SEQUENCE: 62

```
Met Gly Trp Tyr Arg Gln Ala Pro Gly Lys Glu Arg Glu
1               5                   10
```

<210> SEQ ID NO 63
<211> LENGTH: 38
<212> TYPE: PRT
<213> ORGANISM: Artificial Sequence
<220> FEATURE:
<223> OTHER INFORMATION: Synthetic Construct

<400> SEQUENCE: 63

```
Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
```

```
                    20                  25                  30

Ala Val Tyr Tyr Cys Ala
         35

<210> SEQ ID NO 64
<211> LENGTH: 12
<212> TYPE: PRT
<213> ORGANISM: Artificial Sequence
<220> FEATURE:
<223> OTHER INFORMATION: Synthetic Construct

<400> SEQUENCE: 64

Tyr Trp Gly Gln Gly Thr Gln Val Thr Val Ser Ser
1               5                   10

<210> SEQ ID NO 65
<211> LENGTH: 7
<212> TYPE: PRT
<213> ORGANISM: Artificial Sequence
<220> FEATURE:
<223> OTHER INFORMATION: Synthetic Construct

<400> SEQUENCE: 65

Thr Ile Phe Ser Pro Gly Thr
1               5

<210> SEQ ID NO 66
<211> LENGTH: 12
<212> TYPE: PRT
<213> ORGANISM: Artificial Sequence
<220> FEATURE:
<223> OTHER INFORMATION: Synthetic Construct

<400> SEQUENCE: 66

Leu Val Ala Ser Ile Gly Asp Gly Ser Thr Thr Asn
1               5                   10

<210> SEQ ID NO 67
<211> LENGTH: 18
<212> TYPE: PRT
<213> ORGANISM: Artificial Sequence
<220> FEATURE:
<223> OTHER INFORMATION: Synthetic Construct

<400> SEQUENCE: 67

Val Pro Val Ser Tyr Tyr Leu Arg Tyr Tyr Pro Tyr Tyr Lys Thr Tyr
1               5                   10                  15

Phe Trp

<210> SEQ ID NO 68
<211> LENGTH: 126
<212> TYPE: PRT
<213> ORGANISM: Artificial Sequence
<220> FEATURE:
<223> OTHER INFORMATION: Synthetic Construct

<400> SEQUENCE: 68

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Ser Pro Gly
                20                  25                  30

Thr Met Gly Trp Tyr Arg Gln Ala Pro Gly Lys Glu Arg Glu Leu Val
        35                  40                  45

Ala Ser Ile Gly Asp Gly Ser Thr Thr Asn Tyr Ala Asp Ser Val Lys
```

```
                    50                  55                  60
Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                     85                  90                  95

Val Pro Val Ser Tyr Tyr Leu Arg Tyr Tyr Pro Tyr Tyr Lys Thr Tyr
                100                 105                 110

Phe Trp Tyr Trp Gly Gln Gly Thr Gln Val Thr Val Ser Ser
            115                 120                 125

<210> SEQ ID NO 69
<211> LENGTH: 26
<212> TYPE: PRT
<213> ORGANISM: Artificial Sequence
<220> FEATURE:
<223> OTHER INFORMATION: Synthetic Construct

<400> SEQUENCE: 69

Gln Val Gln Leu Gln Glu Ser Gly Gly Gly Leu Val Gln Ala Gly Gly
 1               5                  10                  15

Ser Leu Arg Leu Ser Cys Ala Ala Ser Gly
            20                  25

<210> SEQ ID NO 70
<211> LENGTH: 13
<212> TYPE: PRT
<213> ORGANISM: Artificial Sequence
<220> FEATURE:
<223> OTHER INFORMATION: Synthetic Construct

<400> SEQUENCE: 70

Met Gly Trp Tyr Arg Gln Ala Pro Gly Lys Glu Arg Glu
 1               5                  10

<210> SEQ ID NO 71
<211> LENGTH: 38
<212> TYPE: PRT
<213> ORGANISM: Artificial Sequence
<220> FEATURE:
<223> OTHER INFORMATION: Synthetic Construct

<400> SEQUENCE: 71

Tyr Ala Asp Ser Val Lys Gly Arg Phe Thr Ile Ser Arg Asp Asn Ala
 1               5                  10                  15

Lys Asn Thr Val Tyr Leu Gln Met Asn Ser Leu Lys Pro Glu Asp Thr
            20                  25                  30

Ala Val Tyr Tyr Cys Ala
        35

<210> SEQ ID NO 72
<211> LENGTH: 12
<212> TYPE: PRT
<213> ORGANISM: Artificial Sequence
<220> FEATURE:
<223> OTHER INFORMATION: Synthetic Construct

<400> SEQUENCE: 72

Tyr Trp Gly Gln Gly Thr Gln Val Thr Val Ser Ser
 1               5                  10

<210> SEQ ID NO 73
<211> LENGTH: 7
<212> TYPE: PRT
```

<213> ORGANISM: Artificial Sequence
<220> FEATURE:
<223> OTHER INFORMATION: Synthetic Construct

<400> SEQUENCE: 73

Asn Ile Phe Ser Arg Ala Thr
1               5

<210> SEQ ID NO 74
<211> LENGTH: 12
<212> TYPE: PRT
<213> ORGANISM: Artificial Sequence
<220> FEATURE:
<223> OTHER INFORMATION: Synthetic Construct

<400> SEQUENCE: 74

Phe Val Ala Gly Ile Gly Tyr Gly Gly Asn Thr Tyr
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthetic Construct

<400> SEQUENCE: 75

Val Arg Val Tyr Gly Ala Phe Gly His Val
1               5                   10

<210> SEQ ID NO 76
<211> LENGTH: 118
<212> TYPE: PRT
<213> ORGANISM: Artificial Sequence
<220> FEATURE:
<223> OTHER INFORMATION: Synthetic Construct

<400> SEQUENCE: 76

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Phe Ser Arg Ala
            20                  25                  30

Thr Met Gly Trp Tyr Arg Gln Ala Pro Gly Lys Glu Arg Glu Phe Val
        35                  40                  45

Ala Gly Ile Gly Tyr Gly Gly Asn Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Arg Val Tyr Gly Ala Phe Gly His Val Tyr Trp Gly Gln Gly Thr
            100                 105                 110

Gln Val Thr Val Ser Ser
        115

<210> SEQ ID NO 77
<211> LENGTH: 26
<212> TYPE: PRT
<213> ORGANISM: Artificial Sequence
<220> FEATURE:
<223> OTHER INFORMATION: Synthetic Construct

<400> SEQUENCE: 77

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly
            20                  25
```

<210> SEQ ID NO 78
<211> LENGTH: 13
<212> TYPE: PRT
<213> ORGANISM: Artificial Sequence
<220> FEATURE:
<223> OTHER INFORMATION: Synthetic Construct

<400> SEQUENCE: 78

```
Met Gly Trp Tyr Arg Gln Ala Pro Gly Lys Glu Arg Glu
1               5                   10
```

<210> SEQ ID NO 79
<211> LENGTH: 38
<212> TYPE: PRT
<213> ORGANISM: Artificial Sequence
<220> FEATURE:
<223> OTHER INFORMATION: Synthetic Construct

<400> SEQUENCE: 79

```
Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala
        35
```

<210> SEQ ID NO 80
<211> LENGTH: 12
<212> TYPE: PRT
<213> ORGANISM: Artificial Sequence
<220> FEATURE:
<223> OTHER INFORMATION: Synthetic Construct

<400> SEQUENCE: 80

```
Tyr Trp Gly Gln Gly Thr Gln Val Thr Val Ser Ser
1               5                   10
```

<210> SEQ ID NO 81
<211> LENGTH: 8
<212> TYPE: PRT
<213> ORGANISM: Artificial Sequence
<220> FEATURE:
<223> OTHER INFORMATION: Synthetic Construct

<400> SEQUENCE: 81

```
Glu Arg Asn Asn Asn Ile Asn Ala
1               5
```

<210> SEQ ID NO 82
<211> LENGTH: 12
<212> TYPE: PRT
<213> ORGANISM: Artificial Sequence
<220> FEATURE:
<223> OTHER INFORMATION: Synthetic Construct

<400> SEQUENCE: 82

```
Phe Val Ala Arg Val Ala Val Gly Gly Ser Thr Ala
1               5                   10
```

<210> SEQ ID NO 83

<211> LENGTH: 13
<212> TYPE: PRT
<213> ORGANISM: Artificial Sequence
<220> FEATURE:
<223> OTHER INFORMATION: Synthetic Construct

<400> SEQUENCE: 83

Ala Ala Leu Lys Tyr Glu Val Gly Gly Val Tyr Asp Tyr
1               5                   10

<210> SEQ ID NO 84
<211> LENGTH: 122
<212> TYPE: PRT
<213> ORGANISM: Artificial Sequence
<220> FEATURE:
<223> OTHER INFORMATION: Synthetic Construct

<400> SEQUENCE: 84

Glu Val Gln Leu Val Glu Ser Gly Gly Gly Leu Val Gln Ala Gly Glu
1               5                   10                  15

Ser Leu Arg Leu Ser Cys Ala Ala Ser Glu Arg Asn Asn Asn Ile Asn
            20                  25                  30

Ala Met Gly Trp Phe Arg Gln Pro Pro Gly Lys Gln Arg Glu Phe Val
        35                  40                  45

Ala Arg Val Ala Val Gly Gly Ser Thr Ala Tyr Ala Asp Ser Val Lys
    50                  55                  60

Gly Arg Phe Thr Ile Ser Arg Asp Asn Ala Lys Asn Met Val Tyr Leu
65                  70                  75                  80

Gln Met Asp Ser Leu Lys Val Glu Asp Thr Ala Val Tyr Tyr Cys Tyr
                85                  90                  95

Ala Ala Leu Lys Tyr Glu Val Gly Gly Val Tyr Asp Tyr Trp Gly Gln
            100                 105                 110

Gly Thr Gln Val Thr Val Ser Ser Ala Ala
        115                 120

<210> SEQ ID NO 85
<211> LENGTH: 25
<212> TYPE: PRT
<213> ORGANISM: Artificial Sequence
<220> FEATURE:
<223> OTHER INFORMATION: Synthetic Construct

<400> SEQUENCE: 85

Glu Val Gln Leu Val Glu Ser Gly Gly Gly Leu Val Gln Ala Gly Glu
1               5                   10                  15

Ser Leu Arg Leu Ser Cys Ala Ala Ser
            20                  25

<210> SEQ ID NO 86
<211> LENGTH: 13
<212> TYPE: PRT
<213> ORGANISM: Artificial Sequence
<220> FEATURE:
<223> OTHER INFORMATION: Synthetic Construct

<400> SEQUENCE: 86

Met Gly Trp Phe Arg Gln Pro Pro Gly Lys Gln Arg Glu
1               5                   10

<210> SEQ ID NO 87
<211> LENGTH: 38
<212> TYPE: PRT
<213> ORGANISM: Artificial Sequence

```
<220> FEATURE:
<223> OTHER INFORMATION: Synthetic Construct

<400> SEQUENCE: 87

Tyr Ala Asp Ser Val Lys Gly Arg Phe Thr Ile Ser Arg Asp Asn Ala
1               5                   10                  15

Lys Asn Met Val Tyr Leu Gln Met Asp Ser Leu Lys Val Glu Asp Thr
            20                  25                  30

Ala Val Tyr Tyr Cys Tyr
        35

<210> SEQ ID NO 88
<211> LENGTH: 13
<212> TYPE: PRT
<213> ORGANISM: Artificial Sequence
<220> FEATURE:
<223> OTHER INFORMATION: Synthetic Construct

<400> SEQUENCE: 88

Trp Gly Gln Gly Thr Gln Val Thr Val Ser Ser Ala Ala
1               5                   10

<210> SEQ ID NO 89
<211> LENGTH: 8
<212> TYPE: PRT
<213> ORGANISM: Artificial Sequence
<220> FEATURE:
<223> OTHER INFORMATION: Synthetic Construct

<400> SEQUENCE: 89

Glu Arg Thr Phe Ser Tyr Tyr Val
1               5

<210> SEQ ID NO 90
<211> LENGTH: 13
<212> TYPE: PRT
<213> ORGANISM: Artificial Sequence
<220> FEATURE:
<223> OTHER INFORMATION: Synthetic Construct

<400> SEQUENCE: 90

Phe Val Ala Gly Ile Ser Met Asn Gly Asp Ser Thr Lys
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Synthetic Construct

<400> SEQUENCE: 91

Ala Asp Arg Asp Ile Arg Gly Asn Phe Arg Ser
1               5                   10

<210> SEQ ID NO 92
<211> LENGTH: 121
<212> TYPE: PRT
<213> ORGANISM: Artificial Sequence
<220> FEATURE:
<223> OTHER INFORMATION: Synthetic Construct

<400> SEQUENCE: 92

Glu Val Gln Leu Val Glu Ser Gly Gly Gly Leu Val Gln Ala Gly Gly
1               5                   10                  15
```

```
Ser Leu Thr Leu Ser Cys Ala Ala Ser Glu Arg Thr Phe Ser Tyr Tyr
            20                  25                  30

Val Met Gly Trp Phe Arg Gln Ala Pro Gly Lys Glu Arg Glu Phe Val
        35                  40                  45

Ala Gly Ile Ser Met Asn Gly Asp Ser Thr Lys Tyr Ala Asp Ser Val
    50                  55                  60

Lys Gly Arg Phe Thr Ile Ser Arg Asp Asn Ala Glu Met Thr Gly Tyr
65                  70                  75                  80

Leu Gln Met Asn Ser Leu Lys Pro Glu Asp Thr Ala Val Tyr Tyr Cys
                85                  90                  95

Ala Ala Asp Arg Asp Ile Arg Gly Asn Phe Arg Ser Trp Gly Gln Gly
            100                 105                 110

Thr Gln Val Thr Val Ser Ser Ala Ala
        115                 120

<210> SEQ ID NO 93
<211> LENGTH: 25
<212> TYPE: PRT
<213> ORGANISM: Artificial Sequence
<220> FEATURE:
<223> OTHER INFORMATION: Synthetic Construct

<400> SEQUENCE: 93

Glu Val Gln Leu Val Glu Ser Gly Gly Gly Leu Val Gln Ala Gly Gly
1               5                   10                  15

Ser Leu Thr Leu Ser Cys Ala Ala Ser
            20                  25

<210> SEQ ID NO 94
<211> LENGTH: 13
<212> TYPE: PRT
<213> ORGANISM: Artificial Sequence
<220> FEATURE:
<223> OTHER INFORMATION: Synthetic Construct

<400> SEQUENCE: 94

Met Gly Trp Phe Arg Gln Ala Pro Gly Lys Glu Arg Glu
1               5                   10

<210> SEQ ID NO 95
<211> LENGTH: 38
<212> TYPE: PRT
<213> ORGANISM: Artificial Sequence
<220> FEATURE:
<223> OTHER INFORMATION: Synthetic Construct

<400> SEQUENCE: 95

Tyr Ala Asp Ser Val Lys Gly Arg Phe Thr Ile Ser Arg Asp Asn Ala
1               5                   10                  15

Glu Met Thr Gly Tyr Leu Gln Met Asn Ser Leu Lys Pro Glu Asp Thr
            20                  25                  30

Ala Val Tyr Tyr Cys Ala
        35

<210> SEQ ID NO 96
<211> LENGTH: 13
<212> TYPE: PRT
<213> ORGANISM: Artificial Sequence
<220> FEATURE:
<223> OTHER INFORMATION: Synthetic Construct

<400> SEQUENCE: 96
```

```
Trp Gly Gln Gly Thr Gln Val Thr Val Ser Ser Ala Ala
1               5                   10
```

<210> SEQ ID NO 97
<211> LENGTH: 8
<212> TYPE: PRT
<213> ORGANISM: Artificial Sequence
<220> FEATURE:
<223> OTHER INFORMATION: Synthetic Construct

<400> SEQUENCE: 97

```
Ser Arg Thr Phe Asn His Tyr Asn
1               5
```

<210> SEQ ID NO 98
<211> LENGTH: 13
<212> TYPE: PRT
<213> ORGANISM: Artificial Sequence
<220> FEATURE:
<223> OTHER INFORMATION: Synthetic Construct

<400> SEQUENCE: 98

```
Phe Ala Ala Ala Ile Thr Trp Asn Gly Arg Ser Thr Leu
1               5                   10
```

<210> SEQ ID NO 99
<211> LENGTH: 13
<212> TYPE: PRT
<213> ORGANISM: Artificial Sequence
<220> FEATURE:
<223> OTHER INFORMATION: Synthetic Construct

<400> SEQUENCE: 99

```
Thr Leu Thr Thr Trp Glu His Lys Trp Glu Tyr Asn Ser
1               5                   10
```

<210> SEQ ID NO 100
<211> LENGTH: 123
<212> TYPE: PRT
<213> ORGANISM: Artificial Sequence
<220> FEATURE:
<223> OTHER INFORMATION: Synthetic Construct

<400> SEQUENCE: 100

```
Glu Val Gln Leu Val Glu Ser Gly Gly Leu Val Gln Ala Gly Gly
1               5                   10                  15

Ser Leu Arg Leu Ser Cys Ala Ala Ser Ser Arg Thr Phe Asn His Tyr
                20                  25                  30

Asn Ile Gly Trp Phe Arg Gln Ala Pro Gly Lys Glu Arg Glu Phe Ala
            35                  40                  45

Ala Ala Ile Thr Trp Asn Gly Arg Ser Thr Leu Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Thr Leu Thr Thr Trp Glu His Lys Trp Glu Tyr Asn Ser Gln Gly
            100                 105                 110

Gln Gly Thr Gln Val Thr Val Ser Ser Ala Ala
            115                 120
```

<210> SEQ ID NO 101
<211> LENGTH: 25

```
<212> TYPE: PRT
<213> ORGANISM: Artificial Sequence
<220> FEATURE:
<223> OTHER INFORMATION: Synthetic Construct

<400> SEQUENCE: 101

Glu Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 102
<211> LENGTH: 13
<212> TYPE: PRT
<213> ORGANISM: Artificial Sequence
<220> FEATURE:
<223> OTHER INFORMATION: Synthetic Construct

<400> SEQUENCE: 102

Ile Gly Trp Phe Arg Gln Ala Pro Gly Lys Glu Arg Glu
1               5                   10

<210> SEQ ID NO 103
<211> LENGTH: 38
<212> TYPE: PRT
<213> ORGANISM: Artificial Sequence
<220> FEATURE:
<223> OTHER INFORMATION: Synthetic Construct

<400> SEQUENCE: 103

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala
        35

<210> SEQ ID NO 104
<211> LENGTH: 13
<212> TYPE: PRT
<213> ORGANISM: Artificial Sequence
<220> FEATURE:
<223> OTHER INFORMATION: Synthetic Construct

<400> SEQUENCE: 104

Gln Gly Gln Gly Thr Gln Val Thr Val Ser Ser Ala Ala
1               5                   10

<210> SEQ ID NO 105
<211> LENGTH: 8
<212> TYPE: PRT
<213> ORGANISM: Artificial Sequence
<220> FEATURE:
<223> OTHER INFORMATION: Synthetic Construct

<400> SEQUENCE: 105

Gly Arg Ser Asn Asn Ile Asn Ala
1               5

<210> SEQ ID NO 106
<211> LENGTH: 12
<212> TYPE: PRT
<213> ORGANISM: Artificial Sequence
<220> FEATURE:
<223> OTHER INFORMATION: Synthetic Construct
```

<400> SEQUENCE: 106

Phe Val Ala Arg Val Ala Val Gly Gly Ser Thr Asn
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Synthetic Construct

<400> SEQUENCE: 107

Ala Ala Leu Lys Tyr Glu Leu Gly Gly Val Tyr Asp Tyr
1               5                   10

<210> SEQ ID NO 108
<211> LENGTH: 122
<212> TYPE: PRT
<213> ORGANISM: Artificial Sequence
<220> FEATURE:
<223> OTHER INFORMATION: Synthetic Construct

<400> SEQUENCE: 108

Glu Val Gln Leu Val Glu Ser Gly Gly Gly Leu Val Gln Ala Gly Glu
1               5                   10                  15

Ser Leu Arg Leu Ser Cys Ala Ala Ser Gly Arg Ser Asn Asn Ile Asn
            20                  25                  30

Ala Met Gly Trp Phe Arg Gln Pro Pro Gly Lys Gln Arg Glu Phe Val
        35                  40                  45

Ala Arg Val Ala Val Gly Gly Ser Thr Asn Tyr Ala Asp Ser Val Lys
    50                  55                  60

Gly Arg Phe Thr Ile Ser Arg Asp Asn Ala Lys Asn Met Val Tyr Leu
65                  70                  75                  80

Gln Met Asp Ser Leu Lys Val Glu Asp Thr Ala Val Tyr Tyr Cys Tyr
                85                  90                  95

Ala Ala Leu Lys Tyr Glu Leu Gly Gly Val Tyr Asp Tyr Trp Gly Gln
            100                 105                 110

Gly Thr Gln Val Thr Val Ser Ser Ala Ala
        115                 120

<210> SEQ ID NO 109
<211> LENGTH: 25
<212> TYPE: PRT
<213> ORGANISM: Artificial Sequence
<220> FEATURE:
<223> OTHER INFORMATION: Synthetic Construct

<400> SEQUENCE: 109

Glu Val Gln Leu Val Glu Ser Gly Gly Gly Leu Val Gln Ala Gly Glu
1               5                   10                  15

Ser Leu Arg Leu Ser Cys Ala Ala Ser
            20                  25

<210> SEQ ID NO 110
<211> LENGTH: 13
<212> TYPE: PRT
<213> ORGANISM: Artificial Sequence
<220> FEATURE:
<223> OTHER INFORMATION: Synthetic Construct

<400> SEQUENCE: 110

Met Gly Trp Phe Arg Gln Pro Pro Gly Lys Gln Arg Glu

```
1               5                   10

<210> SEQ ID NO 111
<211> LENGTH: 38
<212> TYPE: PRT
<213> ORGANISM: Artificial Sequence
<220> FEATURE:
<223> OTHER INFORMATION: Synthetic Construct

<400> SEQUENCE: 111

Tyr Ala Asp Ser Val Lys Gly Arg Phe Thr Ile Ser Arg Asp Asn Ala
1               5                   10                  15

Lys Asn Met Val Tyr Leu Gln Met Asp Ser Leu Lys Val Glu Asp Thr
            20                  25                  30

Ala Val Tyr Tyr Cys Tyr
        35

<210> SEQ ID NO 112
<211> LENGTH: 13
<212> TYPE: PRT
<213> ORGANISM: Artificial Sequence
<220> FEATURE:
<223> OTHER INFORMATION: Synthetic Construct

<400> SEQUENCE: 112

Trp Gly Gln Gly Thr Gln Val Thr Val Ser Ser Ala Ala
1               5                   10

<210> SEQ ID NO 113
<211> LENGTH: 7
<212> TYPE: PRT
<213> ORGANISM: Artificial Sequence
<220> FEATURE:
<223> OTHER INFORMATION: Synthetic Construct

<400> SEQUENCE: 113

Tyr Ser Tyr Thr Ala Pro Val
1               5

<210> SEQ ID NO 114
<211> LENGTH: 13
<212> TYPE: PRT
<213> ORGANISM: Artificial Sequence
<220> FEATURE:
<223> OTHER INFORMATION: Synthetic Construct

<400> SEQUENCE: 114

Phe Val Ala Ala Ile Ser Ser Arg Thr Gly Val Thr Lys
1               5                   10

<210> SEQ ID NO 115
<211> LENGTH: 16
<212> TYPE: PRT
<213> ORGANISM: Artificial Sequence
<220> FEATURE:
<223> OTHER INFORMATION: Synthetic Construct

<400> SEQUENCE: 115

Ser Thr Phe Asn Trp Ile Ile Pro Thr Val Glu Ser Gly Tyr Asn Asp
1               5                   10                  15

<210> SEQ ID NO 116
<211> LENGTH: 125
<212> TYPE: PRT
<213> ORGANISM: Artificial Sequence
<220> FEATURE:
```

-continued

<223> OTHER INFORMATION: Synthetic Construct

<400> SEQUENCE: 116

Glu Val Gln Leu Val Glu Ser Gly Gly Gly Leu Val Gln Ala Gly Gly
1               5                   10                  15

Ser Leu Arg Leu Ser Cys Val Ala Ser Tyr Tyr Thr Ala Pro Val
            20                  25                  30

Met Gly Trp Phe Arg Gln Ala Pro Gly Lys Asp Arg Glu Phe Val Ala
        35                  40                  45

Ala Ile Ser Ser Arg Thr Gly Val Thr Lys Tyr Ala Asp Ser Val Lys
    50                  55                  60

Gly Arg Phe Ser Ile Pro Gly Asp Asp Ala Lys Asn Thr Met Phe Leu
65                  70                  75                  80

Gln Met Ser Ser Val Gln Pro Asp Asp Thr Ala Val Tyr Tyr Cys Ala
                85                  90                  95

Ser Thr Phe Asn Trp Ile Ile Pro Thr Val Glu Ser Gly Tyr Asn Asp
            100                 105                 110

Trp Gly Gln Gly Thr Gln Val Thr Val Ser Ser Ala Ala
        115                 120                 125

<210> SEQ ID NO 117
<211> LENGTH: 25
<212> TYPE: PRT
<213> ORGANISM: Artificial Sequence
<220> FEATURE:
<223> OTHER INFORMATION: Synthetic Construct

<400> SEQUENCE: 117

Glu Val Gln Leu Val Glu Ser Gly Gly Gly Leu Val Gln Ala Gly Gly
1               5                   10                  15

Ser Leu Arg Leu Ser Cys Val Ala Ser
            20                  25

<210> SEQ ID NO 118
<211> LENGTH: 13
<212> TYPE: PRT
<213> ORGANISM: Artificial Sequence
<220> FEATURE:
<223> OTHER INFORMATION: Synthetic Construct

<400> SEQUENCE: 118

Met Gly Trp Phe Arg Gln Ala Pro Gly Lys Asp Arg Glu
1               5                   10

<210> SEQ ID NO 119
<211> LENGTH: 38
<212> TYPE: PRT
<213> ORGANISM: Artificial Sequence
<220> FEATURE:
<223> OTHER INFORMATION: Synthetic Construct

<400> SEQUENCE: 119

Tyr Ala Asp Ser Val Lys Gly Arg Phe Ser Ile Pro Gly Asp Asp Ala
1               5                   10                  15

Lys Asn Thr Met Phe Leu Gln Met Ser Ser Val Gln Pro Asp Asp Thr
            20                  25                  30

Ala Val Tyr Tyr Cys Ala
        35

<210> SEQ ID NO 120
<211> LENGTH: 13

```
<212> TYPE: PRT
<213> ORGANISM: Artificial Sequence
<220> FEATURE:
<223> OTHER INFORMATION: Synthetic Construct

<400> SEQUENCE: 120

Trp Gly Gln Gly Thr Gln Val Thr Val Ser Ser Ala Ala
1               5                   10

<210> SEQ ID NO 121
<211> LENGTH: 5
<212> TYPE: PRT
<213> ORGANISM: Artificial Sequence
<220> FEATURE:
<223> OTHER INFORMATION: Synthetic Construct

<400> SEQUENCE: 121

Asp Ser Phe Ser Val
1               5

<210> SEQ ID NO 122
<211> LENGTH: 13
<212> TYPE: PRT
<213> ORGANISM: Artificial Sequence
<220> FEATURE:
<223> OTHER INFORMATION: Synthetic Construct

<400> SEQUENCE: 122

Phe Val Ala Ala Ile Ser Ser Ser Thr Gly Val Thr Lys
1               5                   10

<210> SEQ ID NO 123
<211> LENGTH: 16
<212> TYPE: PRT
<213> ORGANISM: Artificial Sequence
<220> FEATURE:
<223> OTHER INFORMATION: Synthetic Construct

<400> SEQUENCE: 123

Ser Thr Val Asn Trp Ile Ile Pro Thr Val Gln Ser Gly Tyr Tyr Asn
1               5                   10                  15

<210> SEQ ID NO 124
<211> LENGTH: 123
<212> TYPE: PRT
<213> ORGANISM: Artificial Sequence
<220> FEATURE:
<223> OTHER INFORMATION: Synthetic Construct

<400> SEQUENCE: 124

Glu Val Gln Leu Val Glu Ser Gly Gly Gly Leu Val Gln Ala Gly Asp
1               5                   10                  15

Ser Leu Arg Leu Ser Cys Val Ala Ser Asp Ser Phe Ser Val Met Gly
            20                  25                  30

Trp Phe Arg Gln Ala Pro Gly Lys Asp Arg Glu Phe Val Ala Ala Ile
        35                  40                  45

Ser Ser Ser Thr Gly Val Thr Lys Tyr Ala Asp Ser Val Lys Gly Arg
    50                  55                  60

Phe Ser Ile Ser Arg Asp Asn Ala Lys Asn Thr Met Tyr Leu Gln Met
65                  70                  75                  80

Ser Arg Leu Gln Pro Asp Asp Thr Ala Val Tyr Tyr Cys Ala Ser Thr
                85                  90                  95

Val Asn Trp Ile Ile Pro Thr Val Gln Ser Gly Tyr Tyr Asn Trp Gly
            100                 105                 110
```

Gln Gly Thr Gln Val Thr Val Ser Ser Ala Ala
        115                 120

<210> SEQ ID NO 125
<211> LENGTH: 25
<212> TYPE: PRT
<213> ORGANISM: Artificial Sequence
<220> FEATURE:
<223> OTHER INFORMATION: Synthetic Construct

<400> SEQUENCE: 125

Glu Val Gln Leu Val Glu Ser Gly Gly Gly Leu Val Gln Ala Gly Asp
1               5                   10                  15

Ser Leu Arg Leu Ser Cys Val Ala Ser
            20                  25

<210> SEQ ID NO 126
<211> LENGTH: 13
<212> TYPE: PRT
<213> ORGANISM: Artificial Sequence
<220> FEATURE:
<223> OTHER INFORMATION: Synthetic Construct

<400> SEQUENCE: 126

Met Gly Trp Phe Arg Gln Ala Pro Gly Lys Asp Arg Glu
1               5                   10

<210> SEQ ID NO 127
<211> LENGTH: 38
<212> TYPE: PRT
<213> ORGANISM: Artificial Sequence
<220> FEATURE:
<223> OTHER INFORMATION: Synthetic Construct

<400> SEQUENCE: 127

Tyr Ala Asp Ser Val Lys Gly Arg Phe Ser Ile Ser Arg Asp Asn Ala
1               5                   10                  15

Lys Asn Thr Met Tyr Leu Gln Met Ser Arg Leu Gln Pro Asp Asp Thr
            20                  25                  30

Ala Val Tyr Tyr Cys Ala
        35

<210> SEQ ID NO 128
<211> LENGTH: 13
<212> TYPE: PRT
<213> ORGANISM: Artificial Sequence
<220> FEATURE:
<223> OTHER INFORMATION: Synthetic Construct

<400> SEQUENCE: 128

Trp Gly Gln Gly Thr Gln Val Thr Val Ser Ser Ala Ala
1               5                   10

<210> SEQ ID NO 129
<211> LENGTH: 8
<212> TYPE: PRT
<213> ORGANISM: Artificial Sequence
<220> FEATURE:
<223> OTHER INFORMATION: Synthetic Construct

<400> SEQUENCE: 129

Val Arg Ser Leu Ser Thr Tyr Val
1               5

<210> SEQ ID NO 130
<211> LENGTH: 12
<212> TYPE: PRT
<213> ORGANISM: Artificial Sequence
<220> FEATURE:
<223> OTHER INFORMATION: Synthetic Construct

<400> SEQUENCE: 130

Phe Val Gly Thr Ile Asn Trp Ser Ser Ile Thr Asn
1               5                   10

<210> SEQ ID NO 131
<211> LENGTH: 16
<212> TYPE: PRT
<213> ORGANISM: Artificial Sequence
<220> FEATURE:
<223> OTHER INFORMATION: Synthetic Construct

<400> SEQUENCE: 131

Thr Gly Pro Asn Gly Arg Asp Pro Gly Arg Ala Thr Ser Tyr Asp Tyr
1               5                   10                  15

<210> SEQ ID NO 132
<211> LENGTH: 125
<212> TYPE: PRT
<213> ORGANISM: Artificial Sequence
<220> FEATURE:
<223> OTHER INFORMATION: Synthetic Construct

<400> SEQUENCE: 132

Glu Val Gln Leu Val Glu Ser Gly Gly Gly Leu Val Gln Ala Gly Ala
1               5                   10                  15

Ser Leu Arg Leu Ser Cys Ala Pro Ser Val Arg Ser Leu Ser Thr Tyr
                20                  25                  30

Val Met Ala Trp Phe Arg Gln Ala Pro Gly Lys Glu Arg Glu Phe Val
            35                  40                  45

Gly Thr Ile Asn Trp Ser Ser Ile Thr Asn Tyr Ala Asp Ser Val Lys
        50                  55                  60

Gly Arg Phe Ala Ile Ser Arg Asp Asn Asp Lys Asn Thr Val Tyr Leu
65                  70                  75                  80

Gln Met Asn Asn Leu Lys Pro Glu Asp Thr Ala Ile Tyr Tyr Cys Ala
                85                  90                  95

Thr Gly Pro Asn Gly Arg Asp Pro Gly Arg Ala Thr Ser Tyr Asp Tyr
            100                 105                 110

Trp Gly Gln Gly Thr Gln Val Thr Val Ser Ser Ala Ala
        115                 120                 125

<210> SEQ ID NO 133
<211> LENGTH: 25
<212> TYPE: PRT
<213> ORGANISM: Artificial Sequence
<220> FEATURE:
<223> OTHER INFORMATION: Synthetic Construct

<400> SEQUENCE: 133

Glu Val Gln Leu Val Glu Ser Gly Gly Gly Leu Val Gln Ala Gly Ala
1               5                   10                  15

Ser Leu Arg Leu Ser Cys Ala Pro Ser
                20                  25

<210> SEQ ID NO 134
<211> LENGTH: 13
<212> TYPE: PRT

<213> ORGANISM: Artificial Sequence
<220> FEATURE:
<223> OTHER INFORMATION: Synthetic Construct

<400> SEQUENCE: 134

Met Ala Trp Phe Arg Gln Ala Pro Gly Lys Glu Arg Glu
1               5                   10

<210> SEQ ID NO 135
<211> LENGTH: 38
<212> TYPE: PRT
<213> ORGANISM: Artificial Sequence
<220> FEATURE:
<223> OTHER INFORMATION: Synthetic Construct

<400> SEQUENCE: 135

Tyr Ala Asp Ser Val Lys Gly Arg Phe Ala Ile Ser Arg Asp Asn Asp
1               5                   10                  15

Lys Asn Thr Val Tyr Leu Gln Met Asn Asn Leu Lys Pro Glu Asp Thr
            20                  25                  30

Ala Ile Tyr Tyr Cys Ala
        35

<210> SEQ ID NO 136
<211> LENGTH: 13
<212> TYPE: PRT
<213> ORGANISM: Artificial Sequence
<220> FEATURE:
<223> OTHER INFORMATION: Synthetic Construct

<400> SEQUENCE: 136

Trp Gly Gln Gly Thr Gln Val Thr Val Ser Ser Ala Ala
1               5                   10

<210> SEQ ID NO 137
<211> LENGTH: 8
<212> TYPE: PRT
<213> ORGANISM: Artificial Sequence
<220> FEATURE:
<223> OTHER INFORMATION: Synthetic Construct

<400> SEQUENCE: 137

Glu Arg Thr Phe Arg Tyr Tyr Val
1               5

<210> SEQ ID NO 138
<211> LENGTH: 13
<212> TYPE: PRT
<213> ORGANISM: Artificial Sequence
<220> FEATURE:
<223> OTHER INFORMATION: Synthetic Construct

<400> SEQUENCE: 138

Phe Val Ala Gly Ile Ser Met Ser Gly Asp Ser Thr Lys
1               5                   10

<210> SEQ ID NO 139
<211> LENGTH: 11
<212> TYPE: PRT
<213> ORGANISM: Artificial Sequence
<220> FEATURE:
<223> OTHER INFORMATION: Synthetic Construct

<400> SEQUENCE: 139

Ala Asp Arg Asp Ile Arg Gly Asn Phe Arg Ser
1               5                   10

<210> SEQ ID NO 140
<211> LENGTH: 121
<212> TYPE: PRT
<213> ORGANISM: Artificial Sequence
<220> FEATURE:
<223> OTHER INFORMATION: Synthetic Construct

<400> SEQUENCE: 140

Glu Val Gln Leu Val Glu Ser Gly Gly Gly Leu Val Gln Ala Gly Gly
1               5                   10                  15

Ser Leu Thr Leu Ser Cys Ala Ala Ser Glu Arg Thr Phe Arg Tyr Tyr
            20                  25                  30

Val Met Ala Trp Phe Arg Gln Ala Pro Gly Lys Glu Arg Glu Phe Val
        35                  40                  45

Ala Gly Ile Ser Met Ser Gly Asp Ser Thr Lys Tyr Ala Asp Ser Val
    50                  55                  60

Lys Gly Arg Phe Thr Ile Ser Arg Asp Asn Ala Glu Asn Thr Gly Tyr
65                  70                  75                  80

Leu Gln Met Asn Ser Leu Lys Pro Glu Asp Thr Ala Val Tyr Tyr Cys
                85                  90                  95

Ala Ala Asp Arg Asp Ile Arg Gly Asn Phe Arg Ser Trp Gly Gln Gly
            100                 105                 110

Thr Gln Val Thr Val Ser Ser Ala Ala
        115                 120

<210> SEQ ID NO 141
<211> LENGTH: 25
<212> TYPE: PRT
<213> ORGANISM: Artificial Sequence
<220> FEATURE:
<223> OTHER INFORMATION: Synthetic Construct

<400> SEQUENCE: 141

Glu Val Gln Leu Val Glu Ser Gly Gly Gly Leu Val Gln Ala Gly Gly
1               5                   10                  15

Ser Leu Thr Leu Ser Cys Ala Ala Ser
            20                  25

<210> SEQ ID NO 142
<211> LENGTH: 13
<212> TYPE: PRT
<213> ORGANISM: Artificial Sequence
<220> FEATURE:
<223> OTHER INFORMATION: Synthetic Construct

<400> SEQUENCE: 142

Met Ala Trp Phe Arg Gln Ala Pro Gly Lys Glu Arg Glu
1               5                   10

<210> SEQ ID NO 143
<211> LENGTH: 38
<212> TYPE: PRT
<213> ORGANISM: Artificial Sequence
<220> FEATURE:
<223> OTHER INFORMATION: Synthetic Construct

<400> SEQUENCE: 143

Tyr Ala Asp Ser Val Lys Gly Arg Phe Thr Ile Ser Arg Asp Asn Ala
1               5                   10                  15

Glu Asn Thr Gly Tyr Leu Gln Met Asn Ser Leu Lys Pro Glu Asp Thr
            20                  25                  30

```
Ala Val Tyr Tyr Cys Ala
        35

<210> SEQ ID NO 144
<211> LENGTH: 13
<212> TYPE: PRT
<213> ORGANISM: Artificial Sequence
<220> FEATURE:
<223> OTHER INFORMATION: Synthetic Construct

<400> SEQUENCE: 144

Trp Gly Gln Gly Thr Gln Val Thr Val Ser Ser Ala Ala
1               5                   10

<210> SEQ ID NO 145
<211> LENGTH: 8
<212> TYPE: PRT
<213> ORGANISM: Artificial Sequence
<220> FEATURE:
<223> OTHER INFORMATION: Synthetic Construct

<400> SEQUENCE: 145

Glu Arg Thr Phe Ser Tyr Tyr Val
1               5

<210> SEQ ID NO 146
<211> LENGTH: 13
<212> TYPE: PRT
<213> ORGANISM: Artificial Sequence
<220> FEATURE:
<223> OTHER INFORMATION: Synthetic Construct

<400> SEQUENCE: 146

Phe Val Ala Gly Ile Ser Met Ser Gly Asp Ser Thr Lys
1               5                   10

<210> SEQ ID NO 147
<211> LENGTH: 11
<212> TYPE: PRT
<213> ORGANISM: Artificial Sequence
<220> FEATURE:
<223> OTHER INFORMATION: Synthetic Construct

<400> SEQUENCE: 147

Ala Asp Arg Asp Ile Arg Gly Asn Phe Arg Ser
1               5                   10

<210> SEQ ID NO 148
<211> LENGTH: 121
<212> TYPE: PRT
<213> ORGANISM: Artificial Sequence
<220> FEATURE:
<223> OTHER INFORMATION: Synthetic Construct

<400> SEQUENCE: 148

Glu Val Gln Leu Val Glu Ser Gly Gly Gly Leu Val Gln Ala Gly Gly
1               5                   10                  15

Ser Leu Thr Leu Ser Cys Ala Ala Ser Glu Arg Thr Phe Ser Tyr Tyr
            20                  25                  30

Val Met Ala Trp Phe Arg Gln Ala Pro Gly Lys Glu Arg Glu Phe Val
        35                  40                  45

Ala Gly Ile Ser Met Ser Gly Asp Ser Thr Lys Tyr Ala Asp Ser Val
    50                  55                  60

Lys Gly Arg Phe Thr Ile Ser Arg Asp Asn Ala Glu Asn Thr Gly Tyr
```

```
                65                  70                  75                  80
Leu Gln Met Asn Gly Leu Lys Pro Glu Asp Thr Ala Val Tyr Tyr Cys
                    85                  90                  95

Ala Ala Asp Arg Asp Ile Arg Gly Asn Phe Arg Ser Trp Gly Arg Gly
            100                 105                 110

Ala Gln Val Thr Val Ser Ser Ala Ala
        115                 120

<210> SEQ ID NO 149
<211> LENGTH: 25
<212> TYPE: PRT
<213> ORGANISM: Artificial Sequence
<220> FEATURE:
<223> OTHER INFORMATION: Synthetic Construct

<400> SEQUENCE: 149

Glu Val Gln Leu Val Glu Ser Gly Gly Gly Leu Val Gln Ala Gly Gly
1               5                   10                  15

Ser Leu Thr Leu Ser Cys Ala Ala Ser
            20                  25

<210> SEQ ID NO 150
<211> LENGTH: 13
<212> TYPE: PRT
<213> ORGANISM: Artificial Sequence
<220> FEATURE:
<223> OTHER INFORMATION: Synthetic Construct

<400> SEQUENCE: 150

Met Ala Trp Phe Arg Gln Ala Pro Gly Lys Glu Arg Glu
1               5                   10

<210> SEQ ID NO 151
<211> LENGTH: 38
<212> TYPE: PRT
<213> ORGANISM: Artificial Sequence
<220> FEATURE:
<223> OTHER INFORMATION: Synthetic Construct

<400> SEQUENCE: 151

Tyr Ala Asp Ser Val Lys Gly Arg Phe Thr Ile Ser Arg Asp Asn Ala
1               5                   10                  15

Glu Asn Thr Gly Tyr Leu Gln Met Asn Gly Leu Lys Pro Glu Asp Thr
            20                  25                  30

Ala Val Tyr Tyr Cys Ala
        35

<210> SEQ ID NO 152
<211> LENGTH: 13
<212> TYPE: PRT
<213> ORGANISM: Artificial Sequence
<220> FEATURE:
<223> OTHER INFORMATION: Synthetic Construct

<400> SEQUENCE: 152

Trp Gly Arg Gly Ala Gln Val Thr Val Ser Ser Ala Ala
1               5                   10

<210> SEQ ID NO 153
<211> LENGTH: 8
<212> TYPE: PRT
<213> ORGANISM: Artificial Sequence
<220> FEATURE:
<223> OTHER INFORMATION: Synthetic Construct
```

<400> SEQUENCE: 153

Gly Arg Thr Phe Ser Ile Tyr His
1               5

<210> SEQ ID NO 154
<211> LENGTH: 13
<212> TYPE: PRT
<213> ORGANISM: Artificial Sequence
<220> FEATURE:
<223> OTHER INFORMATION: Synthetic Construct

<400> SEQUENCE: 154

Phe Ile Gly Ala Ile Ile Lys Asn Ala Gly Ser Thr Phe
1               5                   10

<210> SEQ ID NO 155
<211> LENGTH: 16
<212> TYPE: PRT
<213> ORGANISM: Artificial Sequence
<220> FEATURE:
<223> OTHER INFORMATION: Synthetic Construct

<400> SEQUENCE: 155

Ala Lys Tyr Phe Gly Ala Ser His Ala Asp Gln Thr Ser Tyr Val Tyr
1               5                   10                  15

<210> SEQ ID NO 156
<211> LENGTH: 126
<212> TYPE: PRT
<213> ORGANISM: Artificial Sequence
<220> FEATURE:
<223> OTHER INFORMATION: Synthetic Construct

<400> SEQUENCE: 156

Glu Val Gln Leu Val Glu Ser Gly Gly Gly Leu Val Gln Ala Gly Gly
1               5                   10                  15

Ser Leu Arg Leu Ala Cys Ala Val Ser Gly Arg Thr Phe Ser Ile Tyr
            20                  25                  30

His Val Gly Trp Phe Arg Gln Pro Pro Gly Lys Glu Arg Glu Phe Ile
        35                  40                  45

Gly Ala Ile Ile Lys Asn Ala Gly Ser Thr Phe Tyr Ala Asp Phe Val
    50                  55                  60

Glu Gly Arg Phe Thr Ile Ser Thr Asp Asn Ala Lys Asn Thr Val Tyr
65                  70                  75                  80

Leu Gln Met Asp His Leu Gln Pro Glu Asp Thr Ala Val Tyr Tyr Cys
                85                  90                  95

Ala Ala Lys Tyr Phe Gly Ala Ser His Ala Asp Gln Thr Ser Tyr Val
            100                 105                 110

Tyr Trp Gly Gln Gly Thr Gln Val Thr Val Ser Ser Ala Ala
        115                 120                 125

<210> SEQ ID NO 157
<211> LENGTH: 25
<212> TYPE: PRT
<213> ORGANISM: Artificial Sequence
<220> FEATURE:
<223> OTHER INFORMATION: Synthetic Construct

<400> SEQUENCE: 157

Glu Val Gln Leu Val Glu Ser Gly Gly Gly Leu Val Gln Ala Gly Gly
1               5                   10                  15

Ser Leu Arg Leu Ala Cys Ala Val Ser
            20                  25

<210> SEQ ID NO 158
<211> LENGTH: 13
<212> TYPE: PRT
<213> ORGANISM: Artificial Sequence
<220> FEATURE:
<223> OTHER INFORMATION: Synthetic Construct

<400> SEQUENCE: 158

Val Gly Trp Phe Arg Gln Pro Pro Gly Lys Glu Arg Glu
1               5                   10

<210> SEQ ID NO 159
<211> LENGTH: 38
<212> TYPE: PRT
<213> ORGANISM: Artificial Sequence
<220> FEATURE:
<223> OTHER INFORMATION: Synthetic Construct

<400> SEQUENCE: 159

Tyr Ala Asp Phe Val Glu Gly Arg Phe Thr Ile Ser Thr Asp Asn Ala
1               5                   10                  15

Lys Asn Thr Val Tyr Leu Gln Met Asp His Leu Gln Pro Glu Asp Thr
            20                  25                  30

Ala Val Tyr Tyr Cys Ala
        35

<210> SEQ ID NO 160
<211> LENGTH: 13
<212> TYPE: PRT
<213> ORGANISM: Artificial Sequence
<220> FEATURE:
<223> OTHER INFORMATION: Synthetic Construct

<400> SEQUENCE: 160

Trp Gly Gln Gly Thr Gln Val Thr Val Ser Ser Ala Ala
1               5                   10

<210> SEQ ID NO 161
<211> LENGTH: 8
<212> TYPE: PRT
<213> ORGANISM: Artificial Sequence
<220> FEATURE:
<223> OTHER INFORMATION: Synthetic Construct

<400> SEQUENCE: 161

Gly Arg Ala Phe Ser Ile Tyr His
1               5

<210> SEQ ID NO 162
<211> LENGTH: 13
<212> TYPE: PRT
<213> ORGANISM: Artificial Sequence
<220> FEATURE:
<223> OTHER INFORMATION: Synthetic Construct

<400> SEQUENCE: 162

Phe Ile Gly Ala Ile Ile Lys Asn Ala Gly Ser Thr Phe
1               5                   10

<210> SEQ ID NO 163
<211> LENGTH: 16
<212> TYPE: PRT
<213> ORGANISM: Artificial Sequence

```
<220> FEATURE:
<223> OTHER INFORMATION: Synthetic Construct

<400> SEQUENCE: 163

Ala Lys Tyr Phe Gly Ala Ser His Val Asp Gln Thr Ser Tyr Val Tyr
1               5                   10                  15

<210> SEQ ID NO 164
<211> LENGTH: 126
<212> TYPE: PRT
<213> ORGANISM: Artificial Sequence
<220> FEATURE:
<223> OTHER INFORMATION: Synthetic Construct

<400> SEQUENCE: 164

Glu Val Gln Leu Val Glu Ser Gly Gly Gly Leu Val Gln Ala Gly Gly
1               5                   10                  15

Ser Leu Arg Leu Ala Cys Ala Val Ser Gly Arg Ala Phe Ser Ile Tyr
            20                  25                  30

His Val Gly Trp Phe Arg Gln Pro Pro Gly Lys Glu Arg Glu Phe Ile
        35                  40                  45

Gly Ala Ile Ile Lys Asn Ala Gly Ser Thr Phe Tyr Ala Asp Phe Val
    50                  55                  60

Glu Gly Arg Phe Thr Ile Ser Thr Asp Asn Ala Lys Asn Thr Val Tyr
65                  70                  75                  80

Leu Gln Met Asp His Leu Gln Pro Glu Asp Thr Ala Val Tyr Tyr Cys
                85                  90                  95

Ala Ala Lys Tyr Phe Gly Ala Ser His Val Asp Gln Thr Ser Tyr Val
            100                 105                 110

Tyr Trp Gly Gln Gly Thr Gln Val Thr Val Ser Ser Ala Ala
        115                 120                 125

<210> SEQ ID NO 165
<211> LENGTH: 25
<212> TYPE: PRT
<213> ORGANISM: Artificial Sequence
<220> FEATURE:
<223> OTHER INFORMATION: Synthetic Construct

<400> SEQUENCE: 165

Glu Val Gln Leu Val Glu Ser Gly Gly Gly Leu Val Gln Ala Gly Gly
1               5                   10                  15

Ser Leu Arg Leu Ala Cys Ala Val Ser
            20                  25

<210> SEQ ID NO 166
<211> LENGTH: 13
<212> TYPE: PRT
<213> ORGANISM: Artificial Sequence
<220> FEATURE:
<223> OTHER INFORMATION: Synthetic Construct

<400> SEQUENCE: 166

Val Gly Trp Phe Arg Gln Pro Pro Gly Lys Glu Arg Glu
1               5                   10

<210> SEQ ID NO 167
<211> LENGTH: 38
<212> TYPE: PRT
<213> ORGANISM: Artificial Sequence
<220> FEATURE:
<223> OTHER INFORMATION: Synthetic Construct
```

```
<400> SEQUENCE: 167

Tyr Ala Asp Phe Val Glu Gly Arg Phe Thr Ile Ser Thr Asp Asn Ala
1               5                   10                  15

Lys Asn Thr Val Tyr Leu Gln Met Asp His Leu Gln Pro Glu Asp Thr
            20                  25                  30

Ala Val Tyr Tyr Cys Ala
        35

<210> SEQ ID NO 168
<211> LENGTH: 13
<212> TYPE: PRT
<213> ORGANISM: Artificial Sequence
<220> FEATURE:
<223> OTHER INFORMATION: Synthetic Construct

<400> SEQUENCE: 168

Trp Gly Gln Gly Thr Gln Val Thr Val Ser Ser Ala Ala
1               5                   10

<210> SEQ ID NO 169
<211> LENGTH: 8
<212> TYPE: PRT
<213> ORGANISM: Artificial Sequence
<220> FEATURE:
<223> OTHER INFORMATION: Synthetic Construct

<400> SEQUENCE: 169

Glu Arg Thr Phe Ser Tyr Tyr Val
1               5

<210> SEQ ID NO 170
<211> LENGTH: 13
<212> TYPE: PRT
<213> ORGANISM: Artificial Sequence
<220> FEATURE:
<223> OTHER INFORMATION: Synthetic Construct

<400> SEQUENCE: 170

Phe Val Ala Gly Ile Ser Met Ser Gly Asp Ser Thr Lys
1               5                   10

<210> SEQ ID NO 171
<211> LENGTH: 11
<212> TYPE: PRT
<213> ORGANISM: Artificial Sequence
<220> FEATURE:
<223> OTHER INFORMATION: Synthetic Construct

<400> SEQUENCE: 171

Ala Asp Arg Asp Ile Arg Gly Asn Phe Arg Ser
1               5                   10

<210> SEQ ID NO 172
<211> LENGTH: 121
<212> TYPE: PRT
<213> ORGANISM: Artificial Sequence
<220> FEATURE:
<223> OTHER INFORMATION: Synthetic Construct

<400> SEQUENCE: 172

Glu Val Gln Leu Val Glu Ser Gly Gly Gly Leu Val Gln Ala Gly Gly
1               5                   10                  15

Ser Leu Thr Leu Ser Cys Ala Ala Ser Glu Arg Thr Phe Ser Tyr Tyr
            20                  25                  30
```

Val Met Ala Trp Phe Arg Gln Ala Pro Gly Lys Glu Arg Glu Phe Val
         35                  40                  45

Ala Gly Ile Ser Met Ser Gly Asp Ser Thr Lys Tyr Ala Asp Ser Val
 50                  55                  60

Lys Gly Arg Phe Thr Ile Ser Arg Asp Asn Ala Glu Asn Thr Gly Tyr
 65                  70                  75                  80

Leu Gln Met Asn Gly Leu Lys Pro Glu Asp Thr Ala Val Tyr Tyr Cys
                 85                  90                  95

Ala Ala Asp Arg Asp Ile Arg Gly Asn Phe Arg Ser Trp Gly Arg Gly
            100                 105                 110

Thr Gln Val Thr Val Ser Ser Ala Ala
        115                 120

<210> SEQ ID NO 173
<211> LENGTH: 25
<212> TYPE: PRT
<213> ORGANISM: Artificial Sequence
<220> FEATURE:
<223> OTHER INFORMATION: Synthetic Construct

<400> SEQUENCE: 173

Glu Val Gln Leu Val Glu Ser Gly Gly Gly Leu Val Gln Ala Gly Gly
1               5                   10                  15

Ser Leu Thr Leu Ser Cys Ala Ala Ser
            20                  25

<210> SEQ ID NO 174
<211> LENGTH: 13
<212> TYPE: PRT
<213> ORGANISM: Artificial Sequence
<220> FEATURE:
<223> OTHER INFORMATION: Synthetic Construct

<400> SEQUENCE: 174

Met Ala Trp Phe Arg Gln Ala Pro Gly Lys Glu Arg Glu
1               5                   10

<210> SEQ ID NO 175
<211> LENGTH: 38
<212> TYPE: PRT
<213> ORGANISM: Artificial Sequence
<220> FEATURE:
<223> OTHER INFORMATION: Synthetic Construct

<400> SEQUENCE: 175

Tyr Ala Asp Ser Val Lys Gly Arg Phe Thr Ile Ser Arg Asp Asn Ala
1               5                   10                  15

Glu Asn Thr Gly Tyr Leu Gln Met Asn Gly Leu Lys Pro Glu Asp Thr
            20                  25                  30

Ala Val Tyr Tyr Cys Ala
        35

<210> SEQ ID NO 176
<211> LENGTH: 13
<212> TYPE: PRT
<213> ORGANISM: Artificial Sequence
<220> FEATURE:
<223> OTHER INFORMATION: Synthetic Construct

<400> SEQUENCE: 176

Trp Gly Arg Gly Thr Gln Val Thr Val Ser Ser Ala Ala
1               5                   10

<210> SEQ ID NO 177
<211> LENGTH: 8
<212> TYPE: PRT
<213> ORGANISM: Artificial Sequence
<220> FEATURE:
<223> OTHER INFORMATION: Synthetic Construct

<400> SEQUENCE: 177

Glu Arg Thr Phe Ser Tyr Tyr Val
1               5

<210> SEQ ID NO 178
<211> LENGTH: 13
<212> TYPE: PRT
<213> ORGANISM: Artificial Sequence
<220> FEATURE:
<223> OTHER INFORMATION: Synthetic Construct

<400> SEQUENCE: 178

Phe Val Ala Gly Ile Ser Met Gly Gly Asp Ser Thr Lys
1               5                   10

<210> SEQ ID NO 179
<211> LENGTH: 11
<212> TYPE: PRT
<213> ORGANISM: Artificial Sequence
<220> FEATURE:
<223> OTHER INFORMATION: Synthetic Construct

<400> SEQUENCE: 179

Ala Asp Arg Asp Ile Arg Gly Asn Phe Arg Ser
1               5                   10

<210> SEQ ID NO 180
<211> LENGTH: 121
<212> TYPE: PRT
<213> ORGANISM: Artificial Sequence
<220> FEATURE:
<223> OTHER INFORMATION: Synthetic Construct

<400> SEQUENCE: 180

Glu Val Gln Leu Val Glu Ser Gly Gly Gly Leu Val Gln Ala Gly Gly
1               5                   10                  15

Ser Leu Thr Leu Ser Cys Ala Ala Ser Glu Arg Thr Phe Ser Tyr Tyr
            20                  25                  30

Val Met Ala Trp Phe Arg Gln Ala Pro Gly Lys Glu Arg Glu Phe Val
        35                  40                  45

Ala Gly Ile Ser Met Gly Gly Asp Ser Thr Lys Tyr Ala Asp Ser Val
    50                  55                  60

Lys Gly Arg Phe Thr Ile Ser Arg Asp Asn Ala Glu Asn Thr Gly Tyr
65                  70                  75                  80

Leu Gln Met Asn Gly Leu Lys Pro Glu Asp Thr Ala Val Tyr Tyr Cys
                85                  90                  95

Ala Ala Asp Arg Asp Ile Arg Gly Asn Phe Arg Ser Trp Gly Arg Gly
            100                 105                 110

Thr Gln Val Thr Val Ser Ser Ala Ala
        115                 120

<210> SEQ ID NO 181
<211> LENGTH: 25
<212> TYPE: PRT
<213> ORGANISM: Artificial Sequence
<220> FEATURE:

<223> OTHER INFORMATION: Synthetic Construct

<400> SEQUENCE: 181

Glu Val Gln Leu Val Glu Ser Gly Gly Gly Leu Val Gln Ala Gly Gly
1               5                   10                  15

Ser Leu Thr Leu Ser Cys Ala Ala Ser
            20                  25

<210> SEQ ID NO 182
<211> LENGTH: 13
<212> TYPE: PRT
<213> ORGANISM: Artificial Sequence
<220> FEATURE:
<223> OTHER INFORMATION: Synthetic Construct

<400> SEQUENCE: 182

Met Ala Trp Phe Arg Gln Ala Pro Gly Lys Glu Arg Glu
1               5                   10

<210> SEQ ID NO 183
<211> LENGTH: 38
<212> TYPE: PRT
<213> ORGANISM: Artificial Sequence
<220> FEATURE:
<223> OTHER INFORMATION: Synthetic Construct

<400> SEQUENCE: 183

Tyr Ala Asp Ser Val Lys Gly Arg Phe Thr Ile Ser Arg Asp Asn Ala
1               5                   10                  15

Glu Asn Thr Gly Tyr Leu Gln Met Asn Gly Leu Lys Pro Glu Asp Thr
            20                  25                  30

Ala Val Tyr Tyr Cys Ala
        35

<210> SEQ ID NO 184
<211> LENGTH: 13
<212> TYPE: PRT
<213> ORGANISM: Artificial Sequence
<220> FEATURE:
<223> OTHER INFORMATION: Synthetic Construct

<400> SEQUENCE: 184

Trp Gly Arg Gly Thr Gln Val Thr Val Ser Ser Ala Ala
1               5                   10

<210> SEQ ID NO 185
<211> LENGTH: 8
<212> TYPE: PRT
<213> ORGANISM: Artificial Sequence
<220> FEATURE:
<223> OTHER INFORMATION: Synthetic Construct

<400> SEQUENCE: 185

Gly Arg Thr Phe Ser Arg Tyr Ala
1               5

<210> SEQ ID NO 186
<211> LENGTH: 14
<212> TYPE: PRT
<213> ORGANISM: Artificial Sequence
<220> FEATURE:
<223> OTHER INFORMATION: Synthetic Construct

<400> SEQUENCE: 186

Phe Val Ala Ala Thr Ser Thr Trp Thr Gly Gly Pro Ser Tyr

```
1               5                   10
```

<210> SEQ ID NO 187
<211> LENGTH: 16
<212> TYPE: PRT
<213> ORGANISM: Artificial Sequence
<220> FEATURE:
<223> OTHER INFORMATION: Synthetic Construct

<400> SEQUENCE: 187

Ala Met Lys Gly Asn Trp Gly Thr Arg Val Glu Val Asp Phe Gly Ser
1               5                   10                  15

<210> SEQ ID NO 188
<211> LENGTH: 127
<212> TYPE: PRT
<213> ORGANISM: Artificial Sequence
<220> FEATURE:
<223> OTHER INFORMATION: Synthetic Construct

<400> SEQUENCE: 188

Glu Val Gln Leu Val Glu Ser Gly Gly Gly Leu Val Gln Asp Gly Gly
1               5                   10                  15

Ser Leu Ser Leu Ser Cys Thr Ala Ser Gly Arg Thr Phe Ser Arg Tyr
            20                  25                  30

Ala Met Gly Trp Phe Arg Gln Ala Pro Gly Lys Glu Arg Glu Phe Val
        35                  40                  45

Ala Ala Thr Ser Thr Trp Thr Gly Gly Pro Ser Tyr Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Gly Ala Met Lys Gly Asn Trp Gly Thr Arg Val Glu Val Asp Phe
            100                 105                 110

Gly Ser Trp Gly Gln Gly Thr Gln Val Thr Val Ser Ser Ala Ala
        115                 120                 125

<210> SEQ ID NO 189
<211> LENGTH: 25
<212> TYPE: PRT
<213> ORGANISM: Artificial Sequence
<220> FEATURE:
<223> OTHER INFORMATION: Synthetic Construct

<400> SEQUENCE: 189

Glu Val Gln Leu Val Glu Ser Gly Gly Gly Leu Val Gln Asp Gly Gly
1               5                   10                  15

Ser Leu Ser Leu Ser Cys Thr Ala Ser
            20                  25

<210> SEQ ID NO 190
<211> LENGTH: 13
<212> TYPE: PRT
<213> ORGANISM: Artificial Sequence
<220> FEATURE:
<223> OTHER INFORMATION: Synthetic Construct

<400> SEQUENCE: 190

Met Gly Trp Phe Arg Gln Ala Pro Gly Lys Glu Arg Glu
1               5                   10

```
<210> SEQ ID NO 191
<211> LENGTH: 38
<212> TYPE: PRT
<213> ORGANISM: Artificial Sequence
<220> FEATURE:
<223> OTHER INFORMATION: Synthetic Construct

<400> SEQUENCE: 191

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Gly
        35

<210> SEQ ID NO 192
<211> LENGTH: 13
<212> TYPE: PRT
<213> ORGANISM: Artificial Sequence
<220> FEATURE:
<223> OTHER INFORMATION: Synthetic Construct

<400> SEQUENCE: 192

Trp Gly Gln Gly Thr Gln Val Thr Val Ser Ser Ala Ala
1               5                   10

<210> SEQ ID NO 193
<211> LENGTH: 8
<212> TYPE: PRT
<213> ORGANISM: Artificial Sequence
<220> FEATURE:
<223> OTHER INFORMATION: Synthetic Construct

<400> SEQUENCE: 193

Gly Gly Ile Phe Ser Ile Ser Ala
1               5

<210> SEQ ID NO 194
<211> LENGTH: 12
<212> TYPE: PRT
<213> ORGANISM: Artificial Sequence
<220> FEATURE:
<223> OTHER INFORMATION: Synthetic Construct

<400> SEQUENCE: 194

Arg Ile Ala Thr Ile Gly Ile Gly Gly Asn Pro Ser
1               5                   10

<210> SEQ ID NO 195
<211> LENGTH: 13
<212> TYPE: PRT
<213> ORGANISM: Artificial Sequence
<220> FEATURE:
<223> OTHER INFORMATION: Synthetic Construct

<400> SEQUENCE: 195

Ala Arg Phe Lys Gly Pro Ser His Tyr Gly Met Asn Asp
1               5                   10

<210> SEQ ID NO 196
<211> LENGTH: 125
<212> TYPE: PRT
<213> ORGANISM: Artificial Sequence
<220> FEATURE:
<223> OTHER INFORMATION: Synthetic Construct

<400> SEQUENCE: 196
```

-continued

Glu Val Gln Leu Val Glu Ser Gly Gly Gly Leu Val Gln Pro Gly Gly
1               5                   10                  15

Ser Leu Lys Leu Ser Cys Val His Ser Gly Gly Ile Phe Ser Ile Ser
            20                  25                  30

Ala Met Gly Trp Phe Arg Gln Ala Pro Gly Lys Glu Arg Glu Arg Ile
        35                  40                  45

Ala Thr Ile Gly Ile Gly Gly Asn Pro Ser Tyr Ala Asp Ser Val Lys
    50                  55                  60

Gly Arg Phe Thr Ile Ser Thr Ile Thr Ser Val Asn Thr Asn Asn Thr
65                  70                  75                  80

Met Ser Leu Gln Met Asn Asp Leu Lys Pro Glu Asp Thr Gly Val Tyr
            85                  90                  95

Tyr Cys Lys Ala Arg Phe Lys Gly Pro Ser His Tyr Gly Met Asn Asp
            100                 105                 110

Trp Gly Lys Gly Thr Leu Val Thr Val Ser Ser Ala Ala
        115                 120                 125

<210> SEQ ID NO 197
<211> LENGTH: 25
<212> TYPE: PRT
<213> ORGANISM: Artificial Sequence
<220> FEATURE:
<223> OTHER INFORMATION: Synthetic Construct

<400> SEQUENCE: 197

Glu Val Gln Leu Val Glu Ser Gly Gly Gly Leu Val Gln Pro Gly Gly
1               5                   10                  15

Ser Leu Lys Leu Ser Cys Val His Ser
            20                  25

<210> SEQ ID NO 198
<211> LENGTH: 13
<212> TYPE: PRT
<213> ORGANISM: Artificial Sequence
<220> FEATURE:
<223> OTHER INFORMATION: Synthetic Construct

<400> SEQUENCE: 198

Met Gly Trp Phe Arg Gln Ala Pro Gly Lys Glu Arg Glu
1               5                   10

<210> SEQ ID NO 199
<211> LENGTH: 41
<212> TYPE: PRT
<213> ORGANISM: Artificial Sequence
<220> FEATURE:
<223> OTHER INFORMATION: Synthetic Construct

<400> SEQUENCE: 199

Tyr Ala Asp Ser Val Lys Gly Arg Phe Thr Ile Ser Thr Ile Thr Ser
1               5                   10                  15

Val Asn Thr Asn Asn Thr Met Ser Leu Gln Met Asn Asp Leu Lys Pro
            20                  25                  30

Glu Asp Thr Gly Val Tyr Tyr Cys Lys
        35                  40

<210> SEQ ID NO 200
<211> LENGTH: 13
<212> TYPE: PRT
<213> ORGANISM: Artificial Sequence
<220> FEATURE:

```
<223> OTHER INFORMATION: Synthetic Construct

<400> SEQUENCE: 200

Trp Gly Lys Gly Thr Leu Val Thr Val Ser Ser Ala Ala
 1               5                  10

<210> SEQ ID NO 201
<211> LENGTH: 8
<212> TYPE: PRT
<213> ORGANISM: Artificial Sequence
<220> FEATURE:
<223> OTHER INFORMATION: Synthetic Construct

<400> SEQUENCE: 201

Glu Arg Thr Phe Ser Tyr Tyr Val
 1               5

<210> SEQ ID NO 202
<211> LENGTH: 13
<212> TYPE: PRT
<213> ORGANISM: Artificial Sequence
<220> FEATURE:
<223> OTHER INFORMATION: Synthetic Construct

<400> SEQUENCE: 202

Phe Val Ala Gly Ile Ser Met Asn Gly Asp Ser Thr Lys
 1               5                  10

<210> SEQ ID NO 203
<211> LENGTH: 11
<212> TYPE: PRT
<213> ORGANISM: Artificial Sequence
<220> FEATURE:
<223> OTHER INFORMATION: Synthetic Construct

<400> SEQUENCE: 203

Ala Asp Arg Asp Ile Arg Gly Asn Phe Arg Ser
 1               5                  10

<210> SEQ ID NO 204
<211> LENGTH: 121
<212> TYPE: PRT
<213> ORGANISM: Artificial Sequence
<220> FEATURE:
<223> OTHER INFORMATION: Synthetic Construct

<400> SEQUENCE: 204

Glu Val Gln Leu Val Glu Ser Gly Gly Leu Val Gln Ala Gly Gly
 1               5                  10                  15

Ser Leu Thr Leu Ser Cys Ala Ala Ser Glu Arg Thr Phe Ser Tyr Tyr
                 20                  25                  30

Val Met Gly Trp Phe Arg Gln Ala Pro Gly Lys Glu Arg Glu Phe Val
             35                  40                  45

Ala Gly Ile Ser Met Asn Gly Asp Ser Thr Lys Tyr Ala Asp Ser Val
         50                  55                  60

Lys Gly Arg Phe Thr Ile Ser Arg Asp Asn Ala Glu Met Thr Gly Tyr
 65                  70                  75                  80

Leu Gln Met Asn Ser Leu Lys Pro Glu Asp Thr Ala Val Tyr Tyr Cys
                 85                  90                  95

Ala Ala Asp Arg Asp Ile Arg Gly Asn Phe Arg Ser Trp Gly Gln Gly
            100                 105                 110

Thr Gln Val Thr Val Ser Ser Ala Ala
            115                 120
```

<210> SEQ ID NO 205
<211> LENGTH: 25
<212> TYPE: PRT
<213> ORGANISM: Artificial Sequence
<220> FEATURE:
<223> OTHER INFORMATION: Synthetic Construct

<400> SEQUENCE: 205

Glu Val Gln Leu Val Glu Ser Gly Gly Gly Leu Val Gln Ala Gly Gly
1               5                   10                  15

Ser Leu Thr Leu Ser Cys Ala Ala Ser
            20                  25

<210> SEQ ID NO 206
<211> LENGTH: 13
<212> TYPE: PRT
<213> ORGANISM: Artificial Sequence
<220> FEATURE:
<223> OTHER INFORMATION: Synthetic Construct

<400> SEQUENCE: 206

Met Gly Trp Phe Arg Gln Ala Pro Gly Lys Glu Arg Glu
1               5                   10

<210> SEQ ID NO 207
<211> LENGTH: 38
<212> TYPE: PRT
<213> ORGANISM: Artificial Sequence
<220> FEATURE:
<223> OTHER INFORMATION: Synthetic Construct

<400> SEQUENCE: 207

Tyr Ala Asp Ser Val Lys Gly Arg Phe Thr Ile Ser Arg Asp Asn Ala
1               5                   10                  15

Glu Met Thr Gly Tyr Leu Gln Met Asn Ser Leu Lys Pro Glu Asp Thr
            20                  25                  30

Ala Val Tyr Tyr Cys Ala
        35

<210> SEQ ID NO 208
<211> LENGTH: 13
<212> TYPE: PRT
<213> ORGANISM: Artificial Sequence
<220> FEATURE:
<223> OTHER INFORMATION: Synthetic Construct

<400> SEQUENCE: 208

Trp Gly Gln Gly Thr Gln Val Thr Val Ser Ser Ala Ala
1               5                   10

<210> SEQ ID NO 209
<211> LENGTH: 22
<212> TYPE: PRT
<213> ORGANISM: Artificial Sequence
<220> FEATURE:
<223> OTHER INFORMATION: Synthetic Construct

<400> SEQUENCE: 209

Ala Ser Pro Val Pro Ser Thr Pro Pro Thr Pro Ser Pro Ser Thr Pro
1               5                   10                  15

Pro Thr Pro Ser Pro Ser
            20

-continued

<210> SEQ ID NO 210
<211> LENGTH: 10
<212> TYPE: PRT
<213> ORGANISM: Artificial Sequence
<220> FEATURE:
<223> OTHER INFORMATION: Synthetic Construct

<400> SEQUENCE: 210

Ala Ser Pro Val Pro Pro Pro Pro Pro Pro
1               5                   10

<210> SEQ ID NO 211
<211> LENGTH: 205
<212> TYPE: PRT
<213> ORGANISM: Artificial Sequence
<220> FEATURE:
<223> OTHER INFORMATION: Synthetic Construct

<400> SEQUENCE: 211

Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
                20                  25                  30

Thr Asn Thr Ile Gly Pro His Asp Arg Gly Gly Ser Ser Pro Ile Tyr
            35                  40                  45

Asn Ile Leu Asn Ser Tyr Leu Thr Ala Tyr Asn Gly Ser His His Leu
        50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln
        195                 200                 205

<210> SEQ ID NO 212
<211> LENGTH: 192
<212> TYPE: PRT
<213> ORGANISM: Artificial Sequence
<220> FEATURE:
<223> OTHER INFORMATION: Synthetic Construct

<400> SEQUENCE: 212

Gly Arg Tyr Pro Glu Thr Thr Val Gly Asn Leu Thr Lys Ser Phe Gln
1               5                   10                  15

Ala Pro Arg Gln Asp Arg Ser Val Gln Ser Pro Ile Tyr Asn Ile Phe
                20                  25                  30

Thr Asn His Val Ala Gly Tyr Ser Leu Ser His Asn Leu Tyr Asp Arg
            35                  40                  45

```
Ile Val Phe Leu Cys Thr Ser Ser Asn Pro Val Asn Gly Ala Cys
        50                  55                  60

Pro Thr Leu Gly Thr Ser Gly Val Gln Tyr Gly Thr Thr Ile Thr
 65              70                  75                  80

Leu Gln Phe Thr Glu Lys Arg Ser Leu Ile Lys Arg Asn Ile Asn Leu
                 85                  90                  95

Ala Gly Asn Lys Lys Pro Ile Trp Glu Asn Gln Ser Cys Asp Thr Ser
            100                 105                 110

Asn Leu Met Val Leu Asn Ser Lys Ser Trp Ser Cys Gly His Tyr Gly
            115                 120                 125

Asn Ala Asn Gly Thr Leu Leu Asn Leu Tyr Ile Pro Ala Gly Glu Ile
            130                 135                 140

Asn Lys Leu Pro Phe Gly Gly Ile Trp Glu Ala Thr Leu Ile Leu Arg
145                 150                 155                 160

Leu Ser Arg Tyr Gly Glu Val Ser Ser Thr His Tyr Gly Asn Tyr Thr
                165                 170                 175

Val Asn Ile Thr Val Asp Leu Thr Asp Lys Gly Asn Ile Gln Val Trp
            180                 185                 190

<210> SEQ ID NO 213
<211> LENGTH: 184
<212> TYPE: PRT
<213> ORGANISM: Artificial Sequence
<220> FEATURE:
<223> OTHER INFORMATION: Synthetic Construct

<400> SEQUENCE: 213

Asp Lys Ile Pro Gly Asp Glu Ser Ile Thr Asn Ile Phe Gly Pro Arg
 1               5                  10                  15

Asp Arg Asn Glu Ser Ser Pro Lys His Asn Ile Leu Asn Asn His Ile
                 20                  25                  30

Thr Ala Tyr Ser Glu Ser His Thr Leu Tyr Asp Arg Met Thr Phe Leu
             35                  40                  45

Cys Leu Ser Ser His Asn Thr Leu Asn Gly Ala Cys Pro Thr Ser Glu
 50                  55                  60

Asn Pro Ser Ser Ser Val Ser Gly Glu Thr Asn Ile Thr Leu Gln
 65              70                  75                  80

Phe Thr Glu Lys Arg Ser Leu Ile Lys Arg Glu Leu Gln Ile Lys Gly
                 85                  90                  95

Tyr Lys Gln Leu Leu Phe Lys Ser Val Asn Cys Pro Ser Gly Leu Thr
            100                 105                 110

Leu Asn Ser Ala His Phe Asn Cys Asn Lys Asn Ala Ala Ser Gly Ala
            115                 120                 125

Ser Leu Tyr Leu Tyr Ile Pro Ala Gly Glu Leu Lys Asn Leu Pro Phe
            130                 135                 140

Gly Gly Ile Trp Asp Ala Thr Leu Lys Leu Arg Val Lys Arg Arg Tyr
145                 150                 155                 160

Ser Glu Thr Tyr Gly Thr Tyr Thr Ile Asn Ile Thr Ile Lys Leu Thr
                165                 170                 175

Asp Lys Gly Asn Ile Gln Ile Trp
            180

<210> SEQ ID NO 214
<211> LENGTH: 192
<212> TYPE: PRT
<213> ORGANISM: Artificial Sequence
```

<220> FEATURE:
<223> OTHER INFORMATION: Synthetic Construct

<400> SEQUENCE: 214

```
Gly Arg Tyr Pro Glu Thr Thr Val Gly Asn Leu Thr Lys Ser Phe Gln
1               5                   10                  15

Ala Pro Arg Leu Asp Arg Ser Val Gln Ser Pro Ile Tyr Asn Ile Phe
            20                  25                  30

Thr Asn His Val Ala Gly Tyr Ser Leu Ser His Arg Leu Tyr Asp Arg
        35                  40                  45

Ile Val Phe Val Cys Thr Ser Ser Asn Pro Val Asn Gly Ala Cys
    50                  55                  60

Pro Thr Ile Gly Thr Ser Gly Val Glu Tyr Gly Thr Thr Ile Thr
65              70                  75                  80

Leu Gln Phe Thr Glu Lys Arg Ser Leu Ile Lys Arg Asn Ile Asn Leu
                85                  90                  95

Ala Gly Asn Lys Lys Pro Ile Trp Glu Asn Gln Ser Cys Asp Phe Ser
            100                 105                 110

Asn Leu Met Val Leu Asn Ser Lys Ser Trp Ser Cys Gly Ala Gln Gly
        115                 120                 125

Asn Ala Asn Gly Thr Leu Leu Asn Leu Tyr Ile Pro Ala Gly Glu Ile
    130                 135                 140

Asn Lys Leu Pro Phe Gly Gly Ile Trp Glu Ala Thr Leu Ile Leu Arg
145             150                 155                 160

Leu Ser Arg Tyr Gly Glu Val Ser Ser Thr His Tyr Gly Asn Tyr Thr
                165                 170                 175

Val Asn Ile Thr Val Asp Leu Thr Asp Lys Gly Asn Ile Gln Val Trp
            180                 185                 190
```

<210> SEQ ID NO 215
<211> LENGTH: 184
<212> TYPE: PRT
<213> ORGANISM: Artificial Sequence
<220> FEATURE:
<223> OTHER INFORMATION: Synthetic Construct

<400> SEQUENCE: 215

```
Asp Lys Ile Pro Gly Asp Glu Asn Ile Thr Asn Ile Phe Gly Pro Arg
1               5                   10                  15

Asp Arg Asn Glu Ser Ser Pro Lys His Asn Ile Leu Asn Asp Tyr Ile
            20                  25                  30

Thr Ala Tyr Ser Glu Ser His Thr Leu Tyr Asp Arg Met Ile Phe Leu
        35                  40                  45

Cys Leu Ser Ser Gln Asn Thr Leu Asn Gly Ala Cys Pro Thr Ser Glu
    50                  55                  60

Asn Pro Ser Ser Ser Val Ser Gly Glu Thr Asn Ile Thr Leu Gln
65              70                  75                  80

Phe Thr Glu Lys Arg Ser Leu Ile Lys Arg Glu Leu Gln Ile Lys Gly
                85                  90                  95

Tyr Lys Arg Leu Leu Phe Lys Gly Ala Asn Cys Pro Ser Tyr Leu Thr
            100                 105                 110

Leu Asn Ser Ala His Tyr Thr Cys Asn Arg Asn Ser Ala Ser Gly Ala
        115                 120                 125

Ser Leu Tyr Leu Tyr Ile Pro Ala Gly Glu Leu Lys Asn Leu Pro Phe
    130                 135                 140

Gly Gly Ile Trp Asp Ala Thr Leu Lys Leu Arg Val Lys Arg Arg Tyr
```

```
                145                 150                 155                 160
Asp Gln Thr Tyr Gly Thr Tyr Thr Ile Asn Ile Thr Val Lys Leu Thr
                    165                 170                 175

Asp Lys Gly Asn Ile Gln Ile Trp
            180

<210> SEQ ID NO 216
<211> LENGTH: 192
<212> TYPE: PRT
<213> ORGANISM: Artificial Sequence
<220> FEATURE:
<223> OTHER INFORMATION: Synthetic Construct

<400> SEQUENCE: 216

Gly Arg Tyr Pro Glu Thr Thr Val Gly Asn Leu Thr Lys Ser Phe Gln
1               5                   10                  15

Ala Pro Arg Leu Asp Arg Ser Val Gln Ser Pro Ile Tyr Asn Ile Phe
                20                  25                  30

Thr Asn His Val Ala Gly Tyr Ser Leu Ser His Arg Leu Tyr Asp Arg
            35                  40                  45

Ile Val Phe Val Cys Thr Ser Ser Asn Pro Val Asn Gly Ala Cys
    50                  55                  60

Pro Thr Ile Gly Thr Ser Arg Val Glu Tyr Gly Thr Thr Ile Thr
65                  70                  75                  80

Leu Gln Phe Thr Glu Lys Arg Ser Leu Ile Lys Arg Asn Ile Asn Leu
                85                  90                  95

Ala Gly Asn Lys Lys Pro Ile Trp Glu Asn Gln Ser Cys Asp Thr Ser
            100                 105                 110

Asn Leu Met Val Leu Asn Ser Lys Ser Trp Ser Cys Gly Ala Leu Gly
        115                 120                 125

Asn Ala Asn Gly Thr Leu Leu Asn Leu Tyr Ile Pro Ala Gly Glu Ile
    130                 135                 140

Asn Lys Leu Pro Phe Gly Gly Ile Trp Glu Ala Thr Leu Ile Leu Arg
145                 150                 155                 160

Leu Ser Arg Tyr Gly Glu Val Ser Ser Thr His Tyr Gly Asn Tyr Thr
                165                 170                 175

Val Asn Ile Thr Val Asp Leu Thr Asp Lys Gly Asn Ile Gln Val Trp
            180                 185                 190

<210> SEQ ID NO 217
<211> LENGTH: 192
<212> TYPE: PRT
<213> ORGANISM: Artificial Sequence
<220> FEATURE:
<223> OTHER INFORMATION: Synthetic Construct

<400> SEQUENCE: 217

Gly Arg Tyr Pro Glu Thr Thr Val Gly Asn Leu Thr Lys Ser Phe Gln
1               5                   10                  15

Ala Pro Arg Leu Asp Arg Ser Val Gln Ser Pro Ile Tyr Asn Ile Phe
                20                  25                  30

Thr Asn His Val Ala Gly Tyr Ser Leu Ser His Ser Leu Tyr Asp Arg
            35                  40                  45

Ile Val Phe Leu Cys Thr Ser Ser Asn Pro Val Asn Gly Ala Cys
    50                  55                  60

Pro Thr Ile Gly Thr Ser Gly Val Gln Tyr Gly Thr Thr Ile Thr
65                  70                  75                  80
```

```
Leu Gln Phe Thr Glu Lys Arg Ser Leu Ile Lys Arg Asn Ile Asn Leu
                85                  90                  95

Ala Gly Asn Lys Lys Pro Ile Trp Glu Asn Gln Ser Cys Asp Phe Ser
            100                 105                 110

Asn Leu Met Val Leu Asn Ser Lys Ser Trp Ser Cys Gly Ala His Gly
            115                 120                 125

Asn Ala Asn Gly Thr Leu Leu Asn Leu Tyr Ile Pro Ala Gly Glu Ile
            130                 135                 140

Asn Lys Leu Pro Phe Gly Gly Ile Trp Glu Ala Thr Leu Ile Leu Arg
145                 150                 155                 160

Leu Ser Arg Tyr Gly Glu Val Ser Ser Thr His Tyr Gly Asn Tyr Thr
                165                 170                 175

Val Asn Ile Thr Val Asp Leu Thr Asp Lys Gly Asn Ile Gln Val Trp
            180                 185                 190

<210> SEQ ID NO 218
<211> LENGTH: 192
<212> TYPE: PRT
<213> ORGANISM: Artificial Sequence
<220> FEATURE:
<223> OTHER INFORMATION: Synthetic Construct

<400> SEQUENCE: 218

Gln Ser Trp His Thr Asn Val Glu Ala Gly Ser Ile Asn Lys Thr Glu
1               5                   10                  15

Ser Ile Gly Pro Ile Asp Arg Ser Ala Ala Ser Tyr Pro Ala His
            20                  25                  30

Tyr Ile Phe His Glu His Val Ala Gly Tyr Asn Lys Asp His Ser Leu
            35                  40                  45

Phe Asp Arg Met Thr Phe Leu Cys Met Ser Ser Thr Asp Ala Ser Lys
        50                  55                  60

Gly Ala Cys Pro Thr Gly Glu Asn Ser Lys Ser Ser Gln Gly Glu Thr
65                  70                  75                  80

Asn Ile Lys Leu Ile Phe Thr Glu Lys Lys Ser Leu Ala Arg Lys Thr
                85                  90                  95

Leu Asn Leu Lys Gly Tyr Lys Arg Phe Leu Tyr Glu Ser Asp Arg Cys
            100                 105                 110

Ile His Tyr Val Asp Lys Met Asn Leu Asn Ser His Thr Val Lys Cys
            115                 120                 125

Val Gly Ser Phe Thr Arg Gly Val Asp Phe Thr Leu Tyr Ile Pro Gln
            130                 135                 140

Gly Glu Ile Asp Gly Leu Leu Thr Gly Gly Ile Trp Glu Ala Thr Leu
145                 150                 155                 160

Glu Leu Arg Val Lys Arg His Tyr Asp Tyr Asn His Gly Thr Tyr Lys
                165                 170                 175

Val Asn Ile Thr Val Asp Leu Thr Asp Lys Gly Asn Ile Gln Val Trp
            180                 185                 190

<210> SEQ ID NO 219
<211> LENGTH: 5
<212> TYPE: PRT
<213> ORGANISM: Artificial Sequence
<220> FEATURE:
<223> OTHER INFORMATION: Synthetic Construct

<400> SEQUENCE: 219

Gly Gly Gly Gly Ser
1               5
```

```
<210> SEQ ID NO 220
<211> LENGTH: 15
<212> TYPE: PRT
<213> ORGANISM: Artificial Sequence
<220> FEATURE:
<223> OTHER INFORMATION: Synthetic Construct

<400> SEQUENCE: 220

Gly Gly Gly Gly Ser Gly Gly Gly Gly Ser Gly Gly Gly Gly Ser
1               5                   10                  15

<210> SEQ ID NO 221
<211> LENGTH: 30
<212> TYPE: PRT
<213> ORGANISM: Artificial Sequence
<220> FEATURE:
<223> OTHER INFORMATION: Synthetic Construct

<400> SEQUENCE: 221

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 222
<211> LENGTH: 4
<212> TYPE: PRT
<213> ORGANISM: Artificial Sequence
<220> FEATURE:
<223> OTHER INFORMATION: Synthetic Construct

<400> SEQUENCE: 222

Gly Ser Gly Ser
1

<210> SEQ ID NO 223
<211> LENGTH: 6
<212> TYPE: PRT
<213> ORGANISM: Artificial Sequence
<220> FEATURE:
<223> OTHER INFORMATION: Synthetic Construct

<400> SEQUENCE: 223

Gly Ser Gly Ser Gly Ser
1               5

<210> SEQ ID NO 224
<211> LENGTH: 8
<212> TYPE: PRT
<213> ORGANISM: Artificial Sequence
<220> FEATURE:
<223> OTHER INFORMATION: Synthetic Construct

<400> SEQUENCE: 224

Gly Ser Gly Ser Gly Ser Gly Ser
1               5

<210> SEQ ID NO 225
<211> LENGTH: 10
<212> TYPE: PRT
<213> ORGANISM: Artificial Sequence
<220> FEATURE:
<223> OTHER INFORMATION: Synthetic Construct

<400> SEQUENCE: 225
```

Gly Ser Gly Ser Gly Ser Gly Ser Gly Ser
1               5                   10

<210> SEQ ID NO 226
<211> LENGTH: 12
<212> TYPE: PRT
<213> ORGANISM: Artificial Sequence
<220> FEATURE:
<223> OTHER INFORMATION: Synthetic Construct

<400> SEQUENCE: 226

Gly Ser Gly Ser Gly Ser Gly Ser Gly Ser Gly Ser
1               5                   10

<210> SEQ ID NO 227
<211> LENGTH: 14
<212> TYPE: PRT
<213> ORGANISM: Artificial Sequence
<220> FEATURE:
<223> OTHER INFORMATION: Synthetic Construct

<400> SEQUENCE: 227

Gly Ser Gly Ser Gly Ser Gly Ser Gly Ser Gly Ser Gly Ser
1               5                   10

<210> SEQ ID NO 228
<211> LENGTH: 16
<212> TYPE: PRT
<213> ORGANISM: Artificial Sequence
<220> FEATURE:
<223> OTHER INFORMATION: Synthetic Construct

<400> SEQUENCE: 228

Gly Ser Gly Ser Gly Ser Gly Ser Gly Ser Gly Ser Gly Ser Gly Ser
1               5                   10                  15

<210> SEQ ID NO 229
<211> LENGTH: 18
<212> TYPE: PRT
<213> ORGANISM: Artificial Sequence
<220> FEATURE:
<223> OTHER INFORMATION: Synthetic Construct

<400> SEQUENCE: 229

Gly Ser Gly Ser Gly Ser Gly Ser Gly Ser Gly Ser Gly Ser Gly Ser
1               5                   10                  15

Gly Ser

<210> SEQ ID NO 230
<211> LENGTH: 20
<212> TYPE: PRT
<213> ORGANISM: Artificial Sequence
<220> FEATURE:
<223> OTHER INFORMATION: Synthetic Construct

<400> SEQUENCE: 230

Gly Ser Gly Ser Gly Ser Gly Ser Gly Ser Gly Ser Gly Ser Gly Ser
1               5                   10                  15

Gly Ser Gly Ser
            20

<210> SEQ ID NO 231
<211> LENGTH: 6
<212> TYPE: PRT
<213> ORGANISM: Artificial Sequence
<220> FEATURE:

```
<223> OTHER INFORMATION: Synthetic Construct

<400> SEQUENCE: 231

Gly Gly Ser Gly Gly Ser
1               5

<210> SEQ ID NO 232
<211> LENGTH: 9
<212> TYPE: PRT
<213> ORGANISM: Artificial Sequence
<220> FEATURE:
<223> OTHER INFORMATION: Synthetic Construct

<400> SEQUENCE: 232

Gly Gly Ser Gly Gly Ser Gly Gly Ser
1               5

<210> SEQ ID NO 233
<211> LENGTH: 12
<212> TYPE: PRT
<213> ORGANISM: Artificial Sequence
<220> FEATURE:
<223> OTHER INFORMATION: Synthetic Construct

<400> SEQUENCE: 233

Gly Gly Ser Gly Gly Ser Gly Gly Ser Gly Gly Ser
1               5                   10

<210> SEQ ID NO 234
<211> LENGTH: 15
<212> TYPE: PRT
<213> ORGANISM: Artificial Sequence
<220> FEATURE:
<223> OTHER INFORMATION: Synthetic Construct

<400> SEQUENCE: 234

Gly Gly Ser Gly Gly Ser Gly Gly Ser Gly Gly Ser Gly Gly Ser
1               5                   10                  15

<210> SEQ ID NO 235
<211> LENGTH: 18
<212> TYPE: PRT
<213> ORGANISM: Artificial Sequence
<220> FEATURE:
<223> OTHER INFORMATION: Synthetic Construct

<400> SEQUENCE: 235

Gly Gly Ser Gly Gly Ser Gly Gly Ser Gly Gly Ser Gly Gly Ser Gly
1               5                   10                  15

Gly Ser

<210> SEQ ID NO 236
<211> LENGTH: 21
<212> TYPE: PRT
<213> ORGANISM: Artificial Sequence
<220> FEATURE:
<223> OTHER INFORMATION: Synthetic Construct

<400> SEQUENCE: 236

Gly Gly Ser Gly Gly Ser Gly Gly Ser Gly Gly Ser Gly Gly Ser Gly
1               5                   10                  15

Gly Ser Gly Gly Ser
            20

<210> SEQ ID NO 237
```

```
<211> LENGTH: 24
<212> TYPE: PRT
<213> ORGANISM: Artificial Sequence
<220> FEATURE:
<223> OTHER INFORMATION: Synthetic Construct

<400> SEQUENCE: 237

Gly Gly Ser Gly Gly Ser Gly Gly Ser Gly Gly Ser Gly Gly Ser Gly
1               5                   10                  15

Gly Ser Gly Gly Ser Gly Gly Ser
            20

<210> SEQ ID NO 238
<211> LENGTH: 27
<212> TYPE: PRT
<213> ORGANISM: Artificial Sequence
<220> FEATURE:
<223> OTHER INFORMATION: Synthetic Construct

<400> SEQUENCE: 238

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser
            20                  25

<210> SEQ ID NO 239
<211> LENGTH: 30
<212> TYPE: PRT
<213> ORGANISM: Artificial Sequence
<220> FEATURE:
<223> OTHER INFORMATION: Synthetic Construct

<400> SEQUENCE: 239

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30

<210> SEQ ID NO 240
<211> LENGTH: 10
<212> TYPE: PRT
<213> ORGANISM: Artificial Sequence
<220> FEATURE:
<223> OTHER INFORMATION: Synthetic Construct

<400> SEQUENCE: 240

Gly Gly Gly Gly Ser Gly Gly Gly Gly Ser
1               5                   10

<210> SEQ ID NO 241
<211> LENGTH: 20
<212> TYPE: PRT
<213> ORGANISM: Artificial Sequence
<220> FEATURE:
<223> OTHER INFORMATION: Synthetic Construct

<400> SEQUENCE: 241

Gly Gly Gly Gly Ser Gly Gly Gly Gly Ser Gly Gly Gly Gly Ser Gly
1               5                   10                  15

Gly Gly Gly Ser
            20

<210> SEQ ID NO 242
<211> LENGTH: 25
<212> TYPE: PRT
```

<213> ORGANISM: Artificial Sequence
<220> FEATURE:
<223> OTHER INFORMATION: Synthetic Construct

<400> SEQUENCE: 242

Gly Gly Gly Gly Ser Gly Gly Gly Ser Gly Gly Gly Gly Ser Gly
1               5                  10                  15

Gly Gly Gly Ser Gly Gly Gly Gly Ser
            20                  25

<210> SEQ ID NO 243
<211> LENGTH: 35
<212> TYPE: PRT
<213> ORGANISM: Artificial Sequence
<220> FEATURE:
<223> OTHER INFORMATION: Synthetic Construct

<400> SEQUENCE: 243

Gly Gly Gly Gly Ser Gly Gly Gly Ser Gly Gly Gly Gly Ser Gly
1               5                  10                  15

Gly Gly Gly Ser Gly Gly Gly Ser Gly Gly Gly Gly Ser Gly Gly
            20                  25                  30

Gly Gly Ser
        35

<210> SEQ ID NO 244
<211> LENGTH: 40
<212> TYPE: PRT
<213> ORGANISM: Artificial Sequence
<220> FEATURE:
<223> OTHER INFORMATION: Synthetic Construct

<400> SEQUENCE: 244

Gly Gly Gly Gly Ser Gly Gly Gly Ser Gly Gly Gly Gly Ser Gly
1               5                  10                  15

Gly Gly Gly Ser Gly Gly Gly Ser Gly Gly Gly Gly Ser Gly Gly
            20                  25                  30

Gly Gly Ser Gly Gly Gly Gly Ser
        35                  40

<210> SEQ ID NO 245
<211> LENGTH: 45
<212> TYPE: PRT
<213> ORGANISM: Artificial Sequence
<220> FEATURE:
<223> OTHER INFORMATION: Synthetic Construct

<400> SEQUENCE: 245

Gly Gly Gly Gly Ser Gly Gly Gly Ser Gly Gly Gly Gly Ser Gly
1               5                  10                  15

Gly Gly Gly Ser Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45

<210> SEQ ID NO 246
<211> LENGTH: 50
<212> TYPE: PRT
<213> ORGANISM: Artificial Sequence
<220> FEATURE:
<223> OTHER INFORMATION: Synthetic Construct

<400> SEQUENCE: 246

```
Gly Gly Gly Gly Ser Gly Gly Gly Gly Ser Gly Gly Gly Ser Gly
1               5                   10                  15

Gly Gly Gly Ser Gly Gly Gly Gly Ser Gly Gly Gly Ser Gly Gly
                20                  25                  30

Gly Gly Ser Gly Gly Gly Gly Ser Gly Gly Gly Ser Gly Gly Gly
            35                  40                  45

Gly Ser
    50

<210> SEQ ID NO 247
<211> LENGTH: 4
<212> TYPE: PRT
<213> ORGANISM: Artificial Sequence
<220> FEATURE:
<223> OTHER INFORMATION: Synthetic Construct

<400> SEQUENCE: 247

Gly Gly Ser Gly
1

<210> SEQ ID NO 248
<211> LENGTH: 8
<212> TYPE: PRT
<213> ORGANISM: Artificial Sequence
<220> FEATURE:
<223> OTHER INFORMATION: Synthetic Construct

<400> SEQUENCE: 248

Gly Gly Ser Gly Gly Gly Ser Gly
1               5

<210> SEQ ID NO 249
<211> LENGTH: 12
<212> TYPE: PRT
<213> ORGANISM: Artificial Sequence
<220> FEATURE:
<223> OTHER INFORMATION: Synthetic Construct

<400> SEQUENCE: 249

Gly Gly Ser Gly Gly Gly Ser Gly Gly Gly Ser Gly
1               5                   10

<210> SEQ ID NO 250
<211> LENGTH: 16
<212> TYPE: PRT
<213> ORGANISM: Artificial Sequence
<220> FEATURE:
<223> OTHER INFORMATION: Synthetic Construct

<400> SEQUENCE: 250

Gly Gly Ser Gly Gly Gly Ser Gly Gly Gly Ser Gly Gly Gly Ser Gly
1               5                   10                  15

<210> SEQ ID NO 251
<211> LENGTH: 20
<212> TYPE: PRT
<213> ORGANISM: Artificial Sequence
<220> FEATURE:
<223> OTHER INFORMATION: Synthetic Construct

<400> SEQUENCE: 251

Gly Gly Ser Gly Gly Gly Ser Gly Gly Gly Ser Gly Gly Gly Ser Gly
1               5                   10                  15

Gly Gly Ser Gly
            20
```

<210> SEQ ID NO 252
<211> LENGTH: 24
<212> TYPE: PRT
<213> ORGANISM: Artificial Sequence
<220> FEATURE:
<223> OTHER INFORMATION: Synthetic Construct

<400> SEQUENCE: 252

Gly Gly Ser Gly Gly Gly Ser Gly Gly Gly Ser Gly Gly Gly Ser Gly
1               5                   10                  15

Gly Gly Ser Gly Gly Gly Ser Gly
            20

<210> SEQ ID NO 253
<211> LENGTH: 28
<212> TYPE: PRT
<213> ORGANISM: Artificial Sequence
<220> FEATURE:
<223> OTHER INFORMATION: Synthetic Construct

<400> SEQUENCE: 253

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly
            20                  25

<210> SEQ ID NO 254
<211> LENGTH: 32
<212> TYPE: PRT
<213> ORGANISM: Artificial Sequence
<220> FEATURE:
<223> OTHER INFORMATION: Synthetic Construct

<400> SEQUENCE: 254

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

<210> SEQ ID NO 255
<211> LENGTH: 36
<212> TYPE: PRT
<213> ORGANISM: Artificial Sequence
<220> FEATURE:
<223> OTHER INFORMATION: Synthetic Construct

<400> SEQUENCE: 255

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly
        35

<210> SEQ ID NO 256
<211> LENGTH: 40
<212> TYPE: PRT
<213> ORGANISM: Artificial Sequence
<220> FEATURE:
<223> OTHER INFORMATION: Synthetic Construct

<400> SEQUENCE: 256

Gly Gly Ser Gly Gly Gly Ser Gly Gly Gly Ser Gly Gly Gly Ser Gly

```
                1               5                   10                  15
Gly Gly Ser Gly Gly Gly Ser Gly Gly Gly Ser Gly Gly Gly Ser Gly
                20                  25                  30
Gly Gly Ser Gly Gly Gly Ser Gly
            35                  40

<210> SEQ ID NO 257
<211> LENGTH: 4
<212> TYPE: PRT
<213> ORGANISM: Artificial Sequence
<220> FEATURE:
<223> OTHER INFORMATION: Synthetic Construct

<400> SEQUENCE: 257

Ser Gly Gly Gly
1

<210> SEQ ID NO 258
<211> LENGTH: 8
<212> TYPE: PRT
<213> ORGANISM: Artificial Sequence
<220> FEATURE:
<223> OTHER INFORMATION: Synthetic Construct

<400> SEQUENCE: 258

Ser Gly Gly Gly Ser Gly Gly Gly
1               5

<210> SEQ ID NO 259
<211> LENGTH: 12
<212> TYPE: PRT
<213> ORGANISM: Artificial Sequence
<220> FEATURE:
<223> OTHER INFORMATION: Synthetic Construct

<400> SEQUENCE: 259

Ser Gly Gly Gly Ser Gly Gly Gly Ser Gly Gly Gly
1               5                   10

<210> SEQ ID NO 260
<211> LENGTH: 16
<212> TYPE: PRT
<213> ORGANISM: Artificial Sequence
<220> FEATURE:
<223> OTHER INFORMATION: Synthetic Construct

<400> SEQUENCE: 260

Ser Gly Gly Gly Ser Gly Gly Gly Ser Gly Gly Gly Ser Gly Gly Gly
1               5                   10                  15

<210> SEQ ID NO 261
<211> LENGTH: 20
<212> TYPE: PRT
<213> ORGANISM: Artificial Sequence
<220> FEATURE:
<223> OTHER INFORMATION: Synthetic Construct

<400> SEQUENCE: 261

Ser Gly Gly Gly Ser Gly Gly Gly Ser Gly Gly Gly Ser Gly Gly Gly
1               5                   10                  15

Ser Gly Gly Gly
            20

<210> SEQ ID NO 262
<211> LENGTH: 24
```

```
<212> TYPE: PRT
<213> ORGANISM: Artificial Sequence
<220> FEATURE:
<223> OTHER INFORMATION: Synthetic Construct

<400> SEQUENCE: 262

Ser Gly Gly Gly Ser Gly Gly Gly Ser Gly Gly Gly Ser Gly Gly
1               5                   10                  15

Ser Gly Gly Gly Ser Gly Gly Gly
            20

<210> SEQ ID NO 263
<211> LENGTH: 28
<212> TYPE: PRT
<213> ORGANISM: Artificial Sequence
<220> FEATURE:
<223> OTHER INFORMATION: Synthetic Construct

<400> SEQUENCE: 263

Ser Gly Gly Gly Ser Gly Gly Gly Ser Gly Gly Gly Ser Gly Gly
1               5                   10                  15

Ser Gly Gly Gly Ser Gly Gly Gly Ser Gly Gly Gly
            20                  25

<210> SEQ ID NO 264
<211> LENGTH: 32
<212> TYPE: PRT
<213> ORGANISM: Artificial Sequence
<220> FEATURE:
<223> OTHER INFORMATION: Synthetic Construct

<400> SEQUENCE: 264

Ser Gly Gly Gly Ser Gly Gly Gly Ser Gly Gly Gly Ser Gly Gly
1               5                   10                  15

Ser Gly Gly Gly Ser Gly Gly Gly Ser Gly Gly Gly Ser Gly Gly Gly
            20                  25                  30

<210> SEQ ID NO 265
<211> LENGTH: 36
<212> TYPE: PRT
<213> ORGANISM: Artificial Sequence
<220> FEATURE:
<223> OTHER INFORMATION: Synthetic Construct

<400> SEQUENCE: 265

Ser Gly Gly Gly Ser Gly Gly Gly Ser Gly Gly Gly Ser Gly Gly
1               5                   10                  15

Ser Gly Gly Gly Ser Gly Gly Gly Ser Gly Gly Gly Ser Gly Gly Gly
            20                  25                  30

Ser Gly Gly Gly
        35

<210> SEQ ID NO 266
<211> LENGTH: 40
<212> TYPE: PRT
<213> ORGANISM: Artificial Sequence
<220> FEATURE:
<223> OTHER INFORMATION: Synthetic Construct

<400> SEQUENCE: 266

Ser Gly Gly Gly Ser Gly Gly Gly Ser Gly Gly Gly Ser Gly Gly
1               5                   10                  15

Ser Gly Gly Gly Ser Gly Gly Gly Ser Gly Gly Gly Ser Gly Gly Gly
            20                  25                  30
```

Ser Gly Gly Gly Ser Gly Gly Gly
        35                  40

ANTI-ETEC ADHESIN PROTEIN ANTIBODIES AND METHODS OF USE

CROSS-REFERENCE TO RELATED APPLICATION(S)

This application relates to and claims priority from U.S. Patent Application No. 63/044,691 filed on Jun. 26, 2020, the entire disclosure of which is incorporated herein by reference.

SEQUENCE LISTING

The instant application contains a Sequence Listing which has been submitted electronically in ASCII format and is hereby incorporated by reference in its entirety. Said ASCII copy, created on Mar. 7, 2023, is named 50811-009003_Sequence_Listing_3_7_23_ST25 and is 107,473 bytes in size.

BACKGROUND OF THE INVENTION

Enterotoxigenic *Escherichia coli* (ETEC) is one of the main causes of diarrhea in infants in the developing world, as well as the major cause of traveler's diarrhea. Transmission of ETEC occurs when contaminated food or water is ingested. ETEC infections are characterized by diarrhea, vomiting, stomach cramps, and in some cases mild fever. Symptoms usually occur 1-3 days after infection and last for a few days. When adult travelers develop ETEC-related diarrhea, a short course of antibiotics can decrease the duration and volume of diarrhea. However, ETEC strains are becoming increasingly resistant to antibiotics, and there are currently no licensed vaccines for protecting travelers against ETEC-related diarrhea. Accordingly, there exists a need for improved treatments or prevention of ETEC-related disorders.

SUMMARY OF THE INVENTION

The invention provides anti-enterotoxigenic *Escherichia coli* (ETEC) adhesin protein VHH antibodies and methods of their use.

In one aspect, the invention provides an isolated VHH antibody that binds an enterotoxigenic *E. coli* (ETEC) adhesin protein, wherein the antibody comprises a VHH binding domain comprising the following complementary determining regions (CDRs): (a) a CDR-H1 comprising the amino acid sequence of NIFQDAE (SEQ ID NO: 1); (b) a CDR-H2 comprising the amino acid sequence of FVATIAYGGNTN (SEQ ID NO: 2); and (c) a CDR-H3 comprising the amino acid sequence of VYTGVYYDRTTGGYVAFE (SEQ ID NO: 3). In one embodiment, the VHH binding domain comprises an amino acid sequence having at least 95% (e.g., 96%, 97%, 98%, or 99%) sequence identity to the amino acid sequence of SEQ ID NO: 4. In some embodiments, the VHH binding domain comprises the following framework regions (FRs): (a) an FR-H1 comprising the amino acid sequence of QVQLQESGGGLVQAGGSLRLSCAASG (SEQ ID NO: 5); (b) an FR-H2 comprising the amino acid sequence of MGWYRQAPGKERE (SEQ ID NO: 6); (c) an FR-H3 comprising the amino acid sequence of YADSVKGRFTISRDNAKNTVYLQMNSLKPEDTAVYYCA (SEQ ID NO: 7); and (d) an FR-H4 comprising the amino acid sequence of YWGQGTQVTVSS (SEQ ID NO: 8). In some embodiments, the VHH binding domain comprises the amino acid sequence of SEQ ID NO: 4. In some embodiments, the VHH binding domain consists of the amino acid sequence of SEQ ID NO: 4.

In another aspect, the invention provides an isolated VHH antibody that binds an ETEC adhesin protein, wherein the antibody comprises a VHH binding domain comprising the amino acid sequence of SEQ ID NO: 4.

In another aspect, the invention provides an isolated antibody that binds an ETEC adhesin protein, wherein the antibody competes for binding to an ETEC adhesin protein with a VHH antibody comprising a VHH binding domain comprising the following complementary determining regions (CDRs): (a) a CDR-H1 comprising the amino acid sequence of NIFQDAE (SEQ ID NO: 1); (b) a CDR-H2 comprising the amino acid sequence of FVATIAYGGNTN (SEQ ID NO: 2); and (c) a CDR-H3 comprising the amino acid sequence of VYTGVYYDRTTGGYVAFE (SEQ ID NO: 3).

In another aspect, the invention provides an isolated VHH antibody that binds an ETEC adhesin protein, wherein the antibody comprises a VHH binding domain comprising the following complementary determining regions (CDRs): (a) a CDR-H1 comprising the amino acid sequence of ERTFSYYV (SEQ ID NO: 9); (b) a CDR-H2 comprising the amino acid sequence of FVAGISMSGDSTK (SEQ ID NO: 10); and (c) a CDR-H3 comprising the amino acid sequence of ADRDIRGNFRS (SEQ ID NO: 11). In some embodiments, the VHH binding domain comprises an amino acid sequence having at least 95% (e.g., 96%, 97%, 98%, or 99%) sequence identity to the amino acid sequence of SEQ ID NO: 12. In some embodiments, the VHH binding domain comprises the following FRs: (a) an FR-H1 comprising the amino acid sequence of EVQLVESGGGLVQAGGSLTLSCAAS (SEQ ID NO: 13); (b) an FR-H2 comprising the amino acid sequence of MAWFRQAPGKERE (SEQ ID NO: 14); (c) an FR-H3 comprising the amino acid sequence of YADSVKGRFTISRDNAENTGYLQMNGLKPEDTAVYYCA (SEQ ID NO: 15); and (d) an FR-H4 comprising the amino acid sequence of WGRGTQVTVSSAA (SEQ ID NO: 16). In some embodiments, the VHH binding domain comprises the amino acid sequence of SEQ ID NO: 12. In some embodiments, the VHH binding domain consists of the amino acid sequence of SEQ ID NO: 12.

In one aspect, the invention provides an isolated VHH antibody that binds an ETEC adhesin protein, wherein the antibody comprises a VHH binding domain comprising the amino acid of SEQ ID NO: 12.

In one aspect, the invention provides an isolated antibody that binds an ETEC adhesin protein, wherein the antibody competes for binding to an ETEC adhesin protein with a VHH antibody comprising a VHH binding domain comprising the following complementary determining regions (CDRs): (a) a CDR-H1 comprising the amino acid sequence of ERTFSYYV (SEQ ID NO: 9); (b) a CDR-H2 comprising the amino acid sequence of FVAGISMSGDSTK (SEQ ID NO: 10); and (c) a CDR-H3 comprising the amino acid sequence of ADRDIRGNFRS (SEQ ID NO: 11).

In one aspect, the invention provides an isolated VHH antibody that binds an ETEC adhesin protein, wherein the antibody comprises a VHH binding domain comprising the following CDRs: (a) a CDR-H1 comprising the amino acid sequence of YIFWSYGY (SEQ ID NO: 17); (b) a CDR-H2 comprising the amino acid sequence of LVATISRGGTTN (SEQ ID NO: 18); (c) a CDR-H3 comprising the amino acid sequence of AGRYAFGYFK (SEQ ID NO: 19). In some embodiments, the VHH binding domain comprises an amino acid sequence having at least 95% (e.g., 96%, 97%, 98%, or 99%) sequence identity to the amino acid sequence of SEQ ID NO: 20. In some embodiments, the VHH binding domain comprises the following FRs: (a) an FR-H1 comprising the amino acid sequence of QVQLQESGGGLVQAGGSLRLS-CAASG (SEQ ID NO: 21); (b) an FR-H2 comprising the amino acid sequence of MGWYRQAPGKERE (SEQ ID NO: 22); (c) an FR-H3 comprising the amino acid sequence of YADSVKGRFTISRDNAKNTVYLQMNSLKPED-TAVYYCA (SEQ ID NO: 23); and (d) an FR-H4 comprising the amino acid sequence of YWGQGTQVTVSS (SEQ ID NO: 24). In some embodiments, the VHH binding domain comprises the amino acid sequence of SEQ ID NO: 20. In certain embodiments, the VHH binding domain consists of the amino acid sequence of SEQ ID NO: 20.

In one aspect, the invention provides an isolated VHH antibody that binds an ETEC adhesin protein, wherein the antibody comprises a VHH binding domain comprising the amino acid of SEQ ID NO: 20.

In one aspect, the invention provides an isolated antibody that binds an ETEC adhesin protein, wherein the antibody competes for binding to an ETEC adhesin protein with a VHH antibody comprising a VHH binding domain comprising the following CDRs: (a) a CDR-H1 comprising the amino acid sequence of YIFWSYGY (SEQ ID NO: 17); (b) a CDR-H2 comprising the amino acid sequence of LVATIS-RGGTTN (SEQ ID NO: 18); and (c) a CDR-H3 comprising the amino acid sequence of AGRYAFGYFK (SEQ ID NO: 19).

In one aspect, the invention provides an isolated VHH antibody that binds an ETEC adhesin protein, wherein the antibody comprises a VHH binding domain comprising the following CDRs: (a) a CDR-H1 comprising the amino acid sequence of SRTFNHYN (SEQ ID NO: 25); (b) a CDR-H2 comprising the amino acid sequence of FAAAITWN-GRSTL (SEQ ID NO: 26); and (c) a CDR-H3 comprising the amino acid sequence of TLTTWEHKWEYNS (SEQ ID NO: 27). In one embodiment, the VHH binding domain comprises an amino acid sequence having at least 95% (e.g., 96%, 97%, 98%, or 99%) sequence identity to the amino acid sequence of SEQ ID NO: 28. In some embodiments, the VHH binding domain comprises the following FRs: (a) an FR-H1 comprising the amino acid sequence of EVQLVES-GGGLVQAGGSLRLSCAAS (SEQ ID NO: 29); (b) an FR-H2 comprising the amino acid sequence of IGWFRQAPGKERE (SEQ ID NO: 30); (c) an FR-H3 comprising the amino acid sequence of YADSVKGRFTIS-RDNAKNTVYLQMNSLKPEDTAVYYCA (SEQ ID NO: 31); and (d) an FR-H4 comprising the amino acid sequence of QGQGTQVTVSSAA (SEQ ID NO: 32). In some embodiments, the VHH binding domain comprises the amino acid sequence of SEQ ID NO: 28. In some embodiments, the VHH binding domain consists of the amino acid sequence of SEQ ID NO: 28.

In one aspect, the invention provides an isolated VHH antibody that binds an ETEC adhesin protein, wherein the antibody comprises a VHH binding domain comprising the amino acid of SEQ ID NO: 28.

In one aspect, the invention provides an isolated antibody that binds to an ETEC adhesin protein, wherein the antibody competes for binding to an ETEC adhesin protein with a VHH antibody comprising a VHH binding domain comprising the following CDRs: (a) a CDR-H1 comprising the amino acid sequence of SRTFNHYN (SEQ ID NO: 25); (b) a CDR-H2 comprising the amino acid sequence of FAAAIT-WNGRSTL (SEQ ID NO: 26); and (c) a CDR-H3 comprising the amino acid sequence of TLTTWEHKWEYNS (SEQ ID NO: 27).

In some embodiments of any of the aspects herein, the antibody comprises multiple VHH binding domains.

In some embodiments, the antibody includes the following N-terminal-to-C-terminal structure:

$$(P_3\text{-}L_3)_{n3}\text{-}P_2\text{-}(L_1\text{-}P_1)_{n1}$$

$P_1$, $P_2$, and $P_3$ are each independently selected from the antibody of any one of claims 1-44; $L_1$ and $L_3$ are each independently a linker; and $n_1$ and $n_3$ are each independently 0 or 1, wherein at least one of $n_1$ and $n_3$ are 1.

In some embodiments, $n_1$ is 1 and $n_3$ is 0, and the antibody comprises the following N-terminal-to-C-terminal structure:

$$P_2\text{-}L_1\text{-}P_1.$$

In certain embodiments, $L_1$ is a peptide linker comprising between 2 and 200 amino acids (e.g., between 5 and 50 (e.g., between 5 and 20, 15 and 30, 25 and 40, or 35 and 50), between 45 and 100 (e.g., between 45 and 60, 55 and 70, 65 and 80, 75 and 90, or 85 and 100), 95 and 150 (e.g., between 95 and 110, 105 and 120, 115 and 130, 125 and 140, or 135 and 150), or 145 and 200 amino acids (e.g., between 145 and 160, 155 and 170, 165 and 180, 175 and 190, or 185 and 200)). In some embodiments, $L_1$ is a peptide linker comprising glycine (G) and serine (S) residues. In certain embodiments, $L_1$ is a peptide linker comprising the amino acid sequence of $(GS)_x$ (SEQ ID NOs: 222-230), $(GGS)_x$ (SEQ ID NOs: 231-239), or $(GGGGS$ (SEQ ID NO: 219)$)_x$ (SEQ ID NOs: 219-221 and 240-246), wherein x is an integer from 1 to 10. In some embodiments, $L_1$ is a peptide linker comprising the amino acid sequence of $(GGGGS)_6$ (SEQ ID NO: 221). In some embodiments, $L_1$ is a peptide linker consisting of the amino acid sequence of $(GGGGS)_6$ (SEQ ID NO: 221). In certain embodiments, $P_1$ and $P_2$ each comprise different VHH binding domains. In some embodiments, $P_1$ and $P_2$ each comprise identical VHH binding domains. In some embodiments, the identical VHH binding domains comprise the amino acid sequence of SEQ ID NO: 4. In some embodiments, the identical VHH binding domains comprise the amino acid sequence of SEQ ID NO: 12.

In some embodiments, when $n_1$ is 1 and $n_3$ is 1, and the antibody comprises the following N-terminal-to-C-terminal structure:

$$P_3\text{-}L_3\text{-}P_2\text{-}L_1\text{-}P_1.$$

In some embodiments, $L_1$ and $L_2$ are each an independently selected peptide linker comprising between 2 and 200 amino acids (e.g., between 5 and 50 (e.g., between 5 and 20, 15 and 30, 25 and 40, or 35 and 50), between 45 and 100 (e.g., between 45 and 60, 55 and 70, 65 and 80, 75 and 90, or 85 and 100), 95 and 150 (e.g., between 95 and 110, 105 and 120, 115 and 130, 125 and 140, or 135 and 150), or 145 and 200 amino acids (e.g., between 145 and 160, 155 and 170, 165 and 180, 175 and 190, or 185 and 200)). In some embodiments, $L_1$ and $L_2$ are each an independently selected peptide linker comprising glycine (G) and serine (S) residues. In some embodiments, $L_1$ and $L_2$ are each an independently selected peptide linker comprising the amino acid sequence of $(GS)_x$ (SEQ ID NOs: 222-230), $(GGS)_x$ (SEQ ID NOs: 231-239), or $(GGGGS$ (SEQ ID NO: 219)$)_x$ (SEQ ID NOs: 219-221 and 240-246), wherein x is an integer from 1 to 10. In some embodiments, $L_1$ and $L_2$ are each a peptide linker comprising the amino acid sequence of $(GGGGS)_3$ (SEQ ID NO: 220). In certain embodiments, $L_1$ and $L_2$ are each a peptide linker consisting of the amino acid sequence of $(GGGGS)_3$ (SEQ ID NO: 221). In some embodiments, $P_1$, $P_2$, and $P_3$ each comprise different VHH binding domains. In some embodiments, $P_1$, $P_2$, and $P_3$ each comprise identical VHH binding domains. In some embodiments, the identical VHH binding domains comprise the amino acid sequence of SEQ ID NO: 4. In some embodiments, the identical VHH binding domains comprise the amino acid sequence of SEQ ID NO: 12.

In some embodiments, the antibody does not comprise an Fc region. In some embodiments, the antibody comprises a single VHH binding domain. In some embodiments, the antibody consists of a single VHH binding domain. In some embodiments, the antibody is a monoclonal antibody. In some embodiments, the antibody is a humanized or chimeric antibody. In some embodiments, the antibody is an IgA class antibody (e.g., an IgA1 or IgA1 subclass antibody). In some embodiments, the antibody is an IgG class antibody (e.g., an IgG1 subclass antibody).

In some embodiments, the antibody comprises an Fc domain comprising a first Fc domain subunit and a second Fc domain subunit, wherein the first Fc domain subunit and the second Fc domain subunit are capable of stable association. In some embodiments, each Fc domain subunit is linked to a single VHH binding domain and positioned relative to each other in an N-terminal-to-C-terminal direction as follows: VHH binding domain-Fc domain subunit. In some embodiments, each Fc domain subunit is linked to a single VHH binding domain by a hinge region and positioned relative to each other in an N-terminal-to-C-terminal direction as follows: VHH binding domain-hinge region-Fc domain subunit. In some embodiments, the antibody is an IgA class antibody and each VHH binding domain comprises the amino acid sequence of SEQ ID NO: 4. In some embodiments, the antibody is an IgA class antibody and each VHH binding domain comprises the amino acid sequence of SEQ ID NO: 12.

In some embodiments, each Fc domain subunit is further linked to a single CH1 domain. In some embodiments, each VHH binding domain, CCH$_H$1 domain, and Fc domain subunit is positioned relative to each other in an N-terminal-to-C-terminal direction as follows: VHH binding domain-CH1 domain-Fc domain subunit. In some embodiments, each CH1 domain is linked to a single VHH binding domain by a hinge region and positioned relative to each other in an N-terminal-to-C-terminal direction as follows: VHH binding domain-CH1 domain-hinge region-Fc domain subunit. In some embodiments, each CH1 domain is linked to a single VHH binding domain by a hinge region and positioned relative to each other in an N-terminal-to-C-terminal direction as follows: VHH binding domain-hinge region-CH1 domain-Fc domain subunit. In some embodiments, the hinge region comprises the amino acid sequence of ASPVPSTPPTPSPSTPPTPSPS (SEQ ID NO: 209) or ASPVPPPPPP (SEQ ID NO: 210). In some embodiments, the hinge region consists of the amino acid sequence of ASPVPSTPPTPSPSTPPTPSPS (SEQ ID NO: 209). In some embodiments, the hinge region consists of the amino acid sequence of ASPVPPPPPP (SEQ ID NO: 210).

In some embodiments, the antibody is a full-length antibody. In some embodiments, the antibody is a VHH antibody fragment that binds an ETEC adhesin protein. In some embodiments, the antibody is capable of inhibiting mannose-resistant hemagglutination of human group A erythrocytes with a maximal inhibitory concentration (IC$_{100}$) of between about 0.10 µg/mL and about 250 µg/mL (e.g., between about 0.5 µg/mL and about 30 µg/mL, about 25 µg/mL and about 50 µg/mL, about 45 µg/mL and about 100 µg/mL, about 95 µg/mL and about 150 µg/mL, about 145 µg/mL and about 200 µg/mL, or about 195 µg/mL and about 250 µg/mL). In some embodiments, the IC$_{100}$ is between about 6 µg/mL and about 200 µg/mL. In some embodiments, the inhibiting is measured using a mannose-resistant hemagglutination (MRHA) assay.

In some embodiments, the ETEC adhesin protein is a fimbrial adhesin protein (e.g., a class 5 fimbrial adhesin protein (e.g., a class 5a fimbrial adhesin protein (e.g., colonization factor antigen I adhesin subunit E (CfaE), coli surface antigen 4 (CS4), or coli surface antigen 14 (CS14)), a class 5b fimbrial adhesin protein (e.g., coli surface antigen 1 (CS1), coli surface antigen 17 (CS17), coli surface antigen 19 (CS19), or PCF071), a class 5c fimbrial adhesin protein (e.g., coli surface antigen 2 (CS2)).

In some embodiments, the ETEC adhesin protein is a non-fimbrial adhesin protein (e.g., a helical adhesin protein (e.g., coli surface antigen 5 (CS5)), a fibrillary adhesin protein (e.g., coli surface antigen 3 (e.g., CS3)), a bundle-forming adhesin protein (e.g., coli surface antigen 21 (CS21)), coli surface antigen 6 (CS6)).

In some embodiments, the antibody binds at least one (e.g., at least two, at least three, at least four, at least five, at least 6, or at least 7) of CfaE, CS4, CS14, CS1, CS17, CS19, CS2, and PCF071. In some embodiments, the antibody binds all eight of the following ETEC adhesin proteins: CfaE, CS4, CS14, CS1, CS17, CS19, CS2, and PCF071.

In some embodiments, the antibody binds CfaE with a $K_D$ of between about 0.1 nM and about 100 nM (e.g., between about 0.5 nM and about 30 nM, about 25 nM and about 50 nM, about 45 nM and about 60 nM, about 55 nM and about 70 nM, about 65 nM and about 80 nM, about 75 nM and about 90 nM, or about 85 nM about 100 nM). In some embodiments, the antibody binds CfaE with a $K_D$ of between about 1 nM and about 50 nM (e.g., between about 1 nM and about 20 nM (e.g., about 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM or 20 nM)). In some embodiments, the $K_D$ is measured by surface plasmon resonance at 25° C.

In some embodiments, the antibody is capable of inhibiting the binding of ETEC bacteria to intestinal cells with a 50% inhibitory concentration (IC$_{50}$) of between about 0.10 µM and about 10 µM (e.g., between about 0.50 µM and about 6 µM, about 3 µM and about 8 µM, or about 5 µM and about 10 µM). In some embodiments, the intestinal cells are Caco-2 human intestinal epithelial cells. In some embodiments, the inhibiting is measured using a Caco-2 adhesion assay at 37° C.

In one aspect, the invention provides an isolated nucleic acid encoding the antibody of any one of the above aspects.

In one aspect, the invention provides a vector comprising the nucleic acid of the above aspect.

In one aspect, the invention provides a host cell comprising the vector of the above aspect. In some embodiments, the host cell is a eukaryotic cell (e.g., a mammalian cell (e.g., a Chinese hamster ovary (CHO) cell or a human embryonic kidney (HEK) 239 cell), a yeast cell, a plant cell (e.g., a tobacco plant cell, a soybean plant cell, or a rice plant cell)).

In some embodiments, the host cell is a prokaryotic cell (e.g., an *E. coli* cell).

In one aspect, the invention provides a method of producing a VHH antibody, the method comprising culturing a host cell comprising the nucleic acid of any one of the aspects described herein in a culture medium. In some embodiments, the method further comprises recovering the antibody from the host cell or the culture medium.

In one aspect, the invention provides a composition comprising the antibody of any one of the aspects described herein.

In one aspect, the invention provides a pharmaceutical composition comprising the antibody of any one of the aspects described herein. In some embodiments, the pharmaceutical composition further includes a pharmaceutically acceptable carrier, excipient, or diluent. In some embodiments, the pharmaceutical composition is formulated for treating a disorder associated with an ETEC infection in a subject. In some embodiments, the disorder associated with an ETEC infection is ETEC-related diarrhea. In some embodiments, the pharmaceutical composition is formulated for oral administration comprising from 2% to 60% (w/v) of the antibody (e.g., from 5% to 20%, 15% to 30%, 25% to 40%, 35% to 50%, or 45% to 60%, from 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% (w/v) of the antibody).

In one aspect, the invention provides a method of treating a subject having a disorder associated with an ETEC infection comprising administering to the subject an effective about of the antibody of any one of the aspects described herein or the pharmaceutical composition of any one of the aspects described herein, thereby treating the subject.

In one embodiments, the invention provides a method of treating a subject at risk of developing a disorder associated with an ETEC infection comprising administering to the subject an effective about of the antibody of any one of the aspects described herein or the pharmaceutical composition of any one of the aspects described herein, thereby treating the subject.

In some embodiments, the antibody is administered to the subject at a dosage of about 0.1 mg/kg to about 100 mg/kg (e.g., about 1 mg/kg to about 80 mg/kg, about 1 mg/kg to about 40 mg/kg, about 5 mg/kg to about 20 mg/kg, or about 10 mg/kg). In some embodiments, the subject is administered at least one dose of the antibody or the pharmaceutical composition. In some embodiments, the subject is administered at least two doses of the antibody or the pharmaceutical composition.

In some embodiments, the disorder associated with an ETEC infection is ETEC-related diarrhea.

In some embodiments, the antibody is administered orally to the subject. In some embodiments, the antibody is administered subcutaneously to the subject.

In one aspect, the invention provides a method of detecting an ETEC in a sample from a subject, the method comprising contacting the sample with the antibody of any one of claims 1-126 under conditions permissive for binding of the antibody to an ETEC and detecting whether a complex is formed between the antibody and the ETEC (e.g., a fimbrial adhesin protein (e.g., a class 5 fimbrial adhesin protein (e.g., a class 5a fimbrial adhesin protein (e.g., colonization factor antigen I adhesin subunit E (CfaE), coli surface antigen 4 (CS4), or coli surface antigen 14 (CS14)), a class 5b fimbrial adhesin protein (e.g., coli surface antigen 1 (CS1), coli surface antigen 17 (CS17), coli surface antigen 19 (CS19), or PCF071), a class 5c fimbrial adhesin protein (e.g., coli surface antigen 2 (CS2)), a non-fimbrial adhesin protein (e.g., a helical adhesin protein (e.g., coli surface antigen 5 (CS5)), a fibrillary adhesin protein (e.g., coli surface antigen 3 (e.g., CS3)), a bundle-forming adhesin protein (e.g., coli surface antigen 21 (CS21)), coli surface antigen 6 (CS6))).

In some embodiments, the sample is a swab sample, a lavage sample, a blood sample, a plasma sample, a sputum sample, a urine sample, a stool sample, a sample from the mucosal lining of the small intestine, or a mucosal secretion sample. In certain embodiments, the sample is a sample from the mucosal lining of the small intestine. In some embodiments, the sample is a stool sample.

In some embodiments, the subject is presumed to have an ETEC infection. In some embodiments, the subject is a mammal (e.g., a human).

In one aspect, the invention provides a kit comprising the antibody of any one of the aspects described herein and a package insert comprising instructions for using the antibody to treat a subject having or at risk of developing a disorder associated with an ETEC infection.

In one aspect, the invention provides a kit for detecting ETEC, the kit comprising the antibody of any one of the aspects described herein and a package insert comprising instructions for using the antibody to detect ETEC. In some embodiments, the antibody is conjugated to a label or a tag.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A is a diagram showing the method of generating VHH antibody binding domains of the invention by llama immunization.

FIG. 1B is a diagram showing the method of generating VHH antibody binding domains of the invention using a naïve yeast surface display library.

FIG. 3A is a graph showing representative weak binders of Alexa-647 labeled CfaE.

FIG. 3B is a graph showing moderate binders of Alexa-647 labeled CfaE. FIG. 3C is a graph showing representative strong binders of Alexa-647 labeled CfaE.

FIG. 6A is a graph showing the binding of VHH antibody 2R215 to class 5 colonization factors. FIG. 6B is a graph showing the binding of VHH antibody 1D7 to class 5 colonization factors. FIG. 6C is a graph showing the binding of VHH antibody 2R23 to class 5 colonization factors. FIG. 6D is a graph showing the binding of VHH antibody 1H4 to class 5 colonization factors. Error bars represent the range in OD values observed in two independent experiments.

FIG. 10 is a table indicating CfaE residues of the putative receptor binding pocket in the surface of CfaE involved in binding of VHH antibodies 2R215, 1D7, 2R23, and 1H4. +++=very strong requirement for antibody binding (reduction in ELISA signal is more than 50% compared to wild-type CfaE protein), ++=strong requirement (50-80% reduction in ELISA signal compared to wild-type CfaE protein), +=weak requirement (20-50% reduction in ELISA signal compared to wild-type CfaE protein), and —=no requirement (reduction in ELISA signal is less than 20% compared to wild-type CfaE protein).

FIG. 11C is a gel showing, from left to right, a standard ladder, monomeric VHH antibody 2R215, trimeric 2R215, and dimeric 2R215. FIG. 11D is a gel showing, from left to right, monomeric VHH antibody 1D7, dimeric 1D7, trimeric 1D7, and a standard ladder.

FIG. 13A shows the efficacy of multimerized VHH 2R215 when administered together with ETEC, while FIG. 13B shows the efficacy of multimerized VHH 2R215 when administered two hours prior to ETEC challenge. ns=not significant (P>0.05), =P<0.01, *=P<0.001, and ****=P<0.0001.

DETAILED DESCRIPTION OF EMBODIMENTS OF THE INVENTION

I. Definitions

Figure 2A:
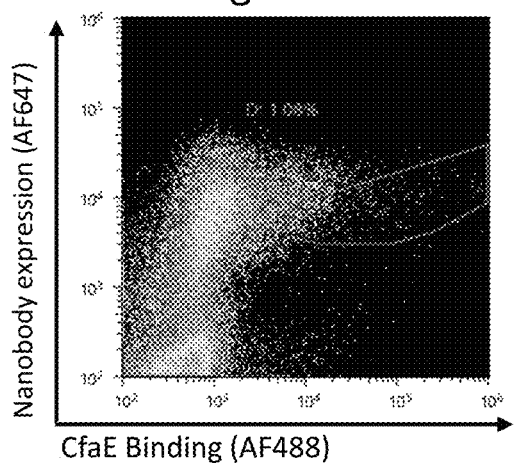
FIGS. 2A-2B are graphs depicting VHH antibody binding to CfaE (FIG. 2A) compared to a known CfaE binding full-length antibody, 68-61 IgG (FIG. 2B).

The terms "anti-ETEC adhesin protein antibody," "an antibody that binds to an ETEC adhesin protein," and "an antibody that specifically binds to an ETEC adhesin protein," or variants thereof, refer to an antibody that is capable of binding to an ETEC adhesin protein (e.g., one or more of CfaE, CS4, CS14, CS1, CS17, CS19, PCF071, and CS2) with sufficient affinity such that the antibody is useful as a preventative, diagnostic, and/or therapeutic agent in targeting an ETEC adhesin protein. In one embodiment, the extent of binding of an anti-ETEC adhesin protein antibody to an unrelated, non-ETEC adhesin protein is less than about 10% of the binding of the antibody to an ETEC adhesin protein as measured, e.g., by a radioimmunoassay (RIA) or surface plasmon resonance (SPR). In certain embodiments, an antibody that binds to an ETEC adhesin protein has a dissociation constant ($K_D$) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

The term "antibody" as used herein in the broadest sense encompasses various antibody structures, including but not limited to VHH antibodies, including single-domain VHH antibodies (e.g., nanobodies), monoclonal antibodies, polyclonal antibodies, multispecific antibodies (e.g., bispecific antibodies), and antibody fragments so long as they exhibit the desired antigen-binding activity (e.g., binding to at least one ETEC adhesin protein). In some embodiments, the VHH antibody can comprise a VHH binding domain linked to an Fc domain subunit.

The term "VHH antibody" refers to an antibody fragment or full-length antibody that includes at least one VHH binding domain.

The term "VHH binding domain" refers to a heavy chain variable domain that is does not require domain pairing with a light chain variable domain. In some embodiments, a VHH binding domain is capable of binding to an ETEC adhesin protein (e.g., one or more of CfaE, CS4, CS14, CS1, CS17, CS19, PCF071, and CS2)). VHH binding domains can be further subdivided into regions of hypervariability, termed "complementarity determining regions" (CDRs), interspersed with regions that are more conserved, termed "framework regions" (FRs). Each VHH binding domain may be composed, for example, of three CDRs and four FRs, arranged from amino-terminus to carboxyl-terminus in the following order: FR1, CDR1, FR2, CDR2, FR3, CDR3, and FR4. The CDR3 region of VHH binding domains is often longer than that of conventional VH domains and has the capacity to form finger-like extensions, allowing for the targeting of conserved clefts and pocket regions (typically binding sites) on hypervariable pathogens. The variable regions of the VHH binding domain contain a binding domain that interacts with at least one ETEC adhesin protein.

The term "class 5 fimbrial adhesin protein" refers to the largest class of ETEC colonization factors in humans. Class 5 includes eight serologically discrete colonization factors of ETEC that mediate small intestinal adhesion, and are subdivided into three sub-classes, class 5a, class 5b, and class 5c. Class 5a includes CfaE, CS4, and CS14; class 5b includes CS1, CS17, CS19, and PCF071; and class 5c includes CS2.

The term "colonization factor antigen I adhesin subunit E" or "CfaE" refers to subunit E of colonization factor antigen I (CFA/I). CFA/I is a filamentous structure on the surface of ETEC that is involved with ETEC adhesion to the small intestine, which allows the bacteria to cause infection.

The term "coli surface antigen 1" or "CS1" refers to colonization factor antigen 1 (CFA/II) class 5b fimbrial adhesin protein.

The term "coli surface antigen 2" or "CS2" refers to colonization factor antigen 2 belonging to colonization factor antigen group II (CFA/II) and is a class 5c fimbrial adhesin protein.

The term "coli surface antigen 3" or "CS3" refers to colonization factor antigen 3 belonging to colonization factor antigen group II (CFA/II) and is a fibrillary adhesin protein. CS3 assembles into fine wiry helical fibrillae encoded by the cstA-H gene cluster.

The term "coli surface antigen 4" or "CS4" refers to colonization factor antigen 4 belonging to colonization factor antigen group IV (CFA/IV) and is a class 5a fimbrial adhesin protein.

The term "coli surface antigen 5" or "CS5" refers to colonization factor antigen 5 belonging to colonization factor antigen group IV (CFA/IV).

The term "coli surface antigen 6" or "CS6" refers to colonization factor antigen 6 belonging to colonization factor antigen group IV (CFA/IV). The CS6 operon encodes two structural subunit proteins, CssA and CssB, a chaperon, CssC, and an usher, CssD.

The term "coli surface antigen 14" or "CS14" refers to colonization factor antigen 14 belonging to colonization factor antigen group III (CFA/III) and is a class 5a fimbrial adhesin protein.

The term "coli surface antigen 17" or "CS17" refers to colonization factor antigen 17 belonging to colonization factor antigen group III (CFA/III) and is a class 5b fimbrial adhesin protein.

The term "coli surface antigen 19" or "CS19" refers to colonization factor antigen 19 and is a class 5b fimbrial adhesin protein.

The term "coli surface antigen 21" or "CS21" refers to colonization factor antigen 21 and is a class 5b fimbrial adhesin protein, also a type IV pilus (T4P), with >20 µm in length.

The term "PCF071" refers to putative colonization factor antigen 071 and is a class 5b fimbrial adhesin protein closely related to CS1.

The terms "full-length antibody," "intact antibody," and "whole antibody" are used herein interchangeably to refer to an antibody having a structure including a VHH binding domain and having heavy chains that contain Fc domain subunits forming or capable of forming an Fc domain as defined herein. The term "Fc domain subunit" refers to a polypeptide chain that includes at least a second and a third antibody constant domains (CH2 and CH3) or functional fragments thereof (e.g., fragments that are capable of (i) dimerizing with another Fc domain subunit to form an Fc domain, and (ii) binding to an Fc receptor). In certain instances, the Fc domain subunit can include a hinge region linked to the second and third antibody constant domains. The term "Fc domain" refers to a dimer of two Fc domain subunits that dimerize by an interaction between the two CH3 constant domains; in some instances, one or more disulfide bonds form between the hinge regions of the two dimerizing Fc domain subunits. The full-length antibody can further include a first constant domain (CH1) linked to the second and third antibody constant domain. The Fc domain subunit or Fc domain can be an IgA subtype, in particular a secretory IgA (sIgA) or dimeric IgA (dIgA). In some instances, the Fc domain subunit of Fc domain may be of any IgA subtype (e.g., dIgA1, dIgA2, sIgA1, and sIgA2). Alternatively, the Fc domain subunit or Fc domain can be an IgG subtype (e.g., IgG1, IgG2a, or IgG2b) (e.g., IgG1). In some instances, the full-length antibody includes an Fc domain including a first Fc domain subunit and a second Fc domain subunit, wherein the first Fc domain subunit and the second Fc domain subunit are capable of stable association. In some embodiments, each Fc domain subunit is linked to a single VHH binding domain and positioned relative to each other in an N-terminal-to-C-terminal direction as follows: VHH binding domain-Fc domain subunit. In some instances, each Fc domain subunit is linked to a single VHH binding domain by a hinge region and positioned relative to each other in an N-terminal-to-C-terminal direction as follows: VHH binding domain-hinge region-Fc domain subunit. In some instances, the antibody is an IgA class antibody. In some instances, each Fc domain subunit is further linked to a single CH1 domain. In some embodiments, each VHH binding domain, CH1 domain, and Fc domain subunit is positioned relative to each other in an N-terminal-to-C-terminal direction as follows: VHH binding domain-CH1 domain-Fc domain subunit. In some instances, each CH1 domain is linked to a single VHH binding domain by a hinge region and positioned relative to each other in an N-terminal-to-C-terminal direction as follows: VHH binding domain-CH1 domain-hinge region-Fc domain subunit. In some instances, each CH1 domain is linked to a single VHH binding domain by a hinge region and positioned relative to each other in an N-terminal-to-C-terminal direction as follows: VHH binding domain-hinge region-CH1 domain-Fc domain subunit. In certain instances, the hinge region includes the amino acid sequence of ASPVPSTPPTPSPSTPPTPSPS (SEQ ID NO: 209) or ASPVPPPPPP (SEQ ID NO: 210).

The term "monoclonal antibody," as used herein, refers to an antibody obtained from a population of substantially homogenous antibodies that displays binding affinity for an epitope on one or more ETEC adhesin proteins.

An "antibody fragment" refers to a molecule other than an intact antibody that comprises a portion of an intact antibody that specifically binds to the antigen (e.g., an ETEC adhesin protein) to which the intact antibody binds. Examples of antibody fragments include, but are not limited to, Fv, Fab, Fab', Fab'-SH, F(ab')$_2$; nanobodies (e.g., VHH nanobodies), diabodies; linear antibodies; single-chain antibody molecules (e.g., scFv); and multispecific antibodies formed from antibody fragments. These antibody fragments are obtained using conventional techniques, and the fragments are screened for utility in the same manner as are intact antibodies. Antibody fragments can be produced by recombinant DNA techniques, or by enzymatic or chemical cleavage of intact immunoglobulins.

The term "about" as used herein refers to the usual error range for the respective value readily known to the skilled person in this technical field. Reference to "about" a value or parameter herein includes (and describes) embodiments that are directed to that value or parameter per se.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described below.

The term "$K_D$," as used herein, is intended to refer to the dissociation equilibrium constant of a particular antibody-antigen interaction. Typically, the antibodies of the invention bind to an ETEC adhesin protein (e.g., CfaE, CS4, CS14, CS1, CS17, CS19, CS2, CS3, CS5, CS6, CS21, or PCF071) with a dissociation equilibrium constant ($K_D$) of less than about $10^{-6}$ M, such as less than approximately $10^{-7}$ M, $10^{-8}$ M, $10^{-9}$ M, or $10^{-10}$ M or even lower when determined by surface plasmon resonance (SPR) technology in a BIA-CORE 3000 instrument using recombinant ETEC adhesin protein as the analyte and the antibody as the ligand.

A "disorder" is any condition that would benefit from treatment including, but not limited to, chronic and acute disorders or diseases including those pathological conditions which predispose the mammal to the disorder in question.

As used herein, the term "disorder associated with an enterotoxigenic Escherichia coli infection" or "disorder associated with an ETEC infection" refers to any disease, the onset, progression, or the persistence of the symptoms of which requires the participation of ETEC. An exemplary disorder associated with an ETEC infection is, for example, diarrhea.

The term "IC50," as used herein, refers to the concentration of an antibody or an antigen-binding portion thereof, which induces a response, either in an in vivo or an in vitro assay, needed to inhibit 50% of the maximal response (i.e., halfway between the maximal response and the baseline), for example, of ETEC adhesion to Caco-2 cells as compared to an irrelevant antibody.

The term "$IC_{100}$," as used herein, refers to the maximal inhibitory concentration of an antibody or an antigen-binding portion thereof, either in an in vivo or an in vitro assay.

The terms "effective amount," "effective dose," and "effective dosage" as used herein are defined as an amount sufficient to achieve, or at least partially achieve, the desired effect. The term "therapeutically effective dose" or "therapeutically effective amount" is defined as an amount sufficient to prevent, cure, or at least partially arrest, the disease (e.g., diarrhea) and its complications in a patient already suffering from the disease or at risk of developing the disease. Amounts effective for this use will depend upon the severity of the disorder being treated and the general state of the patient's own immune system.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography and 2-dimensional nuclear magnetic resonance. See, for example, Epitope Mapping Protocols in Methods in Molecular Biology, Vol. 66, G. E. Morris, Ed. (1996). Epitopes can also be defined by point mutations in the target protein (e.g., an ETEC adhesin protein (e.g., CfaE, CS4, CS14, CS1, CS17, CS19, CS2, CS3, CS5, CS6, CS21, or PCF071)), which affect the binding of the antibody (e.g., monoclonal antibody).

The term "host cell," as used herein, is intended to refer to a cell into which an expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

An "isolated antibody" or "isolated VHH antibody" is one which has been identified and separated and/or recovered from a component of its natural environment and/or is substantially free of other antibodies having different antigenic specificities (e.g., an isolated antibody that binds to an ETEC adhesin protein is substantially free of antibodies that bind antigens other than an ETEC adhesin protein). Contaminant components of its natural environment are materials which would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie™ blue or, preferably, silver stain. Isolated antibody includes the antibody in situ within recombinant cells since at least one component of the antibody's natural environment will not be present. Similarly, isolated antibody includes the antibody in medium around recombinant cells. Ordinarily, however, isolated antibody will be prepared by at least one purification step.

The term "nucleic acid molecule," as used herein, is intended to include DNA molecules and RNA molecules. A nucleic acid molecule may be single-stranded or double-stranded, but preferably is double-stranded DNA.

The term "isolated nucleic acid," as used herein in reference to nucleic acids molecules encoding antibodies or antibody portions (e.g., VHH antibodies or fragments thereof) that bind to an ETEC adhesin protein (e.g., CfaE, CS4, CS14, CS1, CS17, CS19, CS2, CS3, CS5, CS6, CS21, and PCF071), is intended to refer to a nucleic acid molecule in which the nucleotide sequences encoding the antibody or antibody portion are free of other nucleotide sequences encoding antibodies that bind antigens other than an ETEC adhesin protein, which other sequences may naturally flank the nucleic acid in human genomic DNA.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, the terms "specific binding," "selective binding," "selectively binds," and "specifically binds," refer to antibody binding to an epitope on a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE 3000 instrument, which can be performed, for example, using recombinant ETEC adhesin protein (e.g., recombinant CfaE) as the analyte and the antibody as the ligand. In some embodiments, binding by the antibody to the predetermined antigen is with an affinity that is at least two-fold greater than its affinity for binding to a non-specific antigen (e.g., BSA, casein) other than the predetermined antigen or a closely related antigen. The phrases "an antibody recognizing an antigen" and "an antibody specific for an antigen" are used interchangeably herein with the term "an antibody which binds specifically to an antigen."

A "subject" or an "individual" is a mammal. Mammals include, but are not limited to, domesticated animals (e.g., cows, sheep, cats, dogs, and horses), primates (e.g., humans and non-human primates such as monkeys), rabbits, deer, and rodents (e.g., mice and rats). In certain embodiments, the subject or individual is a human.

The terms "treat," "treating," and "treatment," as used herein, refer to preventative or therapeutic measures described herein. The methods of "treatment" involve administration to a subject in need of such treatment a VHH antibody of the present invention or pharmaceutical composition including a VHH antibody of the present invention, for example, administration to a subject at risk of developing a disorder associated with ETEC infection or a subject having a disorder associated with ETEC infection, in order to prevent, cure, delay, reduce the severity of, or ameliorate one or more symptoms of the disorder or recurring disorder, or in order to prolong the survival of a subject beyond that expected in the absence of such treatment. In some embodiments, for example, the anti-ETEC adhesin protein antibodies of the invention would be administered to a subject at risk of developing a disorder associated with ETEC infection (e.g., a subject residing or traveling to a geographical location in which pathogenic ETEC is found). Accordingly, desirable effects of treatment include, but are not limited to, preventing occurrence of disease or disorder, such as a disorder associated with ETEC infection (e.g., ETEC-related diarrhea). Other desirable effects of treatment may include preventing recurrence of disease, alleviation of symptoms, diminishment of any direct or indirect pathological consequences of the disease, decreasing the rate of disease progression, amelioration or palliation of the disease state, and improved prognosis.

As used herein, "administering" is meant a method of giving a dosage of a compound (e.g., an anti-ETEC adhesin protein antibody of the invention or a nucleic acid encoding an anti-ETEC adhesin protein VHH antibody of the invention) or a composition (e.g., a pharmaceutical composition including an anti-ETEC adhesin protein VHH antibody of the invention) to a subject. The compositions utilized in the methods described herein can be administered or formulated for administration, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. The method of administration can vary depending on various factors (e.g., the compound or composition being administered and the severity of the condition, disease, or disorder being treated). Preferably, the compound (e.g., VHH antibodies including anti-ETEC adhesin protein VHH binding domains 2R215, 1D7, 2R23, and/or 1H4) or composition (e.g., pharmaceutical composition comprising VHH antibodies including anti-ETEC adhesin protein VHH binding domains 2R215, 1D7, 2R23, and/or 1H4) is administered orally or formulated for oral administration.

As used herein, the term "vector" is meant to include, but is not limited to, a nucleic acid molecule (e.g., a nucleic acid molecule that is capable of transporting another nucleic acid to which it has been linked), a virus (e.g., a lentivirus or an adenovirus, e.g., a recombinant adeno-associated virus (rAAV)), cationic lipid (e.g., liposome), cationic polymer (e.g., polysome), virosome, nanoparticle, or dendrimer. In a preferred embodiment, the vector is a "plasmid," which refers to a circular double stranded DNA loop into which additional DNA segments may be ligated. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby be replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids.

II. Compositions and Methods

In one aspect, the invention is based, in part, on anti-enterotoxigenic *Escherichia coli* (ETEC) adhesin protein VHH antibodies. Antibodies of the invention are useful, for example, for treating a subject having, or at risk of developing, a disorder associated with an ETEC infection.

A. Anti-ETEC Adhesin Protein VHH Antibodies

The invention provides isolated VHH antibodies that bind one or more ETEC adhesin proteins (e.g., CfaE, CS4, CS14, CS1, CS17, CS19, CS2, CS3, CS5, CS6, CS21, and PCF071).

In one aspect, the invention provides isolated VHH antibodies that bind an ETEC adhesin protein and include a VHH binding domain including the following complementarity determining regions (CDRs): (a) a CDR-H1 comprising the amino acid sequence of NIFQDAE (SEQ ID NO: 1); (b) a CDR-H2 comprising the amino acid sequence of FVATIAYGGNTN (SEQ ID NO: 2); (c) a CDR-H3 comprising the amino acid sequence of VYTGVYYDRTTGGY-VAFE (SEQ ID NO: 3), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1-3, and/or (ii) one, two, or three amino acid substitutions relative to the amino acid sequence of any one of SEQ ID NOs: 1-3. In some embodiments, the antibody may include a VHH binding domain including a sequence having at least 95% sequence identity (e.g., 96%, 97%, 98%, or 99% identity) to the amino acid sequence of SEQ ID NO: 4, and/or may include one, two, three, four, five, or six amino acid substitutions relative to the amino acid sequence of SEQ ID NO: 4. In some instances, the anti-ETEC adhesin protein antibody may include a VHH binding domain including the following framework regions (FRs): (a) an FR-H1 comprising the amino acid sequence of QVQLQESGGGLVQAGGSLRLSCAASG (SEQ ID NO: 5); (b) an FR-H2 comprising the amino acid sequence of MGWYRQAPGKERE (SEQ ID NO: 6); (c) an FR-H3 comprising the amino acid sequence of YADSVKGRFTIS-RDNAKNTVYLQMNSLKPEDTAVYYCA (SEQ ID NO: 7); and (d) an FR-H4 comprising the amino acid sequence of YWGQGTQVTVSS (SEQ ID NO: 8), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 5-8. In some instances, the anti-ETEC adhesin protein antibody may include a VHH binding domain including the amino acid sequence of SEQ ID NO: 4. In particular instances, the anti-ETEC adhesin protein antibody includes a VHH binding domain of VHH antibody 2R215.

In another aspect, the invention provides isolated VHH antibodies that bind an ETEC adhesin protein and include a VHH binding domain including the following complementarity determining regions (CDRs): (a) a CDR-H1 comprising the amino acid sequence of ERTFSYYV (SEQ ID NO: 9); (b) a CDR-H2 comprising the amino acid sequence of FVAGISMSGDSTK (SEQ ID NO: 10); (c) a CDR-H3 comprising the amino acid sequence of ADRDIRGNFRS (SEQ ID NO: 11), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 9-11, and/or (ii) one, two, or three amino acid substitutions relative to the amino acid sequence of any one of SEQ ID NOs: 9-11. In some embodiments, the antibody may include a VHH binding domain including a sequence having at least 95% sequence identity (e.g., 96%, 97%, 98%, or 99% identity) to the amino acid sequence of SEQ ID NO: 12, and/or may include one, two, three, four, five, or six amino acid substitutions relative to the amino acid sequence of SEQ ID NO: 12. In some instances, the anti-ETEC adhesin protein antibody may include a VHH binding domain including the following framework regions (FRs): (a) an FR-H1 comprising the amino acid sequence of EVQLVESGGGLVQAGGSLTLSCAAS (SEQ ID NO: 13); (b) an FR-H2 comprising the amino acid sequence of MAWFRQAPGKERE (SEQ ID NO: 14); (c) an FR-H3 comprising the amino acid sequence of YADSVKGRFTIS-RDNAENTGYLQMNGLKPEDTAVYYCA (SEQ ID NO: 15); and (d) an FR-H4 comprising the amino acid sequence of WGRGTQVTVSSAA (SEQ ID NO: 16), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 13-16. In some instances, the anti-ETEC adhesin protein antibody may include a VHH binding domain including the amino acid sequence of SEQ ID NO: 12. In particular instances, the anti-ETEC adhesin protein antibody includes a VHH binding domain of VHH antibody 1D7.

In another aspect, the invention provides isolated VHH antibodies that bind an ETEC adhesin protein and include a VHH binding domain including the following complementarity determining regions (CDRs): (a) a CDR-H1 comprising the amino acid sequence of YIFWSYGY (SEQ ID NO: 17); (b) a CDR-H2 comprising the amino acid sequence of LVATISRGGTTN (SEQ ID NO: 18); (c) a CDR-H3 comprising the amino acid sequence of AGRYAFGYFK (SEQ ID NO: 19), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 17-19, and/or (ii) one, two, or three amino acid substitutions relative to the amino acid sequence of any one of SEQ ID NOs: 17-19. In some embodiments, the antibody may include a VHH binding domain including a sequence having at least 95% sequence identity (e.g., 96%, 97%, 98%, or 99% identity) to the amino acid sequence of SEQ ID NO: 20, and/or may include one, two, three, four, five, or six amino acid substitutions relative to the amino acid sequence of SEQ ID NO: 20. In some instances, the anti-ETEC adhesin protein antibody may include a VHH binding domain including the following framework regions (FRs): (a) an FR-H1 comprising the amino acid sequence of QVQLQESGGGLVQAGGSLRLSCAASG (SEQ ID NO: 21); (b) an FR-H2 comprising the amino acid sequence of MGWYRQAPGKERE (SEQ ID NO: 22); (c) an FR-H3 comprising the amino acid sequence of YADSVKGRFTISRDNAKNTVYLQMNSLKPEDTAVYYCA (SEQ ID NO: 23); and (d) an FR-H4 comprising the amino acid sequence of YWGQGTQVTVSS (SEQ ID NO: 24), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 21-24. In some instances, the anti-ETEC adhesin protein antibody may include a VHH binding domain including the amino acid sequence of SEQ ID NO: 20. In particular instances, the anti-ETEC adhesin protein antibody includes a VHH binding domain of VHH antibody 2R23.

In another aspect, the invention provides isolated VHH antibodies that bind an ETEC adhesin protein and include a VHH binding domain including the following CDRs: (a) a CDR-H1 comprising the amino acid sequence of SRTFNHYN (SEQ ID NO: 25); (b) a CDR-H2 comprising the amino acid sequence of FAAAITWNGRSTL (SEQ ID NO: 26); (c) a CDR-H3 comprising the amino acid sequence of TLTTWEHKWEYNS (SEQ ID NO: 27), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 25-27, and/or (ii) one, two, or three amino acid substitutions relative to the amino acid sequence of any one of SEQ ID NOs: 25-27. In some embodiments, the antibody may include a VHH binding domain including a sequence having at least 95% sequence identity (e.g., 96%, 97%, 98%, or 99% identity) to the amino acid sequence of SEQ ID NO: 28, and/or may include one, two, three, four, five, or six amino acid substitutions relative to the amino acid sequence of SEQ ID NO: 28. In some instances, the anti-ETEC adhesion protein antibody may include a VHH binding domain including the following framework regions (FRs): (a) an FR-H1 comprising the amino acid sequence of EVQLVESGGGLVQAGGSLRLSCAAS (SEQ ID NO: 29); (b) an FR-H2 comprising the amino acid sequence of IGWFRQAPGKERE (SEQ ID NO: 30); (c) an FR-H3 comprising the amino acid sequence of YADSVKGRFTISRDNAKNTVYLQMNSLKPEDTAVYYCA (SEQ ID NO: 31); (d) an FR-H4 comprising the amino acid sequence of QGQGTQVTVSSAA (SEQ ID NO: 32), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 29-32, and/or (ii) one, two, or three amino acid substitutions relative to the amino acid sequence of any one of SEQ ID NOs: 29-32. In some instances, the anti-ETEC adhesin protein antibody may include a VHH binding domain including the amino acid sequence of SEQ ID NO: 28. In particular instances, the anti-ETEC adhesin protein antibody includes a VHH binding domain of VHH antibody 1H4.

In another aspect, the invention provides isolated VHH antibodies that bind an ETEC adhesin protein and include a VHH binding domain including the following CDRs: (a) a CDR-H1 comprising the amino acid sequence of SRTFNHYN (SEQ ID NO: 33); (b) a CDR-H2 comprising the amino acid sequence of FAAAITWNGRSTL (SEQ ID NO: 34); (c) a CDR-H3 comprising the amino acid sequence of TLTTWEHKWEYNS (SEQ ID NO: 35), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 33-35, and/or (ii) one, two, or three amino acid substitutions relative to the amino acid sequence of any one of SEQ ID NOs: 33-35. In some embodiments, the antibody may include a VHH binding domain including a sequence having at least 95% sequence identity (e.g., 96%, 97%, 98%, or 99% identity) to the amino acid sequence of SEQ ID NO: 36, and/or may include one, two, three, four, five, or six amino acid substitutions relative to the amino acid sequence of SEQ ID NO: 36. In some instances, the anti-ETEC adhesion protein antibody may include a VHH binding domain including the following framework regions (FRs): (a) an FR-H1 comprising the amino acid sequence of EVQLVESGGGLVQAGGSLRLSCAAS (SEQ ID NO: 37); (b) an FR-H2 comprising the amino acid sequence of IGWFRQAPGKERE (SEQ ID NO: 38); (c) an FR-H3 comprising the amino acid sequence of YADSVKGRFTISRDNAKNTVYLQMNSLKPEDTAVYYCA (SEQ ID NO: 39); (d) an FR-H4 comprising the amino acid sequence of QGQGTQVTVSSAA (SEQ ID NO: 40), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 37-40, and/or (ii) one, two, or three amino acid substitutions relative to the amino acid sequence of any one of SEQ ID NOs: 37-40. In some instances, the anti-ETEC adhesin protein antibody may include a VHH binding domain including the amino acid sequence of SEQ ID NO: 36. In particular instances, the anti-ETEC adhesin protein antibody includes a VHH binding domain of VHH antibody 2R275.

In another aspect, the invention provides isolated VHH antibodies that bind an ETEC adhesin protein and include a VHH binding domain including the following CDRs: (a) a CDR-H1 comprising the amino acid sequence of SRTFNHYN (SEQ ID NO: 41); (b) a CDR-H2 comprising the amino acid sequence of FAAAITWNGRSTL (SEQ ID NO: 42); (c) a CDR-H3 comprising the amino acid sequence of TLTTWEHKWEYNS (SEQ ID NO: 43), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 41-43, and/or (ii) one, two, or three amino acid substitutions relative to the amino acid sequence of any one of SEQ ID NOs: 41-43. In some embodiments, the antibody may include a VHH binding domain including a sequence having at least 95% sequence identity (e.g., 96%, 97%, 98%, or 99% identity) to the amino acid sequence of SEQ ID NO: 44, and/or may include one, two, three, four, five, or six amino acid substitutions relative to the amino acid sequence of SEQ ID NO: 44. In some instances, the anti-ETEC adhesion protein antibody may include a VHH binding domain including the following framework regions (FRs): (a) an FR-H1 comprising the amino acid sequence of EVQLVESGGGLVQAGGSLRLS-CAAS (SEQ ID NO: 45); (b) an FR-H2 comprising the amino acid sequence of IGWFRQAPGKERE (SEQ ID NO: 46); (c) an FR-H3 comprising the amino acid sequence of YADSVKGRFTISRDNAKNTVYLQMNSLKPED-TAVYYCA (SEQ ID NO: 47); (d) an FR-H4 comprising the amino acid sequence of QGQGTQVTVSSAA (SEQ ID NO: 48), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 45-48, and/or (ii) one, two, or three amino acid substitutions relative to the amino acid sequence of any one of SEQ ID NOs: 45-48. In some instances, the anti-ETEC adhesin protein antibody may include a VHH binding domain including the amino acid sequence of SEQ ID NO: 44. In particular instances, the anti-ETEC adhesin protein antibody includes a VHH binding domain of VHH antibody 2R12.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 49); (b) a CDR-H2 comprising the amino acid sequence of FAAAITWNGRSTL (SEQ ID NO: 50); (c) a CDR-H3 comprising the amino acid sequence of TLTTWEHKWEYNS (SEQ ID NO: 51), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 49-51, and/or (ii) one, two, or three amino acid substitutions relative to the amino acid sequence of any one of SEQ ID NOs: 49-51. In some embodiments, the antibody may include a VHH binding domain including a sequence having at least 95% sequence identity (e.g., 96%, 97%, 98%, or 99% identity) to the amino acid sequence of SEQ ID NO: 52, and/or may include one, two, three, four, five, or six amino acid substitutions relative to the amino acid sequence of SEQ ID NO: 52. In some instances, the anti-ETEC adhesion protein antibody may include a VHH binding domain including the following framework regions (FRs): (a) an FR-H1 comprising the amino acid sequence of EVQLVESGGGLVQAGGSLRLS-CAAS (SEQ ID NO: 53); (b) an FR-H2 comprising the amino acid sequence of IGWFRQAPGKERE (SEQ ID NO: 54); (c) an FR-H3 comprising the amino acid sequence of YADSVKGRFTISRDNAKNTVYLQMNSLKPED-TAVYYCA (SEQ ID NO: 55); (d) an FR-H4 comprising the amino acid sequence of QGQGTQVTVSSAA (SEQ ID NO: 56), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 53-56, and/or (ii) one, two, or three amino acid substitutions relative to the amino acid sequence of any one of SEQ ID NOs: 53-56. In some instances, the anti-ETEC adhesin protein antibody may include a VHH binding domain including the amino acid sequence of SEQ ID NO: 52. In particular instances, the anti-ETEC adhesin protein antibody includes a VHH binding domain of VHH antibody 2R65.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 57); (b) a CDR-H2 comprising the amino acid sequence of FAAAITWNGRSTL (SEQ ID NO: 58); (c) a CDR-H3 comprising the amino acid sequence of TLTTWEHKWEYNS (SEQ ID NO: 59), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 57-59, and/or (ii) one, two, or three amino acid substitutions relative to the amino acid sequence of any one of SEQ ID NOs: 57-59. In some embodiments, the antibody may include a VHH binding domain including a sequence having at least 95% sequence identity (e.g., 96%, 97%, 98%, or 99% identity) to the amino acid sequence of SEQ ID NO: 60, and/or may include one, two, three, four, five, or six amino acid substitutions relative to the amino acid sequence of SEQ ID NO: 60. In some instances, the anti-ETEC adhesion protein antibody may include a VHH binding domain including the following framework regions (FRs): (a) an FR-H1 comprising the amino acid sequence of EVQLVESGGGLVQAGGSLRLS-CAAS (SEQ ID NO: 61); (b) an FR-H2 comprising the amino acid sequence of IGWFRQAPGKERE (SEQ ID NO: 62); (c) an FR-H3 comprising the amino acid sequence of YADSVKGRFTISRDNAKNTVYLQMNSLKPED-TAVYYCA (SEQ ID NO: 63); (d) an FR-H4 comprising the amino acid sequence of QGQGTQVTVSSAA (SEQ ID NO: 64), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 61-64, and/or (ii) one, two, or three amino acid substitutions relative to the amino acid sequence of any one of SEQ ID NOs: 61-64. In some instances, the anti-ETEC adhesin protein antibody may include a VHH binding domain including the amino acid sequence of SEQ ID NO: 60. In particular instances, the anti-ETEC adhesin protein antibody includes a VHH binding domain of VHH antibody 2R67.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 65); (b) a CDR-H2 comprising the amino acid sequence of FAAAITWNGRSTL (SEQ ID NO: 66); (c) a CDR-H3 comprising the amino acid sequence of TLTTWEHKWEYNS (SEQ ID NO: 67), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 65-67, and/or (ii) one, two, or three amino acid substitutions relative to the amino acid sequence of any one of SEQ ID NOs: 65-67. In some embodiments, the antibody may include a VHH binding domain including a sequence having at least 95% sequence identity (e.g., 96%, 97%, 98%, or 99% identity) to the amino acid sequence of SEQ ID NO: 68, and/or may include one, two, three, four, five, or six amino acid substitutions relative to the amino acid sequence of SEQ ID NO: 68. In some instances, the anti-ETEC adhesion protein antibody may include a VHH binding domain including the following framework regions (FRs): (a) an FR-H1 comprising the amino acid sequence of EVQLVESGGGLVQAGGSLRLS-CAAS (SEQ ID NO: 69); (b) an FR-H2 comprising the amino acid sequence of IGWFRQAPGKERE (SEQ ID NO: 70); (c) an FR-H3 comprising the amino acid sequence of YADSVKGRFTISRDNAKNTVYLQMNSLKPED-TAVYYCA (SEQ ID NO: 71); (d) an FR-H4 comprising the amino acid sequence of QGQGTQVTVSSAA (SEQ ID NO: 72), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 69-72, and/or (ii) one, two, or three amino acid substitutions relative to the amino acid sequence of any one of SEQ ID NOs: 69-72. In some instances, the anti-ETEC adhesin protein antibody may include a VHH binding domain including the amino acid sequence of SEQ ID NO: 68. In particular instances, the anti-ETEC adhesin protein antibody includes a VHH binding domain of VHH antibody 2R221.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 73); (b) a CDR-H2 comprising the amino acid sequence of FAAAITWNGRSTL (SEQ ID NO: 74); (c) a CDR-H3 comprising the amino acid sequence of TLTTWEHKWEYNS (SEQ ID NO: 75), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 73-75, and/or (ii) one, two, or three amino acid substitutions relative to the amino acid sequence of any one of SEQ ID NOs: 73-75. In some embodiments, the antibody may include a VHH binding domain including a sequence having at least 95% sequence identity (e.g., 96%, 97%, 98%, or 99% identity) to the amino acid sequence of SEQ ID NO: 76, and/or may include one, two, three, four, five, or six amino acid substitutions relative to the amino acid sequence of SEQ ID NO: 76. In some instances, the anti-ETEC adhesion protein antibody may include a VHH binding domain including the following framework regions (FRs): (a) an FR-H1 comprising the amino acid sequence of EVQLVESGGGLVQAGGSLRLS-CAAS (SEQ ID NO: 77); (b) an FR-H2 comprising the amino acid sequence of IGWFRQAPGKERE (SEQ ID NO: 78); (c) an FR-H3 comprising the amino acid sequence of YADSVKGRFTISRDNAKNTVYLQMNSLKPED-TAVYYCA (SEQ ID NO: 79); (d) an FR-H4 comprising the amino acid sequence of QGQGTQVTVSSAA (SEQ ID NO: 80), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 77-80, and/or (ii) one, two, or three amino acid substitutions relative to the amino acid sequence of any one of SEQ ID NOs: 77-80. In some instances, the anti-ETEC adhesin protein antibody may include a VHH binding domain including the amino acid sequence of SEQ ID NO: 76. In particular instances, the anti-ETEC adhesin protein antibody includes a VHH binding domain of VHH antibody 2R267.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 81); (b) a CDR-H2 comprising the amino acid sequence of FAAAITWNGRSTL (SEQ ID NO: 82); (c) a CDR-H3 comprising the amino acid sequence of TLTTWEHKWEYNS (SEQ ID NO: 83), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 81-83, and/or (ii) one, two, or three amino acid substitutions relative to the amino acid sequence of any one of SEQ ID NOs: 81-83. In some embodiments, the antibody may include a VHH binding domain including a sequence having at least 95% sequence identity (e.g., 96%, 97%, 98%, or 99% identity) to the amino acid sequence of SEQ ID NO: 84, and/or may include one, two, three, four, five, or six amino acid substitutions relative to the amino acid sequence of SEQ ID NO: 84. In some instances, the anti-ETEC adhesion protein antibody may include a VHH binding domain including the following framework regions (FRs): (a) an FR-H1 comprising the amino acid sequence of EVQLVESGGGLVQAGGSLRLS-CAAS (SEQ ID NO: 85); (b) an FR-H2 comprising the amino acid sequence of IGWFRQAPGKERE (SEQ ID NO: 86); (c) an FR-H3 comprising the amino acid sequence of YADSVKGRFTISRDNAKNTVYLQMNSLKPED-TAVYYCA (SEQ ID NO: 87); (d) an FR-H4 comprising the amino acid sequence of QGQGTQVTVSSAA (SEQ ID NO: 88), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 85-88, and/or (ii) one, two, or three amino acid substitutions relative to the amino acid sequence of any one of SEQ ID NOs: 85-88. In some instances, the anti-ETEC adhesin protein antibody may include a VHH binding domain including the amino acid sequence of SEQ ID NO: 84. In particular instances, the anti-ETEC adhesin protein antibody includes a VHH binding domain of VHH antibody 1A6.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 89); (b) a CDR-H2 comprising the amino acid sequence of FAAAITWNGRSTL (SEQ ID NO: 90); (c) a CDR-H3 comprising the amino acid sequence of TLTTWEHKWEYNS (SEQ ID NO: 91), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 89-91, and/or (ii) one, two, or three amino acid substitutions relative to the amino acid sequence of any one of SEQ ID NOs: 89-91. In some embodiments, the antibody may include a VHH binding domain including a sequence having at least 95% sequence identity (e.g., 96%, 97%, 98%, or 99% identity) to the amino acid sequence of SEQ ID NO: 92, and/or may include one, two, three, four, five, or six amino acid substitutions relative to the amino acid sequence of SEQ ID NO: 92. In some instances, the anti-ETEC adhesion protein antibody may include a VHH binding domain including the following framework regions (FRs): (a) an FR-H1 comprising the amino acid sequence of EVQLVESGGGLVQAGGSLRLS-CAAS (SEQ ID NO: 93); (b) an FR-H2 comprising the amino acid sequence of IGWFRQAPGKERE (SEQ ID NO: 94); (c) an FR-H3 comprising the amino acid sequence of YADSVKGRFTISRDNAKNTVYLQMNSLKPED-TAVYYCA (SEQ ID NO: 95); (d) an FR-H4 comprising the amino acid sequence of QGQGTQVTVSSAA (SEQ ID NO: 96), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 93-96, and/or (ii) one, two, or three amino acid substitutions relative to the amino acid sequence of any one of SEQ ID NOs: 93-96. In some instances, the anti-ETEC adhesin protein antibody may include a VHH binding domain including the amino acid sequence of SEQ ID NO: 92. In particular instances, the anti-ETEC adhesin protein antibody includes a VHH binding domain of VHH antibody 1B8.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 97); (b) a CDR-H2 comprising the amino acid sequence of FAAAITWNGRSTL (SEQ ID NO: 98); (c) a CDR-H3 comprising the amino acid sequence of TLTTWEHKWEYNS (SEQ ID NO: 99), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 97-99, and/or (ii) one, two, or three amino acid substitutions relative to the amino acid sequence of any one of SEQ ID NOs: 97-99. In some embodiments, the antibody may include a VHH binding domain including a sequence having at least 95% sequence identity (e.g., 96%, 97%, 98%, or 99% identity) to the amino acid sequence of SEQ ID NO: 100, and/or may include one, two, three, four, five, or six amino acid substitutions relative to the amino acid sequence of SEQ ID NO: 100. In some instances, the anti-ETEC adhesion protein antibody may include a VHH binding domain including the following framework regions (FRs): (a) an FR-H1 comprising the amino acid sequence of EVQLVESGGGLVQAGGSLRLS-CAAS (SEQ ID NO: 101); (b) an FR-H2 comprising the amino acid sequence of IGWFRQAPGKERE (SEQ ID NO: 102); (c) an FR-H3 comprising the amino acid sequence of YADSVKGRFTISRDNAKNTVYLQMNSLKPED-TAVYYCA (SEQ ID NO: 103); (d) an FR-H4 comprising the amino acid sequence of QGQGTQVTVSSAA (SEQ ID NO: 104), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 101-104, and/or (ii) one, two, or three amino acid substitutions relative to the amino acid sequence of any one of SEQ ID NOs: 101-104. In some instances, the anti-ETEC adhesin protein antibody may include a VHH binding domain including the amino acid sequence of SEQ ID NO: 100. In particular instances, the anti-ETEC adhesin protein antibody includes a VHH binding domain of VHH antibody 2B4.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 105); (b) a CDR-H2 comprising the amino acid sequence of FAAAITWNGRSTL (SEQ ID NO: 106); (c) a CDR-H3 comprising the amino acid sequence of TLTTWEHKWEYNS (SEQ ID NO: 107), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 105-107, and/or (ii) one, two, or three amino acid substitutions relative to the amino acid sequence of any one of SEQ ID NOs: 105-107. In some embodiments, the antibody may include a VHH binding domain including a sequence having at least 95% sequence identity (e.g., 96%, 97%, 98%, or 99% identity) to the amino acid sequence of SEQ ID NO: 108, and/or may include one, two, three, four, five, or six amino acid substitutions relative to the amino acid sequence of SEQ ID NO: 108. In some instances, the anti-ETEC adhesion protein antibody may include a VHH binding domain including the following framework regions (FRs): (a) an FR-H1 comprising the amino acid sequence of EVQLVESGG-GLVQAGGSLRLSCAAS (SEQ ID NO: 109); (b) an FR-H2 comprising the amino acid sequence of IGWFRQAPGKERE (SEQ ID NO: 110); (c) an FR-H3 comprising the amino acid sequence of YADSVKGRFTIS-RDNAKNTVYLQMNSLKPEDTAVYYCA (SEQ ID NO: 111); (d) an FR-H4 comprising the amino acid sequence of QGQGTQVTVSSAA (SEQ ID NO: 112), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 109-112, and/or (ii) one, two, or three amino acid substitutions relative to the amino acid sequence of any one of SEQ ID NOs: 109-112. In some instances, the anti-ETEC adhesin protein antibody may include a VHH binding domain including the amino acid sequence of SEQ ID NO: 108. In particular instances, the anti-ETEC adhesin protein antibody includes a VHH binding domain of VHH antibody 2D4.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 113); (b) a CDR-H2 comprising the amino acid sequence of FAAAITWNGRSTL (SEQ ID NO: 114); (c) a CDR-H3 comprising the amino acid sequence of TLTTWEHKWEYNS (SEQ ID NO: 115), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 113-115, and/or (ii) one, two, or three amino acid substitutions relative to the amino acid sequence of any one of SEQ ID NOs: 113-115. In some embodiments, the antibody may include a VHH binding domain including a sequence having at least 95% sequence identity (e.g., 96%, 97%, 98%, or 99% identity) to the amino acid sequence of SEQ ID NO: 116, and/or may include one, two, three, four, five, or six amino acid substitutions relative to the amino acid sequence of SEQ ID NO: 116. In some instances, the anti-ETEC adhesion protein antibody may include a VHH binding domain including the following framework regions (FRs): (a) an FR-H1 comprising the amino acid sequence of EVQLVESGG- GLVQAGGSLRLSCAAS (SEQ ID NO: 117); (b) an FR-H2 comprising the amino acid sequence of IGWFRQAPGKERE (SEQ ID NO: 118); (c) an FR-H3 comprising the amino acid sequence of YADSVKGRFTIS-RDNAKNTVYLQMNSLKPEDTAVYYCA (SEQ ID NO: 119); (d) an FR-H4 comprising the amino acid sequence of QGQGTQVTVSSAA (SEQ ID NO: 120), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 117-120, and/or (ii) one, two, or three amino acid substitutions relative to the amino acid sequence of any one of SEQ ID NOs: 117-120. In some instances, the anti-ETEC adhesin protein antibody may include a VHH binding domain including the amino acid sequence of SEQ ID NO: 116. In particular instances, the anti-ETEC adhesin protein antibody includes a VHH binding domain of VHH antibody 1E1.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 121); (b) a CDR-H2 comprising the amino acid sequence of FAAAITWNGRSTL (SEQ ID NO: 122); (c) a CDR-H3 comprising the amino acid sequence of TLTTWEHKWEYNS (SEQ ID NO: 123), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 121-123, and/or (ii) one, two, or three amino acid substitutions relative to the amino acid sequence of any one of SEQ ID NOs: 121-123. In some embodiments, the antibody may include a VHH binding domain including a sequence having at least 95% sequence identity (e.g., 96%, 97%, 98%, or 99% identity) to the amino acid sequence of SEQ ID NO: 124, and/or may include one, two, three, four, five, or six amino acid substitutions relative to the amino acid sequence of SEQ ID NO: 124. In some instances, the anti-ETEC adhesion protein antibody may include a VHH binding domain including the following framework regions (FRs): (a) an FR-H1 comprising the amino acid sequence of EVQLVESGG-GLVQAGGSLRLSCAAS (SEQ ID NO: 125); (b) an FR-H2 comprising the amino acid sequence of IGWFRQAPGKERE (SEQ ID NO: 126); (c) an FR-H3 comprising the amino acid sequence of YADSVKGRFTIS-RDNAKNTVYLQMNSLKPEDTAVYYCA (SEQ ID NO: 127); (d) an FR-H4 comprising the amino acid sequence of QGQGTQVTVSSAA (SEQ ID NO: 128), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 125-128, and/or (ii) one, two, or three amino acid substitutions relative to the amino acid sequence of any one of SEQ ID NOs: 125-128. In some instances, the anti-ETEC adhesin protein antibody may include a VHH binding domain including the amino acid sequence of SEQ ID NO: 124. In particular instances, the anti-ETEC adhesin protein antibody includes a VHH binding domain of VHH antibody 2D2.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 129); (b) a CDR-H2 comprising the amino acid sequence of FAAAITWNGRSTL (SEQ ID NO: 130); (c) a CDR-H3 comprising the amino acid sequence of TLTTWEHKWEYNS (SEQ ID NO: 131), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 129-131, and/or (ii) one, two, or three amino acid substitutions relative to the amino acid sequence of any one of SEQ ID NOs: 129-131. In some embodiments, the antibody may include a VHH binding domain including a sequence having at least 95% sequence identity (e.g., 96%, 97%, 98%, or 99% identity) to the amino acid sequence of SEQ ID NO: 132, and/or may include one, two, three, four, five, or six amino acid substitutions relative to the amino acid sequence of SEQ ID NO: 132. In some instances, the anti-ETEC adhesion protein antibody may include a VHH binding domain including the following framework regions (FRs): (a) an FR-H1 comprising the amino acid sequence of EVQLVESGG-GLVQAGGSLRLSCAAS (SEQ ID NO: 133); (b) an FR-H2 comprising the amino acid sequence of IGWFRQAPGKERE (SEQ ID NO: 134); (c) an FR-H3 comprising the amino acid sequence of YADSVKGRFTIS-RDNAKNTVYLQMNSLKPEDTAVYYCA (SEQ ID NO: 135); (d) an FR-H4 comprising the amino acid sequence of QGQGTQVTVSSAA (SEQ ID NO: 136), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 133-136, and/or (ii) one, two, or three amino acid substitutions relative to the amino acid sequence of any one of SEQ ID NOs: 133-136. In some instances, the anti-ETEC adhesin protein antibody may include a VHH binding domain including the amino acid sequence of SEQ ID NO: 132. In particular instances, the anti-ETEC adhesin protein antibody includes a VHH binding domain of VHH antibody 3E7.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 137); (b) a CDR-H2 comprising the amino acid sequence of FAAAITWNGRSTL (SEQ ID NO: 138); (c) a CDR-H3 comprising the amino acid sequence of TLTTWEHKWEYNS (SEQ ID NO: 139), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 137-139, and/or (ii) one, two, or three amino acid substitutions relative to the amino acid sequence of any one of SEQ ID NOs: 137-139. In some embodiments, the antibody may include a VHH binding domain including a sequence having at least 95% sequence identity (e.g., 96%, 97%, 98%, or 99% identity) to the amino acid sequence of SEQ ID NO: 140, and/or may include one, two, three, four, five, or six amino acid substitutions relative to the amino acid sequence of SEQ ID NO: 140. In some instances, the anti-ETEC adhesion protein antibody may include a VHH binding domain including the following framework regions (FRs): (a) an FR-H1 comprising the amino acid sequence of EVQLVESGG-GLVQAGGSLRLSCAAS (SEQ ID NO: 141); (b) an FR-H2 comprising the amino acid sequence of IGWFRQAPGKERE (SEQ ID NO: 142); (c) an FR-H3 comprising the amino acid sequence of YADSVKGRFTIS-RDNAKNTVYLQMNSLKPEDTAVYYCA (SEQ ID NO: 143); (d) an FR-H4 comprising the amino acid sequence of QGQGTQVTVSSAA (SEQ ID NO: 144), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 141-144, and/or (ii) one, two, or three amino acid substitutions relative to the amino acid sequence of any one of SEQ ID NOs: 141-144. In some instances, the anti-ETEC adhesin protein antibody may include a VHH binding domain including the amino acid sequence of SEQ ID NO: 140. In particular instances, the anti-ETEC adhesin protein antibody includes a VHH binding domain of VHH antibody 4A3.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 145); (b) a CDR-H2 comprising the amino acid sequence of FAAAITWNGRSTL (SEQ ID NO: 146); (c) a CDR-H3 comprising the amino acid sequence of TLTTWEHKWEYNS (SEQ ID NO: 147), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 145-147, and/or (ii) one, two, or three amino acid substitutions relative to the amino acid sequence of any one of SEQ ID NOs: 145-147. In some embodiments, the antibody may include a VHH binding domain including a sequence having at least 95% sequence identity (e.g., 96%, 97%, 98%, or 99% identity) to the amino acid sequence of SEQ ID NO: 148, and/or may include one, two, three, four, five, or six amino acid substitutions relative to the amino acid sequence of SEQ ID NO: 148. In some instances, the anti-ETEC adhesion protein antibody may include a VHH binding domain including the following framework regions (FRs): (a) an FR-H1 comprising the amino acid sequence of EVQLVESGG-GLVQAGGSLRLSCAAS (SEQ ID NO: 149); (b) an FR-H2 comprising the amino acid sequence of IGWFRQAPGKERE (SEQ ID NO: 150); (c) an FR-H3 comprising the amino acid sequence of YADSVKGRFTIS-RDNAKNTVYLQMNSLKPEDTAVYYCA (SEQ ID NO: 151); (d) an FR-H4 comprising the amino acid sequence of QGQGTQVTVSSAA (SEQ ID NO: 152), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 149-152, and/or (ii) one, two, or three amino acid substitutions relative to the amino acid sequence of any one of SEQ ID NOs: 149-152. In some instances, the anti-ETEC adhesin protein antibody may include a VHH binding domain including the amino acid sequence of SEQ ID NO: 148. In particular instances, the anti-ETEC adhesin protein antibody includes a VHH binding domain of VHH antibody 4C3.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 153); (b) a CDR-H2 comprising the amino acid sequence of FAAAITWNGRSTL (SEQ ID NO: 154); (c) a CDR-H3 comprising the amino acid sequence of TLTTWEHKWEYNS (SEQ ID NO: 155), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 153-155, and/or (ii) one, two, or three amino acid substitutions relative to the amino acid sequence of any one of SEQ ID NOs: 153-155. In some embodiments, the antibody may include a VHH binding domain including a sequence having at least 95% sequence identity (e.g., 96%, 97%, 98%, or 99% identity) to the amino acid sequence of SEQ ID NO: 156, and/or may include one, two, three, four, five, or six amino acid substitutions relative to the amino acid sequence of SEQ ID NO: 156. In some instances, the anti-ETEC adhesion protein antibody may include a VHH binding domain including the following framework regions (FRs): (a) an FR-H1 comprising the amino acid sequence of EVQLVESGG-GLVQAGGSLRLSCAAS (SEQ ID NO: 157); (b) an FR-H2 comprising the amino acid sequence of IGWFRQAPGKERE (SEQ ID NO: 158); (c) an FR-H3 comprising the amino acid sequence of YADSVKGRFTIS-RDNAKNTVYLQMNSLKPEDTAVYYCA (SEQ ID NO: 159); (d) an FR-H4 comprising the amino acid sequence of QGQGTQVTVSSAA (SEQ ID NO: 160), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 157-160, and/or (ii) one, two, or three amino acid substitutions relative to the amino acid sequence of any one of SEQ ID NOs: 157-160. In some instances, the anti-ETEC adhesin protein antibody may include a VHH binding domain including the amino acid sequence of SEQ ID NO: 156. In particular instances, the anti-ETEC adhesin protein antibody includes a VHH binding domain of VHH antibody 4B7.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 161); (b) a CDR-H2 comprising the amino acid sequence of FAAAITWNGRSTL (SEQ ID NO: 162); (c) a CDR-H3 comprising the amino acid sequence of TLTTWEHKWEYNS (SEQ ID NO: 163), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 161-163, and/or (ii) one, two, or three amino acid substitutions relative to the amino acid sequence of any one of SEQ ID NOs: 161-163. In some embodiments, the antibody may include a VHH binding domain including a sequence having at least 95% sequence identity (e.g., 96%, 97%, 98%, or 99% identity) to the amino acid sequence of SEQ ID NO: 164, and/or may include one, two, three, four, five, or six amino acid substitutions relative to the amino acid sequence of SEQ ID NO: 164. In some instances, the anti-ETEC adhesion protein antibody may include a VHH binding domain including the following framework regions (FRs): (a) an FR-H1 comprising the amino acid sequence of EVQLVESGG-GLVQAGGSLRLSCAAS (SEQ ID NO: 165); (b) an FR-H2 comprising the amino acid sequence of IGWFRQAPGKERE (SEQ ID NO: 166); (c) an FR-H3 comprising the amino acid sequence of YADSVKGRFTIS- RDNAKNTVYLQMNSLKPEDTAVYYCA (SEQ ID NO: 167); (d) an FR-H4 comprising the amino acid sequence of QGQGTQVTVSSAA (SEQ ID NO: 168), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 165-168, and/or (ii) one, two, or three amino acid substitutions relative to the amino acid sequence of any one of SEQ ID NOs: 165-168. In some instances, the anti-ETEC adhesin protein antibody may include a VHH binding domain including the amino acid sequence of SEQ ID NO: 164. In particular instances, the anti-ETEC adhesin protein antibody includes a VHH binding domain of VHH antibody 4B8.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 169); (b) a CDR-H2 comprising the amino acid sequence of FAAAITWNGRSTL (SEQ ID NO: 170); (c) a CDR-H3 comprising the amino acid sequence of TLTTWEHKWEYNS (SEQ ID NO: 171), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 169-171, and/or (ii) one, two, or three amino acid substitutions relative to the amino acid sequence of any one of SEQ ID NOs: 169-171. In some embodiments, the antibody may include a VHH binding domain including a sequence having at least 95% sequence identity (e.g., 96%, 97%, 98%, or 99% identity) to the amino acid sequence of SEQ ID NO: 172, and/or may include one, two, three, four, five, or six amino acid substitutions relative to the amino acid sequence of SEQ ID NO: 172. In some instances, the anti-ETEC adhesion protein antibody may include a VHH binding domain including the following framework regions (FRs): (a) an FR-H1 comprising the amino acid sequence of EVQLVESGG-GLVQAGGSLRLSCAAS (SEQ ID NO: 173); (b) an FR-H2 comprising the amino acid sequence of IGWFRQAPGKERE (SEQ ID NO: 174); (c) an FR-H3 comprising the amino acid sequence of YADSVKGRFTIS-RDNAKNTVYLQMNSLKPEDTAVYYCA (SEQ ID NO: 175); (d) an FR-H4 comprising the amino acid sequence of QGQGTQVTVSSAA (SEQ ID NO: 176), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 173-176, and/or (ii) one, two, or three amino acid substitutions relative to the amino acid sequence of any one of SEQ ID NOs: 173-176. In some instances, the anti-ETEC adhesin protein antibody may include a VHH binding domain including the amino acid sequence of SEQ ID NO: 172. In particular instances, the anti-ETEC adhesin protein antibody includes a VHH binding domain of VHH antibody 4H2.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 177); (b) a CDR-H2 comprising the amino acid sequence of FAAAITWNGRSTL (SEQ ID NO: 178); (c) a CDR-H3 comprising the amino acid sequence of TLTTWEHKWEYNS (SEQ ID NO: 179), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 177-179, and/or (ii) one, two, or three amino acid substitutions relative to the amino acid sequence of any one of SEQ ID NOs: 177-179. In some embodiments, the antibody may include a VHH binding domain including a sequence having at least 95% sequence identity (e.g., 96%, 97%, 98%, or 99% identity) to the amino acid sequence of SEQ ID NO: 180, and/or may include one, two, three, four, five, or six amino acid substitutions relative to the amino acid sequence of SEQ ID NO: 180. In some instances, the anti-ETEC adhesion protein antibody may include a VHH binding domain including the following framework regions (FRs): (a) an FR-H1 comprising the amino acid sequence of EVQLVESGG-GLVQAGGSLRLSCAAS (SEQ ID NO: 181); (b) an FR-H2 comprising the amino acid sequence of IGWFRQAPGKERE (SEQ ID NO: 182); (c) an FR-H3 comprising the amino acid sequence of YADSVKGRFTIS-RDNAKNTVYLQMNSLKPEDTAVYYCA (SEQ ID NO: 183); (d) an FR-H4 comprising the amino acid sequence of QGQGTQVTVSSAA (SEQ ID NO: 184), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 181-184, and/or (ii) one, two, or three amino acid substitutions relative to the amino acid sequence of any one of SEQ ID NOs: 181-184. In some instances, the anti-ETEC adhesin protein antibody may include a VHH binding domain including the amino acid sequence of SEQ ID NO: 180. In particular instances, the anti-ETEC adhesin protein antibody includes a VHH binding domain of VHH antibody 4H4.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 185); (b) a CDR-H2 comprising the amino acid sequence of FAAAITWNGRSTL (SEQ ID NO: 186); (c) a CDR-H3 comprising the amino acid sequence of TLTTWEHKWEYNS (SEQ ID NO: 187), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 185-187, and/or (ii) one, two, or three amino acid substitutions relative to the amino acid sequence of any one of SEQ ID NOs: 185-187. In some embodiments, the antibody may include a VHH binding domain including a sequence having at least 95% sequence identity (e.g., 96%, 97%, 98%, or 99% identity) to the amino acid sequence of SEQ ID NO: 188, and/or may include one, two, three, four, five, or six amino acid substitutions relative to the amino acid sequence of SEQ ID NO: 188. In some instances, the anti-ETEC adhesion protein antibody may include a VHH binding domain including the following framework regions (FRs): (a) an FR-H1 comprising the amino acid sequence of EVQLVESGG-GLVQAGGSLRLSCAAS (SEQ ID NO: 189); (b) an FR-H2 comprising the amino acid sequence of IGWFRQAPGKERE (SEQ ID NO: 190); (c) an FR-H3 comprising the amino acid sequence of YADSVKGRFTIS-RDNAKNTVYLQMNSLKPEDTAVYYCA (SEQ ID NO: 191); (d) an FR-H4 comprising the amino acid sequence of QGQGTQVTVSSAA (SEQ ID NO: 192), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 189-192, and/or (ii) one, two, or three amino acid substitutions relative to the amino acid sequence of any one of SEQ ID NOs: 189-192. In some instances, the anti-ETEC adhesin protein antibody may include a VHH binding domain including the amino acid sequence of SEQ ID NO: 188. In particular instances, the anti-ETEC adhesin protein antibody includes a VHH binding domain of VHH antibody 1H3.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 193); (b) a CDR-H2 comprising the amino acid sequence of FAAAITWNGRSTL (SEQ ID NO: 194); (c) a CDR-H3 comprising the amino acid sequence of TLTTWEHKWEYNS (SEQ ID NO: 195), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 193-195, and/or (ii) one, two, or three amino acid substitutions relative to the amino acid sequence of any one of SEQ ID NOs: 193-195. In some embodiments, the antibody may include a VHH binding domain including a sequence having at least 95% sequence identity (e.g., 96%, 97%, 98%, or 99% identity) to the amino acid sequence of SEQ ID NO: 196, and/or may include one, two, three, four, five, or six amino acid substitutions relative to the amino acid sequence of SEQ ID NO: 196. In some instances, the anti-ETEC adhesion protein antibody may include a VHH binding domain including the following framework regions (FRs): (a) an FR-H1 comprising the amino acid sequence of EVQLVESGG-GLVQAGGSLRLSCAAS (SEQ ID NO: 197); (b) an FR-H2 comprising the amino acid sequence of IGWFRQAPGKERE (SEQ ID NO: 198); (c) an FR-H3 comprising the amino acid sequence of YADSVKGRFTIS-RDNAKNTVYLQMNSLKPEDTAVYYCA (SEQ ID NO: 199); (d) an FR-H4 comprising the amino acid sequence of QGQGTQVTVSSAA (SEQ ID NO: 200), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 197-200, and/or (ii) one, two, or three amino acid substitutions relative to the amino acid sequence of any one of SEQ ID NOs: 197-200. In some instances, the anti-ETEC adhesin protein antibody may include a VHH binding domain including the amino acid sequence of SEQ ID NO: 196. In particular instances, the anti-ETEC adhesin protein antibody includes a VHH binding domain of VHH antibody 2B111.

In another aspect, the invention provides isolated VHH antibodies that bind an ETEC adhesin protein and include a VHH binding domain including the following CDRs: (a) a CDR-H1 comprising the amino acid sequence of SRTFN-HYN (SEQ ID NO: 201); (b) a CDR-H2 comprising the amino acid sequence of FAAAITWNGRSTL (SEQ ID NO: 202); (c) a CDR-H3 comprising the amino acid sequence of TLTTWEHKWEYNS (SEQ ID NO: 203), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 201-203, and/or (ii) one, two, or three amino acid substitutions relative to the amino acid sequence of any one of SEQ ID NOs: 201-203. In some embodiments, the antibody may include a VHH binding domain including a sequence having at least 95% sequence identity (e.g., 96%, 97%, 98%, or 99% identity) to the amino acid sequence of SEQ ID NO: 204, and/or may include one, two, three, four, five, or six amino acid substitutions relative to the amino acid sequence of SEQ ID NO: 204. In some instances, the anti-ETEC adhesion protein antibody may include a VHH binding domain including the following framework regions (FRs): (a) an FR-H1 comprising the amino acid sequence of EVQLVESGG-GLVQAGGSLRLSCAAS (SEQ ID NO: 205); (b) an FR-H2 comprising the amino acid sequence of IGWFRQAPGKERE (SEQ ID NO: 206); (c) an FR-H3 comprising the amino acid sequence of YADSVKGRFTIS-RDNAKNTVYLQMNSLKPEDTAVYYCA (SEQ ID NO: 207); (d) an FR-H4 comprising the amino acid sequence of QGQGTQVTVSSAA (SEQ ID NO: 208), or a combination of one or more of the above FRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 205-208, and/or (ii) one, two, or three amino acid substitutions relative to the amino acid sequence of any one of SEQ ID NOs: 205-208. In some instances, the anti-ETEC adhesin protein antibody may include a VHH binding domain including the amino acid sequence of SEQ ID NO: 204. In particular instances, the anti-ETEC adhesin protein antibody includes a VHH binding domain of VHH antibody 1G7.

Antibodies of the invention may, for example, be monoclonal, human, humanized, or chimeric. The antibodies can be full-length antibodies or antibody fragments thereof (e.g., an antibody fragment that binds an ETEC adhesin protein). The antibody fragment may be selected from the group consisting of Fab, Fab'-SH, Fv, scFv, and (Fab')$_2$ fragments. In some instances, the antibody is an IgA antibody (e.g., an IgA1 or IgA2 antibody). An antibody of the invention may have a half-life of ≥3 days (e.g., ≥1 week, e.g., ≥2 weeks, e.g., ≥1 month, e.g., ≥2 months, e.g., ≥3 months, e.g., ≥4 months, e.g., ≥5 months, e.g., ≥6 months).

The anti-ETEC adhesin protein antibodies of the invention may be any immunoglobulin antibody isotype, including IgG, IgE, IgM, IgA, or IgD (e.g., IgG or IgA). Additionally, the anti-ETEC adhesin protein antibodies may be any IgG subtype (e.g., IgG1, IgG2a, IgG2b, IgG3, or IgG4). In certain embodiments, the anti-ETEC adhesin protein antibodies are IgG1 antibodies. In particular embodiments, the anti-ETEC adhesin protein antibodies are IgA antibodies. IgA is an antibody that plays a crucial role in the immune function of mucous membranes. Subclasses of IgA antibodies include secretory IgA (sIgA) and dimeric IgA (dIgA). In some embodiments, the anti-ETEC adhesin protein antibody may be any IgA subtype (e.g., dIgA1, dIgA2, sIgA1, and sIgA2).

In certain embodiments, the anti-ETEC adhesin protein antibody includes an Fc domain including a first Fc domain subunit and a second Fc domain subunit, and the first Fc domain subunit and the second Fc domain subunit are capable of stable association. In some embodiments, each Fc domain subunit is linked to a single VHH binding domain and positioned relative to each other in an N-terminal-to-C-terminal direction as follows: VHH binding domain-Fc domain subunit. In some embodiments, each Fc domain subunit is linked to a single VHH binding domain by a hinge region and positioned relative to each other in an N-terminal-to-C-terminal direction as follows: VHH binding domain-hinge region-Fc domain subunit. In particular embodiments, the antibody is an IgA class antibody and each VHH binding domain includes the amino acid sequence of SEQ ID NO: 12. In even more particular embodiments, the antibody is an IgA class antibody and each VHH binding domain includes the amino acid sequence of SEQ ID NO: 4.

In certain embodiments, each Fc domain subunit is further linked to a single CH1 domain. In some embodiments, each VHH binding domain, CH1 domain, and Fc domain subunit is positioned relative to each other in an N-terminal-to-C-terminal direction as follows: VHH binding domain-CH1 domain-Fc domain subunit. In some embodiments, each CH1 domain is linked to a single VHH binding domain by a hinge region and positioned relative to each other in an N-terminal-to-C-terminal direction as follows: VHH binding domain-hinge region-CH1 domain-Fc domain subunit. In some embodiments, each CH1 domain is linked to a single VHH binding domain by a hinge region and positioned relative to each other in an N-terminal-to-C-terminal direction as follows: VHH binding domain-hinge region-CH1 domain-Fc domain subunit. In some embodiments, the hinge region includes the amino acid sequence of SEQ ID NO: 209 or 210, or variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to SEQ ID NO: 209 or 210, and/or (ii) one, two, or three amino acid substitutions relative to the amino acid sequence of SEQ ID NO: 209 or 210.

In certain embodiments, the antibody is a full-length antibody. In some embodiments, the antibody is a VHH antibody fragment that binds an ETEC adhesin protein.

In one aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of NIFQDAE (SEQ ID NO: 1); (b) a CDR-H2 comprising the amino acid sequence of FVATIAYGGNTN (SEQ ID NO: 2); and (c) a CDR-H3 comprising the amino acid sequence of VYTGVYYDRTTGGYVAFE (SEQ ID NO: 3), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1-3, and/or (ii) one, two, or three amino acid substitutions relative to the amino acid sequence of any one of SEQ ID NOs: 1-3.

In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to, includes one, two, three, four, five, or six amino acid substitutions relative to, or the sequence of, SEQ ID NO: 4.

In one aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of ERTFSYYV (SEQ ID NO: 9); (b) a CDR-H2 comprising the amino acid sequence of FVAGISMSGDSTK (SEQ ID NO: 10); and (c) a CDR-H3 comprising the amino acid sequence of ADRDIRGNFRS (SEQ ID NO: 11), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 9-11, and/or (ii) one, two, or three amino acid substitutions relative to the amino acid sequence of any one of SEQ ID NOs: 9-11.

In one embodiment, the invention provides an antibody (e.g., a monoclonal antibody) that competes for binding to an ETEC adhesin protein with an isolated VHH antibody that includes VHH binding domain including an amino acid sequence having at least 95% sequence identity (e.g., at least 96%, 97%, 98%, or 99% sequence identity) to, includes one, two, three, four, five, or six amino acid substitutions relative to, or the sequence of, SEQ ID NO: 12.

In one aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of YIFWSYGY (SEQ ID NO: 17); (b) a CDR-H2 comprising the amino acid sequence of LVATISRGGTTN (SEQ ID NO: 18); and (c) a CDR-H3 comprising the amino acid sequence of AGRYAFGYFK (SEQ ID NO: 19), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 17-19, and/or (ii) one, two, or three amino acid substitutions relative to the amino acid sequence of any one of SEQ ID NOs: 17-19.

In one embodiment, the invention provides an antibody (e.g., a monoclonal antibody) that competes for binding to an ETEC adhesin protein with an isolated VHH antibody that includes VHH binding domain including an amino acid sequence having at least 95% sequence identity (e.g., at least 96%, 97%, 98%, or 99% sequence identity) to, includes one, two, three, four, five, or six amino acid substitutions relative to, or the sequence of, SEQ ID NO: 20.

In one aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 25); (b) a CDR-H2 comprising the amino acid sequence of FAAAITWNGRSTL (SEQ ID NO: 26); and (c) a CDR-H3 comprising the amino acid sequence of TLTTWEHKWEYNS (SEQ ID NO: 27), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 25-27, and/or (ii) one, two, or three amino acid substitutions relative to the amino acid sequence of any one of SEQ ID NOs: 25-27.

In one embodiment, the invention provides an antibody (e.g., a monoclonal antibody) that competes for binding to an ETEC adhesin protein with an isolated VHH antibody that includes VHH binding domain including an amino acid sequence having at least 95% sequence identity (e.g., at least 96%, 97%, 98%, or 99% sequence identity) to, includes one, two, three, four, five, or six amino acid substitutions relative to, or the sequence of, SEQ ID NO: 28.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 25); (b) a CDR-H2 comprising the amino acid sequence of FAAAITWNGRSTL (SEQ ID NO: 26); (c) a CDR-H3 comprising the amino acid sequence of TLTTWEHKWEYNS (SEQ ID NO: 27), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 25-27, and/or (ii) one, two, or three amino acid substitutions relative to the amino acid sequence of any one of SEQ ID NOs: 25-27. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 28, and/or may include one, two, three, four, five, or six amino acid substitutions relative to the amino acid sequence of SEQ ID NO: 28.

In some instances, the antibody (e.g., a monoclonal antibody) competes for binding to an ETEC adhesin protein with an isolated VHH antibody that includes a VHH binding domain including the amino acid sequence of SEQ ID NO: 28. In particular instances, the antibody (e.g., a monoclonal antibody) competes for binding to an ETEC adhesin protein with an isolated VHH antibody that includes a VHH binding domain of VHH antibody 1H4.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 33); (b) a CDR-H2 comprising the amino acid sequence of FAAAITWNGRSTL (SEQ ID NO: 34); (c) a CDR-H3 comprising the amino acid sequence of TLTTWEHKWEYNS (SEQ ID NO: 35), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 33-35, and/or (ii) one, two, or three amino acid substitutions relative to the amino acid sequence of any one of SEQ ID NOs: 33-35. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 36, and/or may include one, two, three, four, five, or six amino acid substitutions relative to the amino acid sequence of SEQ ID NO: 36.

In some instances, the antibody (e.g., a monoclonal antibody) competes for binding to an ETEC adhesin protein with an isolated VHH antibody that includes a VHH binding domain including the amino acid sequence of SEQ ID NO: 36. In particular instances, the antibody (e.g., a monoclonal antibody) competes for binding to an ETEC adhesin protein with an isolated VHH antibody that includes a VHH binding domain of VHH antibody 2R275.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 41); (b) a CDR-H2 comprising the amino acid sequence of FAAAITWNGRSTL (SEQ ID NO: 42); (c) a CDR-H3 comprising the amino acid sequence of TLTTWEHKWEYNS (SEQ ID NO: 43), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 41-43, and/or (ii) one, two, or three amino acid substitutions relative to the amino acid sequence of any one of SEQ ID NOs: 41-43. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 44, and/or may include one, two, three, four, five, or six amino acid substitutions relative to the amino acid sequence of SEQ ID NO: 44.

In some instances, the antibody (e.g., a monoclonal antibody) competes for binding to an ETEC adhesin protein with an isolated VHH antibody that includes a VHH binding domain including the amino acid sequence of SEQ ID NO: 44. In particular instances, the antibody (e.g., a monoclonal antibody) competes for binding to an ETEC adhesin protein with an isolated VHH antibody that includes a VHH binding domain of VHH antibody 2R12.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 49); (b) a CDR-H2 comprising the amino acid sequence of FAAAITWNGRSTL (SEQ ID NO: 50); (c) a CDR-H3 comprising the amino acid sequence of TLTTWEHKWEYNS (SEQ ID NO: 51), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 49-51, and/or (ii) one, two, or three amino acid substitutions relative to the amino acid sequence of any one of SEQ ID NOs: 49-51. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 52, and/or may include one, two, three, four, five, or six amino acid substitutions relative to the amino acid sequence of SEQ ID NO: 52.

In some instances, the antibody (e.g., a monoclonal antibody) competes for binding to an ETEC adhesin protein with an isolated VHH antibody that includes a VHH binding domain including the amino acid sequence of SEQ ID NO: 52. In particular instances, the antibody (e.g., a monoclonal antibody) competes for binding to an ETEC adhesin protein with an isolated VHH antibody that includes a VHH binding domain of VHH antibody 2R65.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 57); (b) a CDR-H2 comprising the amino acid sequence of FAAAITWNGRSTL (SEQ ID NO: 58); (c) a CDR-H3 comprising the amino acid sequence of TLTTWEHKWEYNS (SEQ ID NO: 59), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 57-59, and/or (ii) one, two, or three amino acid substitutions relative to the amino acid sequence of any one of SEQ ID NOs: 57-59. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 60, and/or may include one, two, three, four, five, or six amino acid substitutions relative to the amino acid sequence of SEQ ID NO: 60.

In some instances, the antibody (e.g., a monoclonal antibody) competes for binding to an ETEC adhesin protein with an isolated VHH antibody that includes a VHH binding domain including the amino acid sequence of SEQ ID NO: 60. In particular instances, the antibody (e.g., a monoclonal antibody) competes for binding to an ETEC adhesin protein with an isolated VHH antibody that includes a VHH binding domain of VHH antibody 2R67.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 65); (b) a CDR-H2 comprising the amino acid sequence of FAAAITWNGRSTL (SEQ ID NO: 66); (c) a CDR-H3 comprising the amino acid sequence of TLTTWEHKWEYNS (SEQ ID NO: 67), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 65-67, and/or (ii) one, two, or three amino acid substitutions relative to the amino acid sequence of any one of SEQ ID NOs: 65-67. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 68, and/or may include one, two, three, four, five, or six amino acid substitutions relative to the amino acid sequence of SEQ ID NO: 68.

In some instances, the antibody (e.g., a monoclonal antibody) competes for binding to an ETEC adhesin protein with an isolated VHH antibody that includes a VHH binding domain including the amino acid sequence of SEQ ID NO: 68. In particular instances, the antibody (e.g., a monoclonal antibody) competes for binding to an ETEC adhesin protein with an isolated VHH antibody that includes a VHH binding domain of VHH antibody 2R221.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 73); (b) a CDR-H2 comprising the amino acid sequence of FAAAITWNGRSTL (SEQ ID NO: 74); (c) a CDR-H3 comprising the amino acid sequence of TLTTWEHKWEYNS (SEQ ID NO: 75), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 73-75, and/or (ii) one, two, or three amino acid substitutions relative to the amino acid sequence of any one of SEQ ID NOs: 73-75. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 76, and/or may include one, two, three, four, five, or six amino acid substitutions relative to the amino acid sequence of SEQ ID NO: 76.

In some instances, the antibody (e.g., a monoclonal antibody) competes for binding to an ETEC adhesin protein with an isolated VHH antibody that includes a VHH binding domain including the amino acid sequence of SEQ ID NO: 76. In particular instances, the antibody (e.g., a monoclonal antibody) competes for binding to an ETEC adhesin protein with an isolated VHH antibody that includes a VHH binding domain of VHH antibody 2R267.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 81); (b) a CDR-H2 comprising the amino acid sequence of FAAAITWNGRSTL (SEQ ID NO: 82); (c) a CDR-H3 comprising the amino acid sequence of TLTTWEHKWEYNS (SEQ ID NO: 83), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 81-83, and/or (ii) one, two, or three amino acid substitutions relative to the amino acid sequence of any one of SEQ ID NOs: 81-83. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 84, and/or may include one, two, three, four, five, or six amino acid substitutions relative to the amino acid sequence of SEQ ID NO: 84.

In some instances, the antibody (e.g., a monoclonal antibody) competes for binding to an ETEC adhesin protein with an isolated VHH antibody that includes a VHH binding domain including the amino acid sequence of SEQ ID NO: 84. In particular instances, the antibody (e.g., a monoclonal antibody) competes for binding to an ETEC adhesin protein with an isolated VHH antibody that includes a VHH binding domain of VHH antibody 1A6.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 89); (b) a CDR-H2 comprising the amino acid sequence of FAAAITWNGRSTL (SEQ ID NO: 90); (c) a CDR-H3 comprising the amino acid sequence of TLTTWEHKWEYNS (SEQ ID NO: 91), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 89-91, and/or (ii) one, two, or three amino acid substitutions relative to the amino acid sequence of any one of SEQ ID NOs: 89-91. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 92, and/or may include one, two, three, four, five, or six amino acid substitutions relative to the amino acid sequence of SEQ ID NO: 92.

In some instances, the antibody (e.g., a monoclonal antibody) competes for binding to an ETEC adhesin protein with an isolated VHH antibody that includes a VHH binding domain including the amino acid sequence of SEQ ID NO: 92. In particular instances, the antibody (e.g., a monoclonal antibody) competes for binding to an ETEC adhesin protein with an isolated VHH antibody that includes a VHH binding domain of VHH antibody 1B8.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 97); (b) a CDR-H2 comprising the amino acid sequence of FAAAITWNGRSTL (SEQ ID NO: 98); (c) a CDR-H3 comprising the amino acid sequence of TLTTWEHKWEYNS (SEQ ID NO: 99), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 97-99, and/or (ii) one, two, or three amino acid substitutions relative to the amino acid sequence of any one of SEQ ID NOs: 97-99. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 100, and/or may include one, two, three, four, five, or six amino acid substitutions relative to the amino acid sequence of SEQ ID NO: 100.

In some instances, the antibody (e.g., a monoclonal antibody) competes for binding to an ETEC adhesin protein with an isolated VHH antibody that includes a VHH binding domain including the amino acid sequence of SEQ ID NO: 100. In particular instances, the antibody (e.g., a monoclonal antibody) competes for binding to an ETEC adhesin protein with an isolated VHH antibody that includes a VHH binding domain of VHH antibody 2B4.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 105); (b) a CDR-H2 comprising the amino acid sequence of FAAAITWNGRSTL (SEQ ID NO: 106); (c) a CDR-H3 comprising the amino acid sequence of TLTTWEHKWEYNS (SEQ ID NO: 107), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 105-107, and/or (ii) one, two, or three amino acid substitutions relative to the amino acid sequence of any one of SEQ ID NOs: 105-107. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 108, and/or may include one, two, three, four, five, or six amino acid substitutions relative to the amino acid sequence of SEQ ID NO: 108.

In some instances, the antibody (e.g., a monoclonal antibody) competes for binding to an ETEC adhesin protein with an isolated VHH antibody that includes a VHH binding domain including the amino acid sequence of SEQ ID NO: 108. In particular instances, the antibody (e.g., a monoclonal antibody) competes for binding to an ETEC adhesin protein with an isolated VHH antibody that includes a VHH binding domain of VHH antibody 2D4.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 113); (b) a CDR-H2 comprising the amino acid sequence of FAAAITWNGRSTL (SEQ ID NO: 114); (c) a CDR-H3 comprising the amino acid sequence of TLTTWEHKWEYNS (SEQ ID NO: 115), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 113-115, and/or (ii) one, two, or three amino acid substitutions relative to the amino acid sequence of any one of SEQ ID NOs: 113-115. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 116, and/or may include one, two, three, four, five, or six amino acid substitutions relative to the amino acid sequence of SEQ ID NO: 116.

In some instances, the antibody (e.g., a monoclonal antibody) competes for binding to an ETEC adhesin protein with an isolated VHH antibody that includes a VHH binding domain including the amino acid sequence of SEQ ID NO: 116. In particular instances, the antibody (e.g., a monoclonal antibody) competes for binding to an ETEC adhesin protein with an isolated VHH antibody that includes a VHH binding domain of VHH antibody 1E1.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 121); (b) a CDR-H2 comprising the amino acid sequence of FAAAITWNGRSTL (SEQ ID NO: 122); (c) a CDR-H3 comprising the amino acid sequence of TLTTWEHKWEYNS (SEQ ID NO: 123), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 121-123, and/or (ii) one, two, or three amino acid substitutions relative to the amino acid sequence of any one of SEQ ID NOs: 121-123. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 124, and/or may include one, two, three, four, five, or six amino acid substitutions relative to the amino acid sequence of SEQ ID NO: 124.

In some instances, the antibody (e.g., a monoclonal antibody) competes for binding to an ETEC adhesin protein with an isolated VHH antibody that includes a VHH binding domain including the amino acid sequence of SEQ ID NO: 124. In particular instances, the antibody (e.g., a monoclonal antibody) competes for binding to an ETEC adhesin protein with an isolated VHH antibody that includes a VHH binding domain of VHH antibody 2D2.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 129); (b) a CDR-H2 comprising the amino acid sequence of FAAAITWNGRSTL (SEQ ID NO: 130); (c) a CDR-H3 comprising the amino acid sequence of TLTTWEHKWEYNS (SEQ ID NO: 131), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 129-131, and/or (ii) one, two, or three amino acid substitutions relative to the amino acid sequence of any one of SEQ ID NOs: 129-131. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 132, and/or may include one, two, three, four, five, or six amino acid substitutions relative to the amino acid sequence of SEQ ID NO: 132.

In some instances, the antibody (e.g., a monoclonal antibody) competes for binding to an ETEC adhesin protein with an isolated VHH antibody that includes a VHH binding domain including the amino acid sequence of SEQ ID NO: 132. In particular instances, the antibody (e.g., a monoclonal antibody) competes for binding to an ETEC adhesin protein with an isolated VHH antibody that includes a VHH binding domain of VHH antibody 3E7.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 137); (b) a CDR-H2 comprising the amino acid sequence of FAAAITWNGRSTL (SEQ ID NO: 138); (c) a CDR-H3 comprising the amino acid sequence of TLTTWEHKWEYNS (SEQ ID NO: 139), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 137-139, and/or (ii) one, two, or three amino acid substitutions relative to the amino acid sequence of any one of SEQ ID NOs: 137-139. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 140, and/or may include one, two, three, four, five, or six amino acid substitutions relative to the amino acid sequence of SEQ ID NO: 140.

In some instances, the antibody (e.g., a monoclonal antibody) competes for binding to an ETEC adhesin protein with an isolated VHH antibody that includes a VHH binding domain including the amino acid sequence of SEQ ID NO: 140. In particular instances, the antibody (e.g., a monoclonal antibody) competes for binding to an ETEC adhesin protein with an isolated VHH antibody that includes a VHH binding domain of VHH antibody 4A3.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 145); (b) a CDR-H2 comprising the amino acid sequence of FAAAITWNGRSTL (SEQ ID NO: 146); (c) a CDR-H3 comprising the amino acid sequence of TLTTWEHKWEYNS (SEQ ID NO: 147), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 145-147, and/or (ii) one, two, or three amino acid substitutions relative to the amino acid sequence of any one of SEQ ID NOs: 145-147. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 148, and/or may include one, two, three, four, five, or six amino acid substitutions relative to the amino acid sequence of SEQ ID NO: 148.

In some instances, the antibody (e.g., a monoclonal antibody) competes for binding to an ETEC adhesin protein with an isolated VHH antibody that includes a VHH binding domain including the amino acid sequence of SEQ ID NO: 148. In particular instances, the antibody (e.g., a monoclonal antibody) competes for binding to an ETEC adhesin protein with an isolated VHH antibody that includes a VHH binding domain of VHH antibody 4C3.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 153); (b) a CDR-H2 comprising the amino acid sequence of FAAAITWNGRSTL (SEQ ID NO: 154); (c) a CDR-H3 comprising the amino acid sequence of TLTTWEHKWEYNS (SEQ ID NO: 155), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 153-155, and/or (ii) one, two, or three amino acid substitutions relative to the amino acid sequence of any one of SEQ ID NOs: 153-155. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 156, and/or may include one, two, three, four, five, or six amino acid substitutions relative to the amino acid sequence of SEQ ID NO: 156.

In some instances, the antibody (e.g., a monoclonal antibody) competes for binding to an ETEC adhesin protein with an isolated VHH antibody that includes a VHH binding domain including the amino acid sequence of SEQ ID NO: 156. In particular instances, the antibody (e.g., a monoclonal antibody) competes for binding to an ETEC adhesin protein with an isolated VHH antibody that includes a VHH binding domain of VHH antibody 4B7.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 161); (b) a CDR-H2 comprising the amino acid sequence of FAAAITWNGRSTL (SEQ ID NO: 162); (c) a CDR-H3 comprising the amino acid sequence of TLTTWEHKWEYNS (SEQ ID NO: 163), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 161-163, and/or (ii) one, two, or three amino acid substitutions relative to the amino acid sequence of any one of SEQ ID NOs: 161-163. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 164, and/or may include one, two, three, four, five, or six amino acid substitutions relative to the amino acid sequence of SEQ ID NO: 164.

In some instances, the antibody (e.g., a monoclonal antibody) competes for binding to an ETEC adhesin protein with an isolated VHH antibody that includes a VHH binding domain including the amino acid sequence of SEQ ID NO: 164. In particular instances, the antibody (e.g., a monoclonal antibody) competes for binding to an ETEC adhesin protein with an isolated VHH antibody that includes a VHH binding domain of VHH antibody 4B8.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 169); (b) a CDR-H2 comprising the amino acid sequence of FAAAITWNGRSTL (SEQ ID NO: 170); (c) a CDR-H3 comprising the amino acid sequence of TLTTWEHKWEYNS (SEQ ID NO: 171), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 169-171, and/or (ii) one, two, or three amino acid substitutions relative to the amino acid sequence of any one of SEQ ID NOs: 169-171. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 172, and/or may include one, two, three, four, five, or six amino acid substitutions relative to the amino acid sequence of SEQ ID NO: 172.

In some instances, the antibody (e.g., a monoclonal antibody) competes for binding to an ETEC adhesin protein with an isolated VHH antibody that includes a VHH binding domain including the amino acid sequence of SEQ ID NO: 172. In particular instances, the antibody (e.g., a monoclonal antibody) competes for binding to an ETEC adhesin protein with an isolated VHH antibody that includes a VHH binding domain of VHH antibody 4H2.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 177); (b) a CDR-H2 comprising the amino acid sequence of FAAAITWNGRSTL (SEQ ID NO: 178); (c) a CDR-H3 comprising the amino acid sequence of TLTTWEHKWEYNS (SEQ ID NO: 179), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 177-179, and/or (ii) one, two, or three amino acid substitutions relative to the amino acid sequence of any one of SEQ ID NOs: 177-179. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 180, and/or may include one, two, three, four, five, or six amino acid substitutions relative to the amino acid sequence of SEQ ID NO: 180.

In some instances, the antibody (e.g., a monoclonal antibody) competes for binding to an ETEC adhesin protein with an isolated VHH antibody that includes a VHH binding domain including the amino acid sequence of SEQ ID NO: 180. In particular instances, the antibody (e.g., a monoclonal antibody) competes for binding to an ETEC adhesin protein with an isolated VHH antibody that includes a VHH binding domain of VHH antibody 4H4.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 185); (b) a CDR-H2 comprising the amino acid sequence of FAAAITWNGRSTL (SEQ ID NO: 186); (c) a CDR-H3 comprising the amino acid sequence of TLTTWEHKWEYNS (SEQ ID NO: 187), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 185-187, and/or (ii) one, two, or three amino acid substitutions relative to the amino acid sequence of any one of SEQ ID NOs: 185-187. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 188, and/or may include one, two, three, four, five, or six amino acid substitutions relative to the amino acid sequence of SEQ ID NO: 188.

In some instances, the antibody (e.g., a monoclonal antibody) competes for binding to an ETEC adhesin protein with an isolated VHH antibody that includes a VHH binding domain including the amino acid sequence of SEQ ID NO: 188. In particular instances, the antibody (e.g., a monoclonal antibody) competes for binding to an ETEC adhesin protein with an isolated VHH antibody that includes a VHH binding domain of VHH antibody 1H3.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 193); (b) a CDR-H2 comprising the amino acid sequence of FAAAITWNGRSTL (SEQ ID NO: 194); (c) a CDR-H3 comprising the amino acid sequence of TLTTWEHKWEYNS (SEQ ID NO: 195), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 193-195, and/or (ii) one, two, or three amino acid substitutions relative to the amino acid sequence of any one of SEQ ID NOs: 193-195. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 196, and/or may include one, two, three, four, five, or six amino acid substitutions relative to the amino acid sequence of SEQ ID NO: 196.

In some instances, the antibody (e.g., a monoclonal antibody) competes for binding to an ETEC adhesin protein with an isolated VHH antibody that includes a VHH binding domain including the amino acid sequence of SEQ ID NO: 196. In particular instances, the antibody (e.g., a monoclonal antibody) competes for binding to an ETEC adhesin protein with an isolated VHH antibody that includes a VHH binding domain of VHH antibody 2B111.

In another aspect, the invention provides an antibody (e.g., a monoclonal antibody) that competes for binding to an ETEC adhesin protein with an isolated VHH antibody that includes a VHH binding domain including the following CDRs: (a) a CDR-H1 comprising the amino acid sequence of SRTFNHYN (SEQ ID NO: 201); (b) a CDR-H2 comprising the amino acid sequence of FAAAITWNGRSTL (SEQ ID NO: 202); (c) a CDR-H3 comprising the amino acid sequence of TLTTWEHKWEYNS (SEQ ID NO: 203), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 201-203, and/or (ii) one, two, or three amino acid substitutions relative to the amino acid sequence of any one of SEQ ID NOs: 201-203. In one embodiment, the invention provides an antibody (e.g., a monoclonal antibody) that competes for binding to an ETEC adhesin protein with an isolated VHH antibody that includes a VHH binding domain including an amino acid sequence having at least 95% sequence identity (e.g., at least 96%, 97%, 98%, or 99% sequence identity) to the amino acid sequence of SEQ ID NO: 204, and/or may include one, two, three, four, five, or six amino acid substitutions relative to the amino acid sequence of SEQ ID NO: 204.

In some instances, the antibody (e.g., a monoclonal antibody) competes for binding to an ETEC adhesin protein with an isolated VHH antibody that includes a VHH binding domain including the amino acid sequence of SEQ ID NO: 204. In particular instances, the antibody (e.g., a monoclonal antibody) competes for binding to an ETEC adhesin protein with an isolated VHH antibody that includes a VHH binding domain of VHH antibody 1G7.

In some embodiments, the antibody does not include an Fc region.

In certain embodiments, the antibody consists of a single VHH binding domain.

In certain embodiments, labeled anti-ETEC adhesin protein antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In a further aspect, an anti-ETEC adhesin protein antibody according to any of the above embodiments may incorporate any of the features, singly or in combination, as described in Sections 1-6 below.

1. Antibody Affinity

In certain embodiments, an antibody provided herein may have a dissociation constant ($K_D$) of ≤10 μM, ≤1 μM, ≤100 nM, ≤10 nM, ≤1 nM, ≤0.1 nM, or ≤0.01 nM.

In one embodiment, an antibody provided herein may bind an ETEC adhesin protein with a $K_D$ of between about 0.1 nM and about 200 nM (e.g., between about 5 nM and about 100 nM, between about 15 nM and about 100 nM, between about 25 nM and about 100 nM, between about 35 nM and about 100 nM, between about 45 nM and about 100 nM, between about 55 nM and about 100 nM, between about 65 nM and about 100 nM, between about 75 nM and about 100 nM, between about 85 nM and about 100 nM, between about 95 nM and about 100 nM, between about 95 nM and about 200 nM, between about 105 nM and about 200 nM, between about 115 nM and about 200 nM, between about 125 nM and about 200 nM, between about 135 nM and about 200 nM, between about 145 nM and about 200 nM, between about 155 nM and about 200 nM, between about 165 nM and about 200 nM, between about 175 nM and about 200 nM, between about 185 nM and about 200 nM, or between about 195 nM and about 200 nM). In some embodiments, the antibody may bind an ETEC adhesin protein with a $K_D$ between about 1 nM and about 50 nM (e.g., between about 5 nM and about 50 nM, between about 8 nM and about 40 nM, between about 11 nM and about 30 nM, or between about 14 nM and about 20 nM). In particular embodiments, an antibody provided herein may bind an ETEC adhesin protein with a $K_D$ of about 15 nM.

In some embodiments, the antibody may bind ETEC adhesin protein CS4 with a $K_D$ between about 15 and 200 nM (e.g., between about 20 and about 40 nM, between about 35 and about 80 nM, between about 75 and about 90 nM, between about 85 and about 120 nM, between about 115 and about 170 nM, or between about 165 and about 200 nM).

In some embodiments, the antibody may bind ETEC adhesin protein CS14 with a $K_D$ between about 15 and 200 nM (e.g., between about 20 and about 40 nM, between about 35 and about 80 nM, between about 75 and about 90 nM, between about 85 and about 120 nM, between about 115 and about 170 nM, or between about 165 and about 200 nM).

In some embodiments, the antibody may bind ETEC adhesin protein CS1 with a $K_D$ between about 15 and about 200 nM (e.g., between about 20 and about 40 nM, between about 35 and about 80 nM, between about 75 and about 90 nM, between about 85 and about 120 nM, between about 115 and about 170 nM, or between about 165 and about 200 nM).

In some embodiments, the antibody may bind ETEC adhesin protein CS17 with a $K_D$ between about 3 and about 200 nM (e.g., between about 3 and about 20 nM (e.g., about 3 nM, about 4 nM, about 5 nM, about 6 nM, about 7 nM, about 8 nM, about 9 nM, about 10 nM, about 11 nM, about 12 nM, about 13 nM, about 14 nM, about 15 nM, about 16 nM, about 17 nM, about 18 nM, about 19 nM, or about 20 nM), about 3 and about 150 nM, about 3 and about 100 nM, about 3 and about 50 nM, or about 3 and about 35 nM).

In some embodiments, the antibody may bind ETEC adhesin protein CS19 with a $K_D$ between about 80 and 200 nM (e.g., between about 85 and about 110 nM, between about 105 and about 150 nM, between about 145 and about 180 nM, or between about 175 and about 200 nM).

In some embodiments, the antibody may bind ETEC adhesin protein CS2 with a $K_D$ between about 3 and about 200 nM (e.g., between about 5 nM and about 100 nM, between about 15 nM and about 100 nM, between about 25 nM and about 100 nM, between about 35 nM and about 100 nM, between about 45 nM and about 100 nM, between about 55 nM and about 100 nM, between about 65 nM and about 100 nM, between about 75 nM and about 100 nM, between about 85 nM and about 100 nM, between about 95 nM and about 100 nM, between about 95 nM and about 200 nM, between about 105 nM and about 200 nM, between about 115 nM and about 200 nM, between about 125 nM and about 200 nM, between about 135 nM and about 200 nM, between about 145 nM and about 200 nM, between about 155 nM and about 200 nM, between about 165 nM and about 200 nM, between about 175 nM and about 200 nM, between about 185 nM and about 200 nM, or between about 195 nM and about 200 nM).

In some embodiments, the antibody may bind ETEC adhesin protein CS3 with a $K_D$ between about 15 and 200 nM (e.g., between about 20 and about 40 nM, between about 35 and about 80 nM, between about 75 and about 90 nM, between about 85 and about 120 nM, between about 115 and about 170 nM, or between about 165 and about 200 nM).

In some embodiments, the antibody may bind ETEC adhesin protein CS5 with a $K_D$ between about 1 and about 200 nM (e.g., between about 1 and about 20 nM (e.g., about 2 nM, about 3 nM, about 4 nM, about 5 nM, about 6 nM, about 7 nM, about 8 nM, about 9 nM, about 10 nM, about 11 nM, about 12 nM, about 13 nM, about 14 nM, about 15 nM, about 16 nM, about 17 nM, about 18 nM, about 19 nM, or about 20 nM), about 1 and about 150 nM, about 1 and about 100 nM, about 1 and about 50 nM, or about 1 and about 35 nM).

In some embodiments, the antibody may bind ETEC adhesin protein CS6 with a $K_D$ between about 1 and about 200 nM (e.g., between about 7 and about 30 nM (e.g., about 8 nM, about 9 nM, about 10 nM, about 11 nM, about 12 nM, about 12.5 nM, about 13 nM, about 14 nM, about 15 nM, about 16 nM, about 17 nM, about 18 nM, about 19 nM, about 20 nM, about 21 nM, about 22 nM, about 23 nM, about 24 nM, about 25 nM, about 26 nM, about 27 nM, about 28 nM, or about 29 nM), about 1 and about 150 nM, about 1 and about 100 nM, about 1 and about 50 nM, or about 1 and about 35 nM).

In some embodiments, the antibody may bind ETEC adhesin protein CS21 with a $K_D$ between about 10 and about 200 nM (e.g., about 10 and about 150, about 10 and about 100, about 15 and about 50, or about 20 and about 30 nM (e.g., about 21 nM, about 22 nM, about 23 nM, about 24 nM, about 25 nM, about 26 nM, about 27 nM, about 28 nM, or about 29 nM)).

In some embodiments, the antibody binds ETEC adhesin protein CfaE with a $K_D$ between about 40 nM and about 60 nM and includes a VHH binding domain including (i) a CDR-H1 comprising the amino acid sequence of YIFWSYGY (SEQ ID NO: 17), a CDR-H2 comprising the amino acid sequence of LVATISRGGTTN (SEQ ID NO: 18), a CDR-H3 comprising the amino acid sequence of AGRYAFGYFK (SEQ ID NO: 19), and/or (ii) the amino acid sequence of SEQ ID NO: 20.

In some embodiments, the antibody binds ETEC adhesin protein CfaE with a $K_D$ between about 15 nM and about 35 nM and includes a VHH binding domain including (i) a CDR-H1 comprising the amino acid sequence of NIFQDAE (SEQ ID NO: 1), a CDR-H2 comprising the amino acid sequence of FVATIAYGGNTN (SEQ ID NO: 2), a CDR-H3 comprising the amino acid sequence of VYTGVYYDRTTGGYVAFE (SEQ ID NO: 3), and/or (ii) the amino acid sequence of SEQ ID NO: 4.

In some embodiments, the antibody binds ETEC adhesin protein CfaE with a $K_D$ between about 90 nM and about 110 nM and includes a VHH binding domain including (i) a CDR-H1 comprising the amino acid sequence of ERTFSYYV (SEQ ID NO: 9), a CDR-H2 comprising the amino acid sequence of FVAGISMSGDSTK (SEQ ID NO: 10), a CDR-H3 comprising the amino acid sequence of ADRDIRGNFRS (SEQ ID NO: 11), and/or (ii) the amino acid sequence of SEQ ID NO: 12.

In some embodiments, the antibody binds ETEC adhesin protein CfaE with a $K_D$ between about 190 nM and about 200 nM and includes a VHH binding domain including (i) a CDR-H1 including the amino acid sequence of SRTFNHYN (SEQ ID NO: 25), a CDR-H2 including the amino acid sequence of FAAAITWNGRSTL (SEQ ID NO: 26), a CDR-H3 including the amino acid sequence of TLTTWEHKWEYNS (SEQ ID NO: 27), and/or (ii) the amino acid sequence of SEQ ID NO: 28.

In some embodiments, the antibody binds ETEC adhesin protein CS4 with a $K_D$ between about 15 nM and about 35 nM and includes a VHH binding domain including (i) a CDR-H1 comprising the amino acid sequence of YIFWSYGY (SEQ ID NO: 17), a CDR-H2 comprising the amino acid sequence of LVATISRGGTTN (SEQ ID NO: 18), a CDR-H3 comprising the amino acid sequence of AGRYAFGYFK (SEQ ID NO: 19), and/or (ii) the amino acid sequence of SEQ ID NO: 20.

In some embodiments, the antibody binds ETEC adhesin protein CS4 with a $K_D$ between about 90 nM and about 110 nM and includes a VHH binding domain including (i) a CDR-H1 comprising the amino acid sequence of NIFQDAE (SEQ ID NO: 1), a CDR-H2 comprising the amino acid sequence of FVATIAYGGNTN (SEQ ID NO: 2), a CDR-H3 comprising the amino acid sequence of VYTGVYY-DRTTGGYVAFE (SEQ ID NO: 3), and/or (ii) the amino sequence of SEQ ID NO: 4.

In some embodiments, the antibody binds ETEC adhesin protein CS4 with a $K_D$ between about 190 nM and about 200 nM and includes a VHH binding domain including (i) a CDR-H1 comprising the amino acid sequence of ERTFSYYV (SEQ ID NO: 9), a CDR-H2 comprising the amino acid sequence of FVAGISMSGDSTK (SEQ ID NO: 10), a CDR-H3 comprising the amino acid sequence of ADRDIRGNFRS (SEQ ID NO: 11), and/or (ii) the amino acid sequence of SEQ ID NO: 12.

In some embodiments, the antibody binds ETEC adhesin protein CS4 with a $K_D$ between about 15 nM and about 35 nM and includes a VHH binding domain including (i) a CDR-H1 including the amino acid sequence of SRTFNHYN (SEQ ID NO: 25), a CDR-H2 including the amino acid sequence of FAAAITWNGRSTL (SEQ ID NO: 26), a CDR-H3 including the amino acid sequence of TLTTWEHKWEYNS (SEQ ID NO: 27), and/or (ii) the amino acid sequence of SEQ ID NO: 28.

In some embodiments, the antibody binds ETEC adhesin protein CS14 with a $K_D$ between about 15 nM and about 35 nM and includes a VHH binding domain including (i) a CDR-H1 comprising the amino acid sequence of YIFWSYGY (SEQ ID NO: 17), a CDR-H2 comprising the amino acid sequence of LVATISRGGTTN (SEQ ID NO: 18), a CDR-H3 comprising the amino acid sequence of AGRYAFGYFK (SEQ ID NO: 19), and/or (ii) the amino acid sequence of SEQ ID NO: 20.

In some embodiments, the antibody binds ETEC adhesin protein CS14 with a $K_D$ between about 190 nM and about 200 nM and includes a VHH binding domain including (i) a CDR-H1 comprising the amino acid sequence of NIFQ-DAE (SEQ ID NO: 1), a CDR-H2 comprising the amino acid sequence of FVATIAYGGNTN (SEQ ID NO: 2), a CDR-H3 comprising the amino acid sequence of VYTGVYYDRTTGGYVAFE (SEQ ID NO: 3), and/or (ii) the amino sequence of SEQ ID NO: 4.

In some embodiments, the antibody binds ETEC adhesin protein CS14 with a $K_D$ between about 90 nM and about 110 nM and includes a VHH binding domain including (i) a CDR-H1 comprising the amino acid sequence of ERTFSYYV (SEQ ID NO: 9), a CDR-H2 comprising the amino acid sequence of FVAGISMSGDSTK (SEQ ID NO: 10), a CDR-H3 comprising the amino acid sequence of ADRDIRGNFRS (SEQ ID NO: 11), and/or (ii) the amino acid sequence of SEQ ID NO: 12.

In some embodiments, the antibody binds ETEC adhesin protein CS14 with a $K_D$ between about 90 nM and about 110 nM and includes a VHH binding domain including (i) a CDR-H1 including the amino acid sequence of SRTFNHYN (SEQ ID NO: 25), a CDR-H2 including the amino acid sequence of FAAAITWNGRSTL (SEQ ID NO: 26), a CDR-H3 including the amino acid sequence of TLTTWEHKWEYNS (SEQ ID NO: 27), and/or (ii) the amino acid sequence of SEQ ID NO: 28.

In some embodiments, the antibody binds ETEC adhesin protein CS1 with a $K_D$ between about 190 nM and about 200 nM and includes a VHH binding domain including (i) a CDR-H1 comprising the amino acid sequence of YIFWSYGY (SEQ ID NO: 17), a CDR-H2 comprising the amino acid sequence of LVATISRGGTTN (SEQ ID NO: 18), a CDR-H3 comprising the amino acid sequence of AGRYAFGYFK (SEQ ID NO: 19), and/or (ii) the amino acid sequence of SEQ ID NO: 20.

In some embodiments, the antibody binds ETEC adhesin protein CS1 with a $K_D$ between about 190 nM and about 200 nM and includes a VHH binding domain including (i) a CDR-H1 comprising the amino acid sequence of NIFQDAE (SEQ ID NO: 1), a CDR-H2 comprising the amino acid sequence of FVATIAYGGNTN (SEQ ID NO: 2), a CDR-H3 comprising the amino acid sequence of VYTGVYY-DRTTGGYVAFE (SEQ ID NO: 3), and/or (ii) the amino acid sequence of SEQ ID NO: 4.

In some embodiments, the antibody binds ETEC adhesin protein CS1 with a $K_D$ between about 40 nM and about 60 nM and includes a VHH binding domain including (i) a CDR-H1 comprising the amino acid sequence of ERTFSYYV (SEQ ID NO: 9), a CDR-H2 comprising the amino acid sequence of FVAGISMSGDSTK (SEQ ID NO: 10), a CDR-H3 comprising the amino acid sequence of ADRDIRGNFRS (SEQ ID NO: 11), and/or (ii) the amino acid sequence of SEQ ID NO: 12.

In some embodiments, the antibody binds ETEC adhesin protein CS1 with a $K_D$ between about 90 nM and about 110 nM and includes a VHH binding domain including (i) a CDR-H1 including the amino acid sequence of SRTFNHYN (SEQ ID NO: 25), a CDR-H2 including the amino acid sequence of FAAAITWNGRSTL (SEQ ID NO: 26), a CDR-H3 including the amino acid sequence of TLTTWEHKWEYNS (SEQ ID NO: 27), and/or (ii) the amino acid sequence of SEQ ID NO: 28.

In some embodiments, the antibody binds ETEC adhesin protein CS17 with a $K_D$ between about 3 nM and about 9 nM and includes a VHH binding domain including (i) a CDR-H1 comprising the amino acid sequence of YIFWSYGY (SEQ ID NO: 17), a CDR-H2 comprising the amino acid sequence of LVATISRGGTTN (SEQ ID NO: 18), a CDR-H3 comprising the amino acid sequence of AGRYAFGYFK (SEQ ID NO: 19), and/or (ii) the amino acid sequence of SEQ ID NO: 20.

In some embodiments, the antibody binds ETEC adhesin protein CS17 with a $K_D$ between about 3 nM and about 9 nM and includes a VHH binding domain including (i) a CDR-H1 comprising the amino acid sequence of NIFQDAE (SEQ ID NO: 1), a CDR-H2 comprising the amino acid sequence of FVATIAYGGNTN (SEQ ID NO: 2), a CDR-H3 comprising the amino acid sequence of VYTGVYYDRTTGGYVAFE (SEQ ID NO: 3), and/or (ii) the amino sequence of SEQ ID NO: 4.

In some embodiments, the antibody binds ETEC adhesin protein CS17 with a $K_D$ between about 3 nM and about 9 nM and includes a VHH binding domain including (i) a CDR-H1 comprising the amino acid sequence of ERTFSYYV (SEQ ID NO: 9), a CDR-H2 comprising the amino acid sequence of FVAGISMSGDSTK (SEQ ID NO: 10), a CDR-H3 comprising the amino acid sequence of ADRDIRGNFRS (SEQ ID NO: 11), and/or (ii) the amino acid sequence of SEQ ID NO: 12.

In some embodiments, the antibody binds ETEC adhesin protein CS17 with a $K_D$ between about 3 nM and about 9 nM and includes a VHH binding domain including (i) a CDR-H1 including the amino acid sequence of SRTFNHYN (SEQ ID NO: 25), a CDR-H2 including the amino acid sequence of FAAAITWNGRSTL (SEQ ID NO: 26), a CDR-H3 including the amino acid sequence of TLTTWEHKWEYNS (SEQ ID NO: 27), and/or (ii) the amino acid sequence of SEQ ID NO: 28.

In some embodiments, the antibody binds ETEC adhesin protein CS19 with a $K_D$ between about 190 nM and about 200 nM and includes a VHH binding domain including (i) a CDR-H1 comprising the amino acid sequence of YIFWSYGY (SEQ ID NO: 17), a CDR-H2 comprising the amino acid sequence of LVATISRGGTTN (SEQ ID NO: 18), a CDR-H3 comprising the amino acid sequence of AGRYAFGYFK (SEQ ID NO: 19), and/or (ii) the amino acid sequence of SEQ ID NO: 20.

In some embodiments, the antibody binds ETEC adhesin protein CS19 with a $K_D$ between about 190 nM and about 200 nM and includes a VHH binding domain including (i) a CDR-H1 comprising the amino acid sequence of NIFQDAE (SEQ ID NO: 1), a CDR-H2 comprising the amino acid sequence of FVATIAYGGNTN (SEQ ID NO: 2), a CDR-H3 comprising the amino acid sequence of VYTGVYYDRTTGGYVAFE (SEQ ID NO: 3), and/or (ii) the amino sequence of SEQ ID NO: 4.

In some embodiments, the antibody binds ETEC adhesin protein CS19 with a $K_D$ between about 90 nM and about 110 nM and includes a VHH binding domain including (i) a CDR-H1 comprising the amino acid sequence of ERTFSYYV (SEQ ID NO: 9), a CDR-H2 comprising the amino acid sequence of FVAGISMSGDSTK (SEQ ID NO: 10), a CDR-H3 comprising the amino acid sequence of ADRDIRGNFRS (SEQ ID NO: 11), and/or (ii) the amino acid sequence of SEQ ID NO: 12.

In some embodiments, the antibody binds ETEC adhesin protein CS19 with a $K_D$ between about 90 nM and about 110 nM and includes a VHH binding domain including (i) a CDR-H1 including the amino acid sequence of SRTFNHYN (SEQ ID NO: 25), a CDR-H2 including the amino acid sequence of FAAAITWNGRSTL (SEQ ID NO: 26), a CDR-H3 including the amino acid sequence of TLTTWEHKWEYNS (SEQ ID NO: 27), and/or (ii) the amino acid sequence of SEQ ID NO: 28.

In some embodiments, the antibody binds ETEC adhesin protein CS2 with a $K_D$ between about 190 nM and about 200 nM and includes a VHH binding domain including (i) a CDR-H1 comprising the amino acid sequence of YIFWSYGY (SEQ ID NO: 17), a CDR-H2 comprising the amino acid sequence of LVATISRGGTTN (SEQ ID NO: 18), a CDR-H3 comprising the amino acid sequence of AGRYAFGYFK (SEQ ID NO: 19), and/or (ii) the amino acid sequence of SEQ ID NO: 20.

In some embodiments, the antibody binds ETEC adhesin protein CS2 with a $K_D$ between about 3 nM and about 9 nM and includes a VHH binding domain including (i) a CDR-H1 comprising the amino acid sequence of NIFQDAE (SEQ ID NO: 1), a CDR-H2 comprising the amino acid sequence of FVATIAYGGNTN (SEQ ID NO: 2), a CDR-H3 comprising the amino acid sequence of VYTGVYYDRTTGGYVAFE (SEQ ID NO: 3), and/or (ii) the amino sequence of SEQ ID NO: 4.

In some embodiments, the antibody binds ETEC adhesin protein CS2 with a $K_D$ between about 40 nM and about 60 nM and includes a VHH binding domain including (i) a CDR-H1 comprising the amino acid sequence of ERTFSYYV (SEQ ID NO: 9), a CDR-H2 comprising the amino acid sequence of FVAGISMSGDSTK (SEQ ID NO: 10), a CDR-H3 comprising the amino acid sequence of ADRDIRGNFRS (SEQ ID NO: 11), and/or (ii) the amino acid sequence of SEQ ID NO: 12.

In some embodiments, the antibody binds ETEC adhesin protein CS2 with a $K_D$ between about 90 nM and about 110 nM and includes a VHH binding domain including (i) a CDR-H1 including the amino acid sequence of SRTFNHYN (SEQ ID NO: 25), a CDR-H2 including the amino acid sequence of FAAAITWNGRSTL (SEQ ID NO: 26), a CDR-H3 including the amino acid sequence of TLTTWEHKWEYNS (SEQ ID NO: 27), and/or (ii) the amino acid sequence of SEQ ID NO: 28.

In some embodiments, the antibody binds ETEC adhesin protein CS3 with a $K_D$ between about 90 nM and about 110 nM and includes a VHH binding domain including (i) a CDR-H1 comprising the amino acid sequence of YIFWSYGY (SEQ ID NO: 17), a CDR-H2 comprising the amino acid sequence of LVATISRGGTTN (SEQ ID NO: 18), a CDR-H3 comprising the amino acid sequence of AGRYAFGYFK (SEQ ID NO: 19), and/or (ii) the amino acid sequence of SEQ ID NO: 20.

In some embodiments, the antibody binds ETEC adhesin protein CS3 with a $K_D$ between about 90 nM and about 110 nM and includes a VHH binding domain including (i) a CDR-H1 comprising the amino acid sequence of NIFQDAE (SEQ ID NO: 1), a CDR-H2 comprising the amino acid sequence of FVATIAYGGNTN (SEQ ID NO: 2), a CDR-H3 comprising the amino acid sequence of VYTGVYY-DRTTGGYVAFE (SEQ ID NO: 3), and/or (ii) the amino sequence of SEQ ID NO: 4.

In some embodiments, the antibody binds ETEC adhesin protein CS3 with a $K_D$ between about 40 nM and about 60 nM and includes a VHH binding domain including (i) a CDR-H1 comprising the amino acid sequence of ERTFSYYV (SEQ ID NO: 9), a CDR-H2 comprising the amino acid sequence of FVAGISMSGDSTK (SEQ ID NO: 10), a CDR-H3 comprising the amino acid sequence of ADRDIRGNFRS (SEQ ID NO: 11), and/or (ii) the amino acid sequence of SEQ ID NO: 12.

In some embodiments, the antibody binds ETEC adhesin protein CS3 with a $K_D$ between about 90 nM and about 110 nM and includes a VHH binding domain including (i) a CDR-H1 including the amino acid sequence of SRTFNHYN (SEQ ID NO: 25), a CDR-H2 including the amino acid sequence of FAAAITWNGRSTL (SEQ ID NO: 26), a CDR-H3 including the amino acid sequence of TLTTWEHKWEYNS (SEQ ID NO: 27), and/or (ii) the amino acid sequence of SEQ ID NO: 28.

In some embodiments, the antibody binds ETEC adhesin protein CS5 with a $K_D$ between about 9 nM and about 15 nM and includes a VHH binding domain including (i) a CDR-H1 comprising the amino acid sequence of YIFWSYGY (SEQ ID NO: 17), a CDR-H2 comprising the amino acid sequence of LVATISRGGTTN (SEQ ID NO: 18), a CDR-H3 comprising the amino acid sequence of AGRYAFGYFK (SEQ ID NO: 19), and/or (ii) the amino acid sequence of SEQ ID NO: 20.

In some embodiments, the antibody binds ETEC adhesin protein CS5 with a $K_D$ between about 3 nM and about 9 nM and includes a VHH binding domain including (i) a CDR-H1 comprising the amino acid sequence of NIFQDAE (SEQ ID NO: 1), a CDR-H2 comprising the amino acid sequence of FVATIAYGGNTN (SEQ ID NO: 2), a CDR-H3 comprising the amino acid sequence of VYTGVYYDRTTGGYVAFE (SEQ ID NO: 3), and/or (ii) the amino sequence of SEQ ID NO: 4.

In some embodiments, the antibody binds ETEC adhesin protein CS5 with a $K_D$ between about 1 nM and about 5 nM and includes a VHH binding domain including (i) a CDR-H1 comprising the amino acid sequence of ERTFSYYV (SEQ ID NO: 9), a CDR-H2 comprising the amino acid sequence of FVAGISMSGDSTK (SEQ ID NO: 10), a CDR-H3 comprising the amino acid sequence of ADRDIRGNFRS (SEQ ID NO: 11), and/or (ii) the amino acid sequence of SEQ ID NO: 12.

In some embodiments, the antibody binds ETEC adhesin protein CS5 with a $K_D$ between about 1 nM and about 5 nM and includes a VHH binding domain including (i) a CDR-H1 including the amino acid sequence of SRTFNHYN (SEQ ID NO: 25), a CDR-H2 including the amino acid sequence of FAAAITWNGRSTL (SEQ ID NO: 26), a CDR-H3 including the amino acid sequence of TLTTWEHKWEYNS (SEQ ID NO: 27), and/or (ii) the amino acid sequence of SEQ ID NO: 28.

In some embodiments, the antibody binds ETEC adhesin protein CS6 with a $K_D$ between about 9 nM and about 15 nM and includes a VHH binding domain including (i) a CDR-H1 comprising the amino acid sequence of YIFWSYGY (SEQ ID NO: 17), a CDR-H2 comprising the amino acid sequence of LVATISRGGTTN (SEQ ID NO: 18), a CDR-H3 comprising the amino acid sequence of AGRYAFGYFK (SEQ ID NO: 19), and/or (ii) the amino acid sequence of SEQ ID NO: 20.

In some embodiments, the antibody binds ETEC adhesin protein CS6 with a $K_D$ between about 15 nM and about 35 nM and includes a VHH binding domain including (i) a CDR-H1 comprising the amino acid sequence of NIFQDAE (SEQ ID NO: 1), a CDR-H2 comprising the amino acid sequence of FVATIAYGGNTN (SEQ ID NO: 2), a CDR-H3 comprising the amino acid sequence of VYTGVYYDRTTGGYVAFE (SEQ ID NO: 3), and/or (ii) the amino sequence of SEQ ID NO: 4.

In some embodiments, the antibody binds ETEC adhesin protein CS6 with a $K_D$ between about 9 nM and about 15 nM and includes a VHH binding domain including (i) a CDR-H1 comprising the amino acid sequence of ERTFSYYV (SEQ ID NO: 9), a CDR-H2 comprising the amino acid sequence of FVAGISMSGDSTK (SEQ ID NO: 10), a CDR-H3 comprising the amino acid sequence of ADRDIRGNFRS (SEQ ID NO: 11), and/or (ii) the amino acid sequence of SEQ ID NO: 12.

In some embodiments, the antibody binds ETEC adhesin protein CS6 with a $K_D$ between about 15 nM and about 35 nM and includes a VHH binding domain including (i) a CDR-H1 including the amino acid sequence of SRTFNHYN (SEQ ID NO: 25), a CDR-H2 including the amino acid sequence of FAAAITWNGRSTL (SEQ ID NO: 26), a CDR-H3 including the amino acid sequence of TLTTWEHKWEYNS (SEQ ID NO: 27), and/or (ii) the amino acid sequence of SEQ ID NO: 28.

In some embodiments, the antibody binds ETEC adhesin protein CS21 with a $K_D$ between about 15 nM and about 35 nM and includes a VHH binding domain including (i) a CDR-H1 comprising the amino acid sequence of YIFWSYGY (SEQ ID NO: 17), a CDR-H2 comprising the amino acid sequence of LVATISRGGTTN (SEQ ID NO: 18), a CDR-H3 comprising the amino acid sequence of AGRYAFGYFK (SEQ ID NO: 19), and/or (ii) the amino acid sequence of SEQ ID NO: 20.

In some embodiments, the antibody binds ETEC adhesin protein CS21 with a $K_D$ between about 15 nM and about 35 nM and includes a VHH binding domain including (i) a CDR-H1 comprising the amino acid sequence of NIFQDAE (SEQ ID NO: 1), a CDR-H2 comprising the amino acid sequence of FVATIAYGGNTN (SEQ ID NO: 2), a CDR-H3 comprising the amino acid sequence of VYTGVYYDRTTGGYVAFE (SEQ ID NO: 3), and/or (ii) the amino sequence of SEQ ID NO: 4.

In some embodiments, the antibody binds ETEC adhesin protein CS21 with a $K_D$ between about 15 nM and about 35 nM and includes a VHH binding domain including (i) a CDR-H1 comprising the amino acid sequence of ERTFSYYV (SEQ ID NO: 9), a CDR-H2 comprising the amino acid sequence of FVAGISMSGDSTK (SEQ ID NO: 10), a CDR-H3 comprising the amino acid sequence of ADRDIRGNFRS (SEQ ID NO: 11), and/or (ii) the amino acid sequence of SEQ ID NO: 12.

In some embodiments, the antibody binds ETEC adhesin protein CS21 with a $K_D$ between about 15 nM and about 35 nM and includes a VHH binding domain including (i) a CDR-H1 including the amino acid sequence of SRTFNHYN (SEQ ID NO: 25), a CDR-H2 including the amino acid sequence of FAAAITWNGRSTL (SEQ ID NO: 26), a CDR-H3 including the amino acid sequence of TLTTWEHKWEYNS (SEQ ID NO: 27), and/or (ii) the amino acid sequence of SEQ ID NO: 28.

According to another embodiment, $K_D$ is measured using a BIACORE® surface plasmon resonance assay. For example, an assay using a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$. See, for example, Chen et al.,

*J. Mol. Biol.* 293:865-881 (1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

In one embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 µM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

2. Inhibition of Colonization by ETEC

In certain embodiments, an antibody provided herein is an antibody capable of inhibiting colonization of the small intestine by ETEC. In some embodiments, the antibody is capable of inhibiting colonization of the small intestine by CfaE-expressing ETEC (e.g., ETEC strain H10407). In some embodiments, the antibody is capable of inhibiting colonization of the small intestine by CS1-expressing ETEC. In some embodiments, the antibody is capable of inhibiting colonization of the small intestine by CS3-expressing ETEC. In some embodiments, the antibody is capable of inhibiting colonization of the small intestine by CS5-expressing ETEC. In some embodiments, the antibody is capable of inhibiting colonization of the small intestine by CS6-expressing ETEC. In some embodiments, the antibody is capable of inhibiting colonization of the small intestine by CS21-expressing ETEC. In some instances, the antibody of the invention is capable of inhibiting colonization of the small intestine by ETEC by at least 20% (e.g., about 25%, about 30%, about 40%, about 50%, about 55%, about 60%, about 65%, about 70%, about 75%, about 80%, about 85%, about 90%, about 95%, or about 100%). In some embodiments, the antibody of the invention is capable of inhibiting colonization of the small intestine by ETEC by between about 20% and 100% (e.g., between about 20% and about 40%, between about 35% and about 50%, between about 45% and about 60%, between about 55% and about 70%, between about 65% and about 80%, between about 75% and about 90%, or between about 85% and about 100%). In particular embodiments, the antibody is capable of inhibiting colonization of the small intestine by CfaE-expressing ETEC at 100 mg/kg. In particular embodiments, the antibody is capable of inhibiting colonization of the small intestine by CS1-expressing ETEC at 100 mg/kg. In particular embodiments, the antibody is capable of inhibiting colonization of the small intestine by CS3-expressing ETEC at 100 mg/kg. In particular embodiments, the antibody is capable of inhibiting colonization of the small intestine by CS5-expressing ETEC at 100 mg/kg. In particular embodiments, the antibody is capable of inhibiting colonization of the small intestine by CS6-expressing ETEC at 100 mg/kg. In particular embodiments, the antibody is capable of inhibiting colonization of the small intestine by CS21-expressing ETEC at 100 mg/kg.

In some embodiments, the antibody is capable of inhibiting mannose-resistant hemagglutination of human group A erythrocytes with a maximal inhibitory concentration ($IC_{100}$) of between about 0.10 µg/mL and about 250 µg/mL (e.g., between about 0.5 µg/mL and about 30 µg/mL, about 25 µg/mL and about 50 µg/mL, about 45 µg/mL and about 100 µg/mL, about 95 µg/mL and about 150 µg/mL, about 145 µg/mL and about 200 µg/mL, or about 195 µg/mL and about 250 µg/mL). In some embodiments, the $IC_{100}$ is between about 6 µg/mL and about 200 µg/mL. In some embodiments, the inhibiting is measured using a mannose-resistant hemagglutination (MRHA) assay.

In some embodiments, the antibody is capable of inhibiting the binding of ETEC bacteria to intestinal cells with a 50% inhibitory concentration ($IC_{50}$) of between about 0.10 µM and about 10 µM (e.g., between about 0.50 µM and about 6 µM, about 3 µM and about 8 µM, or about 5 µM and about 10 µM). In some embodiments, the intestinal cells are Caco-2 human intestinal epithelial cells. In some embodiments, the inhibiting is measured using a Caco-2 adhesion assay at 37° C.

3. Antibody Fragments

In certain embodiments, an antibody provided herein is an antibody fragment. Antibody fragments include, but are not limited to, Fab, Fab', Fab'-SH, F(ab')$_2$, Fv, and scFv fragments, which are known in the art. Also included are diabodies, which have two antigen-binding sites that may be bivalent or bispecific, as is known in the art. Triabodies and tetrabodies are also known. Single-domain antibodies are also antibody fragments comprising all or a portion of the heavy chain variable domain or all or a portion of the light chain variable domain of an antibody. In certain embodiments, a single-domain antibody is a human single-domain antibody. In particular embodiments, a single-domain antibody is a single-domain VHH antibody.

Antibody fragments can be made by various techniques, including but not limited to proteolytic digestion of an intact antibody as well as production by recombinant host cells (e.g., *E. coli* or phage), as described herein.

4. Multimeric Antibodies

In certain embodiments, an antibody provided herein is a multimeric antibody (e.g., a multimeric VHH antibody). In one example, a multimeric antibody comprises two or more VHH antibodies (e.g., VHH antibodies described herein) connected by way of a linker (e.g., a peptide linker). In some instances, the VHH multimer includes the following N-terminal-to-C-terminal structure:

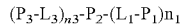

wherein $P_1$, $P_2$, and $P_3$ are each independently selected from any VHH binding domain described herein (e.g., a VHH binding domain of 2R215, 1D7, 2R23, or 1H4); $L_1$ and $L_3$ are each independently a linker; and $n_1$ and $n_3$ are each independently 0 or 1, wherein at least one of $n_1$ and $n_3$ are 1.

In some instances, $n_1$ is 1 and $n_3$ is 0, and the antibody comprises the following N-terminal-to-C-terminal structure:

In some instances, the peptide linker includes between 2 and 200 amino acids (e.g., between 5 and 50 (e.g., between 5 and 20, 15 and 30, 25 and 40, or 35 and 50), between 45 and 100 (e.g., between 45 and 60, 55 and 70, 65 and 80, 75 and 90, or 85 and 100), 95 and 150 (e.g., between 95 and 110, 105 and 120, 115 and 130, 125 and 140, or 135 and 150), or 145 and 200 amino acids (e.g., between 145 and 160, 155 and 170, 165 and 180, 175 and 190, or 185 and 200)). In some instances, the peptide linker comprises glycine (Gly) and serine (Ser) amino acids. In some instances, the peptide linker includes the amino acid sequence of any one of $(GS)_x$ (SEQ ID NOs: 222-230), $(GGS)_x$ (SEQ ID NOs: 231-239), (GGGGS (SEQ ID NO: 219))$_x$ (SEQ ID NOs: 219-221 and 240-246), (GGSG (SEQ ID NO: 247))$_x$ (SEQ ID NOs: 247-256), (SGGG (SEQ ID NO: 257))$_x$ (SEQ ID NOs: 257-266), wherein x is an integer from 1 to 10. In certain embodiments the linker includes the amino acid sequence of (GGGGS (SEQ ID NO: 219))$_x$, wherein x is an integer from 2-5 (SEQ ID NOs: 220 and 240-242). In some instances, $P_2$ and $P_1$ are different VHH binding domains. In some instances, $P_2$ and $P_1$ are identical VHH binding domains. In particular embodiments, $P_1$ and $P_2$ each include identical VHH binding domains including the amino acid sequence of SEQ ID NO: 4. In particular embodiments, $P_1$ and $P_2$ each include identical VHH binding domains including the amino acid sequence of SEQ ID NO: 12.

In some instances, $n_1$ is 1 and $n_3$ is 1, and the antibody comprises the following N-terminal-to-C-terminal structure:

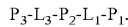

In some instances, each peptide linker independently includes between 2 and 200 amino acids (e.g., between 5 and 50 (e.g., between 5 and 20, 15 and 30, 25 and 40, or 35 and 50), between 45 and 100 (e.g., between 45 and 60, 55 and 70, 65 and 80, 75 and 90, or 85 and 100), 95 and 150 (e.g., between 95 and 110, 105 and 120, 115 and 130, 125 and 140, or 135 and 150), or 145 and 200 amino acids (e.g., between 145 and 160, 155 and 170, 165 and 180, 175 and 190, or 185 and 200)). In some instances, the peptide linker comprises glycine (Gly) and serine (Ser) amino acids. In some instances, the peptide linker includes the amino acid sequence of any one of $(GS)_x$ (SEQ ID NOs: 222-230), $(GGS)_x$ (SEQ ID NOs: 231-239), (GGGGS (SEQ ID NO: 219))$_x$ (SEQ ID NOs: 219-221 and 240-246), (GGSG (SEQ ID NO: 247))$_x$ (SEQ ID NOs: 247-256), (SGGG (SEQ ID NO: 257))$_x$ (SEQ ID NOs: 257-266), wherein x is an integer from 1 to 10. In certain embodiments the linker includes the amino acid sequence of (GGGGS (SEQ ID NO: 219))$_x$, wherein x is an integer from 2-5 (SEQ ID NOs: 220 and 240-242). In some instances, $P_3$, $P_2$, and $P_1$ are different VHH binding domains. In some instances, $P_3$, $P_2$, and $P_1$ are identical VHH binding domains. In particular embodiments, $P_1$, $P_2$, and $P_3$ each include identical VHH binding domains including the amino acid sequence of SEQ ID NO: 4. In particular embodiments, $P_1$, $P_2$, and $P_3$ each include identical VHH binding domains including the amino acid sequence of SEQ ID NO: 12.

Nanobodies (e.g., single-domain VHH antibodies) 2R215 and 1D7 were multimerized to dimeric and trimeric forms with (GGGGS (SEQ ID NO: 219))$_x$ linkers. The dimeric forms were generated using (GGGGS (SEQ ID NO: 219))$_6$ (SEQ ID NO: 221) linker to connect two monomeric VHHs in tandem N-terminus-to-C-terminus orientation. Trimers were generated using two (GGGGS)$_3$ (SEQ ID NO: 220) linkers between monomeric VHH units. The multimers were cloned into pET26b, adding a C-terminal 6×His tag to the nanobody sequence. Nanobodies were purified from the periplasmic fraction by Ni-NTA chromatography (Gold Biotechnology) and dialyzed against PBS to remove imidazole.

5. Chimeric, Humanized, and Fc-Containing Antibodies

In certain embodiments, an antibody provided herein is a chimeric antibody. In one example, a chimeric antibody comprises a non-human variable region (e.g., a VHH binding domain) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs (or portions thereof) are derived from a non-human antibody (e.g., a VHH binding domain antibody), and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA*, 89:4285 (1992); and Presta et al. *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In some instances, an antibody provided herein includes an Fc domain including a first Fc domain subunit and a second Fc domain subunit capable of stable association, with each Fc domain subunit having a CH2 domain and a CH3 domain, or functional fragments thereof (e.g., fragments that are capable of (i) dimerizing with another variant Fc domain monomer to form a variant Fc domain, and (ii) binding to an Fc receptor). In certain instances, each Fc domain subunit can include a hinge region linked to the CH2 domain. In some instances, the hinge regions can include the amino acid sequence of ASPVPSTPPTPSPSTPPTPSPS (SEQ ID NO: 209) or ASPVPPPPPP (SEQ ID NO: 210). In some instances, each Fc domain subunit is further linked to a single CH1 domain. In some embodiments, each VHH binding domain, CH1 domain, and Fc domain subunit is positioned relative to each other in an N-terminal-to-C-terminal direction as follows: VHH binding domain-CH1 domain-Fc domain subunit. In some embodiments, each CH1 domain is linked to a single VHH binding domain by a hinge region and positioned relative to each other in an N-terminal-to-C-terminal direction as follows: VHH binding domain-CH1 domain-hinge region-Fc domain subunit. In some embodiments, each CH1 domain is linked to a single VHH binding domain by a hinge region and positioned relative to each other in an N-terminal-to-C-terminal direction as follows: VHH binding domain-hinge region-CH1 domain-Fc domain subunit. The Fc domain can be an IgA subtype, in particular a secretory IgA (sIgA) or dimeric IgA (dIgA). In some instances, the Fc domain may be of any IgA subtype (e.g., dIgA1, dIgA2, sIgA1, and sIgA2). The Fc domain can be an IgG subtype (e.g., IgG1, IgG2a, or IgG2b) (e.g., IgG1).

In some instances, in the antibodies provided herein VHH binding domains were ligated into a pcDNA 3.1 vector containing heavy constant IgA1 and IgA2 chains without CH1 domain. Each vector was transformed in NEB5 competent cells, and sequences were verified ahead of transient transfection. In other instances, VHH binding domains may be ligated into vectors containing heavy constant IgA1 and IgA2 chains including a CH1 domain. In some instances, each Fc domain subunit is linked to a single VHH binding domain and positioned relative to each other in an N-terminal-to-C-terminal direction as follows: VHH binding domain-Fc domain subunit. In some instances, when each Fc domain subunit is further linked to a single CH1 domain, and each VHH binding domain, CH1 domain, and Fc domain subunit is positioned relative to each other in an N-terminal-to-C-terminal direction as follows: VHH binding domain-CH1 domain-Fc domain subunit.

6. Antibody Variants

In certain embodiments, amino acid sequence variants of the anti-ETEC adhesin protein antibodies of the invention are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

In certain embodiments, antibody variants having one or more amino acid substitutions are provided. Sites of interest for substitutional mutagenesis include the CDRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 1

Exemplary and Preferred Amino Acid Substitutions

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.

Non-conservative substitutions will entail exchanging a member of one of these classes for another class.

One type of substitutional variant involves substituting one or more hypervariable region residues of a parent antibody (e.g., an isolated VHH antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g., binding affinity).

Alterations (e.g., substitutions) may be made in CDRs, for example, to improve antibody affinity. Such alterations may be made in CDR "hotspots," i.e., residues encoded by codons that undergo mutation at high frequency during the somatic maturation process, and/or residues that contact antigen, with the resulting variant VHH binding domain being tested for binding affinity. Affinity maturation by constructing and reselecting from secondary libraries is known in the art. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L$_3$, in particular, are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may, for example, be outside of antigen contacting residues in the CDRs. In certain embodiments of the variant VHH binding domain sequences provided above, each CDR either is unaltered, or contains no more than one, two, or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, And Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, alternations may be made to the Fc region, when present, of an antibody. These alterations can be made alone, or in addition to, alterations to the VHH binding domain or regions thereof (e.g., one or more CDRs or FRs). The alterations to the Fc region, when present, may result in enhanced antibody effector functions (e.g., complement-dependent cytotoxicity (CDC)), for example, by increasing C1q avidity to opsonized cells. Exemplary mutations that enhance CDC include, for example, Fc mutations E345R, E430G, and S440Y. Accordingly, anti-ETEC adhesin protein antibodies of the invention may contain one or more CDC-enhancing Fc mutations, which promote IgG hexamer formation and the subsequent recruitment and activation of C1, the first component of complement (see, e.g., Diebolder et al. *Science*. 343: 1260-1263, 2014).

In certain embodiments, alterations of the amino acid sequences of the Fc region of the antibody may alter the half-life of the antibody in the host. Certain mutations that alter binding to the neonatal Fc receptor (FcRn) may extend half-life of antibodies in serum. For example, antibodies that have tyrosine in heavy chain position 252, threonine in position 254, and glutamic acid in position 256 of the heavy chain can have dramatically extended half-life in serum (see, e.g., U.S. Pat. No. 7,083,784).

B. Production of Anti-ETEC Adhesin Protein VHH Antibodies

1. Immunizations

A mammal from the Camelidae family (e.g., llamas, camels, or alpacas) can be subcutaneously immunized with N-terminal fragments representing class 5 of ETEC antigens. A phage-displayed VHH library can be constructed from PBMC total RNA, retrieved from the mammal, and selection of target-binding VHHs can be performed by phage-display selections as described in Hultberg, A., et al (*PLoS One* 6(4): e17665, 2011), which is incorporated by reference herein in its entirety. The initial screening can be performed with desired antigens (e.g., an ETEC adhesin protein (e.g., CfaE, CS4, CS14, CS1, CS17, CS19, CS2, or PCF071)). Additionally, another round of screening can be performed with a different ETEC adhesin protein antigen.

Identified clones of interest can be completely sequenced and clones including unique sequences can be selected for further characterization.

2. Yeast Library Screening

Yeast library screening can be performed as described in McMahon et al. *Nat. Struct. Mol. Biol.* 25: 289-296, 2018, which is incorporated by reference herein in its entirety. For a first round of magnetic-activated cell sorting (MACS), $1 \times 10^{10}$ *S. cerevisiae* cells expressing a surface displayed library of synthetic nanobodies (see McMahon et al. *Nat. Struct. Mol. Biol.* 25: 289-296, 2018) can be centrifuged, resuspended in binding buffer (20 mM HEPES pH 7.5, 150 mM NaCl, 2.8 mM CaCl$_2$, 0.05% MNG, 0.005% CHS, 0.1% BSA, 0.2% maltose), and then incubated with anti-fluorescein isothiocyanate (FITC) microbeads (Miltenyi Biotec) and FITC labeled MBP for 40 min at 4° C. The selected yeast can then be passed through an LD column (Miltenyi Biotec) to remove any yeast expressing nanobodies which interacted with the microbeads or MBP. Remaining yeast that flow through the column can be centrifuged, resuspended in binding buffer, and incubated with 1 mM of FITC-labeled N-terminal ETEC adhesin (e.g., CfaE, CS4, CS14, CS1, CS17, CS19, CS2, or PCF071) protein for 1 h at 4° C. Yeast can then be centrifuged, resuspended in binding buffer with anti-FITC microbeads, and incubated for 15 min at 4° C. before passing into an LS column (Miltenyi Biotec) and collecting the eluate enriched for ETEC adhesin-binding nanobodies. The eluted yeast can be expanded and used in a subsequent round of MACS to further enrich for ETEC adhesin-binding nanobodies. A second round can be performed similarly to the first, but beginning with $4 \times 10^8$ yeast and substituting FITC-labeled ETEC adhesin protein with AlexaFluor647-labeled ETEC adhesin protein, and anti-FITC microbeads with anti-AlexaFluor647 microbeads. High-affinity binding yeast can be isolated with FACS. In the first round of FACS, yeast binding to 300 nM of AlexaFluor488 labeled ETEC adhesin protein can be collected. The yeast can be grown and subjected to a second round of FACS in the presence of human monoclonal antibody capable of binding to an ETEC adhesin protein (e.g., a human monoclonal antibody of Guintini et al. *Infect. Immun.* 86(8): e00355-18, 2018) that was shown to bind in the proximity of the receptor binding domain of CfaE). Clones that are outcompeted from binding to the antigen can be collected. Individual clones from the two rounds of FACS can be grown, stained in a 96-well plate, assessed via flow cytometry for binding specificity to an ETEC adhesin protein (e.g., CfaE, CS4, CS14, CS1, CS17, CS19, CS2, or PCF071), and subsequently sequenced. Clones with unique sequences can be isolated and chosen for further characterization, that included further panning with FITC-labeled ETEC adhesin proteins (e.g., class 5 adhesins CS1 (class5b) and CS2 (class5c)).

3. Nanobody Purification Nanobody sequences can be ligated into a suitable vector (e.g., a pET26b vector), and a tag (e.g., a C-terminal 6×His tag) can be added to the nanobody sequence to aid in purification. Sequence-verified clones can be transformed into T7 Express lysY BL21 *E. coli*. Bacteria can be grown in Terrific Broth containing 1 mM $MgCl_2$ and 0.01% glucose to an OD600=0.7 before induction with 1 mM IPTG. Cells can be harvested after an overnight incubation at 27° C. Following osmotic shock, nanobodies can be purified from the periplasmic fraction by Ni-NTA chromatography (Gold Biotechnology) and dialyzed against PBS to remove imidazole.

4. Recombinant Generation of VHH Antibodies to an ETEC Adhesin Protein

Anti-ETEC adhesin protein VHH antibodies of the invention (e.g., antibodies including anti-ETEC adhesin protein VHH binding domains 2R215, 1D7, 2R23, and 1H4, or variants thereof) may be produced using recombinant methods and compositions, for example, as described in U.S. Pat. No. 4,816,567. In one embodiment, isolated nucleic acid encoding an anti-ETEC adhesin protein antibody described herein is provided. Such nucleic acid may encode an amino acid sequence comprising the VHH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with) a vector comprising a nucleic acid that encodes an amino acid sequence comprising the VHH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-ETEC adhesin protein antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-ETEC adhesin protein antibody, nucleic acid encoding an antibody, e.g., as described above, can be isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of anti-ETEC adhesin protein antibody-encoding vectors include prokaryotic or eukaryotic cells described herein. For example, antibodies may be produced in bacteria, in particular when glycosylation and Fc effector function are not needed, or when an Fc region is not present. After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern.

Suitable host cells for the expression of anti-ETEC adhesin protein VHH antibodies are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. Furthermore, high expression of IgA-Fc fusions can be easily produced in plant seeds (e.g., *Arabidopsis*, tobacco, rice, and soybean) and are specifically contemplated for the production of anti-ETEC adhesin protein VHH antibodies provided herein.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells, and myeloma cell lines such as Y0, NS0, and Sp2/0.

C. Characterization of Anti-ETEC Adhesin Protein VHH Antibodies

Sequence information for VHH antibodies of the invention can be ascertained using sequencing techniques which are well known in the art.

Similarly, affinity of the antibodies for ETEC adhesin proteins can also be assessed using standard techniques. For example, BIACORE 3000 can be used to determine the affinity of VHH antibodies to ETEC adhesin proteins. VHH antibodies are captured on the surface of a BIACORE® chip (GE healthcare), for example, via amine coupling (Sensor Chip CM5). The captured VHH antibodies can be exposed to various concentrations of ETEC adhesin proteins (e.g., CfaE, CS4, CS14, CS1, CS17, CS19, CS2, or PCF071) in solution, and the $K_{on}$ and $K_{off}$ for an affinity ($K_D$) can be calculated, for example, by BIAevaluation software.

VHH antibodies of the invention can also be characterized for binding to ETEC adhesin proteins using a variety of known techniques, such as ELISA, Western blot, etc. Generally, the antibodies are initially characterized by ELISA. Briefly, microtiter plates can be coated with purified ETEC adhesin protein(s) (e.g., CfaE) in PBS, and then blocked with irrelevant proteins such as bovine serum albumin (BSA) diluted in PBS. Dilutions of plasma from ETEC adhesin protein immunized mammals from the Camelidae family (e.g., llamas, camels, and alpacas), or purified VHHs are added to each well and incubated for 1-2 hours at 37° C. The plates are washed with PBS/Tween 20 and then incubated with a hydroxy peroxidase-conjugated rabbit anti-camelid IgG Fc (1:10,000) for 1 h for staining. After staining, the plates can be developed using TMB Peroxidase substrate (SeraCare) and analyzed at OD of 450.

In some instances, an ELISA assay as described above can be used to screen for antibodies and, thus, hybridomas that produce antibodies that show positive reactivity with the ETEC adhesin protein immunogen (e.g., CfaE, CS4, CS14, CS1, CS17, CS19, CS2, or PCF071). Hybridomas that bind, preferably with high affinity, to an ETEC adhesin protein (e.g., CfaE, CS4, CS14, CS1, CS17, CS19, CS2, or PCF071) can then be subcloned and further characterized. One clone from each hybridoma, which retains the reactivity of the parent cell (by ELISA), can then be chosen for making a cell bank, and for antibody purification.

In some instances, the antibodies can be evaluated by a mannose-resistant hemagglutination (MRHA) assay of human group A erythrocyte inhibition. The MRHA assay is considered a surrogate method for assessment of ETEC adhesion to the intestinal mucosa (Hagberg et al., *Infect. Immun.* 31:564-570, 1981). In summary, the MRHA assay is performed as follows. First, ETEC cultures are taken from frozen cell banks and diluted in saline solution, reaching an $OD_{600nm}$ of 1 for the assay. Human erythrocytes type A+ are washed in saline solution and resuspended in the same solution. Serial antibody dilutions are prepared in a 96-well plate. The diluted ETEC and a solution of D-mannose are added to each well, then incubated at room temperature for 10 minutes. After incubation, the blood solution is added to the plates and mixed well, then allowed to sit stagnant at 4° C. for two hours. Hemagglutination is then observed without the aid of magnification. The absence of a pellet of red blood cells at the bottom of the well is indicative of positive hemagglutination.

In other instances, the antibodies are evaluated for their ability to inhibit binding of ETEC to intestinal cells by a Caco-2 cell adhesion assay. Briefly, Caco-2 cells are seeded and grown in 24-well tissue plates containing Dulbecco's modified Eagle's medium (DMEM), and frozen bacterial banks are streaked on CFA agar plates and grown overnight at 37° C. Bacteria are then resuspended in PBS and diluted until reaching an $OD_{600nm}$ of 0.1. Serial antibody dilutions are also prepared in a deep well plate. The antibody dilutions and bacteria are combined and allowed to shake at 300 rpm for one hour at room temperature. The antibody/bacteria mixture is then added to Caco-2 cells and incubated statically for 3 hours at 37° C. After incubation, cells are washed with PBS to remove non-adherent ETEC cells, then dislodged with trypsin, collected via centrifugation, and resuspended in PBS. Dilutions are plated on CFA agar plates and colonies are counted the next day.

In other instances, competition assays may be used to identify an antibody that competes with an anti-ETEC adhesin protein antibody of the invention for binding to an ETEC adhesin protein. In certain embodiments, such a competing antibody binds to the same epitope (e.g., a linear or a conformational epitope) that is bound by an anti-ETEC adhesin protein antibody of the invention. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized ETEC adhesin protein (e.g., CfaE) can be incubated in a solution comprising a first labeled antibody that binds to an ETEC adhesin protein (e.g., CfaE) and a second unlabeled antibody that is being tested for its ability to compete with the first antibody for binding to the ETEC adhesin protein (e.g., CfaE). As a control, immobilized ETEC adhesin protein (e.g., CfaE) can be incubated in a solution comprising the first labeled antibody but not the second unlabeled antibody. After incubation under conditions permissive for binding of the first antibody to an ETEC adhesin protein (e.g., CfaE), excess unbound antibody can be removed, and the amount of label associated with immobilized ETEC adhesin protein (e.g., CfaE) can be measured. If the amount of label associated with immobilized ETEC adhesin protein (e.g., CfaE) is substantially reduced in the test sample relative to the control sample, then that indicates that the second antibody is competing with the first antibody for binding to an ETEC adhesin protein (e.g., CfaE).

D. Pharmaceutical Compositions

In another aspect, the present invention provides a composition, e.g., a pharmaceutical composition, containing one or more (e.g., 1, 2, 3, or 4 or more) of the anti-ETEC adhesin protein VHH antibodies, or antibody fragments thereof, of the present invention. The pharmaceutical compositions may be formulated together with a pharmaceutically acceptable carrier, excipient, or diluent. In some instances, the pharmaceutical compositions include two or more of the anti-ETEC VHH antibodies of the invention. In some instances, each of the antibodies of the composition binds to distinct ETEC adhesin proteins. Preferably, each of the antibodies of the composition binds to a distinct, preselected epitopes of ETEC adhesin proteins.

A pharmaceutical composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

The anti-ETEC adhesin protein antibodies of the invention may be orally administered as a pharmaceutical composition, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the anti-ETEC adhesin protein antibodies of the invention may be incorporated with an excipient and used in the form of ingestible tablets, buccal tablets, troches, capsules, elixirs, suspensions, syrups, and wafers. Oral formulations including antibodies are described in Jaison et al., *Nutrition Journal*. 14:22 (2015), which is incorporated herein by reference in its entirety. For example, the anti-ETEC adhesin protein antibodies may be formulated in a lyophilized composition, mixed into a liquid or a powder formulation. The anti-ETEC adhesin protein antibodies may also be formulated in enteric-coated capsules containing the antibodies. The composition formulated for oral administration may contain at least 0.01% (w/v) of the antibody. For example, the composition may contain about 0.1% to 70% (w/v) of the antibody, e.g., about 0.1% to 65% (w/v), about 0.1% to 65% (w/v), about 0.1% to 55% (w/v), about 0.1% to 50% (w/v), about 0.1% to 45% (w/v), about 0.1% to 40% (w/v), about 0.1% to 35% (w/v), about 0.1% to 30% (w/v), about 0.1% to 25% (w/v), about 0.1% to 20% (w/v), about 0.1% to 15% (w/v), about 0.1% to 10% (w/v), about 0.1% to 5% (w/v), about 0.1% to 2% (w/v), about 2% to 70% (w/v), or about 2% to 60% (w/v) of the antibody.

Pharmaceutical compositions of the invention also can be administered in combination therapy, i.e., combined with other agents. For example, the combination therapy can include a composition of the present invention with at least one or more additional therapeutic agents as necessary for the particular indication (e.g., ETEC-related diarrhea) being treated.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions.

Sustained-release preparations may be prepared. Suitable examples of sustained-release preparations include semipermeable matrices of solid hydrophobic polymers containing the antibody, which matrices are in the form of shaped articles, for example, films, or microcapsules.

The formulations to be used for in vivo administration are generally sterile. Sterility may be readily accomplished, e.g., by filtration through sterile filtration membranes. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof. Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, such as TWEEN® 80. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Alternatively, genes encoding the anti-ETEC adhesin protein antibodies of the invention may be delivered directly into the subject for expression rather than administering purified antibodies for prevention or therapy. For example, viral vectors, such as recombinant viruses, can be used to deliver the heavy and light chain genes. In one example, rAAV virus particles can be used to deliver anti-ETEC adhesin protein antibodies (Balazs et al. *Nature.* 481: 81, 2012). Antibody genes could also be effectively delivered by electroporation of muscle cells with plasmid DNA containing heavy chain genes (e.g., VHH) (Muthumani et al. *Hum Vaccin Immunother.* 10: 2253, 2013). Lentivirus vectors or other nucleic acids (e.g., RNA) capable of delivering transgenes could also be used to deliver antibody genes to establish serum antibody levels capable of prevention.

Also within the scope of the present invention are kits including human anti-ETEC adhesin protein VHH antibodies of the invention and, optionally, instructions for use. The kits can further contain one or more additional reagents, such as a second, different anti-ETEC adhesin protein VHH antibody having a complementary activity that binds to an epitope on an ETEC adhesin protein (e.g., CfaE) that is distinct from the epitope to which the first anti-ETEC adhesin protein VHH antibody binds.

E. Therapeutic Methods and Related Compositions for Use

Any of the anti-ETEC adhesin protein antibodies of the invention (e.g., antibodies including anti-ETEC adhesin protein VHH binding domains 2R215, 1D7, 2R23, and/or 1H4) and compositions containing the antibodies can be used in a variety of in vitro and in vivo therapeutic applications.

In one aspect, the invention features a method of treating a subject having a disorder associated with an ETEC infection (e.g., ETEC-related diarrhea) comprising administering a therapeutically effective amount of a monoclonal antibody (e.g., a human monoclonal antibody) that specifically binds to an ETEC adhesin protein, or a pharmaceutical composition thereof, thereby treating the subject.

In another aspect, an anti-ETEC adhesin protein VHH antibody of the invention may be used in a method of treating a subject having a disorder associated with an ETEC infection (e.g., ETEC-related diarrhea). In one embodiment, the method comprises administering to a subject having such a disorder associated with an ETEC infection (e.g., ETEC-related diarrhea) a therapeutically effective amount of one or more (e.g., 1, 2, 3, or 4 or more) anti-ETEC adhesin protein antibodies of the invention or a pharmaceutical composition(s) including the one or more anti-ETEC adhesin protein antibodies.

In another aspect, an anti-ETEC adhesin protein antibody of the invention may be used in a method of treating a subject at risk of developing a disorder associated with an ETEC infection (e.g., treating a subject at risk of developing a disorder associated with an ETEC infection with an anti-ETEC adhesin protein antibody of the invention in order to prevent the subject from developing a disorder associated with an ETEC infection, such as ETEC-related diarrhea). In one embodiment, the method comprises administering to a subject at risk of developing a disorder associated with an ETEC infection a therapeutically effective amount of one or more (e.g., 1, 2, 3, or 4 or more) anti-ETEC adhesin protein antibodies of the invention or a pharmaceutical composition(s) including the one or more anti-ETEC adhesin protein antibodies. In some instances, a subject can be considered at risk of an ETEC infection if the subject is in a geographic region in which ETEC is commonly found (e.g., in Asia, the Middle East, Africa, and Central and South America). In other instances, subject can be considered at risk of an ETEC infection if the subject had travelled, or will travel, to a geographic region in which ETEC is commonly found.

Antibodies of the invention can be used either alone or in combination with other agents in a therapy. For instance, an antibody of the invention may be co-administered with at least one additional therapeutic agent. Such combination therapies encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-ETEC adhesin protein antibody (e.g., antibodies including anti-ETEC adhesin protein VHH binding domains 2R215, 1D7, 2R23, and/or 1H4) and administration of an additional therapeutic agent occur within about one month, or within about one, two or three weeks, or within about one, two, three, four, five, or six days, of each other.

An antibody of the invention, such as antibodies including anti-ETEC adhesin protein VHH binding domains 2R215, 1D7, 2R23, and/or 1H4 (and/or any additional therapeutic agent) can be administered by any suitable means, including oral, parenteral, intrapulmonary, and intranasal, and, if desired for local treatment, intralesional administration. Parenteral infusions include intramuscular, intravenous, intraarterial, intraperitoneal, or subcutaneous administration. Preferably, the antibodies are administered orally or subcutaneously. In certain instances, antibody genes (e.g., genes encoding any one or more of the anti-ETEC adhesin protein antibodies of the invention could be administered as a gene therapy to produce the one or more anti-ETEC adhesin protein antibodies in the subject using either DNA vectors or viral vectors (e.g., rAAV vectors). Dosing can be by any suitable route, for example, by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with, one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, such as ETEC-related diarrhea, the appropriate dosage of an antibody of the invention (when used alone or in combination with one or more other additional therapeutic agents) will depend on the type of disease to be prevented/treated, the duration of effective antibody concentration required, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. In some embodiments, a dosing schedule can include delivery, for example oral delivery, 1-3 days before a subject is at risk of developing a disorder associated with an ETEC infection (e.g., −3 days, −2 days, and/or −1 day), on the day a subject is at risk of developing a disorder associated with an ETEC infection (e.g., 0 day), and/or 1-3 days after a subject was at risk of developing a disorder associated with an ETEC infection (e.g., +1 day, +2 days, and/or +3 days). In some embodiments, a dosing schedule can include delivery, for example oral delivery, on the day before a subject is at risk of developing a disorder associated with an ETEC infection (e.g., −1 days), the day a subject is at risk of developing a disorder associated with an ETEC infection (e.g., 0 day), and/or on the day after a subject is at risk of developing a disorder associated with an ETEC infection (e.g., +1 day).

As a general proposition, the therapeutically effective amount of the anti-ETEC adhesin protein antibody administered to human will be in the range of about 0.01 to about 100 mg/kg of patient body weight whether by one or more administrations. In some embodiments, the antibody used is about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.1 to about 10 mg/kg, or about 1 to about 10 mg/kg administered one (single administration) or more times (multiple administrations, e.g., daily administrations). In one example, the antibody used is about 10 mg/kg, preferably administered orally. In one embodiment, an anti-ETEC adhesin protein antibody described herein is administered to a human at a flat dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. For repeated administrations over several days or longer, depending on the condition, the treatment would generally be sustained until a desired suppression of disease symptoms occurs. One exemplary dosage of the antibody would be in the range from about 0.01 mg/kg to about 10 mg/kg. Such doses may be administered intermittently, for example, every week or every three weeks (e.g., such that the patient receives from about two to about twenty, or, for example, about six doses of the anti-ETEC adhesin protein antibody). An initial higher loading dose, followed by one or more lower doses may be administered. The progress of this therapy is easily monitored by conventional techniques and assays.

The anti-ETEC adhesin protein antibodies of the invention may be orally administered as a pharmaceutical composition, for example, with an inert diluent or with an assimilable edible carrier; may be enclosed in hard or soft shell gelatin capsules; may be compressed into tablets; or may be incorporated directly with the food of the diet. For oral therapeutic administration, the anti-ETEC adhesin protein antibodies of the invention may be incorporated with an excipient and used in the form of ingestible tablets, buccal tablets, troches, capsules, elixirs, suspensions, syrups, and wafers. Oral formulations including antibodies are described in Jaison et al., *Nutrition Journal*. 14:22 (2015), which is incorporated herein by reference in its entirety. For example, the anti-ETEC adhesin protein antibodies may be formulated in a lyophilized composition, mixed into a liquid or a powder formulation. The anti-ETEC adhesin protein antibodies may also be formulated in enteric-coated capsules containing the antibodies. The composition formulated for oral administration may contain at least 0.01% (w/v) of the antibody. For example, the composition may contain about 0.1% to 70% (w/v) of the antibody, e.g., about 0.1% to 65% (w/v), about 0.1% to 65% (w/v), about 0.1% to 55% (w/v), about 0.1% to 50% (w/v), about 0.1% to 45% (w/v), about 0.1% to 40% (w/v), about 0.1% to 35% (w/v), about 0.1% to 30% (w/v), about 0.1% to 25% (w/v), about 0.1% to 20% (w/v), about 0.1% to 15% (w/v), about 0.1% to 10% (w/v), about 0.1% to 5% (w/v), about 0.1% to 2% (w/v), about 2% to 70% (w/v), or about 2% to 60% (w/v) of the antibody.

Pharmaceutical compositions of the invention also can be administered in combination therapy, i.e., combined with other agents. For example, the combination therapy can include a composition of the present invention with at least one or more additional therapeutic agents as necessary for the particular indication (e.g., ETEC-related diarrhea) being treated.

Actual dosage levels of the active ingredients in the pharmaceutical compositions of the present invention may be varied so as to obtain an amount of the active ingredient which is effective to achieve the desired therapeutic response and duration for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian can start doses of the compounds of the invention employed in the pharmaceutical composition at levels lower than that required in order to achieve the desired therapeutic effect and gradually increase the dosage until the desired effect is achieved. In general, a suitable daily dose of compositions of the invention will be that amount of the compound which is the lowest dose effective to produce a therapeutic effect. Such an effective dose will generally depend upon the factors described above. If desired, the effective daily dose of therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. The liposomes may comprise one or more moieties which are selectively transported into specific cells or organs, thus enhance targeted drug delivery. Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134), different species of which may comprise the formulations of the inventions, as well as components of the invented molecules; p 120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

In some instances, the antibody-based therapy may be combined with an additional therapy for more efficacious treatment (e.g., additive or synergistic treatment) of the subject. Accordingly, subjects treated with antibodies of the invention can be additionally administered (prior to, simultaneously with, or following administration of a human antibody of the invention) with another therapeutic agent which enhances or augments the therapeutic effect of the human antibodies.

F. Methods and Compositions for Detection or Diagnosis

In certain embodiments, any of the anti-ETEC adhesin protein antibodies of the invention are useful for in vitro or in vivo detection of the presence of an ETEC adhesin protein (e.g., CfaE, CS4, CS14, CS1, CS17, CS19, CS2, CS3, CS5, CS6, CS21, or PCF071) in a biological sample (e.g., a swab sample, a lavage sample, a blood sample, a plasma sample, a sputum sample, a urine sample, a stool sample, a sample from the mucosal lining of the small intestine, or a mucosal secretion sample). The term "detecting" as used herein encompasses quantitative or qualitative detection. In some embodiments, the sample is from a subject presumed to have an ETEC infection (e.g., a subject showing symptoms of an ETEC adhesin protein (e.g., ETEC-related diarrhea)).

In some aspects, an anti-ETEC adhesin protein antibody for use in a method of diagnosis (e.g., diagnosis of a disorder associated with an ETEC infection) or detection (e.g., detection of an ETEC infection) is provided. For example, in one aspect, a method of detecting an ETEC (e.g., detecting the presence of an ETEC adhesin protein (e.g., CfaE, CS4, CS14, CS1, CS17, CS19, CS2, CS3, CS5, CS6, CS21, or PCF071)) in a biological sample is provided. In certain embodiments, the method comprises contacting the biological sample with an anti-ETEC adhesin protein antibody as described herein under conditions permissive for binding of the anti-ETEC adhesin protein antibody to the ETEC adhesin protein (e.g., CfaE, CS4, CS14, CS1, CS17, CS19, CS2, CS3, CS5, CS6, CS21, or PCF071), and detecting whether a complex is formed between the anti-ETEC adhesin protein antibody and ETEC adhesin protein (e.g., CfaE, CS4, CS14, CS1, CS17, CS19, CS2, CS3, CS5, CS6, CS21, or PCF071). Such a method of detection may be an in vitro or in vivo method.

In another aspect, an anti-ETEC adhesin protein VHH antibody for use in a method of diagnosis (e.g., diagnosis of a disorder associated with an ETEC infection) is provided. In certain embodiments, the method includes contacting the biological sample with an anti-ETEC adhesin protein antibody as described herein under conditions permissive for binding of the anti-ETEC adhesin protein antibody to the ETEC adhesin protein (e.g., CfaE, CS4, CS14, CS1, CS17, CS19, CS2, CS3, CS5, CS6, CS21, or PCF071), and detecting whether a complex is formed between the anti-ETEC adhesin protein antibody and ETEC (e.g., CfaE, CS4, CS14, CS1, CS17, CS19, CS2, CS3, CS5, CS6, CS21, or PCF071). Such a diagnostic method may be an in vitro or in vivo method.

In certain embodiments, labeled anti-ETEC adhesin protein antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

G. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. In some embodiments, the invention provides a kit comprising an antibody of the invention and a package insert with instructions for using the antibody for treating a subject having or at risk of developing a disorder associated with an ETEC infection (e.g., ETEC-related diarrhea). In some embodiments, the invention provides a kit for detecting ETEC including an antibody of the invention and a package insert with instructions for using the antibody to detect ETEC. In some embodiments, the antibody is conjugated to a label or a tag. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Other embodiments of the present invention are described in the following Examples. The present invention is further illustrated by the following examples which should not be construed as further limiting. The contents of Sequence Listing, figures and all references, patents and published patent applications cited throughout this application are expressly incorporated herein by reference.

III. EXAMPLES

The following are examples of the methods and compositions of the invention. It is understood that various other embodiments may be practiced, given the description provided herein.

Example 1. Materials and Methods

Antigen Cloning, Expression, Purification

The nucleic acid sequences of N-terminal adhesin domains of CfaE and class 5 adhesins (GenBank M55661) were cloned into a pMAL-C5X vector (Addgene) in-frame with an MBP tag to express as periplasmic proteins with improved solubility (MBP-CfaE-N). The donor strand complement was included to ensure the overall protein expression and stability, as reported previously (Poole S T et al, 2007). All cloned constructs were transformed into SHuffleT7 Competent *Escherichia coli* (NEB), and expression was induced with 1 mM IPTG (isopropyl-D-thiogalactopyranoside). Bacteria were lysed, and proteins were purified with amylose resin (NEB) and eluted with 20 and 50 mM maltose (Sigma).

Alpaca Immunization

Alpaca immunization was performed as described in Section B above. Briefly, two male alpacas were subcutaneously immunized with N-terminal fragments representing class 5 of ETEC antigens. Good immune response was observed against all antigens. A phage-displayed VHH library was constructed from PBMC total RNA and selection of target-binding VHHs was performed by phage-display selections as previously described, for example, in Hultberg, A., et al (supra, 2011). The initial screening was performed with colonization factor antigens CS1 and CS2. Additionally, another round of screening was performed with CfaE antigen.

Two master plates containing 92 clones each were completely sequenced and total of 54 clones with unique sequences were selected for further characterization.

Yeast Library Screening

Yeast display library screening was performed as described in Section B above. Briefly, yeast library screening was performed as previously described (McMahon et al, supra, 2018). For the first round of magnetic-activated cell sorting (MACS), $1\times10^{10}$ S. cerevisiae, cells expressing a surface displayed library of synthetic nanobodies (McMahon et al., id, 2018), were centrifuged, resuspended in binding buffer (20 mM HEPES pH 7.5, 150 mM NaCl, 2.8 mM $CaCl_2$, 0.05% MNG, 0.005% CHS, 0.1% BSA, 0.2% maltose) and then incubated with anti-fluorescein isothiocyanate (FITC) microbeads (Miltenyi Biotec) and FITC labeled MBP for 40 min at 4° C. The selected yeast were then passed through an LD column (Miltenyi Biotec) to remove any yeast expressing nanobodies which interacted with the microbeads or MBP. Remaining yeast that flowed through the column were centrifuged, resuspended in binding buffer, and incubated with 1 mM of FITC-labeled N-terminal CfaE protein for 1 h at 4° C. Yeast were then centrifuged, resuspended in binding buffer with anti-FITC microbeads, and incubated for 15 min at 4° C. before passing them into an LS column (Miltenyi Biotec) and collecting the eluate enriched for CfaE-binding nanobodies. The eluted yeast were expanded and used in a subsequent round of MACS to further enrich for CfaE-binding nanobodies. The second round was performed similarly to the first, but beginning with $4\times10^8$ yeast and substituting FITC-labeled CfaE with AlexaFluor647-labeled CfaE, and anti-FITC microbeads with anti-AlexaFluor647 microbeads. High affinity binding yeast were isolated with FACS. In the first round of FACS, yeast binding to 300 nM of AlexaFluor488 labeled CfaE were collected. The yeast were grown and subjected to second round of FACS in the presence of human monoclonal antibody (Guintini et al, Infect. Immun. 86(8): e00355-18, 2018) that was shown to bind in the proximity of the receptor binding domain. Clones that were outcompeted from binding to the antigen were collected. About 400 individual clones from two rounds of FACS were then grown, stained in a 96-well plate, assessed via flow cytometry for binding specificity to CfaE, and subsequently sequenced. A total of 30 clones with unique sequences were isolated and chosen for further characterization, that included further panning with FITC-labeled class 5 adhesins CS1 (class5b) and CS2 (class5c).

Nanobody Purification

Nanobody sequences were ligated into pET26b, adding a C-terminal 6xHis tag to the nanobody sequence. Sequence-verified clones were transformed into T7 Express lysY BL21 E. coli. Bacteria were grown in Terrific Broth containing 1 mM $MgCl_2$ and 0.01% glucose to an OD600=0.7 before induction with 1 mM IPTG. Cells were harvested after an overnight incubation at 27° C. Following osmotic shock, nanobodies were purified from the periplasmic fraction by Ni-NTA chromatography (Gold Biotechnology) and dialyzed against PBS to remove imidazole.

ETEC Test Strains

ETEC strain H10407 expressing CFA/I fimbrial protein was purchased from ATCC (ATCC 35401). ETEC strain H10407 was cultured on 2% agar containing 1% Casamino Acids (Sigma) and 0.15% yeast extract (Fisher Bioreagents) plus 0.005% $MgSO_4$ (Sigma) and 0.0005% $MnCl_2$ (Sigma) (CFA agar plates) overnight at 37° C. A total of $1\times10^8$ CFU/ml were resuspended in 20% glycerol (Sigma) in phosphate-buffered saline (PBS) solution and kept frozen at −80° C. until needed. Strains expressing other adhesin proteins were obtain from University of Maryland. These strains included: #200145 (expressing ETEC adhesion protein CS1), #700056 (expressing ETEC adhesin protein CS4), #201546 (expressing ETEC adhesion protein CS2), #503046 (expressing ETEC adhesion protein CS4), #400599 (expressing ETEC adhesion protein CS14), #204648 (expressing ETEC adhesion protein CS19), #100483 (expressing ETEC adhesion protein CS3), #204348 (expressing ETEC adhesion protein CS5), #100001 (expressing ETEC adhesion protein CS6), and #100171 (expressing ETEC adhesion protein CS21).

VHH Multimerization

VHH multimerization was performed as described in Section B above. Briefly, nanobodies 2R215 and 1D7 were multimerized to dimeric and trimeric forms with (GGGGS (SEQ ID NO: 219))$_x$ linkers. The dimeric forms were generated using (GGGGS (SEQ ID NO: 219))$_6$ (SEQ ID NO: 221) linker to connect two monomeric VHHs in tandem N-terminus-to-C-terminus orientation. Trimers were generated using two (GGGGS (SEQ ID NO: 219))$_3$ (SEQ ID NO: 220) linkers between monomeric VHH units. The multimers were cloned into pET26b, adding a C-terminal 6xHis tag to the nanobody sequence. Nanobodies were purified from the periplasmic fraction by Ni-NTA chromatography (Gold Biotechnology) and dialyzed against PBS to remove imidazole.

VHH IgA Fc Fusion

VHH IgA Fc fusion antibodies were developed as described in Section B above. Briefly, VHHs were ligated into a pcDNA 3.1 vector containing heavy constant IgA1 and IgA2 chains without CH1 domain. Each vector was transformed in NEB5 competent cells, and sequences were verified ahead of transient transfection.

ELISA

For binding activity of purified VHHs against CfaE and other antigens, 96-well plates (Nunc) were coated overnight at 4° C. with 2 g/ml of purified MBP-CfaE-N. The plates were blocked with 1% BSA plus 0.05% Tween 20 in PBS. Purified VHHs were diluted in 1 PBS and added to the plates for 1 h. The plates were stained with hydroxy peroxidase-conjugated rabbit anti-camelid IgG Fc (1:10,000) for 1 h and developed using TMB Peroxidase substrate (SeraCare). Absorbance at an optical density at 450 nm (OD450) was measured on an Emax precision plate reader (Molecular Devices).

SPR Analysis

Surface plasmon resonance (SPR) technology was used to assess the binding properties of the VHH molecules (BIACORE® T200 instrument; GE Healthcare). Biotinylated CfaE protein was coupled to a CM5 sensor chip using standard amine coupling chemistry. Various concentrations of lead nanobodies ranging from 1 to 10 ug were injected over the chip surface at a flow rate of 30 l/min. An association step of 60 s was followed by a dissociation step of 180 s, and the final dissociation step was 600 s. Regeneration of the sensor chip surface was accomplished using 3 M $MgCl_2$. Experiments were performed at 25° C. Kinetic data were analyzed using BIACORE® T200 Evaluation (version 3.0) software and a 1:1 binding model. All chemicals for the BIACORE® experiment were purchased from GE Healthcare.

Flow Cytometry

Binding of the yeast surface expressed VHH to fluorescently labeled antigens was determined as described previously (McMahon et al, supra, 2018). Briefly, single clone pools were induced by Galactose in Trp-media. $2 \times 10^6$ cells were stained in selection buffer (McMahon et al, id 2018) in the presence of anti AlexaFluor 647 labeled HA antibody to monitor clone expression, and FITC labeled antigens with the final concentration of 100 nM. To determine whether the VHH antibody was competing with our functional antibody, antibody (100 fold of reported Kd) was included in the staining mixture. Yeast cells were washed, resuspended in the selection buffer and subjected to flow cytometry on MACSquant.

Mannose-Resistant Hemagglutination Assay of Human Group A Erythrocytes

ETEC cultures were taken from frozen cell banks and diluted in a sterile 0.15 M saline solution until an OD600 of 1 was reached for the assay. Type A-positive human erythrocytes stored in K3EDTA were washed three times with 0.15 M saline solution and resuspended in the same solution to a final concentration of 1.5% (vol/vol). In a U-bottom 96-well plate (Nunc Thermo Scientific), 100 ul of VHH was added in duplicate to the top row and diluted 1:2 down the plate in a 0.15 M saline solution. To each well, 50 μl of appropriately diluted ETEC was added together with 50 μl of a 0.1 M D-mannose solution (Sigma). The plate was incubated for 10 min at room temperature. After incubation, 50 μl of blood solution was added to the plate and mixed well (200 μl final volume). Plates were allowed to sit stagnant at 4° C. for 2 h. Hemagglutination was then observed without the aid of magnification. The absence of a pellet of erythrocytes at the bottom of the well is indicative of positive hemagglutination. Blood was ordered fresh every other week (Bioreclamation IVT).

Caco-2 Adhesion Assay

Caco-2 cells seeded at $1 \times 10^4$ cells/ml were grown in 96-well tissue culture plates containing Dulbecco's modified Eagle's medium (DMEM), at 37° C. in 5% CO2 statically. H10407 strain of ETEC was grown overnight at 37° C. in ETEC medium containing 1% Casamino Acids (Sigma) and 0.15% yeast extract (Fisher Bioreagents) plus 0.005% $MgSO_4$ (Sigma) and 0.0005% $MnCl_2$ (Sigma). The next day, bacteria were resuspended in PBS and diluted until an OD600 nm of 0.4 was reached. Antibody dilutions were set up in a deep well plate. Antibody dilutions and bacteria were combined at a 1:10 ratio and allowed to shake at 300 rpm for 1 h at room temperature. Meanwhile, Caco-2 cells were washed and incubated in antibiotic free DMEM containing 500 μg/ml of VHH.

After incubation, 0.035 ml of the mixture of antibody and bacteria was added to each well containing Caco-2 cells. The cells were then incubated statically for 3 h at 37° C. Subsequently, the cells were washed four times with 1 ml PBS to remove nonadherent ETEC cells and intensity of luciferase signal was determined using Victor Nivo Multimode Plate reader (PerkinElmer).

Mouse Intestine Colonization Assays

Six- to eight-week-old DBA/2 mice were pretreated with streptomycin (5 g/liter) in the drinking water for 24 to 48 h. Twelve hours prior to bacterial administration, the water was replaced with regular drinking water. One hour prior to bacterial administration, mice received cimetidine (50 mg/kg) intraperitoneally to reduce the effect of stomach acid on ETEC. A total of 107 CFU of ETEC strain H10407 diluted in PBS were incubated with 100 mg/kg of monomeric anti-CfaE VHH or an irrelevant VHH 1 h prior to challenge. For multimer and IgA Fc fusion VHHs, irrelevant and anti ETEC VHHs were used at 10 mg/kg.

In pre-mix model, bacteria and VHH were administered in 200 μl volume by oral gavage using 20-gauge bulb-tip feeding needles.

In pre-treatment model, mice were pre-treated with 200 μl of VHH for 1 or 2 hours. Bacteria were administered in 100 μl of volume following pre-treatment with the antibody.

The mice were allowed to survive for 24 h. At 12 h before euthanasia, food was withdrawn. Following isolation of the small intestine, two segments of ileum (3 cm each), beginning within 0.5 cm of the ileocecal junction and extending proximally 6 cm, were removed and placed in 1 ml sterile PBS (adapted from Allen K P et al, *Infect. Immun.* 74(2): 869-875, 2006). Tissues were mechanically homogenized. Samples were serially diluted on MacConkey agar plates and incubated overnight at 37° C. Bacterial CFU were counted the next day.

Epitope Mapping

BioLuminate software (Schrödinger) was used to identify CfaE residues involved in antibody-antigen recognition. A total of 22 amino acids predicted by the software to be involved in the interaction between anti-CfaE VHHs and the N-terminal portion of CfaE were individually synthesized by Genscript. The genes were cloned into pMAL-C5x vector, and the resulting 22 constructs were transformed, expressed, and purified as described above. An ELISA was performed to determine binding of the VHHs to the mutant ETEC adhesin proteins in comparison to that of the wild type ETEC adhesin protein.

Statistical Analysis

Statistical calculations were performed using the software Prism version 7.03 (GraphPad Software, La Jolla, Calif.). Comparisons between the hemagglutination or Caco-2 titers of respective antibodies were performed using multiple comparisons, the Bonferroni test, and one-way analysis of variance (ANOVA).

Example 2. Identification of Anti-ETEC Adhesin Protein VHH Antibodies from Immunized Llama and Synthetic Yeast Library Immunized Llama To generate a panel of single domain antibodies with a wide range of cross-reactivity against all class 5 antigens of ETEC, two male alpacas were subcutaneously immunized with N-terminal fragments representing class 5 of ETEC antigens (FIG. 1A; Table 2). Good immune response was observed against all antigens. A phage-displayed VHH library was generated from PBMC total RNA and selection of target-binding VHHs was performed by phage-display selections as previously described Hultberg, A., et al. (supra, 2011). The initial screening was performed with colonization factor antigens CS1 and CS2 because of their relatively low sequence homology. Large number of clones showed binding to both antigens. Additionally, another round of screening was performed with CfaE antigen.

TABLE 2

N-terminal fragments of class 5 ETEC antigens

| ETEC Antigen | N-terminal sequence | SEQ ID NO: |
|---|---|---|
| SS + CFA/I, CfaE | MNKILFIFTLFFSSGFFTFAVSADKNPGSENMTNTI GPHDRGGSSPIYNILNSYLTAYNGSHHLYDRMSFLC LSSQNTLNGACPSSDAPGTATIDGETNITLQFTEKR SLIKRELQIKGYKQFLFKNANCPSKLALNSSHFQCN REQASGATLSLYIPAGELNKLPFGGVWNAVLKLNVK RRYDTTYGTYTINITVNLTDKGNIQ | 211 |
| CsdB, CS17 | GRYPETTVGNLTKSFQAPRQDRSVQSPIYNIFTNHV AGYSLSHNLYDRIVFLCTSSSNPVNGACPTLGTSGV QYGTTTITLQFTEKRSLIKRNINLAGNKKPIVVENQ SCDTSNLMVLNSKSWSCGHYGNANGTLLNLYIPAGE INKLPFGGIWEATLILRLSRYGEVSSTHYGNYTVNI TVDLTDKGNIQVW | 212 |
| CsfD, CS4 | DKIPGDESITNIFGPRDRNESSPKHNILNNHITAYS ESHTLYDRMTFLCLSSHNTLNGACPTSENPSSSSVS GETNITLQFTEKRSLIKRELQIKGYKQLLFKSVNCP SGLTLNSAHFNCNKNAASGASLYLYIPAGELKNLPF GGIWDATLKLRVKRRYSETYGTYTINITIKLTDKGN IQIW | 213 |
| CosD, PCF071 | GRYPETTVGNLTKSFQAPRLDRSVQSPIYNIFTNHV AGYSLSHRLYDRIVFVCTSSSNPVNGACPTIGTSGV EYGTTTITLQFTEKRSLIKRNINLAGNKKPIWENQS CDFSNLMVLNSKSWSCGAQGNANGTLLNLYIPAGEI NKLPFGGIWEATLILRLSRYGEVSSTHYGNYTVNIT VDLTDKGNIQVW | 214 |
| CsuD, CS14 | DKIPGDENITNIFGPRDRNESSPKHNILNDYITAYS ESHTLYDRMIFLCLSSQNTLNGACPTSENPSSSSVS GETNITLQFTEKRSLIKRELQIKGYKRLLFKGANCP SYLTLNSAHYTCNRNSASGASLYLYIPAGELKNLPF GGIWDATLKLRVKRRYDQTYGTYTINITVKLTDKGN IQIW | 215 |
| CsdD, CS19 | GRYPETTVGNLTKSFQAPRLDRSVQSPIYNIFTNHV AGYSLSHRLYDRIVFVCTSSSNPVNGACPTIGTSRV EYGTTTITLQFTEKRSLIKRNINLAGNKKPIWENQS CDTSNLMVLNSKSWSCGALGNANGTLLNLYIPAGEI NKLPFGGIWEATLILRLSRYGEVSSTHYGNYTVNIT VDLTDKGNIQVW | 216 |
| CooD, CS21 | GRYPETTVGNLTKSFQAPRLDRSVQSPIYNIFTNHV AGYSLSHSLYDRIVFLCTSSSNPVNGACPTIGTSGV QYGTTTITLQFTEKRSLIKRNINLAGNKKPIVVENQ SCDFSNLMVLNSKSWSCGAHGNANGTLLNLYIPAGE INKLPFGGIWEATLILRLSRYGEVSSTHYGNYTVNI TVDLTDKGNIQVW | 217 |
| CotD, CS2 | QSWHTNVEAGSINKTESIGPIDRSAAASYPAHYIFH EHVAGYNKDHSLFDRMTFLCMSSTDASKGACPTGEN SKSSQGETNIKLIFTEKKSLARKTLNLKGYKRFLYE SDRCIHYVDKMNLNSHTVKCVGSFTRGVDFTLYIPQ GEIDGLLTGGIWEATLELRVKRHYDYNHGTYKVNIT VDLTDKGNIQVW | 218 |

Two master plates, each containing 92 clones, were completely sequenced and a total of 54 clones with unique sequences were selected for further characterization. The sequences of the 54 selected clones were subcloned into production plasmid pET-26b (+) which also provided them with N-terminal His tag.

Synthetic Yeast Library

Figure 2B:
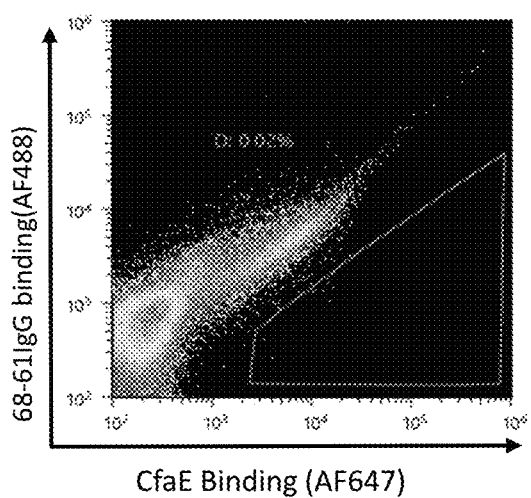

As an alternative approach, we used recently developed library of synthetic nanobodies displayed on the surface of *S. cerevisiae* (McMahon et al, supra, 2018) to identify anti-ETEC VHH antibodies. To enrich for CfaE-binding nanobodies from the naïve library we performed two rounds of magnetic activated cell sorting (MACS) using as antigen FITC and Alexa-Flour 647 labeled N-terminal truncation of CfaE (FIG. 1B). We then performed fluorescent activated cell sorting (FACS) with decreasing concentration of FITC labeled CfaE to enrich for yeast displaying high affinity binders (FIG. 2A). To identify the VHH clones that could potentially bind to receptor binding region of CfaE (Guintini et al, supra, 2018) we performed competition FACS with functional anti-CfaE HuMab 68-61 (Guintini et al, supra, 2018) where we collected the yeast cells expressing VHHs that were outcompeted from binding to the labeled antigen by functional HuMab (FIG. 2B).

Figure 3A:
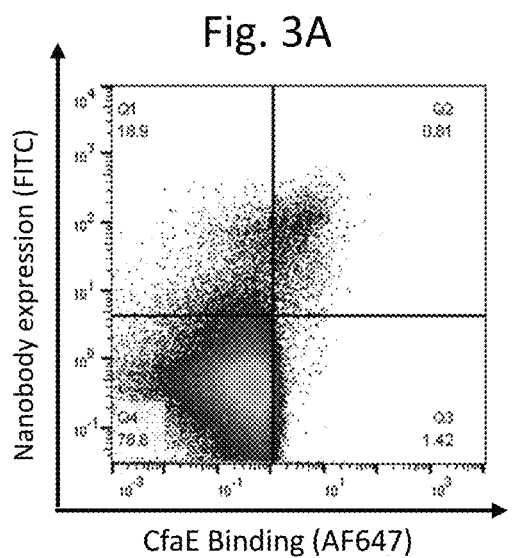
FIGS. 3A-3C are graphs showing representative weak to strong binders of Alexa-647 labeled CfaE using flow cytometry.
Figure 3B:
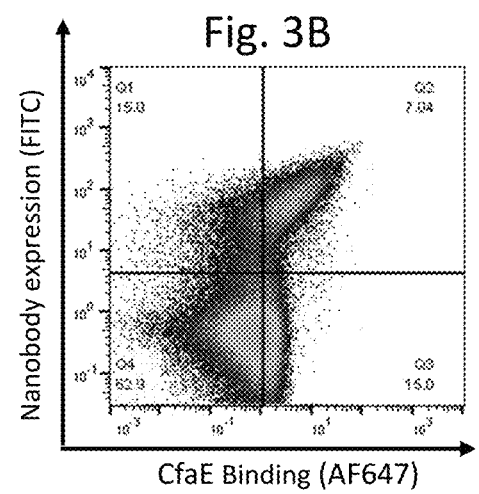
Figure 3C:
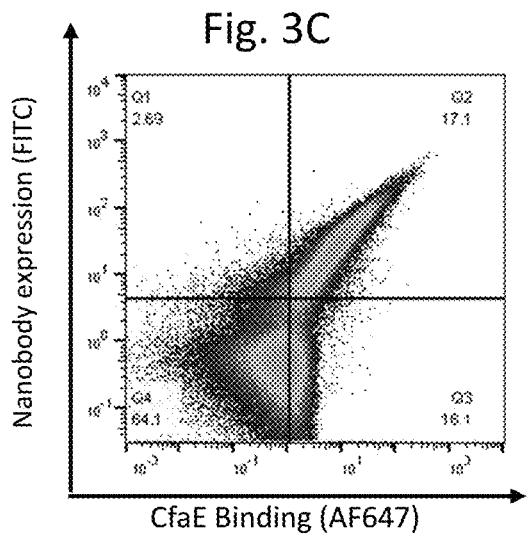
Figure 4A:
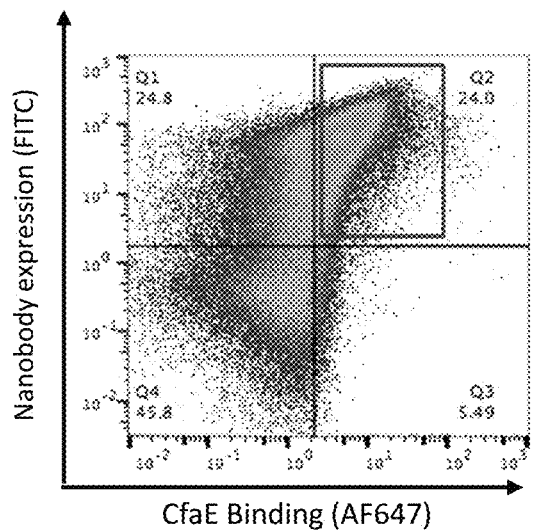
FIGS. 4A-4B are graphs showing clone 2R215 competes for binding in the proximity of the epitope required for the binding of previously described HuMab 68-61.
Figure 4B:
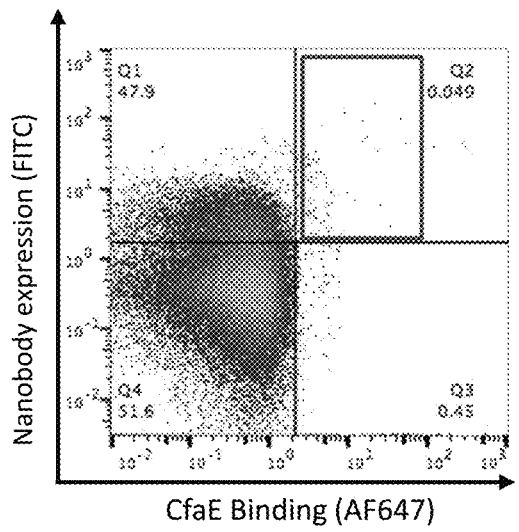

Overall, approximately 300 yeast clones were recovered from naïve library screen. The binding of selected clones expressed on yeast surface to purified Alexa 647 labeled CfaE was verified by flow cytometry. The clones could be classified into weak to strong binders (FIGS. 3A-3C, respectively). Interestingly, only one clone (2R215) competed for the binding in proximity of the epitope required for the binding of previously described functional HuMab 68-61 (FIGS. 4A-4B).

Figure 5A:
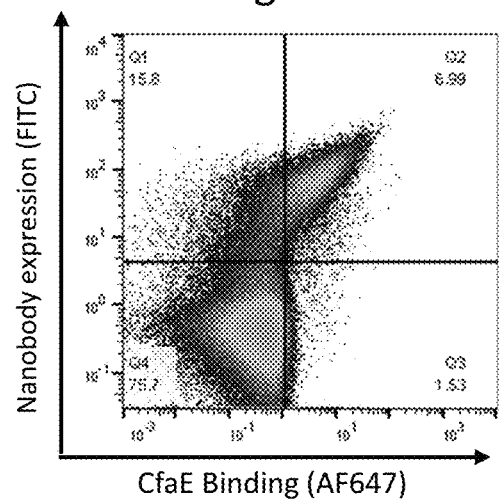
FIGS. 5A-5C are graphs showing VHH antibodies binding to class 5 antigens CfaE (FIG. 5A), coli surface antigen 1 (FIG. 5B), and coli surface antigen 2 (FIG. 5C).
Figure 5B:
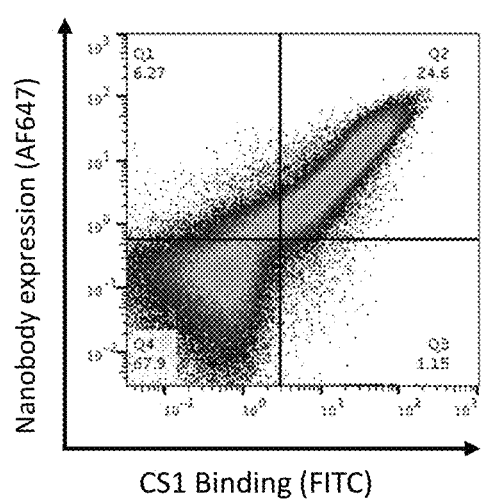
Figure 5C:
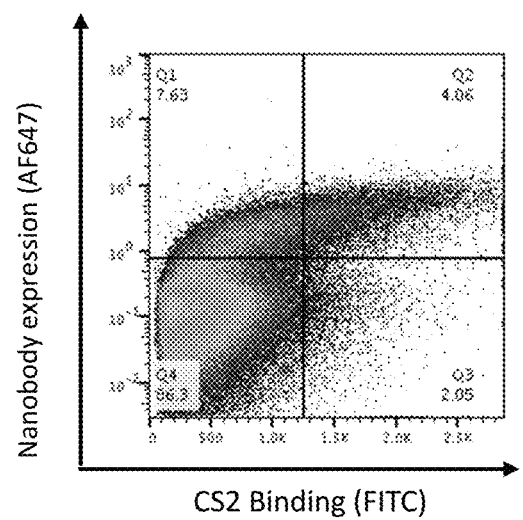

A total of 30 clones were selected based on their CDR3 sequences, and were subsequently screened for binding to two additional class 5 antigens-CS1 and CS2 (FIG. 5A-5C). Yeast clones were then cloned into pET-26b (+) vector for periplasmic expression in *E. coli*.

Example 3. Selected Anti-CfaE VHHs Show Distinct Patterns of Binding to Class 5 Colonization Factors Based on CD3 sequence uniqueness, 2 yeast clones (2R215 and 2R23) and 2 llama-derived clones (1D7 and 1H4) were selected for further characterization.

One of the major advantages of VHH antibodies is the ability to target conserved binding sites on hypervariable pathogens. As a first step of characterization of selected llama- and yeast-derived clones, nanobodies were expressed and purified in *E. coli* and examined in ELISA for binding to recombinant N-terminal truncated CfaE protein and other class 5 colonization factors (FIGS. 6A-6D). An OD below 0.050 was considered as negative binding. All clones showed moderate to strong binding to all ⅞ tested antigens. Interestingly, clone 1D7 did not show binding to recombinant CS2.

Mannose resistant hemagglutination assay (MRHA) has long been considered a surrogate method for the assessment of ETEC adhesion to the intestinal mucosa (Hagberg L U, 1981). Four lead anti-CfaE VHHs were tested for their ability to inhibit MRHA of human group A erythrocytes, as described above.

Figure 6A:
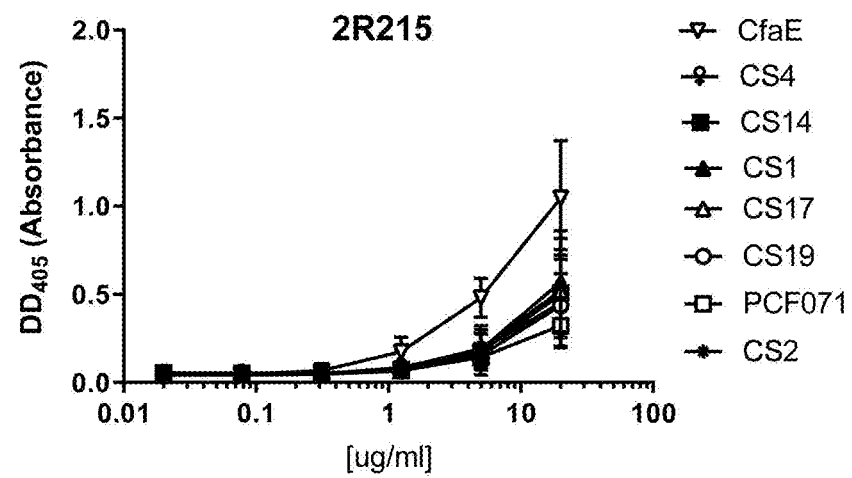
FIGS. 6A-6D are graphs showing anti-ETEC adhesin protein VHH antibodies binding to class 5 colonization factors.
Figure 6B:
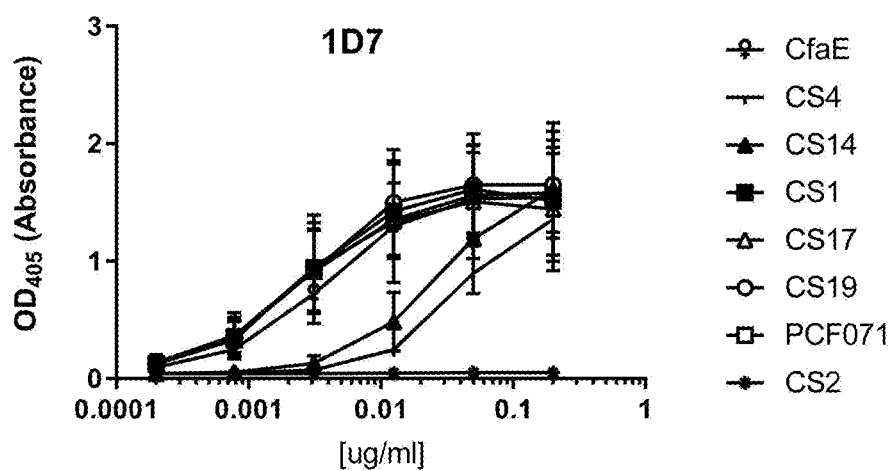
Figure 6C:
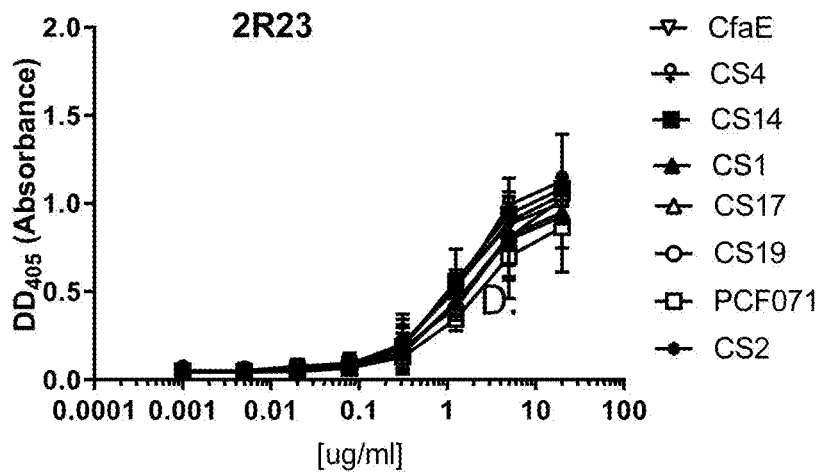
Figure 6D:
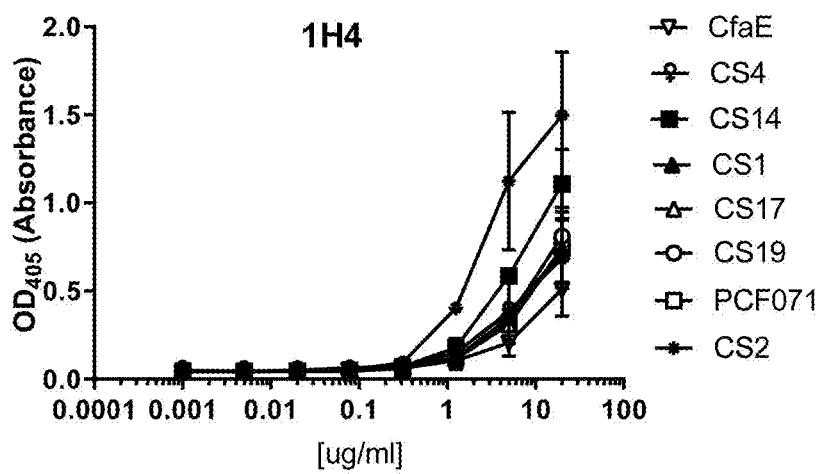
Figure 6E:
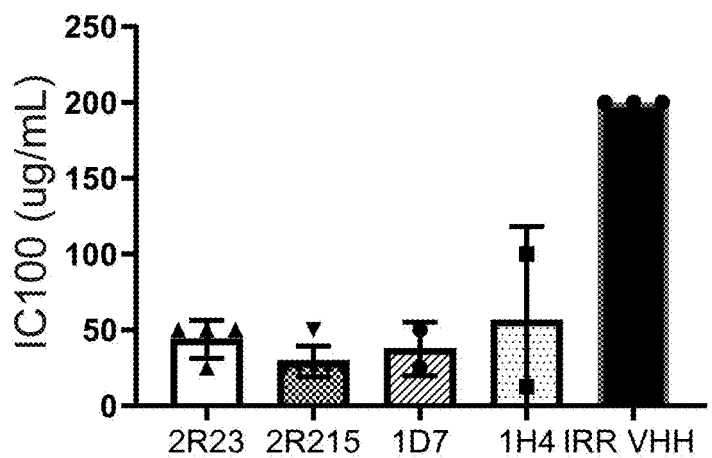
FIG. 6E is a bar graph showing the maximal inhibitory concentration ($IC_{100}$) for the VHH antibodies 2R23, 2R215, 1D7, 1H4, and an irrelevant (IRR) VHH antibody as a control in a mannose-resistant hemagglutination assay (MRHA) against H10407. Error bars represent the range in OD values observed in two independent experiments.

The results of the MRHA assays against CfaE-expressing ETEC strain H10407 were reported as the maximal inhibitory concentration (IC100). VHH 2R240 was used as negative control showing no activity at a concentration 200 ug/ml. All nanobodies showed $IC_{100}$ activity in the micromolar concentration range (12.5 ug/ml and 100 ug/ml) (FIG. 6E). We next examined whether the panel of selected nanobodies is active against ETEC strains expressing other class 5 colonization factors in MRHA assay. Most of the VHH showed activity against other strains that ranged from 6.25 to 200 ug/ml (Table 3). Surprisingly, VHHs were active in MRHA assay despite showing weak or no binding to purified antigens in ELISA. This result may be due to recombinantly expressed and purified protein fragments having different tertiary folding that obscures the antigenic sites present on a full-length protein naturally presented on the surface of ETEC.

In addition to CFA/I and other class 5 colonization factors, bacteria strains that express other fimbrial and non-fimbrial adhesins have been implicated in endemic and traveler diarrheal disease (Isidean, S D., et al, *Vaccine* 29(37): 6167-6178). We further examined the activity of the VHHs against helical CS5, fibrillary CS3 and non-fimbrial CS6 adhesins, as well as another common disease causing adhesin CS21. Surprisingly, the panel of selected VHHs showed activity against strains expressing individual adhesins (Table 3).

TABLE 3

VHH activity against ETEC adhesins

| VHH | Rigid rods | | | | | | | Helical | Fibrillar | Nonfimbrial | Bundle-forming |
| | 5a | | | 5b | | 5c | | | | | |
| | CFA/I | CS4 | CS14 | CS1 | CS17 | CS19 | CS2 | CS3 | CS5 | CS6 | CS21 |
|---|---|---|---|---|---|---|---|---|---|---|---|
| 2R23 | 50 | 25 | 25 | 200 | 6.25 | 200 | 200 | 100 | 12.5 | 12.5 | 25 |
| 2R215 | 25 | 100 | 200 | 200 | 6.25 | 200 | 6.25 | 100 | 6.25 | 25 | 25 |
| 1D7 | 100 | 200 | 100 | 50 | 6.25 | 100 | 50 | 50 | 3.125 | 12.5 | 25 |
| 1H4 | 200 | 25 | 100 | 100 | 6.25 | 100 | 100 | 100 | 3.125 | 25 | 25 |

To differentiate the CfaE-binding activities of VHHs, antibody affinity was analyzed by surface plasmon resonance using recombinant MBP CfaE-N. All VHHs showed high affinities to MBP-CfaE-N with dissociation constant (Kd) values in the nanomolar range (3 nM to 20 nM) (Table 4).

TABLE 4

$K_D$ values of VHH binding to CfaE

| | Ka(1/Ms) | Kd(1/s) | $K_D$(M) | Chi$^2$ |
|---|---|---|---|---|
| 2R23 | 7.13E+09 | 64.58 | 9.06E−09 | 20.4 |
| 2R215 | 1.46E+06 | 0.00315 | 2.16E−09 | 0.35 |
| 1D7 | 1.75E+06 | 0.03106 | 1.77E−08 | 1.69 |
| 1H4 | 2.81E+04 | 5.13E−04 | 1.83E−08 | 0.0251 |

Figure 7A:
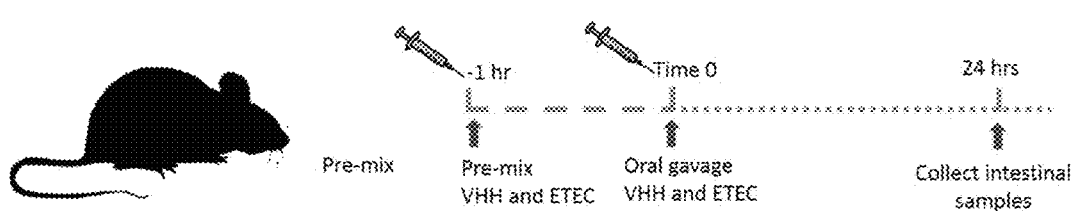
FIG. 7A is a diagram depicting pre-mix of VHH candidates in an animal colonization model of ETEC.

Example 4. Anti-CfaE VHH Prevent ETEC Colonization in the Small Intestine of a Mouse Model Next, we examined lead VHH candidates in animal colonization model (FIG. 7A). Groups of five DBA/2 mice were given a mixture of bacteria and anti-CfaE VHH (100 mg/kg of body weight) by oral gavage. VHH 2R23 could only be tested at 50 mg/kg due to the lower production yields of this yeast derived clone. All other leads were tested at 100 mg/kg.

Figure 7B:
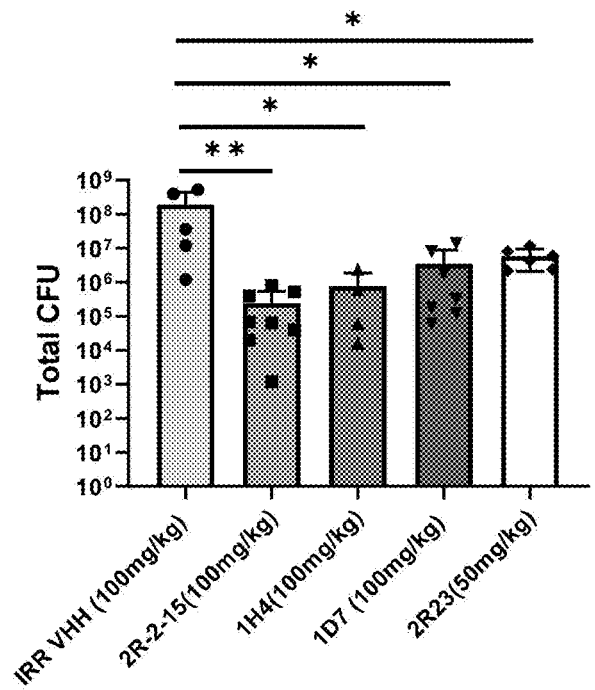
FIG. 7B is a bar graph showing the efficacy of monomeric VHH antibodies against colonization of ETEC strain H10407 expressing class 5 colonization factor CfaE. *=P<0.05 and **=P<0.01.

At 24 h after challenge, the mice were euthanized and the CFU in the small intestine were counted as described in Materials and Methods (FIG. 7B).

The efficacy of the monomeric anti-CfaE VHHs was assessed by determining whether the VHH could prevent adhesion of bacteria to the small intestine, in comparison to the irrelevant control. All VHHs showed activity in preventing colonization by H10407 strain when administered together with the bacteria at a concentration of 100 mg/kg.

Next we determined if our lead VHHs were functional at inhibition of colonization by ETEC strains expressing colonization factors other than CfaE.

Figure 7C:
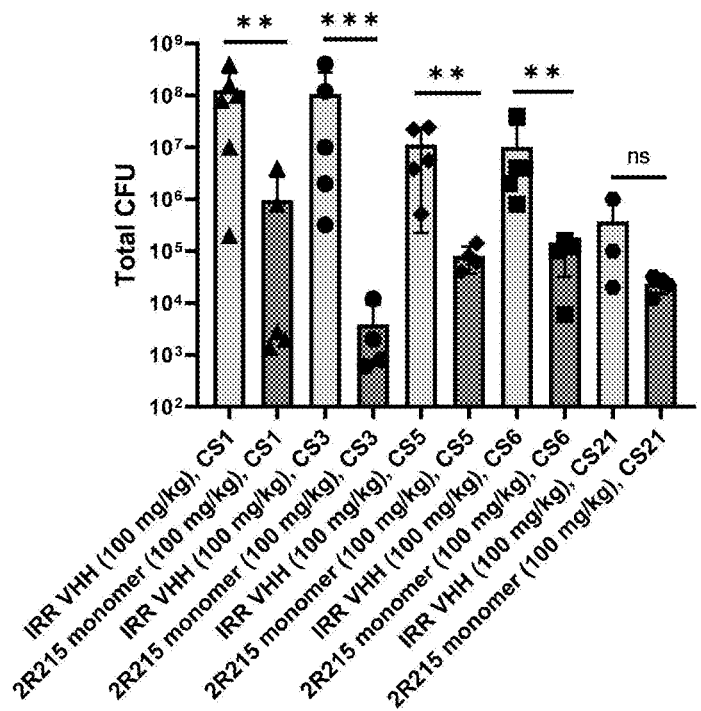
FIG. 7C is a bar graph showing the efficacy of monomeric VHH antibody 2R215 and an irrelevant (IRR) VHH antibody against colonization of ETEC strains expressing coli surface antigen 1 (CS1), coli surface antigen 3 (CS3), coli surface antigen 5 (CS5), coli surface antigen 6 (CS6), or coli surface antigen 21 (CS21). ns=not significant (P>0.05), =P<0.01, *=P<0.001.
Figure 8A:
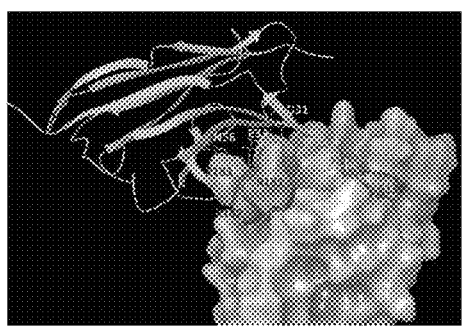
FIGS. 8A-8D are images depicting molecular model docking simulations performed for VHH antibodies 2R215 (FIG. 8A), 1D7 (FIG. 8B), 2R23 (FIG. 8C), and 1H4 (FIG. 8D). The four docking simulations used the previously resolved full-length CfaE structure (PDB ID: 2HBO) and the previously resolved VHH antibody structure (PDB ID: 6H16) to model the binding of N-terminally truncated CfaE with the VHH antibody.
Figure 8B:
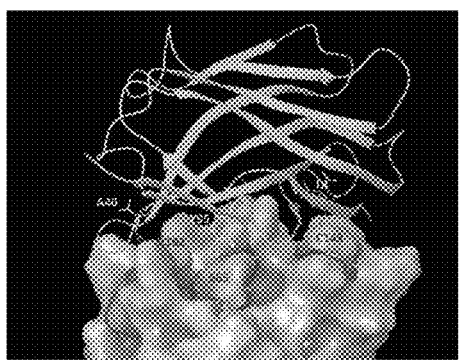
Figure 8C:
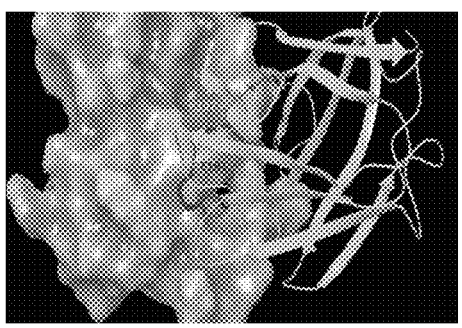
Figure 8D:
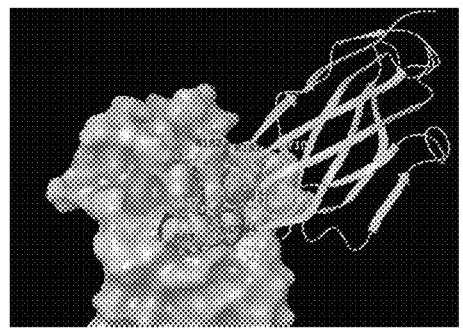
Figure 9A:
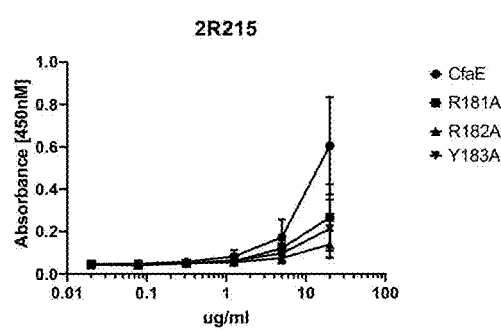
FIGS. 9A-9D are graphs showing binding by ELISA of VHH monomeric antibodies to CfaE using alanine scanning of potential residues for VHH binding to CfaE for 2R215 (FIG. 9A), 1D7 (FIG. 9B), 2R23 (FIG. 9C), and 1H4 (FIG. 9D).
Figure 9B:
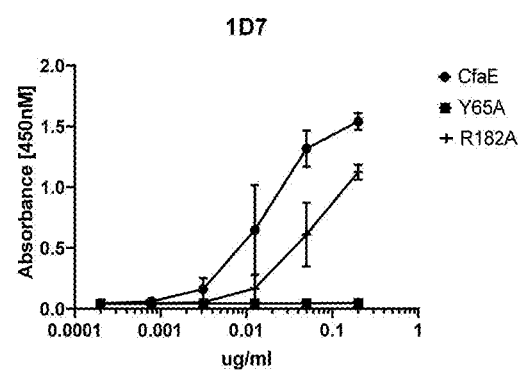
Figure 9C:
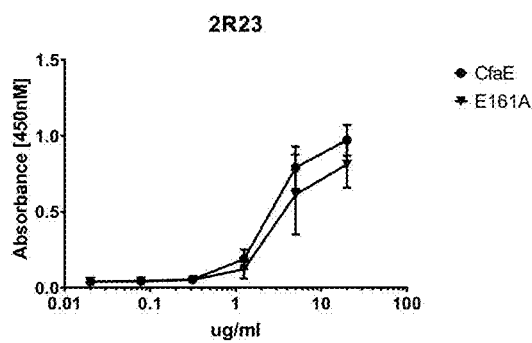
Figure 9D:
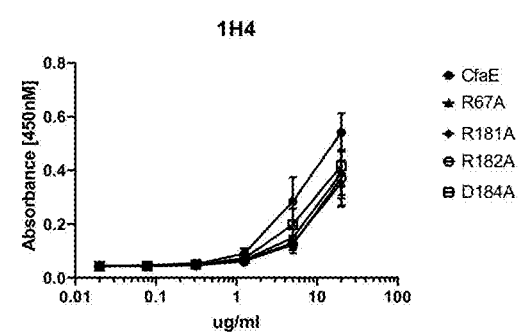

Groups of five DBA/2 mice were given a mixture of bacteria expressing colonization factors commonly implicated in causing disease (Isidean, S D., *Id*) (CS1, CS3, CS5, CS6, CS21) and VHH (100 mg/kg of body weight) by oral gavage (FIG. 7C). At 24 h after challenge, the mice were euthanized and the CFU in the small intestine were counted as described in Example 1.

VHH antibody 2R215 significantly inhibited colonization by *E. coli* strains expressing colonization factors CS1, CS3, CS5 and CS6 and resulted in a small and not significant decrease in colonization induced by *E. coli* strain expressing CS21.

Example 5. Epitope Mapping of Lead Anti-ETEC VHHs

As a visualization exercise of anti-ETEC VHH binding to CfaE, we modeled 4 lead VHHs, performed docking simulations, and in silico alanine scanning. We modeled N-terminal CfaE truncation on a previously resolved full length CfaE structure (PDB ID 2HBO) and the lead VHH sequences on previously resolved structure of a VHH 6H16 for alpaca-derived 1D7 and 1H4 and VHH 5NV for yeast derived 2R215 and 2R23 using BioLuminate (Schrodinger) (FIGS. 8A-8D).

Based on docking results, we identified potential residues for the binding interaction. In silico alanine scanning was then followed by ELISA (FIGS. 9A-9D). ELISA results confirmed that mutating predicted residues Y65, R67, E161, D184, R181, R182, and Y183 to alanine, affected the binding of VHHs to CfaE.

Interestingly, VHHs 2R215, 1D7 and 1H4 bind to the putative receptor binding pocket on the surface of CfaE, that is formed by three arginine residues (R67, R181 and R182) and is highly conserved among the class 5 adhesins (FIG. 10). In addition to the residues forming the binding pocket, we identified several other highly conserved residues, such as S65, L64, Y58, L110, C143, and Y156 that are required for interaction of cross-protective VHHs and adhesin. Interestingly, sequence alignment revealed that these residues are highly conserved among at least eight class 5 adhesins (Sakellaris, H., et al., *PNAS* 96(22): 12828-12832, 1999), which is consistent with our observation that these VHH antibodies are broadly cross protective against multiple ETEC strains.

Example 6. Multimerization Enhances the Potency of 2R215 In Vitro and In Vivo

Figure 11A:
FIGS. 11A-11B are diagram representations of exemplary dimeric (FIG. 11A) and trimeric (FIG. 11B) VHH antibodies.
Figure 11B:
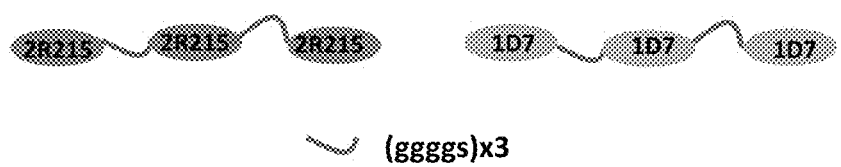
Figure 11C:
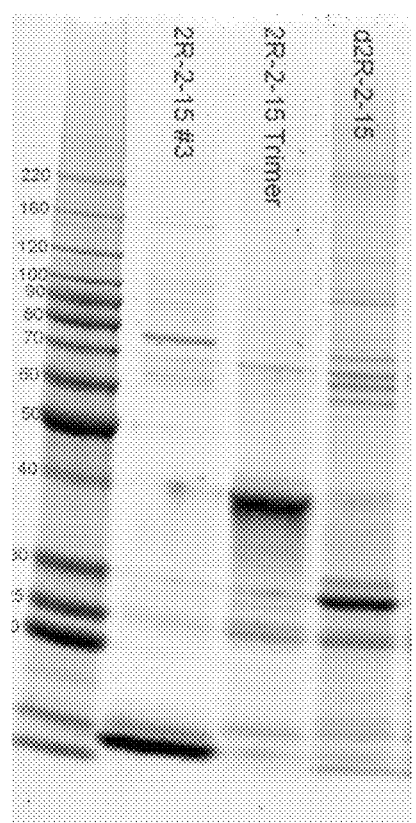
FIGS. 11C-11D are images of protein gels showing the expression and purification of multimerized VHH antibodies 2R215 (FIG. 11C) and 1D7 (FIG. 11D).
Figure 11D:
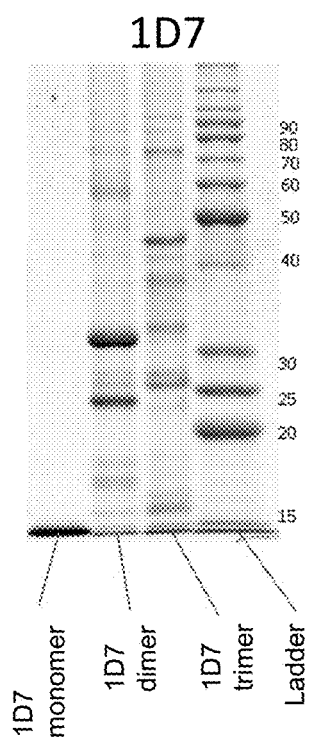

Multimerization of single domain antibodies can be often used to increase their stability and potency. We multimerized 2R215 and 1D7 to dimeric and trimeric forms with (G4S) linkers (FIGS. 11A-11B, respectively). The dimeric forms were generated using 6×(G4S) (SEQ ID NO: 221) linker to connect two monomeric VHHs in tandem N terminus to C terminus orientation. Trimers were generated using two 3×(G4S) (SEQ ID NO: 220) linkers between monomeric VHH units. These formats were successfully expressed and purified from *E. coli* (FIGS. 11C-11D).

Figure 12A:
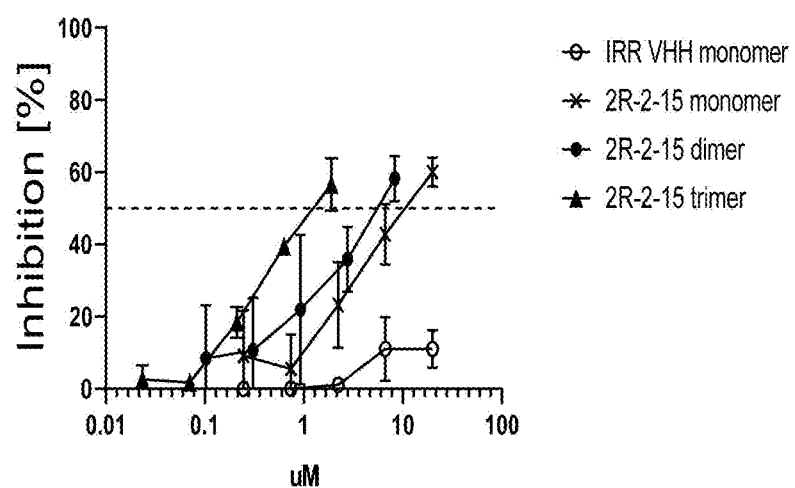
FIG. 12A is a graph showing the efficacy of multimerized VHH 2R215 for the inhibition of ETEC H10407 adhesion to intestinal cells compared to monomeric VHH 2R215 and an irrelevant (IRR) monomeric VHH.
Figure 12B:
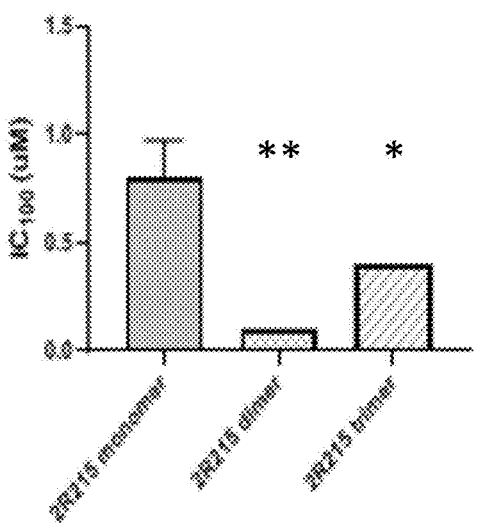
FIG. 12B is a graph showing the efficacy of multimerized VHH 2R215 by MRHA assay. The graph showed improved activity with an $IC_{100}$ of 6.7 µM for monomeric, 1.25 µM for dimeric, and 2.5 µM for trimeric VHH 2R215. *=P<0.05 and **=P<0.0.01.

Both dimeric and trimeric formats of 2R215 increased the potency of the VHH antibody in vitro in Caco2 adhesion assay (FIG. 12A). While irrelevant VHH did not inhibit the adhesion of H10407 to intestinal cells, the various formats of 2R215 when pre-incubated with bacteria, inhibited adhesion at 5.3 µM for monomeric 2R215, 1.8 µM for dimeric 2R215 and 0.567 µM for trimeric form of 2R215. Also, both dimeric and trimeric formats of 2R215 increased the activity of VHH antibody in vitro in MRHA assay (FIG. 12B). While monomeric VHH antibody had an $IC_{100}$ of 6.7 µM for monomeric, dimeric VHH antibody had an $IC_{100}$ of 1.25 µM, and trimeric VHH antibody had an $IC_{100}$ of 2.5 µM.

Figure 13A:
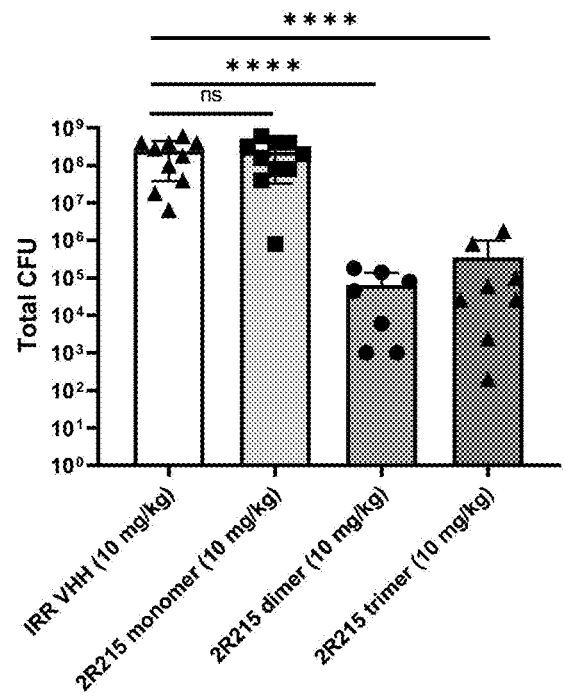
FIGS. 13A-13B are graphs showing the efficacy of multimerized VHH 2R215 for the in vivo inhibition of ETEC colonization.
Figure 13B:
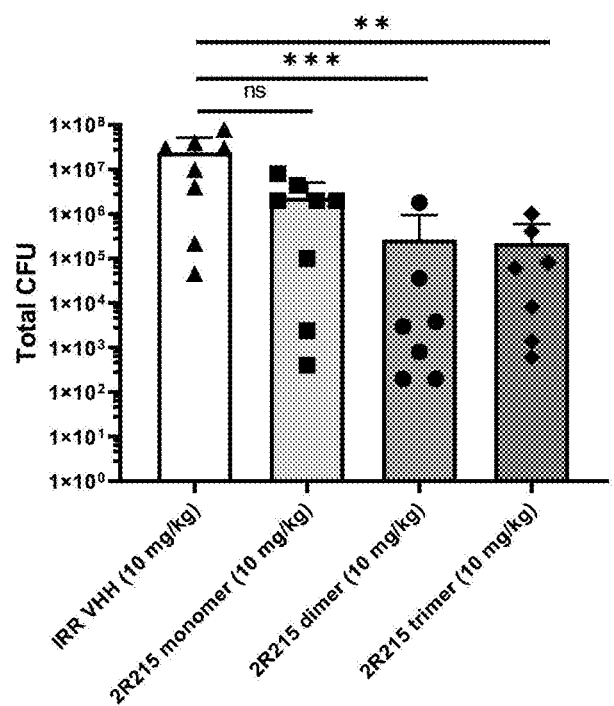

An in vivo colonization assay showed dimeric and trimeric formats of 2R215 actively inhibited colonization at a concentration 10 mg/kg when administered together with ETEC, while monomeric 2R215 had no effect at 10 mg/kg (FIG. 13A). Moreover, the dimeric and trimeric formats of 2R215 retained their activity when administered 2 hours prior to bacteria challenge (FIG. 13B).

Figure 15A:
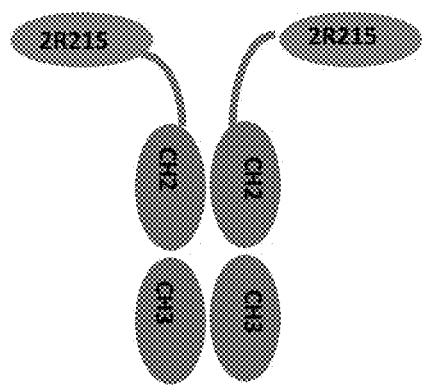
FIG. 15A is diagram representation of a VHH-IgA candidate antibody including 2R215 VHH binding domain.
Figure 15B:
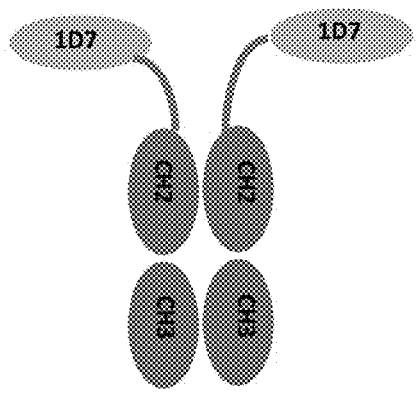
FIG. 15B is diagram representation of a VHH-IgA candidate antibody including a 1D7 VHH binding domain.
Figure 15C:
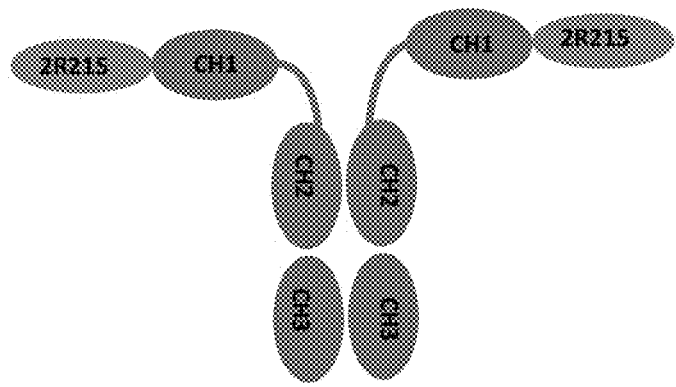
FIG. 15C is a diagram representation of a CH+ VHH-IgA candidate antibody including a 2R215 VHH binding domain.
Figure 15D:
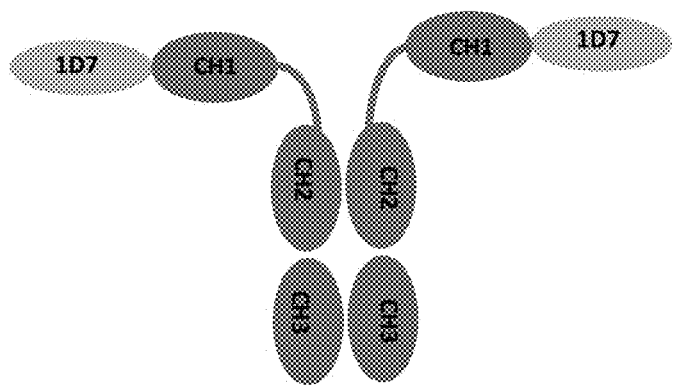
FIG. 15D is a diagram representation of a CH+ VHH-IgA candidate antibody including a 1D7 VHH binding domain.

Example 7. IgA Fc Enhances the Potency of 2R215 and 1D7 in Colonization Assay IgA Fc fusions can be produced in different platforms, as they are encoded by only a single gene and have been demonstrated to enable expression at high levels in plant seeds (e.g. *Arabidopsis* and soybean) and yeast (*Pichia pastoris*). Moreover, the VHH-Fc fusions could gain properties of the Fc region, such as increased half-life and effector functions (FIG. 15A-15C)).

Figure 16:
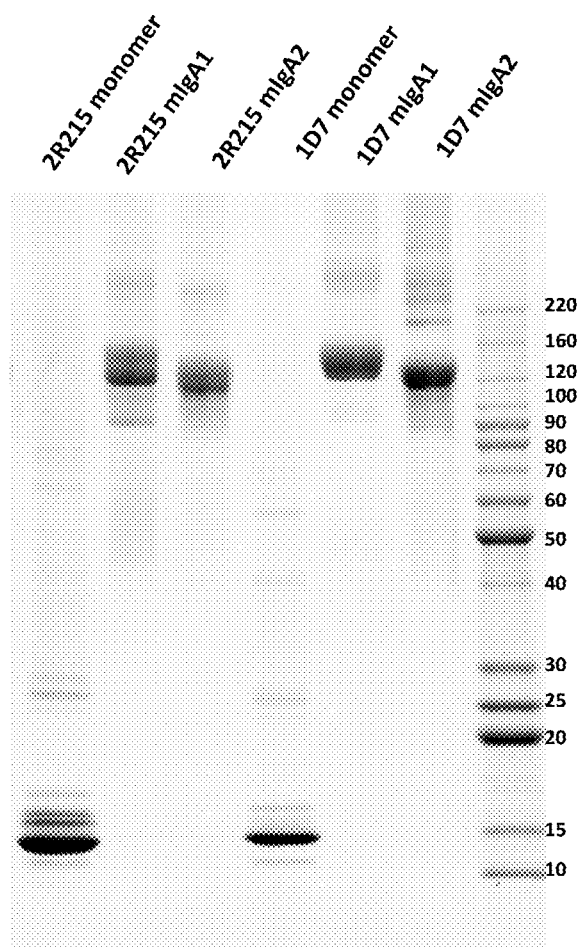
FIG. 16 is an image of a gel showing the expression and purification of VHH-IgA candidate antibodies. The gel shows, from left to right, monomeric VHH binding domain 2R215, monomeric VHH-IgA1 candidate antibody including a 2R215 VHH binding domain, monomeric VHH-IgA2 candidate antibody including a 2R215 VHH binding domain, monomeric VHH binding domain 1D7, monomeric VHH-IgA1 candidate antibody including a 1D7 VHH binding domain, monomeric VHH-IgA2 candidate antibody including a 1D7 VHH binding domain, and a standard ladder.
Figure 17A:
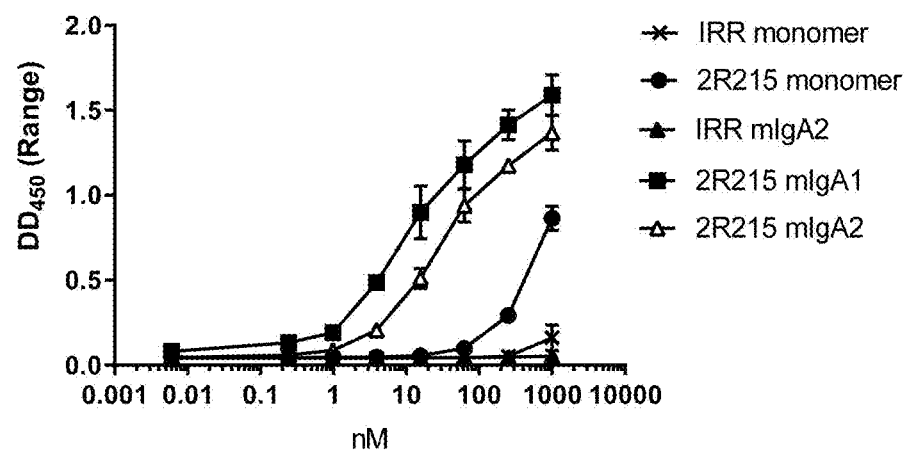
FIGS. 17A and 17B are graphs showing improved binding of VHH-IgA1 and VHH-IgA2 antibodies 2R215 (FIG. 17A) and 1D7 (FIG. 17B) to CfaE antigen by ELISA, as compared to irrelevant (IRR) VHH-IgA2 and monomeric VHH antibodies.
Figure 17B:
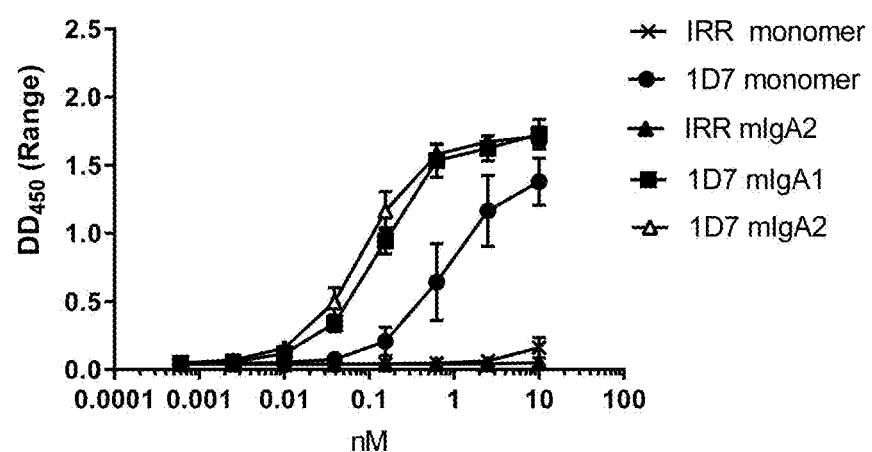

To obtain simplified VHH-Fc antibodies, 2R215 and 1D7 were grafted on to the Fc domain of an IgA1 and IgA2 (VHH-IgA) at the hinge region (Virdi V., et al. *PNAS* 110(29): 11809-11814, 2013). This resulted in bivalent monomeric VHH-Fc fusion proteins that were produced in Expi293 cells (FIG. 16). VHH-IgA fusion bodies showed improved binding to CfaE by ELISA compared to irrelevant (VHH-IgA2) and monomeric nanobody binding (FIGS. 17A-17B).

Figure 14:
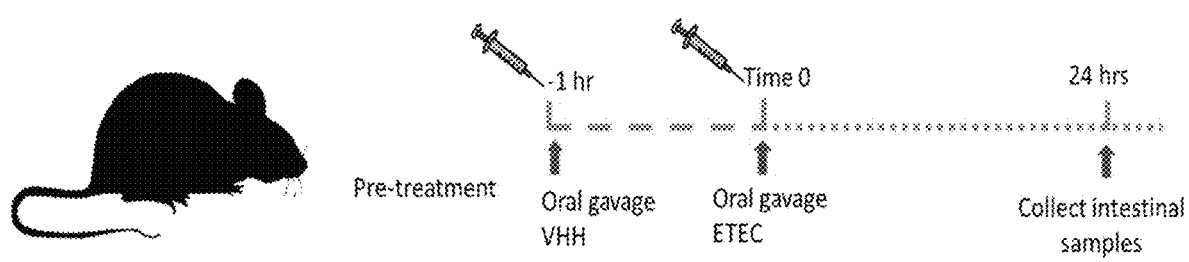
FIG. 14 is a diagram depicting pre-treatment VHH candidates in an animal colonization model of ETEC.
Figure 18A:
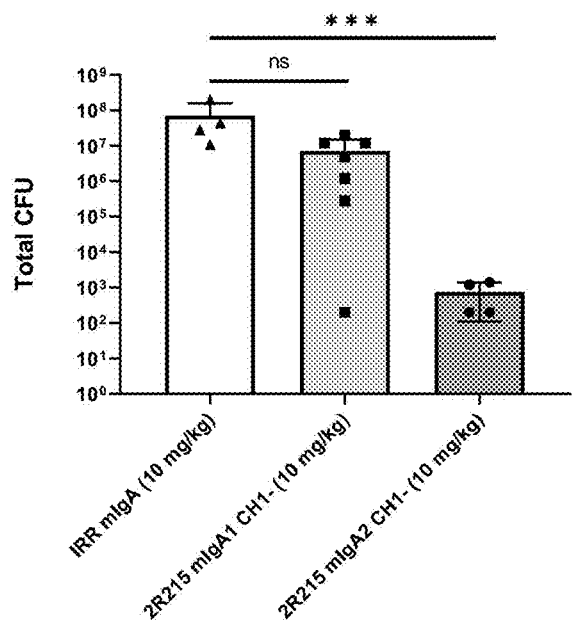
FIGS. 18A-18B are graphs showing the efficacy of treatment with anti-ETEC adhesin protein VHH-IgA fusion antibodies having VHH binding domains 2R215 (FIG. 18A) and 1D7 (FIG. 18B), as compared to an irrelevant (IRR) VHH-IgA antibody in total intestinal CFU. ns=not significant (P>0.05), =P<0.01, *=P<0.001.
Figure 18B:
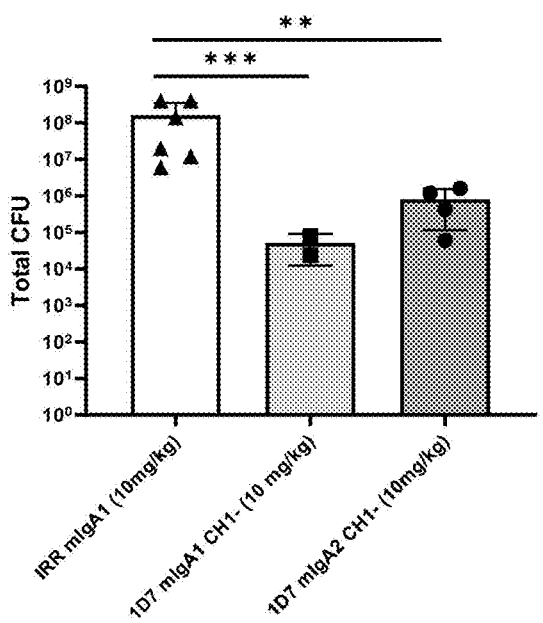
Figure 19:
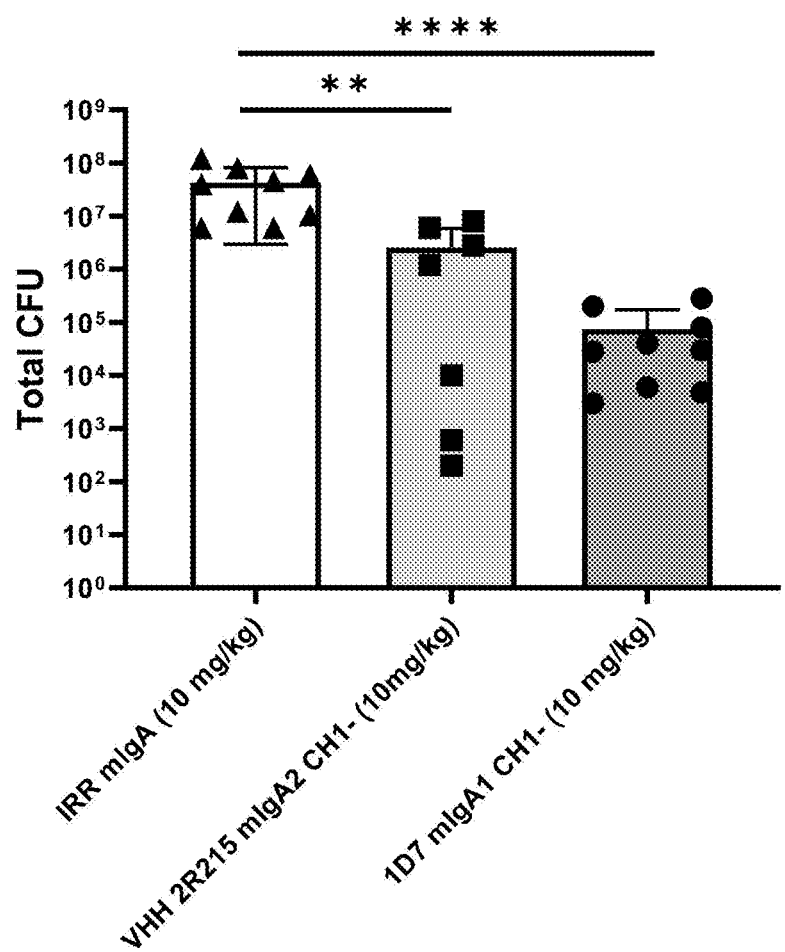
FIG. 19 is a graph showing the efficacy of anti-ETEC adhesin protein VHH-IgA antibodies 2R215 and 1D7 against ETEC compared to irrelevant (IRR) VHH-IgA when administered one hour prior to ETEC challenge. =P<0.01 and **=P<0.0001.
Figure 20A:
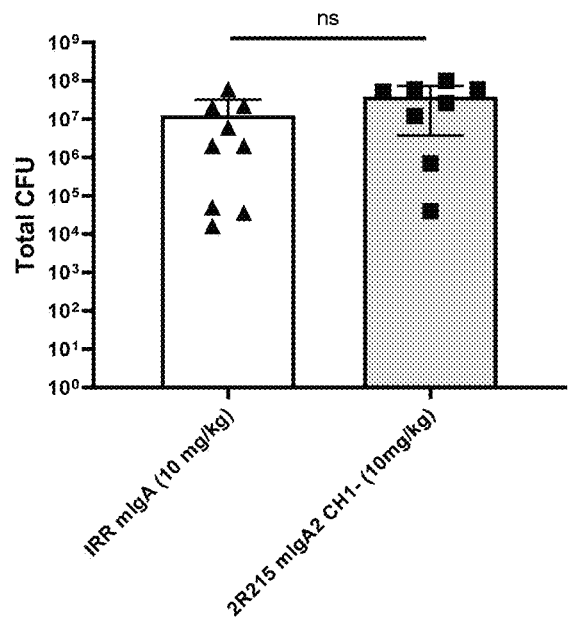
FIGS. 20A-20B are graphs showing the efficacy of CH1 domain-containing VHH-IgA antibodies 2R215 (FIG. 20A) and 1D7 (FIG. 20B) against ETEC compared to irrelevant (IRR) VHH-IgA and Travelan when administered two hours prior to ETEC challenge. ns=not significant (P>0.05), *=P<0.05, and ****=P<0.0001.
Figure 20B:
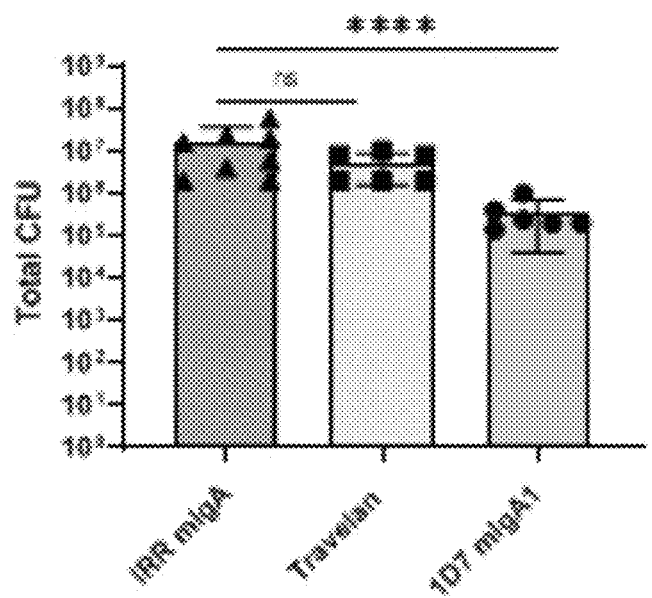
Figure 20C:
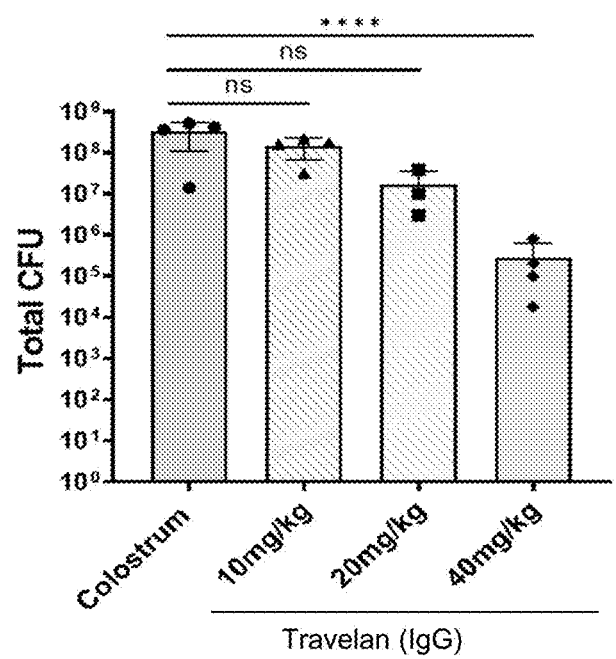
FIG. 20C is a graph showing the efficacy of Travelan, a commercial hyperimmune bovine colostrum (HBS) product, when administered one hour prior to ETEC challenge at 10 mg/kg, 20 mg/kg, and 40 mg/kg as compared with Colostrum. ns=not significant (P>0.05), and ****=P<0.0001.

We demonstrated that fusion of 2R215 with human IgA2 and fusion of 1D7 with human IgA1 or IgA2 Fc fragments significantly increased the potency of VHH to inhibit colonization of mouse intestine when administered together with ETEC in pre-mix model of colonization assay. While monomeric VHHs inhibited colonization at 100 mg/kg (FIG. 7A), the VHH-IgA fusion bodies showed strong inhibitory activity at 10 mg/kg (FIGS. 18A-18B). The 1D7 IgA1 and 2R215 IgA2 fusion bodies were next examined in pre-treatment model (FIG. 14). Both VHH-Fc fusion bodies remained protective when administered 1 hour prior to ETEC challenge (FIG. 19), and 1D7 retained activity in pre-treatment model for up to 2 hours (FIGS. 20A-20B). The activity of the 1D7 VHH-IgA fusion body was also compared to Travelan, a commercial hyperimmune bovine colostrum (HBS) product used for prevention of ETEC-induced diarrhea. While Travelan showed activity in 1 hr pre-treatment when used at 40 mg/kg (FIG. 20C), it did not inhibit colonization at 2 hrs pre-treatment (FIG. 20B).

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

---

What is claimed is:

1. An isolated VHH antibody that binds an ETEC adhesin protein, wherein the antibody comprises a VHH binding domain comprising the following complementarity determining regions (CDRs):
   (a) a CDR-H1 comprising the amino acid sequence of ERTFSYYV (SEQ ID NO: 9);
   (b) a CDR-H2 comprising the amino acid sequence of FVAGISMSGDSTK (SEQ ID NO: 10); and
   (c) a CDR-H3 comprising the amino acid sequence of ADRDIRGNFRS (SEQ ID NO: 11).

2. The antibody of claim 1, wherein the VHH binding domain comprises an amino acid sequence having at least 95% sequence identity to the amino acid sequence of SEQ ID NO: 12.

3. The antibody of claim 1, wherein the antibody comprises multiple VHH binding domains.

4. The antibody of claim 3, comprising the following N-terminal-to-C-terminal structure:

$$(P_3\text{-}L_3)_{n3}\text{-}P_2\text{-}(L_1\text{-}P_1)_{n1}$$

wherein $P_1$, $P_2$, and $P_3$ are each an isolated VHH antibody that binds an ETEC adhesin protein, wherein the antibody comprises a VHH binding domain comprising the following CDRs:
   (a) a CDR-H1 comprising the amino acid sequence of NIFQDAE (SEQ ID NO: 1);
   (b) a CDR-H2 comprising the amino acid sequence of FVATIAYGGNTN (SEQ ID NO: 2); and
   (c) a CDR-H3 comprising the amino acid sequence of VYTGVYYDRTTGGYVAFE (SEQ ID NO: 3);

$L_1$ and $L_3$ are each independently a linker; and $n_1$ and $n_3$ are each independently 0 or 1, wherein at least one of $n_1$ and $n_3$ are 1.

5. The antibody of claim 3, wherein the antibody does not comprise an Fc region.

6. The antibody of claim 1, wherein the antibody comprises a single VHH binding domain.

7. The antibody of claim 6, wherein the antibody consists of a single VHH binding domain.

8. An isolated VHH antibody that binds an ETEC adhesin protein, wherein the antibody comprises a VHH binding domain comprising the following CDRs:
   (a) a CDR-H1 comprising the amino acid sequence of ERTFSYYV (SEQ ID NO: 9);
   (b) a CDR-H2 comprising the amino acid sequence of FVAGISMSGDSTK (SEQ ID NO: 10); and
   (c) a CDR-H3 comprising the amino acid sequence of ADRDIRGNFRS (SEQ ID NO: 11),
   wherein the antibody is a monoclonal antibody, a humanized antibody, or a chimeric antibody.

9. The antibody of claim 8, wherein the antibody is an IgA class antibody or an IgG class antibody.

10. The antibody of claim 3, wherein the antibody comprises an Fc domain comprising a first Fc domain subunit and a second Fc domain subunit, wherein the first Fc domain subunit and the second Fc domain subunit are capable of stable association.

11. The antibody of claim 1, wherein the antibody is a VHH antibody fragment that binds an ETEC adhesin protein.

12. An isolated nucleic acid encoding the antibody of claim 1.

13. A vector comprising the nucleic acid of claim 12.

14. A host cell comprising the vector of claim 13.

15. A method of producing a VHH antibody, the method comprising culturing a host cell comprising an expression vector comprising the nucleic acid of claim 12 in a culture medium.

16. A composition or a pharmaceutical composition comprising the antibody of claim 1.

17. A method of treating a subject having a disorder associated with an ETEC infection or at risk of developing a disorder associated with an ETEC infection comprising administering to the subject an effective amount of the antibody of claim 1, thereby treating the subject.

18. A method of detecting an ETEC in a sample from a subject, the method comprising contacting the sample with the antibody of claim 1 under conditions permissive for binding of the antibody to an ETEC and detecting whether a complex is formed between the antibody and the ETEC.

19. A kit comprising the antibody of claim 1 and a package insert comprising instructions for (a) using the antibody to treat a subject having or at risk of developing a disorder associated with an ETEC infection or (b) using the antibody to detect ETEC.

20. An isolated VHH antibody that binds an ETEC adhesin protein, wherein the antibody comprises a VHH binding domain comprising the amino acid sequence of SEQ ID NO: 12.

21. An isolated nucleic acid encoding the antibody of claim 20.

22. A method of producing a VHH antibody, the method comprising culturing a host cell comprising an expression vector comprising the nucleic acid of claim 21 in a culture medium.

23. A composition or a pharmaceutical composition comprising the antibody of claim 20.

24. A method of treating a subject having a disorder associated with an ETEC infection or at risk of developing a disorder associated with an ETEC infection comprising administering to the subject an effective amount of the antibody of claim 20, thereby treating the subject.

25. A method of detecting an ETEC in a sample from a subject, the method comprising contacting the sample with the antibody of claim 20 under conditions permissive for binding of the antibody to an ETEC and detecting whether a complex is formed between the antibody and the ETEC.

26. A kit comprising the antibody of claim 20 and a package insert comprising instructions for (a) using the antibody to treat a subject having or at risk of developing a disorder associated with an ETEC infection or (b) using the antibody to detect ETEC.

* * * * *